(12) United States Patent
Andersson et al.

(10) Patent No.: US 9,096,901 B2
(45) Date of Patent: Aug. 4, 2015

(54) METHODS AND MATERIALS RELATED TO HAIR PIGMENTATION AND CANCER

(75) Inventors: Leif Andersson, Uppsala (SE); Gerli Rosengren Pielberg, Uppsala (SE); Anna Olegovna Golovko, Uppsala (SE); Kjell Robert Johan Lennartsson, Heby (SE); Carl-Henrik Heldin, Uppsala (SE)

(73) Assignee: Biocistronix AB, Uppsala (SE)

( * ) Notice: Subject to any disclaimer, the term of this patent is extended or adjusted under 35 U.S.C. 154(b) by 248 days.

(21) Appl. No.: 13/603,109

(22) Filed: Sep. 4, 2012

(65) Prior Publication Data
US 2013/0004520 A1    Jan. 3, 2013

Related U.S. Application Data

(63) Continuation of application No. 12/663,138, filed as application No. PCT/EP2008/057034 on Jun. 5, 2008, now Pat. No. 8,278,043.

(60) Provisional application No. 60/942,080, filed on Jun. 5, 2007.

(51) Int. Cl.
*C12N 15/11* (2006.01)
*C12Q 1/68* (2006.01)

(52) U.S. Cl.
CPC ............ *C12Q 1/6881* (2013.01); *C12Q 1/6886* (2013.01); *C12Q 2600/124* (2013.01); *C12Q 2600/136* (2013.01); *C12Q 2600/156* (2013.01); *C12Q 2600/158* (2013.01); *C12Q 2600/172* (2013.01)

(58) Field of Classification Search
CPC .. C12Q 1/6886; C12Q 2600/158; C12Q 1/68; C07K 16/00; C07K 2317/92; A61K 39/3955
See application file for complete search history.

(56) References Cited

U.S. PATENT DOCUMENTS

2003/0175721 A1    9/2003  Box et al.
2005/0245475 A1*  11/2005  Khvorova et al. ............... 514/44

FOREIGN PATENT DOCUMENTS

WO       WO 99/57318       11/1999
WO       WO 2005/075983    8/2005

OTHER PUBLICATIONS

Bailey et al., "Recent Segmental Duplications in the Human Genome" *Science*, 2002, 297:1003-1007.
Bonetto et al., "Isolation and characterization of antagonist and agonist peptides to the human melanocortin 1 receptor," *Peptides*, 2005, 26:2302-2313.
Bonifacino and Glick, "The mechanisms of vesicle budding and fusion," *Cell*, 2004, 116:153-166.
Comfort, "Coat-Colour and Longevity in Thoroughbred Mares," *Nature*, 1958, 182:1531-1532.
De Snoo et al., "Cutaneous melanoma susceptibility and progression genes," *Cancer Letters*, 2005, 230(2):153-186.
Duffy et al., Interactive effects of MC1R and OCA2 on melanoma risk phenotypes, *Human Molecular Genetics*, 2004, 13(4):447-461.
Fleury et al., "The study of cutaneous melanomas in Camargue-type gray-skinned horses (2): epidemiological survey," Pigment Cell Res., Feb 2000, 13(1):47-51.
Green et al., "Production of Polyclonal Antisera," Immunochemical Protocols, 1992, 10:1-5.
Henner et al., "Genetic mapping of the (G)-locus responsible for the coat color phontype progressive graying with age," *Mamm. Genome*, 2002, 13:535-537.
Karolchik et al., "The UCSC Genome Browser Database," *Nucl. Acids Res.*, 2003, 31(1):51-54.
Kohler & Milstein, "Continuous cultures of fused cells secreting antibody of predefined specificity," *Nature* 1975, 256:495-497.
Leevers and Marshall, "Activation of extracellular signal-regulated kinase, ERK2, by p21ras oncoprotein," *EMBO J.*, 1992, 11:569-574.
Locke et al., "Linkage of the grey coat colour locus to microsatellites on horse chromosome 25," *Anim. Genet.*, 2002, 33:329-337.
Maxwell and Muscat,"The NR4A subgroup. immediate early response genes with pleiotropic physiological roles," *Nucl. Recept. Signal.*, 2006, 4:e002.
Mayorov et al., "Effects of macrocycle size and rigidity on melanocortin receptor-1 and -5 selectivity in cyclic lactam alpha-melanocyte-stimulating hormone analogs," *Chem. Biol. Drug Des.*, 2006, 67(5):329-335.
Mossner et al., "Variations in the peroxisome proliferator-activated receptor-gamma gene and melanoma risk," *Cancer Letters*, 2006, 246(1-2):218-223.
Nomiyama et al., "The NR4A Orphan Nuclear Receptor NOR1 Is Induced by Platelet-derived Growth Factor and Mediates Vascular Smooth Muscle Cell Proliferation," *J. Biol. Chem.*, 2006, 281:33467-33476.
Pedersen et al., "Identification and classification of conserved RNA secondary structures in the human genome," *PLoS Computat. Biol.*, 2:e33 (2006.
Pei et al., NR4A orphan nuclear receptors are transcriptional regualtors of hepatic glucose metabolism, *Nature Medicine*, 2006, 12(6):1048-1055.

(Continued)

*Primary Examiner* — Tracy Vivlemore
*Assistant Examiner* — Kate Poliakova
(74) *Attorney, Agent, or Firm* — Fish & Richardson P.C.

(57) ABSTRACT

This document relates to methods and materials for determining whether or not a horse contains a Grey allele. For example, diagnostic methods such as nucleic acid-based detection methods and materials such as nucleic acid probes and primer pairs that can be used to determine whether or not a horse contains a duplication in intron 6 of STX17 nucleic acid are provided. This document also relates to methods and materials for treating a mammal having or being likely to develop cancer (e.g., benign, malignant, or metastatic cancer). For example, methods and materials for treating cancer in a mammal by administering an agent having the ability to reduce expression of an STX17 polypeptide and/or an NR4A polypeptide (e.g., an NR4A1, NR4A2, or NR4A3 polypeptide) in the mammal are provided.

6 Claims, 45 Drawing Sheets

(56) References Cited

OTHER PUBLICATIONS

Pielberg et al., "A cis-acting regulatory mutation causes premature hair greying and susceptibility to melanoma in the horse," *Nature Genetics*, 2008, 40(8):1004-1009.
Pielberg et al., "Comparative linkage mapping of the Grey coat colour gene in horses," *Anim. Genet.*, 2005, 36:390-395
Prince et al., "Robust and Accurate Single Nucleotide Polymorphism Genotyping by Dynamic Allele Specific Hybridization (DASH): Design Criteria and Assay Validation," *Genome Res.*, 2001, 11(1):152-162.
Schafer and Hawkins , "DNA variation and the future of human genetics," *Nat. Biotechnol.*, 1998, 16:33-39.
Seltenhammer et al., "Comparative histopathology of grey-horse-melanoma and human malignant melanoma," *Pigment Cell Res.*, 2004, 17:674-681.
Sponenberg, *Equine Coat Color Genetics*, 2009, Blackwell, Ames, Iowa.
Steegmaier et al., "Three novel proteins of the syntaxin/SNAP-25 family," *J. Biol. Chem.*, 1998, 273:34171-34179.
Stoneking et al., "Population variation of human mtDNA control region sequences detected by enzymatic amplification and sequence-specific oligonucleotide probes," *Am. J. Hum. Genet.*, 1991, 48:3 70-3 82.
Sundstrom et al., "Cis-acting regulatory mutation causes premature hair greying and susceptibility to melanoma in the horse," *Pigment Cell & Melanoma Research*, 2008, 21(2):274-275.
Sutton and Coleman, "Melanoma and the Greying Horse," In: RIRDC Research Paper Series No. 97/55 RIRDC Project No. UQ-28 University of Queensland, 1997.

Swanton, "Cell-cycle targeted therapies," *Lancet*, 2004, 6:27-36.
Swinburne et al., "Assignment of the horse grey colt coulur gene to ECA25 using whole genome scanning," *Animal Genetics*, 2002, 33:338-342.
The Horse Genome Project, EquCab1, released Jan. 2007, http://genome.ucsc.edu.
The Horse Genome Browser Gateway, Jan. 2007, http://genome.ucsc.edu/cgi-bin/hgGateway.
Thirumoorthy et al., "Novel agouti-related-protein-based melanocortin-1 receptor antagonist ," *J. Med. Chem.*, 2001, 44(24):4114-4124.
Underhill et al., "Detection of Numerous Y Chromosome Biallelic Polymorphisms by Denaturing High-Performance Liquid Chromatography," *Genome Res.*, 1997, 7:996-1005.
Vaysberg et al., "Rapamycin Inhibits Proliferation of Epstein-Barr Virus-Positive B-cell Lymphomas Through Modulation of Cell-Cycle Protein Expression," *Transplantation*, 2007, 83(8):1114-1121.
Yin et al., Suberoylanilide Hydroxamic Acid, a Histone Deacetylase Inhibitor: Effects on Gene Expression and Growth of glimoa Cells, *Clin Canc Res.*, 13(3):1045-1052.
Zhang et al., "The Subcellular Localization of Syntaxin 17 Varies Among Different Cell Types and is Altered in Some Malignant Cells," *J. Histochem. Cytochem.*, 2005, 53:1371-1382.
Authorized Officer Anja Bruma, International Search Report in PCT/EP2008/057034, mailed Nov. 14, 2008, 4 pages.
Authorized Officer Anja Bruma, International Preliminary Report on Patentability in PCT/EP2008/057034, mailed Dec. 17, 2009, 10 pages.

\* cited by examiner

FIGURE 11

TGAGTATATAACTGTTTTTGGCTCAGAGACGTTAGATTAATAGGATAAGAGG
CTTTTATAAATCACTAGGCTTTTGATTAGGATTTTAATAGAAGTTACAATTTG
TAAGACTGGTATTGAACCATGGATAGAAGTCTAACTGTCCTCAAATTCCAGA
TCAATTCAATAAACATTTATTAAGCACTTGTTATATAAAAGGCACTGTCTTAG
GTGCTTGGCATTGGGGATCTGACAAGGTTGGATAAAGAAAGAAAGGAAGCA
TGCTGTCTGCCTTCAGGGGTTTACAGTGGGTGGAGATATGCTTGGACCCCCAA
AACTGAAATTTCAAGTGTGATTGTTAAATGCAAAGACAAGGTATGAAGAGAA
GTATTATCCGCTCCAAGGGAAGGAGGCAGGGATTGTGAGGTGGAAGCGTCAA
GGGTAGCTTCACAAGATAGGTAGTATTTGCTTAAGCCTTGAAAACTGAGTAA
AGTTTCCGCAGGTGGGAGAGAGGGAGTGCATTTGAAGAACGCTGAACAAAG
CCTTGGAGTAGTGAAGTGTATGGCCTCCCAGGAATGACAAGTTCTGCAGTGT
AACCAAAGCACAAGGTACCATGGGCAAGCAAAGCAGAGTGGCTGAGGGCCA
GGTTTAGATGGTACTGAAGGCCATACCAAAGAATTTGCACTTTGTAGGCATT
AAGGAGCCAATACAGGTTTTTGAGCAGGTTAGAGTGATGTGATCCTGTCCGT
GTTTCAGGAAGATCACTGTTAGCGGTATGAGTAATGGCCTTAAGAGAGGAGG
AGGTTATAGGCAGGACAGCTAGTTAGGAGTCATTGCAAGAGTTGCACCAAGA
GCAATGGCAATACAAGTGTGAAGGTAAAGGAGAGCTGAGAGGCATTTCTGG
GGTGCACTTATTAGGAATTGGAGGAAGATGAAAGAGTCAAAGATAAGAAAC
ATTAAGGCTTTATTCGGCATAATCGGGTAGACAGTGATACTGTTAACATAGAT
TAGGGAACATAAAGTAGATTTGGTGGGAAAGATAGATTTTCTGTTGTTATTT
TTTAAATTATTCTTATTTTTCCTTCCCAGGAATTATGGGAAGGTTGGATATGTG
GATGTGTGTGTATATGTATGTACATAACAGGCTCGAGCCTGTTTCTGCTTATG
CTTCTCTTAGGTTTAATTCTTTGTTCTTGATCAGACTGTGATTTGAGGGTTGCG
CATCTTTGAGTTAGGGTTTCCCTGACATCTGGCTTTAAATTATAAGAAGTTCC
CAGATCACACAATCTCAGAATTGGAATTGAACTTAAAAGGACAACTAGTCTA
ATCCTTCTGCTCTTGCCCAACTTCTCAAATAGATGGTTTTTGCCTCTTTTTGAA
CAATTACTGCAAGGATGCTTTCTGCTTCAACCATTCCGTTTTGAGGCTCTAAC
TCCAGAAGTTATTCCTTGTACACAGTAAGCTCTGCCCTGTGATAACTTCCCTC
TGGCACTTTGGCCCTCTGGAGCCGTATACTGAACAAATTTTGTCTTTTTCCCAT
ATAAATGTCTCTACTTTTTGAGACCAACATTTTCCTCCTTCACCCTACCCCACC
TCACTGTATTTTCTTCTCTTAAGAACCCTTGACTGTCTAATGTGTTCCTTCTAG
AATGTGATTTCTAGTCTTTTAGTACTGGCCCTTTACTCTGCTTGTTTTCTAGT
TTGTGGATTTTTCTTGAAATGTAATGCAAAAAATTGAATGCAGTAAATTGTTT
AAAGCGTTTTTCTTTTTTGATGGCTTTAAGTCAGAAAAGCAAAATGTTTGAA
GTTTATGGAGTAGATATCTGTACAATATATTAATATATTTACGTATAAAAGGG
AATGATACAAGAATCCCAAACTATTTTTGTTTCTAGAATCAAGATTTATTCAA
TTATTCTAACTCATAATCTCTGATCTAATGTAGTTTTTAAAATCTGTAATGTAT
GATTACACAAATATATACATTTGTCAAAAGTCATCAATATGTACACATTACAA
TGTGTGAGTTACAATGTATGTGAATTATACCCAATAAAATTGATTTAAAAAAC
AAACTAAACATGTATAAAGTTCTTCTCATTCAAGACAAGTACGTTTCCCTCCT
AGTGGGATAGACACATGAAAGGAAAGTTAGGGGTTTGTGGCCATGTAACAGT

FIGURE 11 (continued)

TACATATCCGATTAGGTTACGTAAGCAGCTCCTAACCCCTAATCTAAGGAGGT
TCGTACAGGAAGACTTTGGCCATAGCCATAGCTCTATACAAATGTCCTTTTA
TAATAATCTGTAAGGACATGAGACGGAATGCTATTAGGCAAAAGCTCAAAGG
AGAACCTCTGATTACTATCCCCAGGGTGACTGAGTTCTCGTGACCACATGGTC
AAGGATTCACAGAAGCTCCATTTAGGCACCAAATGACTTGGGAACATAACCA
GAGTGACCACACATCCTCTCGTTATCATCACATGGTCATGGTAGTATCTGGGC
CAATTAACCGTGTGTTTCTGGAGCACTTTCTATGCGCATAGTACTGTGCTAAG
CTCCGTGAAAAACAGAGAATCGTATAAAAAGAACCTATAGGATGGTCGCGGT
AGCTGCACAGCATCGTGGATGCGTTTAATGTACTGAACTGTATATTTAAAACT
GTTAAAAGTTCAAGTTTTATGTTGTGCGTATTTTACCACAATCAAAAAGAAC
CTTCAAGGCCCTTGGGAGATCCAGGTGTGGTCCAGTAGATGTGAATAAATTC
CTATCTACTAAGCACCCTGCATCGTCTTTCCTCTGCCATTATTGCTCAAGTGCC
CTCTTCTCTTCCTGTGACTGTGAAGCCAGCCTTATTTCTAGTCAAGGGGATGT
AAAGAACTGTGGGCCAGTCGCTTAATAGCATGGCACCCTTGGTGCTGGTCCA
GTTTTGTCTCTCCTTTTGCCTTATTCCTTATGGCTTTTATAATCTATTTTACTCT
GGATGCATAAAAACTGGGTTGTGATGGATTAGATCAGATTCCTCCATTTATTA
CCTATGTGACCTTCGGGGTATTGTGTTGACAGCAATGAGCTTTGTAAAATTAA
TCAGAAGACTCAATGAGATAGTGCCTATTACTTCCCACCCCCTTCTCTTCTAC
TGACCCCAACTGCATTTCTGCTTTTGTCCCTCTCTCATTTGATTCCCTCTGTGG
CTCCTTGCTTAGAATTCTGCTTTTGCCACCATCATTATGTTTAAACATTTTAGT
ACGTAGTTCCTGACTCCCTCTTTTATTGCTGGATCTCTTGCTGTCAACATTTA
CTTACCTACTCTGTTTACCGCCTACTCTAGGCCAATATAATTCTTACTGTGCCT
GTATGTCATAGTGTTTGTAAGCTTGTTTCTGGGCTTTTCTGTGTATATAAGTGC
ATGTGATTAAGGAGTATAGATTACTTACCTTTGGAGTTCAGAACCAGGATAG
CTCAGTGTTATCTGGGATGGTCAAGCTGTAAGACTAGAGCTGCTATTGAAAG
TAGCCTGGAAGTTAGAGAGTCAGAAATAAAGGAAAATACCTAGAGTTCTGAT
GTTAGCTTCTTCAAAGAAACCTGTAGCTTTCCAAGCACATTAATAAAACTACA
CAGCCACTAGCAAGACTCTCCGTGGGAGAGCATGTATTATGGCTCCAGAAGG
ATTTGGGGGTGGGTTTGTTGAATGCATTATTGTTGCTTGATGCAGAGAATGCT
GGGCCTACAAGTGTCCACCACAAGCTTTCAAGGGAAAAACTTCTTCATTAGTT
TTGACTTCAGATGCCCAAACTGCATTATAATTGAACAAGTATTAACTTAGTAA
GTCAAATTTTCTTCAAAATCTTAGGTGCTCCTATAACTGCTCATTAAGATTCA
CTTATTTTTTCACGCAGGTAAGGGGACCTAATTCAGTGTTTCTTAAAATGAA
ATTCATAGACATATTCTTAGAGTCTTTGAAAATTCTTTTTCTTTAAAAAGGAA
AGTTTTTATAGTACTCTAGTTTGAGAAACACTACGGTGTCCCTCATAAATGGT
TTAGTTCATTGTTAAAGGGATGCTGAGAACATATATGAGGTGCCAAAGTATA
AAATGTCAGGAAGGGAGTTTGAAGGTTGTCAAATGTTGGAGGCCCAGGGAG
GTGAAAGCAAACATAAGCACATCGGAAGCAAAAAGGGGAGGTTGGTGGATA
GAGGTGAGAAGGCTGCTGAGCCACCATTGCTGTCAGCTTGGTTTCCTATACTG
GGGTAAGTTTGTGTATGTGTGGTTTGGCCCAGCATAAAGAGCCAAAGACATA
GCGGACAAGTGGTGACCAGATTCAGCTCTGAATGGATTCTAGTTTGGCAATC
TCTGGGGAGTGATTAACAACTTTGACACCAGTTTGCTGCCTAACAGTAATTGC

FIGURE 11 (continued)

TGTGTCATTGAGTCCTTCTTACTCAAGAAGCAGAATTTGAAGATATGGGCAA
AGTTTGGGATTCAAACCAAGCAAAATAGGGAAGGAGCAGGCAGATCTGTAC
AATGAGGGACGACTTTTGATCCAGGGTAGAGGCTGGTCTTCCCTCTGCCTTG
TCTCCAGGCCCGTGTTTAAGCAAGCGCCCTGATGTCAGTGAATGAATCCTTAC
AGGTGTGGGCTACTCCCCATGGTGAGACAGGCCTCATCAGGTTCTGGGATTG
CGGTGATGGGGAGCATTGCAGTTCAAATAACCACTGAGCTCAGGCTTCATTT
GGCCCTGTGATCCTTTCTCCAATTATTCTAAAGGATCTTTATGAAAAAATAAT
AAAGTAAAATTTTTAAATTTCACTTAAAAAAACTCATAGAGCTGCAATATGC
AACCTTTTTAGGAAGGAGCATTAAAAAATATTTCCCTGAGGCCTCGAGATTA
CACTTGGGGTACAGAAATGGCAATAATTATGGCAGATTCCACCATCTTGACG
GAACAATTTTGGGGCTGAGAGAAAGACAGTTGGCTATTTTCCCTCTACGCCTC
AACTTGTCAAGATACGGAGGTTGATGATCGAGTTTTACATCTGTGATTTATCT
GGTAGCATAGACTTGATGCAAGAACAGAAAGTGTTGGGGATGTCCCAAATAG
AAACAAGGATAGGGTATCAGAAATCCTGACAAGTGGCACTTATGCTTCTGTG
GGTTGGGAAAGGAGAGCTAACATTAAAGAAGTTTTATTGTCTGAGGAAAATA
AAAACTGAGTACATGAATGCTAGGAGAGATCTAATGTTTAGTGCCCTAGAA
TTTTCAAGCATTATAGGAAAAGTTTAATATTTTTTGATAGCAAAGAATGAT
GAGAGTTAAGCTTTCTTTGGAAGATCAGCATGACTTTTTCTATTTTTCCCCTCA
TATTCTACAGACACTATCTCATTTTATCCTCACTTCAACTCTGTGAGGTATGA
GTATCATTATCCTCACTTGGCAGACGAGAGTACTGACATATAGGGAGCTTGA
GTAGTTTATCCAAGGGCACACAGTGCTCGTGCTGGGATCTGAACACAGGACA
TCCAACCAAAGGTTGTGCCCTTAATCCTATCATATATATATACTTGTGGTTTG
TTTTTTTCTTTGCTTAGGAAGATTCGCCCTGAGCTAACTTCTGTTGCCAACCTT
CCTCTTTTGCTTGAGGAAGATTCGCCCTGAGCTAACATCTGTGCCAGTCTTC
CTTTGTTTTGTATGTGGGTCACCACCACAGTATGGCTGCCAAAGAGTGGTGTA
GGTCTGCACCCAGGAACCAAACCAGGGCCGCCAAAGCGGAGCATGCCGAAC
AACCATGAGGCCATGAGGCTGGCCCTGCTAGTGGCTTTTAAAGTTTGAGAAT
CATGGACTTGTAGTATCAGCACCACCTGGGAACTCATTAGAAATGCAA↓AAT
CTCAGAATTGGAATTGAACTTAAAAGGACAACTAGTCTAATCCTTCTGCTCTT
GCCCAACTTCTCAAATAGATGGTTTTTGCCTCTTTTGAACAATTACTGCAAG
GATGCTTTCTGCTTCAACCATTCCGTTTTGAGGCTCTAACTCCAGAAGTTATTC
CTTGTACACAGTAAGCTCTGCCCTGTGATAACTTCCCTCTGGCACTTTGGCCC
TCTGGAGCCGTATACTGAACAAATTTTGTCTTTTCCCATATAAATGTCTCTAC
TTTTTGAGACCAACATTTTCCTCCTTCACCCTACCCCACCTCACTGTATTTTCT
TCTCTTAAGAACCCTTGACTGTCTAATGTGTTCCTTCTAGAATGTGATTTCTAG
TCTTTTTAGTACTGGCCCTTTACTCTGCTTGTTTTCTAGTTTGTGGATTTTTCTT
GAAATGTAATGCAAAAAATTGAATGCAGTAAATTGTTTAAAGCGTTTTTCTTT
TTTGATGGCTTTAAGTCAGAAAAAGCAAAATGTTTGAAGTTTATGGAGTAGA
TATCTGTACAATATATTAATATATTTACGTATAAAAGGGAATGATACAAGAA
TCCCAAACTATTTTTGTTTCTAGAATCAAGATTTATTCAATTATTCTAACTCAT
AATCTCTGATCTAATGTAGTTTTTAAAATCTGTAATGTATGATTACACAAATA
TATACATTTGTCAAAAGTCATCAATATGTACACATTACAATGTGTGAGTTACA
ATGTATGTGAATTATACCCAATAAAATTGATTTAAAAAACAAACTAAACATG

FIGURE 11 (continued)

```
TATAAAGTTCTTCTCATTCAAGACAAGTACGTTTCCCTCCTAGTGGGATAGAC
ACATGAAAGGAAAGTTAGGGGTTTGTGGCCATGTAACAGTTACATATCCGAT
TAGGTTACGTAAGCAGCTCCTAACCCCTAATCTAAGGAGGTTCGTACAGGAA
GACTTTGGCCATAGCCATAGCTCTATACAAATGTCCTTTTTATAATAATCTGT
AAGGACATGAGACGGAATGCTATTAGGCAAAAGCTCAAAGGAGAACCTCTG
ATTACTATCCCCAGGGTGACTGAGTTCTCGTGACCACATGGTCAAGGATTCAC
AGAAGCTCCATTTAGGCACCAAATGACTTGGGAACATAACCAGAGTGACCAC
ACATCCTCTCGTTATCATCACATGGTCATGGTAGTATCTGGGCCAATTAACCG
TGTGTTTCTGGAGCACTTTCTATGCGCATAGTACTGTGCTAAGCTCCGTGAAA
AACAGAGAATCGTATAAAAGAACCTATAGGATGGTCGCGGTAGCTGCACA
GCATCGTGGATGCGTTTAATGTACTGAACTGTATATTTAAAACTGTTAAAAGT
TCAAGTTTTATGTTGTGCGTATTTTACCACAATCAAAAAGAACCTTCAAGGC
CCTTGGGAGATCCAGGTGTGGTCCAGTAGATGTGAATAAATTCCTATCTACTA
AGCACCCTGCATCGTCTTTCCTCTGCCATTATTGCTCAAGTGCCCTCTTCTCTT
CCTGTGACTGTGAAGCCAGCCTTATTTCTAGTCAAGGGGATGTAAAGAACTG
TGGGCCAGTCGCTTAATAGCATGGCACCCTTGGTGCTGGTCCAGTTTTGTCTC
TCCTTTTGCCTTATTCCTTATGGCTTTTATAATCTATTTTACTCTGGATGCATA
AAAACTGGGTTGTGATGGATTAGATCAGATTCCTCCATTTATTACCTATGTGA
CCTTCGGGGTATTGTGTTGACAGCAATGAGCTTTGTAAAATTAATCAGAAGA
CTCAATGAGATAGTGCCTATTACTTCCCACCCCTTCTCTTCTACTGACCCCA
ACTGCATTTCTGCTTTTGTCCCTCTCTCATTTGATTCCCTCTGTGGCTCCTTGCT
TAGAATTCTGCTTTTGCCACCATCATTATGTTTAAACATTTTAGTACGTAGTTC
CTGACTCCCTCTTTTATTGCTGGATCTCTTGCTGTCAACATTTTACTTACCTAC
TCTGTTTACCGCCTACTCTAGGCCAATATAATTCTTACTGTGCCTGTATGTCAT
AGTGTTTGTAAGCTTGTTTCTGGGCTTTTCTGTGTATATAAGTGCATGTGATTA
AGGAGTATAGATTACTTACCTTTGGAGTTCAGAACCAGGATAGCTCAGTGTT
ATCTGGGATGGTCAAGCTGTAAGACTAGAGCTGCTATTGAAAGTAGCCTGGA
AGTTAGAGAGTCAGAAATAAAGGAAAATACCTAGAGTTCTGATGTTAGCTTC
TTCAAAGAAACCTGTAGCTTTCCAAGCACATTAATAAAACTACACAGCCACT
AGCAAGACTCTCCGTGGGAGAGCATGTATTATGGCTCCAGAAGGATTTGGGG
GTGGGTTTGTTGAATGCATTATTGTTGCTTGATGCAGAGAATGCTGGGCCTAC
AAGTGTCCACCACAAGCTTTCAAGGGAAAAACTTCTTCATTAGTTTTGACTTC
AGATGCCCAAACTGCATTATAATTGAACAAGTATTAACTTAGTAAGTCAAAT
TTTCTTCAAAATCTTAGGTGCTCCTATAACTGCTCATTAAGATTCACTTATTTT
TTTCACGCAGGTAAGGGGACCTAATTCAGTGTTTCTTAAAATGAAATTCATAG
ACATATTCTTAGAGTCTTTGAAAATTCTTTTCTTTAAAAAGGAAAGTTTTTAT
AGTACTCTAGTTTGAGAAACACTACGGTGTCCCTCATAAATGGTTTAGTTCAT
TGTTAAAGGGATGCTGAGAACATATATGAGGTGCCAAAGTATAAAATGTCAG
GAAGGGAGTTTGAAGGTTGTCAAATGTTGGAGGCCCAGGGAGGTGAAAGCA
AACATAAGCACATCGGAAGCAAAAAGGGGAGGTTGGTGGATAGAGGTGAGA
AGGCTGCTGAGCCACCATTGCTGTCAGCTTGGTTTCCTATACTGGGGTAAGTT
TGTGTATGTGTGGTTTGGCCCAGCATAAAGAGCCAAAGACATAGCGGACAAG
TGGTGACCAGATTCAGCTCTGAATGGATTCTAGTTTGGCAATCTCTGGGGAGT
```

FIGURE 11 (continued)

GATTAACAACTTTGACACCAGTTTGCTGCCTAACAGTAATTGCTGTGTCATTG
AGTCCTTCTTACTCAAGAAGCAGAATTTGAAGATATGGGCAAAGTTTGGGAT
TCAAACCAAGCAAAATAGGGAAGGAGCAGGCAGATCTGTACAATGAGGGAC
GACTTTTGATCCCAGGGTAGAGGCTGGTCTTCCCTCTGCCTTGTCTCCAGGCC
CGTGTTTAAGCAAGCGCCCTGATGTCAGTGAATGAATCCTTACAGGTGTGGG
CTACTCCCCATGGTGAGACAGGCCTCATCAGGTTCTGGGATTGCGGTGATGG
GGAGCATTGCAGTTCAAATAACCACTGAGCTCAGGCTTCATTTGGCCCTGTGA
TCCTTTCTCCAATTATTCTAAAGGATCTTTATGAAAAAATAATAAAGTAAAAT
TTTTAAATTTCACTTAAAAAAACTCATAGAGCTGCAATATGCAACCTTTTTAG
GAAGGAGCATTAAAAAATATTTCCCTGAGGCCTCGAGATTACACTTGGGGTA
CAGAAATGGCAATAATTATGGCAGATTCCACCATCTTGACGGAACAATTTTG
GGGCTGAGAGAAAGACAGTTGGCTATTTTCCCTCTACGCCTCAACTTGTCAAG
ATACGGAGGTTGATGATCGAGTTTTACATCTGTGATTTATCTGGTAGCATAGA
CTTGATGCAAGAACAGAAAGTGTTGGGGATGTCCCAAATAGAAACAAGGAT
AGGGTATCAGAAATCCTGACAAGTGGCACTTATGCTTCTGTGGGTTGGGAAA
GGAGAGCTAACATTAAAGAAGTTTTATTGTCTGAGGAAAATAAAAACTGAGT
ACATGAATGCTAGGAGAGATCTAATGTTTAGTGCCCTAGAATTTTCAAGCAT
TATAGGAAAAGTTTAATATTTTTTGATAGCAAAGAATGATGAGAGTTAAG
CTTTCTTTGGAAGATCAGCATGACTTTTTCTATTTTTCCCCTCATATTCTACAG
ACACTATCTCATTTTATCCTCACTTCAACTCTGTGAGGTATGAGTATCATTATC
CTCACTTGGCAGACGAGAGTACTGACATATAGGGAGCTTGAGTAGTTTATCC
AAGGGCACACAGTGCTCGTGCTGGGATCTGAACACAGGACATCCAACCAAA
GGTTGTGCCCTTAATCCTATCATATATATATACTTGTGGTTTGTTTTTTTCTTT
GCTTAGGAAGATTCGCCCTGAGCTAACTTCTGTTGCCAACCTTCCTCTTTTTGC
TTGAGGAAGATTCGCCCTGAGCTAACATCTGTGCCAGTCTTCCTTTGTTTTGT
ATGTGGGTCACCACCACAGTATGGCTGCCAAAGAGTGGTGTAGGTCTGCACC
CAGGAACCAAACCAGGGCCGCCAAAGCGGAGCATGCCGAACAACCATGAGG
CCATGAGGCTGGCCCTGCTAGTGGCTTTTAAAGTTTGAGAATCATGGACTTGT
AGTATCAGCACCACCTGGGAACTCATTAGAAATGCAAATTCTCAGGCCTCAT
CCCAAGCCCCCTGAATCAGAAACTCTGGATGAAGTTCTCCAGGTGATTCTGGT
GCACACTCCAGTGTGGAAACCACTGTTGTATTGGTCTCTGACGACGTTAGAA
GAAGACTTATAGAGGACTTTTTAGGGATTGTGTTAGAGATGTCAAGATGGT
GGAGAATATAGCAATGAAGGGATACCATGAAAGGTCTAACGGTGAAGAGGT
ACATACCTGGCGTCTGAGAAGGGAAGGAATGTCAATAATGTGATAGGAAGC
AACTGTGAGGAAACAATTAGCTGTGTTGTTTGGGTGTCCTGTTCTCGGATGAA
ATGATGATTGGAATTAGAAGAGTGTTGGTCACATACGCTTCACTATAAGTGA
CTAGGTCAGTTATATAAGGACAATCAAATACTTCAGGGTTCAAATTGAATTAT
TTCACAGTCATCGAAGAAGTTGGCATTTAGCTAGGATCAAAGAGGGATTCTC
TTCTTTTTTTCTGTGAATTAAAAAGACTAGTCTGTATATTGATGTGATGGTGGT
TACGTGGGTTTATGCATTTATCAGAAATCATCATACTATACCCTTAAAATGGG
TGCATATTATTATATGTAAATTCTGTCTAAATAAAGTTGATTTAAAAATGGGA
ATGTGGGGGCTGGCCCTGTGTGCCCGAGCGGTTAAGTTCGCGCCCTCCGCTG
CAGGCGGCCCAGTGTTTCGTTGGTTCGAATCCTGGGCACGGACATGACACTG

FIGURE 11 (continued)

CTCATCAAACCACGCTGAGGCAGCATCCCACATGCCACAACTAGAAGGACCC
ACAACAAAGAATATACAACTATGTACCGGGGTGCTTTGGGGAGAAAAAGGA
AAAAATAAAATCTTAAAAAAAAAAAAAAATAGGGTATAGTGTACTCGTGGC
CAGTTAATGAGTTTCTGTCACTGAGGTGTTTGAGCAGAGGTTCAGTAAGCGCT
TGTCAGATATGTCGTAGTGGGGCTTCCCACATCTGAGGGAGAAATCGCACTC
AGCAACCTAAACATTCCTTCTACCCAGAGGTTCCATGAGTCACAATTTCTGTT
GTGTCAGCCGCAGGTGTTGCCATTTTGTGTAGAATGCTTGGTTAATATATTTG
ATCTGAAACATTTTAACTTGTCATGATTTTAAAATGTATTAAAGTGTCCACGT
GTGAAACACAGGACAGTGAATTCATTCACCACTCCCTACTGCATATCACAAG
TAGAAAGATTTCATGGCAGATCAAACCATATTGTATTCTTATTCCTAAAACAG
TAATTTGTATTTATCGTGGCATCAAGGGTGTTTTACTCCTAAGGCAAATTTGC
CTGTTTTAAACTGAATCTTCAAAGAAGATAAGTTAGGGAGGATTTTTGCTTTG
ATCCTGTTTTTGTTTTTTTCCATCAAACCCAACATGACATGTAAATACTTATTT
GGACTTTTTTTCTTTCTCGAAAGCAGATTTATTTGGAGAACAATATGCTTGTA
TGTTTGAATGAAGTTTAGAGTAAGATGCTTTTTCCTATAAAGGTGCCACTCTT
TTATTACTGAATAATTAAGTCACCTTTTTTTATACAAGTGAATTTGTGCTTTCG
ACGTGGTTTGTCAGATGCTGTTAAATGAACTGCTGTTAGACTCCAAGGCTGCG
GCACACAGGCCCTGATTACAGGAGTTAAAATAGTGTGCATTGGCTGACTGCT
GCTCCGCAGCAGGAGCGCTCACTCATAATTCCTTTGCATCTAG

FIGURE 12

TGAGTATATAACTGTTTTTGGCTCAGAGAC/TGTTAGATTAATAGGATAAGAG
GCTTTTATAAATCACTAGGCTTTTGATTAGGATTTTAATAGAAGTTACAATTT
GTAAGACTGGTATTGAACCATGGATAGAAGTCTAACTGTCCTCAAATTCCAG
ATCAATTCAATAAACATTTATTAAGCACTTGTTATATAAAAGGCACTGTCTTA
GGTGCTTGGCATTGGGGATCTGACAAGGTTGGATAAAGAAAGAAAGGAAGC
ATGCTGTCTGCCTTCAGGGGTTTACAGTGGGTGGAGATATGCTTGGACCCCA
AAACTGAAATTTCAAGTGTGATTGTTAAATGCAAAGACAAGGTATGAAGAGA
AGTATTATCCGCTCCAAGGGAAGGAGGCAGGGATTGTGAGGTGGAAGCGTC/
TAAGGGT/CAGCTTCACAAG/CATAGGTAGTATTTGCTTAAGCCTTGAAAAC/T
TGAGTAAAGTT/GTCCGCAGGTGGGAGAGAGGGAGTGCATTTGAAGAACGCT
GAACAAAGCCTTGGAGTAGTGAAGTGTATGGCCTCCCAGGAATGACAAGTTC
TGCAGTGTAACCAAAGCACAAGGTACCAT/CGGGCAAGCAAAGCAGAGT/CG
GCTGAGGGCCAGGTTTAGATGGTACTGAAGGCCATACCAAAGAATTTGCACT
TTGTAGGCATTAAGGAGCCAATACAGGTTTTTGAGCAGGTTAGAGTGATGTG
ATCCTGTCCGTGTTTCAGGAAGATCACTGTTAGCGGTA/GTGA/GA/GTAATGG
CCTTAAGAGAGGAGGAGGTTATAGGCAGGACAGCTAGTTAGGAGTCATTGCA
AGAGTTGCACCAAGAGCAATGGCAATACAAGTGTGAAGGTAAAGGAGAGCT
GAGAGGCATTTCTGGGGTGCACTTATTAGGAATTGGAGGAAGATGAAAGAGT
CAAAGATAAGAAACATTAAGGCTTTATTCGGCATAATCGGGTAGACAGTGAT
ACTGTTAACATAGATTAGGGAACATAAAGTAGATTTGGTGGGAAAGATAGAT
TTTCTGTTGTTATTTTTTAAATTATTCTTATTTTTCCTTCCCAGGAATTATGGG
AAGGTTGGATATGTGGATGTGTGTATATGTATGTACATAACAGGCTCGAG
CCTGTTTCTGCTTATGCTTCTCTTAGGTTTAATTCTTTGTTCTTGATCAGACTGT
GATTTGAGGGTTGCGCATCTTTGAGTTAGGGTTTCCCTGACATCTGGCTTTAA
ATTATAAGAAGTTCCCAGATCACACAATCTCAGAATTGGAATTGAACTTAAA
AGGACAACTAGTCTAATCCTTCTGCTCTTGCCCAACTTCTCAAATAGATGGTT
TTTGCCTCTTTTTGAACAATTACTGCAAGGATGCTTTCTGCTTCAACCATTCCG
TTTTGAGGCTCTAACTCCAGAAGTTATTCCTTGTACACAGTAAGCTCTGCCCT
GTGATAACTTCCCTCTGGCACTTTGGCCCTCTGGAGCCGTATACTGAACAAAT
TTTGTCTTTTCCCATATAAATGTCTCTACTTTTGAGACCAACATTTTCCTCC
TTCACCCTACCCCACCTCACTGTATTTCTTCTCTTAAGAACCCTTGACTGTCT
AATGTGTTCCTTCTAGAATGTGATTTCTAGTCTTTTAGTACTGGCCCTTTACT
CTGCTTGTTTCTAGTTTGTGGATTTTTCTTGAAATGTAATGCAAAAATTGA
ATGCAGTAAATTGTTTAAAGCGTTTTCTTTTTGATGGCTTTAAGTCAGAAA
AAGCAAAATGTTTGAAGTTTATGGAGTAGATATCT/CGTACAATATATTAATA
TATTTACGTATAAAGGGAATGATACAAGAATCCCAAACTATTTTTGTTTCTA
GA/GATCAAGATTTATTCAATTATTCTAACTCATAATCTCTGATCTAATGTAGT
TTTTAAAATCTGTAATGTATGATTACACAAATATATACATTTGTCAAAAGTCA
TCAATATGTACACATTACAATGTGTGAGTTACAATGTATGTGAATTATACCCA

FIGURE 12 (continued)

ATAAAATTGATTTAAAAAACAAACTAAACATGTATAAAGTTCTTCTCATTCAA
GACAAGTACGTTTCCCTCCTAGTGGGATAGACACATGAAAGGAAAGTTAGGG
GTTTGTGGCCATGTAACAGTTACATATCCGATTAGGTTACGTAAGCAGCTCCT
AACCCCTAATCTAAGGAGGTTCGTACAGGAAGACTTTGGCCATAGCCATAGC
TCTATACAAATGTCCTTTTTATAATAATCTGTAAGGACATGAGACGGAATGCT
ATTAGGCAAAAGCTCAAAGGAGAACCTCTGATTACTATCCCCAGGGTGACTG
AGTTCTCGTGACCACATGGTCAAGGATTCACAGAAGCTCCATTTAGGCACCA
AATGACTTGGGAACATAACCAGAGTGACCACACATCCTCTCGTTATCATCAC
ATGGTCATGGTAGTATCTGGGCCAATTAACCGTGTGTTTCTGGAGCACTTTCT
ATGCGCATAGTACTGTGCTAAGCTCCGTGAAA/GAACAGAGAATCG/ATATAA
AAAGAACCTATAGGATGGTCGCGGTAGCTGCACAGCATCGTGGATGCGTTTA
ATGTACTGAACTGTATATTTAAAACTGTTAAAAGTTCAAGTTTTATGTTGTGC
GTATTTTTACCACAATCAAAAAGAACCTTCAAGGCCCTTGGGAGATCCAGGT
GTGGTCCAGTAGATGTGAATAAATTCCTATCTACTAAGCACCCTGCA/GTCGT
CTTTCCTCTGCCA/GTTATTGCTCAAGTGCCCTCTTCTCTTCCTGTGACTGTGAA
GCCAGCCTTATTTCTAGTCAAGGGGATGTAAAGAACTGTGGGCCAGTCGCTT
AATAGCATGGCACCCTTGGTGCTGGTCCAGTTTTGTCTCTCCTTTTGCCTTATT
CCT/CTATGGCTTTTATAATCTATTTTACTCTGGATGCATAAAAACTGGGTTGT
GATGGATTAGATCAGATTCCTCCATTTATTACCTATGTGACCTTCGGGGTATT
GTGTTGACAGCAATGAGCTTTGTAAAATTAATCAGAAGACTCAATGAGATAG
TGC/TCTATTACTTCCCACCCCCTTCTCTTCTACTGACCCCAACTGCATTTCTGC
TTTTGTCCCTCC/TCTCATTTGATTCCCTCTGTGGCTCCTTGCTTAGAATTCTGC
TTTTGCCACCATCATTATGTTTAAACATTTTAGTACGTAGTTCCTGACTCCCTC
TTTTATTGCTGGATCTCTTGCTGTCAACATTTTACTTACCTACTCTGTTTACCG
CCTACTCTAGGCCAATATAATC/TCTTACTGTGCCTGTATGTCATAGTGTTTGT
AAGCTTGTTTCTGGGCTTTTCTGTGTATATAAGTGCATGTGATTAAGGAGTAT
G/AGATTACTTACCTTTGGAGTTCAGAACCAGGATAGCTCAGTGTTATCTGGG
ATGGTCAAGCTGTAAGACTAGAGCTGCTATTGAAAGTAGCCTGGAAGTTAGA
GAGTCAGAAATAAAGGAAAATACCTAGAGTTCTGATGTTAGCTTCTTCAAAG
AAACCTGTAGCTTTCCAAGCACATTAATAAAACTACACAGCCACTAGCAAGA
CTCTCCGTGGGAGAGCATGTATTATGGCTCCAGAAGGATTTGGGGGTGGGTT
TGTTGAATGCATTATTGTTGCTTGATGCAGAGAATGCTGGGCCTACAAGTGTC
CACCACAAGCTTTCAAGGGAAAAACTTCTTCATTAGTTTTGACTTCAGATGCC
CAAACTGCATTATAATTGAACAAGTATTAACTTAGTAAGTCAAATTTTCTTCA
AAATCTTAGGTGCTCCTATAACTGCTCATTAAGATTCACTTATTTTTTCACGC
AGGTAAGGGGACCTAATTCAGTGTTTCTTAAAATGAAATTCATAGACATATTC
TTAGAGTCTTTGAAAATTCTTTTCTTTAAAAAGGAAAGTTTTTATAGTACTCT
AGTTTGAGAAACACTACGGTGTCCCTCATAAATGGTTTAGT/CTCATTGTTAA
AGGGATGCTGAGAACATATATGAGGTGCCAAAGTATAAAATGTCAGGAAGG
GAGTTTGAAGGTTGTCAAATGTTGGAGGCCCAGGGAGGTGAAAGCAAACATA
AGCACATCGGAAGCAAAAAGGGGAGGTTGGTGGATAGAGGTGAGAAGGCTG

FIGURE 12 (continued)

CTGAGCCACCATTGCTGTCAGCTTGGTTTCCTATACTGGGGTAAGTTTGTGTA
TGTGTGGTTTGGCCCAGCATAAAGAGCCAAAGACATAGCGGACAAGTGGTGA
CCAGATTCAGCTCTGAATGGATTCTAGTTTGGCAATCTCTGGGGAGTGATTAA
CAACTTTGACACCAGTTTGCTGCCTAACAGTAATTGCTGTGTCATTGAGTCCT
TCTTACTCAAGAAGCAGAATTTGAAGATATGGGCAAAGTTTGGGATTCAAAC
CAAGCAAAATAGGGAAGGAGCAGGCAGATCTGTACAATGAGGGACGACTTT
TGATCC/TAGGGTAGAGGCTGGTCTTCCCTCTGCCTTGTCTCCAGGCCCGTGT
TTAAGCAAGCGCCTGATGTCAGTGAATGAATCCTTACAGGTGTGGGCTACT
CCCCATGGTGAGACAGGCCTCATCAGGTTCTGGGATTGCGGTGATGGGGAGC
ATTGCAGTTCAAATAACCACTGAGCTCAGGCTTCATTTGGCCCTGTGATCCTT
TCTCCAATTATTCTAAAGGATCTTTATGAAAAAATAATAAAGTAAAATTTTA
AATTTCACTG/TAAAAAAACTCATAGAGCTGCAATATGCAACCTTTTAGGAA
GGAGCATTAAAAAATATTTCCCTGAGGCCTCGAGATTACACTTGGGGTACAG
AAATGGCAATAATTATGGCAGATTCCACCATCTTGACGGAACAATTTTGGGG
CTGAGAGAAAGACAGTTGGCTATTTTCCCTCTACGCCTG/CAACTT/CGTCAAG
ATACGGAGGTTGATGATCGAGTTTTACATCTGTGATTTATCTGGTAGCATAGA
CTTGATGCAAGAACA/GGAAAGTGTTGGGGATGTCCCAAATAGAAACAAGGA
TAGGGTATCAGAAATCCTGACAAGTGGCACTTATGCTTCTGTGGGTTGGGAA
AGGAGAGCTAACATTAAAGAAG/TTTTATTGTCTGAGGAAAATAAAAACTG
AGTA/GCATGAATGCTAGGAGAGATCTAATGTTTTAGTGCCCTAGAATTTTCA
AGCA/TTTATAGGAAAAGTTTAATATTTTTTGATAGCAAAGAATGATGAGA
GTTAAGCTTTCTTTGGAAGATCAGCA/CTGACTTTTTCTATTTTTCCCCTCATAT
TCTACAGACACTATCTCATTTTATCCTCACTTCAACTCTGTGAGGTATGAGTA
TCATTATCCTCACTTGGCAGACGAGAGTACTGACATATAGG/AGAGCTTGAGT
AGTTTATCCAAGGGCACACAGTGCTCGTGCTGGGATCTGAACACAGGACATC
CAACCAAAGGTTGTGCCCTTAATCCTATCATATATATATACTT/CGTGGTTTGT
TTTTTTCTTTGCTTAGGAAGATTCA/GCCCTGAGCTAACTTCTGTTGCCAACCT
TCCTCTTTTTGCTTGAGGAAGATTCGCCCTGAGCTAACATCTGTGCCAGTCTT
CCTT/CTGTTTTGTATGTGGGTCACCACCACAGTATGGCTGCCAAAGAGTGGT/
CGTAGGTCTGCACCCAGGAACCAAACCAGGGCCGCCAAAGCG/AGAGCATGC
CGAACAACCATG/AAGGCCATGAGGCTGGCCCTGCTAGTGGCTTTTAAAGTT/
GTGAGAATCATGGACTTGTAGTATCAGCACCACCTGGGAACTCATTAGAAAT
GCAAATTCTCAGGCCTCAT/CCCCAAGCCCCTGAATCAGAAACTCTGGATGA
AGTTCTCCAGGTGATTCTGGTGCACACTCCAGTGTGGAAACCACTGTTGTATT
GGTCTCTGACGACGTTAGAAGAAGACTTATAGAGGACTTTTTAGGGATTGT
GTTAGAGATGTCAAGATGGTGGAGAATATAGCAATGAAGGGATACCATGAA
AGGTCTAACGGTGAAGAGGTACATACCTGGCGTCTGAGAAGGGAAGGAATG
TCAATAATGTGATAGGAAGCAACTGTGAGGAAACAATTAGCTGTGTTGTTTG
GGTGTCCTGTTCTCGGATGAAATGATGATTGGAATTAGAAGAGTGTTGGTCA
CATACGCTTCACTATAAGTGACTAGGTCAGTTATATAAGGACAATCAAATAC
TTCAGGGTTCAAATTGAATTATTTCACAGTCATCGAAGAAGTTGGCATTTAGC
TAGGATCAAAGAGGGATTCTCTTCTTTTTTCTGTGAATTAAAAAGACTAGTC
TGTATATTGATGTGATGGTGGTTACGTGGGTTTATGCATTTATCAGAAATCAT

FIGURE 12 (continued)

CATACTATACCCTTAAAATGGGTGCATATTATTATATGTAAATTCTGTCTAAA
TAAAGTTGATTTAAAAATGGGAATGTGGGGGCTGGCCCT/CGTGTGCCCGAGC
GGTTAAGTTCGCGCC/GCTCCGCTGCAGGCGGCCCAGTGTTTCGTTGGTTCG/A
AATCCTGGGCACGGACATGACACTGCTCATCAAACCACGCTGAGGCAGCATC
CCACATGCCACAACTAGAAGGACCCACAACAAAGAATATACA/CACTATGTA
CCGGGGTGCTTTGGGGAGAAAAAGGAAAAAATAAAATCTTAAAAAAAAAAA
AAAATAGGGTATAGTGTACTCGTGGCCAGTTAATGAGTTTCTGTCACTGAGGT
GTTTGAGCAGAGGTTCAGTAAGCGCTTGTCAGATATGTCGTAGTGGGGCTTCC
CACATCTGAGGGAGAAATCGCACTCAGCAACCTAAACATTCCTTCTACCCAG
AGGTTCCATGAGTCACAATTTCTGTTGTGTCAGCCGCAGGTGTTGCCATTTTG
TGTAGAATGCTTGGTTAATATATTTGATCTGAAACATTTTAACTTGTCATGAT
TTTAAAATGTATTAAAGTGTCCACGTGTGAAACACAGGACAGT/CGAATTCAT
TCACCA/GCTCCCTACTGCATATCACAAGTAGAAAGATTTCATGGCAGATCAA
ACCATATTGTATTCTTATTCCTAAAACAGTAATTTGTATTTATCGTGGCATCA
AGGGTGTTTACTCCTAAGGCAAATTTGCCTGTTTTAAACTGAATCTTCAAAG
AAGATAAGTTAGGGAGGATTTTTGCTTTGATCCTGTTTTTGTTTTTTTCCATCA
AACCCAACATGACATGTAAATACTTATTTGGACTTTTTTTCTTTCTCGAAAGC
AGATTTATTTGGAGAACAATATGCTTGTATGTTTGAATGAAGTTTAGAGTAAG
ATGCTTTTTCCTATAAAGGTGCCACTCTTTTATTACTGAATAATTAAGTCACCT
TTTTTTATACAAGTGAATTTGTGCTTTCGACGTGGTTTGTCAGATGCTGTTAAA
TGAACTGCTGTTAGACTCCAAGGCTGCGGCACACAGGCCCTGATTA/GCAGGA
GTTAAAATAGTGTGCATTGGCTGACTGCTGCTCCGCAGCAGGAGCGCTCACT
CATAATTCCTTTGCATCTAG

FIGURE 13

GAAATCACCGAAACCGGCCTCCAGCGCCCCGGCCGGAGGTTTTTCTGTATGA
GTGGAGAAGACAGTTGTTACAAGTAGAAGTGACACAACATTTTTTTAGGATG
TCTGAAGATGAAGAAAAGTGAAATTACGCCGTCTTGAGCCAGCTATCCAGA
AATTCATTAAGATAGTAATCCCAACAGACCTGGAGAGGTTAAGAAAGCACCA
GATAAATATTGAGAAGTATCAAAGGTGCAGAATCTGGGATAAGTTACATGAA
GAACATATCAATGCAGGACGTACAGTTCAGCAACTCCGCTCCAATATTCGAG
AAATGGAGAAACTTTGTTTGAAAGTCCGAAAGGATGATGTAGGACTTCTAAA
GAGAATGATAGATCCTGTTAAAGAAGAAGCATCAGTAGCAACAGCAGAATTT
CTCCAGCTCCATCTGGAATCTGTAGAAGAACTTAAGAAACAGTTTAATGATG
AAGAAACTTTGTTACAGCCTTCTCTGACCAGATCCATGACTGTTGGTGGAGCT
TTTCACACTGCTGAAGCTGAAACCGATCCTCAGAGTGTGACTCAGATATACG
CATTGCCTGAAATCCCTCGAGATCAAATGCTGCCGAATCCTGGGAAACCTT
AGAAGCGGACTTAATCGAACTTAGCCAACTGGTCACTGATTTCTCTCTCCTAG
TAAATTCCCAGCAGGAGAAGATTGACAGCATTGAAGACCATGTCAACACTGC
TGCTGTGAATGTTGAAGTGGGAACCAAAAACTTGGGGAAGGCTGCAAAATAC
AAGCTGGCAGCTCTGCCTGTGGCAGGTGCACTCATCGGAGGAGCGGTAGGGG
GTCCGATTGGCCTCCTTGCAGGCTTCAAAGTGGCAGGAATTGCAGCTGCACTT
GGTGGTGGGGTGTTGGGCTTCACAGGTGGAAAATTGATACAAAGAAAAAAA
CAGAAAATGATGGAGAAGCTCGCTTCCAGCTGTCCAGATCTTCCCAGCCAAA
GTGACAAAAAATGCAGTTAAAAACCAAACTTTAGTATTATTGGTGCCAACAT
GTCTATCCTAATGAGGACCTTTTCTGCTGTTGGACACTCAGTCAGCTTTTGGA
ACATGATTATATCAAAATAGTGGCTGTAGATGCTCCAGTGGGACTGAACTGT
GATGAGCGGGTATATTTCGTTGTTACTGGGTTTTTAATGGAGATGTTAGAGA
TCAAGGAGCCTGGGCTGAGGGTGTATAATGGTTGTCAGGTAAAGTTTAAAGA
GTGCCAGGGAGCAGATTTTCTACCTGGAAATATGAAAACTGAACCCATAACT
TTGATAAGGTCTTGAGATGTGTGGACATGTTGGGTTACAGAAGAATAGTTTCT
TCCATAACCTTGACTTGGAAACCCTAGGGCTAAGCATATTGCAAATATGCTTA
TTTGTCTCCTAAATATGGGAGATTATTTAGGCCTGTTAGCAAGGAAAGAATG
GGAGTTCAGGAGCCTATCTTGTCAAATAGGGAGATCAGGATCCAGCGAGATC
CTGGTGAGCTACATAACACAGTCCATTTGGTGAACCCTATTACAGTTGGTCC
AACTGTACTTCTGGTGAAGGAAACTAATAATGTAAGAAAATGGAAAGAGAG
GCCCAGCTTCTCTTTCAGATATCTTAATTTGTGATACTGGCTTCTTCTCTGAAC
TCTTCCTTCTGCCTCTCTTTAAATAAAGAACACTGAATCTCAAATGGTAGGAG
ACTTATTAGCCCAGTCACTAAGCTTGCTCTGTCAGCCTGTATCTTAAGACCTC
AAAGATCCAGTGCCCTGTGTCTTTCCTCCCTTGTAATTTTGAAAAGGTCTTAG
ACTTGTAGGGTGAATTTTACCCATGTGTAATGAGGACTTTTCTCATAATCTCC
TTTTTTGTACTGTCTCCCATCTCTGTTCACCCTTTCCTGTAGCCCCTAGGTGGA
AAAAAAAAAAAAAAAAAAA

FIGURE 14

CATGACACTGCTCATCAAACCACGCTGAGGCAGCATCCCACATGCCACAACT
AGAAGGACCCACAACAAAGAATATACAACTATGTACCGGGGTGCTTTGGGGA
GAAAAAGGAAAAAATAAAATCTTAAAAAAAAAAAAAAAATAGGGTATAGTGT
ACCTGTGGCCAGTAATGAGTTTCTGTCACTGAGGTGTTTGAGCAGAGGTTCAG
TAAGCGCTTGTCAGAATGTCGTAGTGGGGCTTCCCACATCTGAGGGAGAAAT
CGCACTCAGCAACCTAAACATTCCTTCTACCCAGAGGTTCCATGAGTCACAAT
TTCTGTTGTGTCAGCCGCAGGTGTTGCCATTTTGTGTAGAATGCTTGGTTAAT
ATATTTGATCTGAAACATTTTAACTTGTCATGATTTTAAAATGTATAAAGTGT
CCACGTGTGAAACACAGGACAGTGAATTCATTCACCACTCCCTACTGCATAT
CACAAGTAGAAAGATTTCATGGCAGATCAAACCATATTGTATTCTTATTCCTA
AAACAGTAATTTGTATTTATCGTGGCATCAAGGGTGTTTTACTCCTAAGGCAA
ATTTGCCTGTTTTAAACTGAATCTTCAAAGAAGATAAGTTAGGGAGGATTTTT
GCTTTGATCCTGTTTTTGTTTTTTCCATCAAACCCAACATGACATGTAAATAC
TTATTTGGACTTTTTTCTTTCTCGAAAGCAGATTTATTTGGAGAACAATATGC
TTGTATGTTTGAATGAAGTTTAGAGTAAGATGCTTTTCCTATAAAGGTGCCA
CTCTTTATTACTGAATAATTAAGTCACCTTTTTTATACAAGTGAATTTGTGC
TTTCGACGTGGTTTGTCAGATGCTGTTAATGAACTGCTGTTAGACTCCAAGGC
TGCGGCACACAGGCCCTGATTNCAGGAGTTAAAATAGTGTGCATTGGCTGAC
TGCTGCTCCGCAGCAGGAGCGCTCACTCATAATTCCTTTGCATCTAGTCCCAG
CAGGAGAAGATTGACAGCATTGAAGACCATGTCAACACTGCTGCTGTGAATG
TTGAAGTGGGAACCAAAAACTTGGGGAAGGCTGCAAAATACAAGCTGGCAG
CTCTGCCTGTGGCAGGTGCACTCATCGGAGGAGCGGTAGGGGGTCCGATTGG
CCTCCTTGCAGGCTTCAAAGTGGCAGGAATTGCAGCTGCACTTGGTGGTGGG
GTGTTGGGCTTCACAGGTGGAAAATTGATACAAAGAAAAAAACAGAAAATG
ATGGAGAAGCTCGCTTCCAGCTGTCCAGATCTTCCCAGCCAAAGTGACAAAA
AATGCAGTTAAAAACCAAACTTTAGTATTATTGGTGCCAACATGTCTATCCTA
ATGAGGACCTTTTCTGCTGTTGGACACTCAGTCAGCTTTTGGAACATGATTAT
ATCAAAATAGTGGCTGTAGATGCTCCAGTGGGACTGAACTGTGATGAGCGGG
TATATTTCGTTGTTTACTGGGTTTTTAATGGAGATGTTAGAGATCAAGGAGCC
TGGGCTGAGGGTGTATAATGGTTGTCAGGTAAAGTTTAAAGAGTGCCAGGGA
GCAGATTTTCTACCTGGAAATATGAAAACTGAACCCATAACTTTGATAAGGT
CTTGAGATGTGTGGACATGTTGGGTTACAGAAGAATAGTTTCTTCCATAACCT
TGACTTGGAAACCCTAGGGCTAAGCATATTGCAAATATGCTTATTTGTCTCCT
AAATATGGGAGATTATTTAGGCCTGTTAGCAAGGAAAGAATGGGAGTTCAGG
AGCCTATCTTGTCAAATAGGGAGATCAGGATCCAGCGAGATCCTGGTGAGCT
ACATAACACAGTCCATTTGGTGAACCCTATTACAGTTTGGTCCAACTGTACTT
CTGGTGAAGGAAACTAATAATGTAAGAAAATGGAAAGAGAGGCCCAGCTTC
TCTTTCAGATATCTTAATTTGTGATACTGGCTTCTTCTCTGAACTCTTCCTTCT
GCCTCTCTTTAAATAAAGAACACTGAATCTCAAATGGTAGGAGACTTATTAG

FIGURE 14 (continued)

CCCAGTCACTAAGCTTGCTCTGTCAGCCTGTATCTTAAGACCTCAAAGATCCA
GTGCCCTGTGTCTTTCCTCCCTTGTAATTTTGAAAAGGTCTTAGACTTGTAGG
GTGAATTTTACCCATGTGTAATGAGGACTTTTCTCATAATCTCCTTTTTTGTAC
TGTCTCCCATCTCTGTTCACCCTTTCCTGTAGCCCCTAGGTGGAAAAAAAAAA
AAAAAAAAAA

FIGURE 15

MSEDEEKVKLRRLEPAIQKFIKIVIPTDLERLRKHQINIEKYQRCRIWDKLHEEHIN
AGRTVQQLRSNIREMEKLCLKVRKDDVGLLKRMIDPVKEEASVATAEFLQLHLE
SVEELKKQFNDEETLLQPSLTRSMTVGGAFHTAEAETDPQSVTQIYALPEIPRDQ
NAAESWETLEADLIELSQLVTDFSLLVNSQQEKIDSIEDHVNTAAVNVEVGTKNL
GKAAKYKLAALPVAGALIGGAVGGPIGLLAGFKVAGIAAALGGGVLGFTGGKLI
QRKKQKMMEKLASSCPDLPSQSDKKCS

FIGURE 16

ATA<u>ATG</u>CCCTGCGTGCAAGCCCAGTATAGCCCTTCGCCTCCAGGTTCCAGTTAT
GCAGCGCAGACCTACGGCTCAGCGGAATACACCACCGAGATCATGAACCCCG
ACTACACCAAGCTGACCATGGACCTCGGCAGCACCGAGATCACGGCCACGGC
CACCACGTCCCTGCCCAGCTTCAGTACCTTCATGGAGGGCTACTCGAGCAACT
ACGAACTCAAGCCCTCCTGCCTGTACCAAATGCCGCCATCGGGGCCGCGGCC
CTTGATCAAGATGGAGGAGGGCCGCGCGCACGGCTACCACCATCACCACCAT
CACCACCACCACCACCACCATCACCAGCAGCAGCAGCAGCAGCCATCCATTC
CGCCCCCTCCGGCCCGGAGGACGAGGTGCTGCCCAGCACCTCCATGTACTT
CAAGCAGTCCCCGCCGTCCACCCCGACCACGCCGGGCTTCCCCCCGCAGGCG
GGGGCGCTGTGGGACGACGCGCTGCCCTCCGCGCAGGGCTGCCTCGCGCCCG
GCCCGCTGCTCGACCCGCCGATGAAGGCGGTGCCCACGGTGGCCGGCGCGCG
CTTCCCGCTCTTCCACTTCAAGACCTCGCCGCCGCACCCGCCTGCGCCCAGCC
CGGCCGGCGGCCACCACCTGGCCTACGACCCGACGGCCGCCGCCGCGCTCAG
CCTGCCGCTTGGAGCCGCCGCCGCGGGCAGCCAGGCCGCCGCGCTCGAG
GGCCACTCGTACGGGCTGCCGCTGCCCAAGAGGGCGGCCGCGCTGGCCTTCT
CGCCGCTCGGCCTCACCGCCTCCCCCACCGCGTCCAGCCTGCTGGCCGAGAG
CCCCAGCCTGCCGTCGCCGCCCAACAGGAGTTTGTCGTCGGGCGAGGGAACG
TGCGCCGTGTGCGGGGACAACGCCGCCTGCCAGCACTACGGCGTGCGAACCT
GCGAGGGCTGCAAGGGCTTTTTCAAGAGAACGGTGCAGAAAAATGCAAAAT
ATGTTTGCCTGGCAAATAAAAACTGCCCTGTAGACAAGAGACGTCGAAACCG
ATGTCAGTACTGTCGATTTCAGAAGTGTCTCAGTGTCGGAATGGTTAAAGAA
GTTGTCCGTACAGATAGTCTGAAAGGGAGGAGAGGTCGGCTGCCTTCCAAAC
CAAAGAGCCCGTTACAGCAGGAACCTTCTCAGCCCTCTCCACCGTCTCCTCCG
ATCTGCATGATGAATGCCCTTGTCCGAGCTTAACAGACTCAACGCCCAGAG
ATCTCGATTATTCCAGATACTGCCCCACTGACCAGGCCGCTGCCGGCACAGA
TGCTGAGCATGTGCAACAGTTCTACAACCTTCTGACAGCCTCCATTGATGTAT
CCAGAAGCTGGGCAGAAAAGATTCCCGGATTTACTGATCTCCCCAAAGAAGA
TCAGACATTACTTATAGAATCAGCCTTTTGGAGCTGTTTGTTCTCAGACTTTC
CATCAGGTCGAACACTGCTGAAGATAAGTTTGTGTTCTGCAATGGACTTGTCC
TGCATCGACTTCAGTGCCTTCGTGGATTTGGGGAGTGGCTCGACTCCATTAAA
GACTTTTCCTTAAGTTTGCAGAGCCTGAACCTGGATATCCAAGCCTTAGCATG
CCTGTCAGCACTGAGCATGATCACAGAACGACATGGGTTAAAAGAACCAAAG
AGAGTGGAGGAGCTATGCAACAAGATCACAAGCAGCTTAAAAGACCACCAG
AGCAAGGGGCAGGCTTTGGAGCCCACGGAGCCCAAGGTCCTGCGCGCCCTGG
TAGAACTGCGGAAGATATGCACCCTGGGCCTCCAGCGCATCTTCTACCTGAA
GCTGGAAGACTTGGTGTCTCCACCTTCCATCATCGACAAGCTCTTCCTGGACA
CCCTGCCTTTC<u>TGA</u>GCAGGAGCAGCCTCATCTGCTAGCACCTGCTTGCTAAGC
AGCAGAGGGATGGGTCTGGACACCTACCATTTTCTGTCCTTCCTTAAGAGAA

FIGURE 16 (continued)

AAAGCAGCTCCTGTAGAAAAGAAAGACTTTTTTTTTTTTCTGGCACTTTTCCT
TACAAGCTAAAGCCAGAAAACTTGCAGAGTATTGTGTTGGGGTTGTGTTTTAT
ATTTAGGCTTTGGGGTTGGGGTGGGAGGTGGGTATAGTTCATGAGGGTTTTCT
AAGAAATTGCTAACAGAGCACTTTTGGACGATGCTATCCCAGCAGGAAAAAA
AAAAAAAAA

FIGURE 17

MPCVQAQYSPSPPGSSYAAQTYGSAEYTTEIMNPDYTKLTMDLGSTEITATATTS
LPSFSTFMEGYSSNYELKPSCLYQMPPSGPRPLIKMEEGRAHGYHHHHHHHHH
HHHQQQQQPSIPPPSGPEDEVLPSTSMYFKQSPPSTPTTPGFPPQAGALWDDALP
SAQGCLAPGPLLDPPMKAVPTVAGARFPLFHFKTSPPHPPAPSPAGGHHLAYDPT
AAAALSLPLGAAAAAGSQAAALEGHSYGLPLPKRAAALAFSPLGLTASPTASSLL
AESPSLPSPPNRSLSSGEGTCAVCGDNAACQHYGVRTCEGCKGFFKRTVQKNAK
YVCLANKNCPVDKRRRNRCQYCRFQKCLSVGMVKEVVRTDSLKGRRGRLPSKP
KSPLQQEPSQPSPPSPPICMMNALVRALTDSTPRDLDYSRYCPTDQAAAGTDAEH
VQQFYNLLTASIDVSRSWAEKIPGFTDLPKEDQTLLIESAFLELFVLRLSIRSNTAE
DKFVFCNGLVLHRLQCLRGFGEWLDSIKDFSLSLQSLNLDIQALACLSALSMITE
RHGLKEPKRVEELCNKITSSLKDHQSKGQALEPTEPKVLRALVELRKICTLGLQRI
FYLKLEDLVSPPSIIDKLFLDTLPF

FIGURE 18

GGCCTCGAGCGCCCCGGCGGGAGGTTTTTCTATATGAGTGGAGAAGACAGCT
GTTACCAGGGAGGTCATACAACATTTTTTTAGG<u>ATG</u>TCTGAAGATGAAGAAA
AAGTGAAATTACGCCGTCTTGAACCAGCTATCCAGAAATTCATTAAGATAGT
AATCCCAACAAACCTGGAAAGGTTAAGAAAGCACCAGATAAATATTGAGAA
GTATCAAAGGTGCAGAATCTGGGACAAGTTGCATGAAGAGCATATCAATGCA
GGACGTACAGTTCAGCAACTCCGATCCAATATCCGAGAAATTGAGAAACTTT
GTTTGAAAGTCCGAAAGGATGACCTAGTACTTCTGAAGAGAATGATAGATCC
TGTTAAAGAAGAAGCATCAGCAGCAACAGCAGAATTTCTCCAACTCCATTTG
GAATCTGTAGAAGAACTTAAGAAGCAATTTAATGATGAAGAAACTTTGCTAC
AGCCTCCTTTGACCAGATCCATGACTGTTGGTGGAGCATTTCATACTACTGAA
GCTGAAGCTAGTTCTCAGAGTTTGACTCAGATATATGCCTTACCTGAAATTCC
TCAAGATCAAAATGCTGCAGAATCGCGGGAAACCTTAGAAGCGGACTTAATT
GAACTTAGCCAACTGGTCACTGACTTCTCTCTCCTAGTGAACTCTCAGCAGGA
GAAGATTGACAGCATTGCAGACCATGTCAACAGTGCTGCTGTGAATGTTGAA
GAGGGAACCAAAAACTTAGGGAAGGCTGCAAAATACAAGCTGGCAGCTCTG
CCTGTGGCAGGTGCACTCATCGGGGGAATGGTAGGGGGTCCTATTGGCCTCC
TTGCATGCTTCAAAGTGGCAGGAATTGCAGCTGCACTTGGTGGTGGGGTGTT
GGGCTTCACAGGTGGAAAATTGATACAAAGAAAGAAACAGAAAATGATGGA
GAAGCTCACTTCCAGCTGTCCAGATCTTCCCAGCCAAACTGACAAGAAATGC
AGT<u>TAA</u>AAACCAAATTTCAGTATTATTGGTGCCAACATGTCTATCCTGAGGAC
CTTTGCTGCTGTTGGACACTCCGTCACCTTTTGGAACACAAGTATATCAAGAT
AGTGGCTACTGATGTTCAAGTGGGATTGAAGTGTGATAAATGGATATATTTTG
TTGTTTGCTGGGGTGTTCATGGAGATGTTAAGAGATTGAGGCCCTGGGCTGA
GGGTATATAATGTATGTCAGGTAAAGTTTGAAGACTGCCAAGGAGCAGATTT
TCTCCCTGGAAATGTGAAAACTGAACCTATAACTCTGATAAGGACTTGAGAT
GTGTAGAAACGTTGGGTTATGGAAGACTAGTTTCTTCCATAACCCTGAATTGG
AGACCTTAATGCTAAGTGTAGATTATTGAGGTTTGTTAGTGAGGAAAAGAAT
AAGAGTTCAGAAGCCTTTGTTATCAGATAGCGAAATCAGGGCCTAGTGAGGA
GCACAGGTCGACTACATAATGGAGTCCATTGGCGAACCCTATTGCAATTTGG
TCCAACTATATCTTCTGGTGAAGGAAATTAATGATGTAAGAAAATGCAAGAG
GCTCAACTTCTCTTCCAAAAATCTTCTGGCTTCTGAACTCTTCCTCTGCCTCTC
TTTAAATAAATAACACAGAATTTCAAGTGGTAGGAGACTTATTAAGCCAGTC
ACCAAGCTTGGTCTGTCAGCCTGTCTTCTAACACCTCAAAGATCTTGTGCCCT
GTGCTGTCCCTCCCTTGTAATTATGAAAGTTCTTTGGTTTCTGGGGTGAACT
CTACCCATGTATAATGAGGAATTCTCTCATAACCTTTTTGTCTTGTCTGTCAT
CTCTGTTCATCCCCTCCTATAACCTCTAGGTAAAAGAAAAGAAAAAAAGAA
ATTTCGAGATATTTTCAACATTGTTAGAGTTTGGGCTAAAATGAGCAAGGAG
AAAAAAACCACCAAGAACATTTCCTGGGGCATGTTCCAGTTTGAGGGGTGA
TATATCTGCCAGATAGGGGGTATCTGACCCAGTCTTCTTTTCAGCTGGTCTCT
GGGGGGAGCTGAGAACTCGCTTGCTACCTCACATCCTTTTCCCCAGACTTTTT
ATCTCCTATGCATCCCTTGCTTTCTATAGCTGGTGTTTCTTCCCCAAAATGGC
GTTCCCATGCTTACCTTTCTCACATTCTAGACAATGATGGACAAAGACGCATG

FIGURE 18 (continued)

CAAGACTCAGACCCGGGGAATGGTGTGGTGCTAATCTCAACACCTGACATTC
ACAGCAAGCATGGCCCAGCCCAACCGCATGTCTATCTCAAACCGCAGAAAGG
CTTTAATACTGGAAAAAAAGAATTCAAGACTACAGGCAGCTCCCTCTGTAC
CCCAACTCATTTAAAATAGGAGGAATCACTTTTTGCCTTACTTAACGCTTTTTT
CTGAGCACAGGGATGGGCACCTGCACCCAGAAGGTGTGAGCTGTCTCTCTG
CCAGGAGCTAAGGTTCATTAGGGGATTGGATGGTTTATCACTTCTTTCTTTCT
GAGTTTACTTTTAGTAACTTTTATTGATGGCTACCTTTCATGTCCCTGTCTAAA
GAGACTTTCTCTTTCATACGTCTTAAATCTCATCAATGAAATCCAGTGAAACA
GCACCATTTCTTAGTATCATTAAATAACTAGAAAGTATCAAAAAAAAAAAAA
AAAAA

FIGURE 19

TCATACTATACCATTAAAAGCAGTACTTGTTATATGTAAATTCTATCTAAATA
AAGTTGAATTAAAAATGGGAATGTGTTCCTACAGCAAGTAATGAGTTCGTGT
CACTGGAGGTATCTGAGCAGAGGTTCAGTAACCACTTGTCAGGAATGTTACA
GTAGGGCTTCGCACATCAGAGAGGAGATTGACCTGATGACCTCAACATTCCT
TCTACCCAGAGATTCCATGAGTCACAGTTGCTGTTGTGCCAGCACAGGTGTTG
CCATTTTATGTAGAATGCTTTATTAATATATTTGATCTGAAACATTTTAAACTG
TCATGATTTTAAAATGTATTAAGATACACAGGTGTAAAGCACAGAACAGTGA
TTTCATTCACTGTTCCCTACTGCATATTACAAATGGAAAGATCTCATAATAGA
TCAAACCGTATTGTAGTCTTGTTCCTGAAACATAACAATTTGTATTTATTGGA
CCAAGGGCATTTTACTCCTAAGGTAAATGTGCCTGATTTAAACTGAATCCTCA
AAGAAGGTAAGTTAGGGAGGTATTTTGGGGTTTGATTTTGTTGGGTTTTTTT
TTCCATCAAACCCAACATGACATGTAAATGCTTATTGGATTTTTTTTTCTGG
AAAGTAGATTCATTTGGAGAATAATATGTTTGTATGTTTGAGTGAATTTAGC
GTGAGATGCTTTTGCTGTAAAGTTGCCACCCTTTTATTACCTAATAATTAAG
ACCCCCCCCTTTTTTTTATGAAAGTTAATTTGTCCTTTCGACATGGCTTATCAG
ATGCTATTAATGAACCACTATTAAGATGGCAAGGCTGCAGTACCCAGGGCCC
TGATTACAGGAATTAAAATAGTGTGTGTTGGCTCCCTGCTGCTCCCAGCAGG
ACCGCTCACTCATAATTCCTTTGCATCTAGTCTCAGCAGGAGAAGATTGACAG
CATTGCAGACCATGTCAACAGTGCTGCTGTGAATGTTGAAGAGGGAACCAAA
AACTTAGGGAAGGCTGCAAAATACAAG<u>CT</u>GGCAGCTCTGCCTGTGGCAGGTG
CACTCATCGGGGGAATGGTAGGGGGTCCTATTGGCCTCCTTGCAGGCTTCAA
AGTGGCAGGAATTGCAGCTGCACTTGGTGGTGGGGTGTTGGGCTTCACAGGT
GGAAAATTGATACAAAGAAAGAAACAGAAAATGATGGAGAAGCTCACTTCC
AGCTGTCCAGATCTTCCCAGCCAAACTGACAAGAAATGCAGT<u>TAA</u>AAACCAA
ATTTCAGTATTATTGGTGCCAACATGTCTATCCTGAGGACCTTTGCTGCTGTT
GGACACTCCGTCACCTTTTGGAACACAAGTATATCAAGATAGTGGCTACTGA
TGTTCAAGTGGGATTGAAGTGTGATAAATGGATATATTTGTTGTTTGCTGGG
GTGTTCATGGAGATGTTAAGAGATTGAGGCCCTGGGCTGAGGGTATATAATG
TATGTCAGGTAAAGTTTGAAGACTGCCAAGGAGCAGATTTTCTCCCTGGAAA
TGTGAAAACTGAACCTATAACTCTGATAAGGACTTGAGATGTGTAGAAACGT
TGGGTTATGGAAGACTAGTTTCTTCCATAACCCTGAATTGGAGACCTTAATGC
TAAGTGTAGATTATTGAGGTTTGTTAGTGAGGAAAAGAATAAGAGTTCAGAA
GCCTTTGTTATCAGATAGCGAAATCAGGGCCTAGTGAGGAGCACAGGTCGAC
TACATAATGGAGTCCATTGGCGAACCCTATTGCAATTTGGTCCAACTATATCT
TCTGGTGAAGGAAATTAATGATGTAAGAAAATGCAAGAGGCTCAACTTCTCT
TCCAAAAATCTTCTGGCTTCTGAACTCTTCCTCTGCCTCTCTTTAAATAAATAA
CACAGAATTTCAAGTGGTAGGAGACTTATTAAGCCAGTCACCAAGCTTGGTC
TGTCAGCCTGTCTTCTAACACCTCAAAGATCTTGTGCCCTGTGCTGTCCCTCC
CTTGTAATTATGAAAAGTTCTTTGGTTTCTGGGGTGAACTCTACCCATGTATA
ATGAGGAATTCTCTCATAACCTTTTTTGTCTTGTCTGTCATCTCTGTTCATCCC
CTCCTATAACCTCTAGGTAAAAGAAAGAAAAAAGAAATTTCGAGATATT

FIGURE 19 (continued)

TTCAACATTGTTAGAGTTTGGGCTAAAATGAGCAAGGAGAAAAAAACCACCA
AGAACATTTCCTGGGGCATGTTCCAGTTTTGAGGGGTGATATATCTGCCAGAT
AGGGGGTATCTGACCCAGTCTTCTTTTCAGCTGGTCTCTGGGGGGAGCTGAGA
ACTCGCTTGCTACCTCACATCCTTTTCCCCAGACTTTTTATCTCCTATGCATCC
CTTTGCTTTCTATAGCTGGTGTTTCTTCCCCAAAATGGCGTTCCCATGCTTACC
TTTCTCACATTCTAGACAATGATGGACAAAGACGCATGCAAGACTCAGACCC
GGGGAATGGTGTGGTGCTAATCTAACACCTGACATTCACAGCAAGCATGGC
CCAGCCCAACCGCATGTCTATCTCAAACCGCAGAAAGGCTTTAATACTGGAA
AAAAAGAATTCAAGACTACAGGCAGCTCCCTCTGTACCCCAACTCATTTAA
AATAGGAGGAATCACTTTTTGCCTTACTTAACGCTTTTTCTGAGCACAGGGA
TGGGCACCTGCACCCCAGAAGGTGTGAGCTGTCTCTCTGCCAGGAGCTAAGG
TTCATTAGGGGATTGGATGGTTTATCACTTCTTTCTTTCTGAGTTTACTTTTAG
TAACTTTTATTGATGGCTACCTTTCATGTCCCTGTCTAAAGAGACTTTCTCTTT
CATACGTCTTAAATCTCATCAATGAAATCCAGTGAAACAGCACCATTTCTTAG
TATCATTAAATAACTAGAAAGTATCAAAAAAAAAAAAAAAAAA

FIGURE 20

MSEDEEKVKLRRLEPAIQKFIKIVIPTNLERLRKHQINIEKYQRCRIWDKLHEEHIN
AGRTVQQLRSNIREIEKLCLKVRKDDLVLLKRMIDPVKEEASAATAEFLQLHLES
VEELKKQFNDEETLLQPPLTRSMTVGGAFHTTEAEASSQSLTQIYALPEIPQDQNA
AESRETLEADLIELSQLVTDFSLLVNSQQEKIDSIADHVNSAAVNVEEGTKNLGK
AAKYKLAALPVAGALIGGMVGGPIGLLACFKVAGIAAALGGGVLGFTGGKLIQR
KKQKMMEKLTSSCPDLPSQTDKKCS

FIGURE 21

ATAAATGACGTGCCGAGAGAGCGAGCGAACGCGCAGCCGGGAGAGCGGAGT
CTCCTGCCTCCCGCCCCCACCCCTCCAGCTCCTGCTCCTCCTCCGCTCCCCAT
ACACAGACGCGCTCACACCCGCTCCCTCACTCGCACACACAGACACAAGCGC
GCACACAGGCTCCGCACACACACTTCGCTCTCCCGCGCGCTCACACCCCTCTT
GCCCTGAGCCCTTGCCGGTGCAGCGCGGCGCCGCAGCTGGACGCCCTCCCG
GGCTCACTTTGCAACGCTGACGGTGCCGGCAGTGGCCGTGGAGGTGGGAACA
GCGGCGGCATCCTCCCCCCTGGTCACAGCCCAAGCCAGGACGCCCGCGGAAC
CTCTCGGCTGTGCTCTCCCATGAGTCGGGATCGCAGCATCCCCCACCAGCCGC
TCACCGCCTCCGGGAGCCGCTGGGCTTGTACACCGCAGCCCTTCCGGGACAG
CAGCTGTGACTCCCCCCAGTGCAGATTTCGGGACAGCTCTCTAGAAACTCG
CTCTAAAGACGGAACCGCCACAGCACTCAAAGCCCACTGCGGAAGAGGGCA
GCCCGGCAAGCCCGGGCCCTGAGCCTGGACCCTTAGCGGTGCCGGGCAGCAC
TGCCGGCGCTTCGCCTCGCCGGACGTCCGCTCCTCCTACACTCTCAGCCTCCG
CTGGAGAGACCCCCAGCCCCACCATTCAGCGCGCAAGATAGTGTGTATATAT
ATATATATGGGTGGGTGTTTTGTTGCAGCTGCTGATCTTTTTCTTTGCAGATGG
TACAAACTCTCCCGAGTCAATTTCTGGGCCTATGTCCCCACCTAGCTGACTG
AAGTTATCAACAGGGGTCCAGTTTGTGCAGGCTGCTAGCCCTATTGGAAGAG
TGGGGATGAGGTGGGAGAAAGCAACCACAACGTGTGTGGGCAACCTCAATT
GGCACTCATAAAATGTTAGAATGTCAACTCTCTCCCTTGGCCACTAAATCTCT
CACAGGGTAGTTTTTCTTGCCTAACTCAGGTTTACAAATCAATGTGTATGCCT
TGGGGGACCAATGGCCTCTTTCCTCCCAAATAAACCACTGGCTTTCTCTTTGT
CCCCCTAGGTTATAGCTGAGGAGCCCACTCCAATTAGTTTATAGGATTCAAAG
CCTCTTTTTAAAAACATCTCTGAGCTTATGAGGAAAGACTTCAAGTTTCCCAA
ATCTAGTGGAGGACAGGGCAAGGGAGGAAAGATAGGTACAGGAGTCCACAG
GAGGCCAGGTTTTGGCACCCCTTTGTCAGGAATTCAGCTTCCTTACTAGGGAT
GAAGAAAATAAGTGTGGGGCTTTGTGTCTATGCTACCAGAAGGAGGAGAGG
ATGACACTTCCTCTCTGTTTCCCAGATTAGAGAACAGTGAACCCAATGCTGCC
TGTTGGCTAGAAAACAAGTGTTAACTTGCTTCTGAGAGACCCTTTTCTCTGTC
CCTGCAGAT<u>ATG</u>CCCTGCGTCCAAGCCCAATATAGCCCTTCCCCTCCAGGTTC
CAGTTATGCGGCGCAGACATACAGCTCGGAATACACCACGGAGATCATGAAC
CCCGACTACACCAAGCTGACCATGGACCTTGGCAGCACTGAGATCACGGCTA
CAGCCACCACGTCCCTGCCCAGCATCAGTACCTTCGTGGAGGGCTACTCGAG
CAACTACGAACTCAAGCCTTCCTGCGTGTACCAAATGCAGCGGCCCTTGATC
AAAGTGGAGGAGGGGCGGGCGCCCAGCTACCATCACCATCACCACCACCAC
CACCACCACCACCACCATCACCAGCAGCAGCATCAGCAGCCATCCATTCCTC
CAGCCTCCAGCCCGGAGGACGAGGTGCTGCCCAGCACCTCCATGTACTTCAA
GCAGTCCCCACCGTCCACCCCCACCACGCCGGCCTTCCCCCCGCAGGCGGGG
GCGTTATGGGACGAGGCACTGCCCTCGGCGCCCGGCTGCATCGCACCCGGCC
CGCTGCTGGACCCGCCGATGAAGGCGGTCCCCACGGTGGCCGGCGCGCGCTT
CCCGCTCTTCCACTTCAAGCCCTCGCCGCCGCATCCCCCGCGCCCAGCCCGG
CCGGCGGCCACCACCTCGGCTACGACCCGACGGCCGCTGCCGCGCTCAGCCT
GCCGCTGGGAGCCGCAGCCGCCGCGGGCAGCCAGGCCGCCGCGCTTGAGAG

FIGURE 21 (continued)

CCACCCGTACGGGCTGCCGCTGGCCAAGAGGGCGGCCCCGCTGGCCTTCCCG
CCTCTCGGCCTCACGCCCTCCCCTACCGCGTCCAGCCTGCTGGGCGAGAGTCC
CAGCCTGCCGTCGCCGCCCAGCAGGAGCTCGTCGTCTGGCGAGGGCACGTGT
GCCGTGTGCGGGGACAACGCCGCCTGCCAGCACTACGGCGTGCGAACCTGCG
AGGGCTGCAAGGGCTTTTTCAAGAGAACAGTGCAGAAAAATGCAAAATATGT
TTGCCTGGCAAATAAAAACTGCCCAGTAGACAAGAGACGTCGAAACCGATGT
CAGTACTGTCGATTTCAGAAGTGTCTCAGTGTTGGAATGGTAAAAGAAGTTG
TCCGTACAGATAGTCTGAAAGGGAGGAGAGGTCGTCTGCCTTCCAAACCAAA
GAGCCCATTACAACAGGAACCTTCTCAGCCCTCTCCACCTTCTCCTCCAATCT
GCATGATGAATGCCCTTGTCCGAGCTTTAACAGACTCAACACCCAGAGATCTT
GATTATTCCAGATACTGTCCCACTGACCAGGCTGCTGCAGGCACAGATGCTG
AGCATGTGCAACAATTCTACAACCTCCTGACAGCCTCCATTGATGTATCCAGA
AGCTGGGCAGAAAAGATTCCGGGATTTACTGATCTCCCCAAAGAAGATCAGA
CATTACTTATTGAATCAGCCTTTTGGAGCTGTTTGTCCTCAGACTTTCCATCA
GGTCAAACACTGCTGAAGATAAGTTTGTGTTCTGCAATGGACTTGTCCTGCAT
CGACTTCAGTGCCTTCGTGGATTTGGGGAGTGGCTCGACTCTATTAAAGACTT
TTCCTTAAATTTGCAGAGCCTGAACCTTGATATCCAAGCCTTAGCCTGCCTGT
CAGCACTGAGCATGATCACAGAAAGACATGGGTTAAAAGAACCAAAGAGAG
TCGAAGAGCTATGCAACAAGATCACAAGCAGTTTAAAAGACCACCAGAGTA
AGGGACAGGCTCTGGAGCCCACCGAGTCCAAGGTCCTGGGTGCCCTGGTAGA
ACTGAGGAAGATCTGCACCCTGGGCCTCCAGCGCATCTTCTACCTGAAGCTG
GAAGACTTGGTGTCTCCACCTTCCATCATTGACAAGCTCTTCCTGGACACCCT
ACCTTTC<u>TAA</u>TCAGGAGCAGTGGAGCAGTGAGCTGCCTCCTCTCCTAGCACCT
GCTTGCTACGCAGCAAAGGGATAGGTTTGGAAACCTATCATTTCCTGTCCTTC
CTTAAGAGGAAAAGCAGCTCCTGTAGAAAGCAAAGACTTTCTTTTTTTCTGG
CTCTTTTCCTTACAACCTAAAGCCAGAAAACTTGCAGAGTATTGTGTTGGGGT
TGTGTTTTATATTTAGGCATTGGGGGATGGGGTGGAGGGGGTTATAGTTCAT
GAGGGTTTTCTAAGAAATTGCTAACAAAGCACTTTTGGACAATGCTATCCCA
GCAGGAAAAAAAGGATAATATAACTGTTTTAAAACTCTTTCTGGGGAATCC
AATTATAGTTGCTTTGTATTTAAAAACAAGAACAGCCAAGGGTTGTTCGCCA
GGGTAGGATGTGTCTTAAAGATTGGTCCCTTGAAAATATGCTTCCTGTATCAA
AGGTACGTATGTGGTGCAAACAAGGCAGAAACTTCCTTTTAATTTCCTTCTTC
CTTTATTTTAACAAATGGTGAAAGATGGAGGATTACCTACAAATCAGACATG
GCAAAACAATAATGGCTGTTTGCTTCCATAAACAAGTGCAATTTTTTAAAGTG
CTGTCTTACTAAGTCTTGTTTATTAACTCTCCTTTATTCTATATGGAAATAAAA
AGGAGGCAGTCATGTTAGCAAATGACACGTTAATATCCCTAGCAGAGGCTGT
GTTCACCTTCCCTGTCGATCCCTTCTGAGGTATGGCCCATCCAAGACTTTTAG
GCCATTCTTGATGGAACCAGATCCCTGCCCTGACTGTCCAGCTATCCTGAAAG
TGGATCAGATTATAAACTGGATTACATGTAACTGTTTTGGTTGTGTTCTATCA
ACCCCACCAGAGTTCCCTAAACTTGCTTCAGTTATAGTAACTGACTGGTATAT

FIGURE 21 (continued)

TCATTCAGAAGCGCCATAAGTCAGTTGAGTATTTGATCCCTAGATAAGAACA
TGCAAATCAGCAGGAACTGGTCATACAGGGTAAGCACCAGGGACAATAAGG
ATTTTTATAGATATAATTTAATTTTTGTTATTGGTTAAGGAGACAATTTTGGA
GAGCAAGCAAATCTTTTTAAAAAATAGTATGAATGTGAATACTAGAAAAGAT
TTAAAAAATAGTATGAGTGTGAGTACTAGGAAGGATTAGTGGGCTGCGTTTC
AACATTCCGTGTTCGTACTCCCTTTTGTATGTTTCTACTGTTAATGCCATATTA
CTATGAGATAATTGTTGCATAGTGTCCTTATTTGTATAAACATTTGTATGCA
CGTTATATTGTAATAGCTTTGCCTGTATTTATTGCAAGACCACCAGCTCCTGG
AAGCTGAGTTACAGAGTAATTAAATGGGGTGTTCACAGTGACTTGGATACAC
CAATTAGAAATTAAATAAGCAAATATATATATATATAAATATAGCAGGTT
ACATATATATATTTATAATGTGTCTTTTTATTAACCATTTGTACAATAAATGTC
ACTTCCCATGCCGTTATTTATGGTTCATTTGCAGTGACTTTTAAGGCAGTACT
GTTTAGCACTTTGATATTAAAATTTTGCTTATGTTTTGCTAAATTCGAATAATG
TTTGAAGATTTTTAGGTCTAAAAGTCTTTATATTATATACTCTGTATCAAGTCA
AAATATCTTTGGCCATTTTGCTAAGAAACAAACTTTGAATGTCAAACTGATGT
CACAGTAGTTTTTGTTAGCTTTAAATCATTTTTGCTTTAGTCTTTTTAAAGGAA
AATAACAAAACTATGCTGTTTATATTGTCATTAAATTATACAATCAAACAAAT
GCCAAATGAATTGCCTAATTGCTGCAAAGTATAACCCAGATAGGAAATCATA
TGTTTTTTTCCAAGAGTCATTCTAATATTTGATTATGTTATGTGTGCTTTTATG
AAAGATTGTTATTTTATATATCAAGATGATAGAACCTGGAATGTTAGGATTT
TGAAATGTTAGACTTGGAAGGGGCCTGGTCTGTCAACTAGTCCAACCCCTTA
AAATTCATAGAGGAGCAAACTGGGGCCCATTGAAGGGTGAAGAGTTACTCAA
GGTCAAACAGCTGGTAACAGAATCAAGACTAAGACCTAATTTACCTTTCCAT
ACTCTTTTTTTTTCTCAACTTCATCTATATAAAATCAGGCTTTTAAACATAACC
ACTAATATTTACCTGAAGATAACCATGAGTAAAGTATACTTTTGCATTAATTT
TTTGAGCTTATATGCAAACATAATAAATATTATTAAATATCAGGAAAGCTAA
CATTTCATACAAGATAGCTTCAGACCAAATTCAAATTGAATTTGAATAAATTA
GAAATACTGTGCATACATAACCTTCTTGTGCACCATGAGTATTTGGAAAGTTA
ATCCTTGTTTTTGTCGTGTCTATAAAGGAAGAACAAAACAAAATAAAAACAG
AGCCCTAGAGAAATGCTGTTACTTTTATTTTACACCCATCAGATTTAAGGA
AAAGACTTTTTAGCCATTATAATCTAGTGGTTGGAAGGAATGAAGAAGCTTTT
TTAGTAATAGGTCCAGATATGAGTGCTAAAAATAAAGATGATAGCATGTTCT
TCTGTCTTCCATAGTTATTACAACTATGAGAGCCTCCCAAGTCATCTTATCAA
CTCAACTCCCTTTTTTTGTCTTAATGTTGCACATAAGTTTATACAGAGTGGAT
GACCACACTAGCACAGAAGAGAACAACATGTATTAAAGCAGGTGATTCCTCC
CCTTGGCGGGAGAGCTCTCTCAGTGTGAACATGCCTTCTGTGGGCGGAAATC
AGGAAGCCACCAGCTGTTAATGGAGAGTGCCTTGCTTTTATTTCAGACAGCA
GAGTTTTCCAAAGTTTCTCTGCTCCTCTAACAGCATTGCTCTTAGTGTGTGTT
AACCTGTGGTTTGAAAGAAATGCTCTTGTACATTAACAATGTAAATTTAAATG
ATTAAATTACATTTTATCAATGGCA

FIGURE 22

MPCVQAQYSPSPPGSSYAAQTYSSEYTTEIMNPDYTKLTMDLGSTEITATATTSL
PSISTFVEGYSSNYELKPSCVYQMQRPLIKVEEGRAPSYHHHHHHHHHHHHHHQ
QQHQQPSIPPASSPEDEVLPSTSMYFKQSPPSTPTTPAFPPQAGALWDEALPSAPG
CIAPGPLLDPPMKAVPTVAGARFPLFHFKPSPPHPPAPSPAGGHHLGYDPTAAAA
LSLPLGAAAAAGSQAAALESHPYGLPLAKRAAPLAFPPLGLTPSPTASSLLGESPS
LPSPPSRSSSSGEGTCAVCGDNAACQHYGVRTCEGCKGFFKRTVQKNAKYVCLA
NKNCPVDKRRRNRCQYCRFQKCLSVGMVKEVVRTDSLKGRRGRLPSKPKSPLQ
QEPSQPSPPSPPICMMNALVRALTDSTPRDLDYSRYCPTDQAAAGTDAEHVQQF
YNLLTASIDVSRSWAEKIPGFTDLPKEDQTLLIESAFLELFVLRLSIRSNTAEDKFV
FCNGLVLHRLQCLRGFGEWLDSIKDFSLNLQSLNLDIQALACLSALSMITERHGL
KEPKRVEELCNKITSSLKDHQSKGQALEPTESKVLGALVELRKICTLGLQRIFYLK
LEDLVSPPSIIDKLFLDTLPF

FIGURE 23

```
human     MSEDEEKVKLRRLEPAIQKFIKIVIPTNLERLRKHQINIEKYQRCRIWDKLHEEHINAGR
horse     MSEDEEKVKLRRLEPAIQKFIKIVIPTDLERLRKHQINIEKYQRCRIWDKLHEEHINAGR
          *************************:****************************** human     TVQQLRSNIREIEKLCLKVRKDDLVLLKRMIDPVKEEASAATAEFLQLHLESVEELKKQF
horse     TVQQLRSNIREMEKLCLKVRKDDVGLLKRMIDPVKEEASVATAEFLQLHLESVEELKKQF
          *********:*******: **********.****************** human     NDEETLLQPPLTRSMTVGGAFHTTEAEASSQSLTQIYALPEIPQDQNAAESRETLEADLI
horse     NDEETLLQPSLTRSMTVGGAFHTAEAETDPQSVTQIYALPEIPRDQNAAESWETLEADLI
          *******.*********:*: ..:*****:** ****** human     ELSQLVTDFSLLVNSQQEKIDSIADHVNSAAVNVEEGTKNLGKAAKYKLAALPVAGALIG
horse     ELSQLVTDFSLLVNSQQEKIDSIEDHVNTAAVNVEVGTKNLGKAAKYKLAALPVAGALIG
          *********************  :** ********************* human     GMVGGPIGLLACFKVAGIAAALGGGVLGFTGGKLIQRKKQKMMEKLTSSCPDLPSQTDKK
horse     GAVGGPIGLLAGFKVAGIAAALGGGVLGFTGGKLIQRKKQKMMEKLASSCPDLPSQSDKK
          * ******* *****************************:*****:* human     CS
horse     CS
          **
```

FIGURE 24

```
human    MPCVQAQYSPSPPGSSYAAQTY-SSEYTTEIMNPDYTKLTMDLGSTEITATATTSLPSIS
horse    MPCVQAQYSPSPPGSSYAAQTYGSAEYTTEIMNPDYTKLTMDLGSTEITATATTSLPSFS
         ******************** *:***********************************:* human    TFVEGYSSNYELKPSCVYQMQR----PLIKVEEGRAPSYHHHHHHHHHHHHHQQQHQQP
horse    TFMEGYSSNYELKPSCLYQMPPSGPRPLIKMEEGRAHGYHHHHHHHHHHHHHQQQQQQ-P
         :********:*        **:** .*********:*:* * human    SIPPASSPEDEVLPSTSMYFKQSPPSTPTTPAFPPQAGALWDEALPSAPGCIAPGPLLDP
horse    SIPPPSGPEDEVLPSTSMYFKQSPPSTPTTPGFPPQAGALWDDALPSAQGCLAPGPLLDP
         ****.*.**********************.*****:* .******** human    PMKAVPTVAGARFPLFHFKPSPPHPPAPSPAGGHHLGYDPTAAAALSLPLGAAAAAGSQA
horse    PMKAVPTVAGARFPLFHFKTSPPHPPAPSPAGGHHLAYDPTAAAALSLPLGAAAAAGSQA
         *****************.************.********************* human    AALESHPYGLPLAKRAAPLAFPPLGLTPSPTASSLLGESPSLPSPPSRSSSSGEGTCAVC
horse    AALEGHSYGLPLPKRAAALAFSPLGLTASPTASSLLAESPSLPSPPNRSLSSGEGTCAVC
         ****.*.*** .* .***.***.*****..********* human    GDNAACQHYGVRTCEGCKGFFKRTVQKNAKYVCLANKNCPVDKRRRNRCQYCRFQKCLSV
horse    GDNAACQHYGVRTCEGCKGFFKRTVQKNAKYVCLANKNCPVDKRRRNRCQYCRFQKCLSV
         ************************************************************ human    GMVKEVVRTDSLKGRRGRLPSKPKSPLQQEPSQPSPPSPPICMMNALVRALTDSTPRDLD
horse    GMVKEVVRTDSLKGRRGRLPSKPKSPLQQEPSQPSPPSPPICMMNALVRALTDSTPRDLD
         ************************************************************ human    YSRYCPTDQAAAGTDAEHVQQFYNLLTASIDVSRSWAEKIPGFTDLPKEDQTLLIESAFL
horse    YSRYCPTDQAAAGTDAEHVQQFYNLLTASIDVSRSWAEKIPGFTDLPKEDQTLLIESAFL
         ************************************************************ human    ELFVLRLSIRSNTAEDKFVFCNGLVLHRLQCLRGFGEWLDSIKDFSLNLQSLNLDIQALA
horse    ELFVLRLSIRSNTAEDKFVFCNGLVLHRLQCLRGFGEWLDSIKDFSLSLQSLNLDIQALA
         *********************************************.********** human    CLSALSMITERHGLKEPKRVEELCNKITSSLKDHQSKGQALEPTESKVLGALVELRKICT
horse    CLSALSMITERHGLKEPKRVEELCNKITSSLKDHQSKGQALEPTEPKVLRALVELRKICT
         ******************************************.*.********* human    LGLQRIFYLKLEDLVSPPSIIDKLFLDTLPF
horse    LGLQRIFYLKLEDLVSPPSIIDKLFLDTLPF
         *******************************
```

FIGURE 25

MPCIQAQYGTPAPSPGPRDHLASDPLTPEFIKPTMDLASPEAAPAAPTALPSFSTF
MDGYTGEFDTFLYQLPGTVQPCSSASSSASSTSSSSATSPASASFKFEDFQVYGCY
PGPLSGPVDEALSSSGSDYYGSPCSAPSPSTPSFQPPQLSPWDGSFGHFSPSQTYEG
LRAWTEQLPKASGPPQPPAFFSFSPPTGPSPSLAQSPLKLFPSQATHQLGEGESYS
MPTAFPGLAPTSPHLEGSGILDTPVTSTKARSGAPGGSEGRCAVCGDNASCQHYG
VRTCEGCKGFFKRTVQKNAKYICLANKDCPVDKRRRNRCQFCRFQKCLAVGMV
KEVVRTDSLKGRRGRLPSKPKQPPDASPANLLTSLVRAHLDSGPSTAKLDYSKFQ
ELVLPHFGKEDAGDVQQFYDLLSGSLEVIRKWAEKIPGFAELSPADQDLLLESAF
LELFILRLAYRSKPGEGKLIFCSGLVLHRLQCARGFGDWIDSILAFSRSLHSLLVD
VPAFACLSALVLITDRHGLQEPRRVEELQNRIASCLKEHVAAVAGEPQPASCLSR
LLGKLPELRTLCTQGLQRIFYLKLEDLVPPPPIIDKIFMDTLPF

FIGURE 26

MPCVQAQYGSSPQGASPASQSYSYHSSGEYSSDFLTPEFVKFSMDLTNTEITATTS
LPSFSTFMDNYSTGYDVKPPCLYQMPLSGQQSSIKVEDIQMHNYQQHSHLPPQSE
EMMPHSGSVYYKPSSPPTPTTPGFQVQHSPMWDDPGSLHNFHQNYVATTHMIEQ
RKTPVSRLSLFSFKQSPPGTPVSSCQMRFDGPLHVPMNPEPAGSHHVVDGQTFAV
PNPIRKPASMGFPGLQIGHASQLLDTQVPSPPSRGSPSNEGLCAVCGDNAACQHY
GVRTCEGCKGFFKRTVQKNAKYVCLANKNCPVDKRRRNRCQYCRFQKCLAVG
MVKEVVRTDSLKGRRGRLPSKPKSPQEPSPPSPPVSLISALVRAHVDSNPAMTSL
DYSRFQANPDYQMSGDDTQHIQQFYDLLTGSMEIIRGWAEKIPGFADLPKADQD
LLFESAFLELFVLRLAYRSNPVEGKLIFCNGVVLHRLQCVRGFGEWIDSIVEFSSN
LQNMNIDISAFSCIAALAMVTERHGLKEPKRVEELQNKIVNCLKDHVTFNNGGL
NRPNYLSKLLGKLPELRTLCTQGLQRIFYLKLEDLVPPPAIIDKLFLDTLPF

FIGURE 27

```
NR4A2    MPCVQAQYGSSPQGASPASQSYSYHSSGEYSSDFLTPEFVKFSMDLTNTEITATTS--LP
NR4A3    MPCVQAQYSPSPPGSSYAAQTYS----SEYTTEIMNPDYTKLTMDLGSTEITATATTSLP
NR4A1    MPCIQAQYGTPAPSPGPRDHLAS---------DPLTPEFIKPTMDLASPEAAPAAPTALP
         ***:****....  ...    :  *        : :.*:: * :*** ..* :.::.  **

NR4A2    SFSTFMDNYS---TGYDVKPPCLYQMP------LSGQQSSIKVEDIQMHNYQQHSHLPPQ
NR4A3    SISTFVEGYS---SNYELKPSCVYQMQRPLIKVEEGRAPSYHHHHHHHHHHHHHQQQHQ
NR4A1    SFSTFMDGYTGEFDTFLYQLPGTVQPCSSASSSASSTSSSSATSPASASFKFEDFQVYGC
         *:***:..*:       :  : .   *         ..  .*           .. :

NR4A2    SEEMMPHSG---------SVYYKPSSPPTPTTPGFQVQHSPMWDDPGSLHN--FHQNYVA
NR4A3    QPSIPPASSPEDEVLPSTSMYFKQSPPSTPTTPAFPPQAGALWDEALPSAPGCIAPGPLL
NR4A1    YPGPLSGPVDEALSSSGSDYYGSPCSAPSPSTPSFQPPQLSPWDGSFGHFSP-SQTYEGL
              . .           . *  . ....:*:**.*      . **  .

NR4A2    TTHMIEQRKTPVSRLSLFSFKQSPPGTPVSSCQMRFDG--------PLHVPMNPEPAGSH
NR4A3    DPPMKAVPTVAGARFPLFHFKPSPPHPPAPSPAGGHHLGYDPTAAAALSLPLGAAAAAGS
NR4A1    RAWTEQLPKASGPPQPPAFFSFSPPTGPSPSLAQSPLKLFP--------------SQATH
                . ....  .  *. *** * .*                             . .

NR4A2    HVVDGQTFAVPNPIR---KPAS------MGFPGLQIGHASQLLDTQVPSPPSRGSPSNEG
NR4A3    QAAALESHPYGLPLA---KRAAPLAFPPLGLTPSPTASSLLGESPSLPSPPSRSSSSGEG
NR4A1    QLGEGESYSMPTAFPGLAP-----------TSPHLEGSGILDTPVTSTKARSGAPGGSEG
         :     ::..   .:              .       . ..         ... * .. ..**

NR4A2    LCAVCGDNAACQHYGVRTCEGCKGFFKRTVQKNAKYVCLANKNCPVDKRRRNRCQYCRFQ
NR4A3    TCAVCGDNAACQHYGVRTCEGCKGFFKRTVQKNAKYVCLANKNCPVDKRRRNRCQYCRFQ
NR4A1    RCAVCGDNASCQHYGVRTCEGCKGFFKRTVQKNAKYICLANKDCPVDKRRRNRCQFCRFQ
          ********:*****************************:*****:**********:****

NR4A2    KCLAVGMVKEVVRTDSLKGRRGRLPSKPKS-----PQEPSPPSPPVSLISALVRAHVDSN
NR4A3    KCLSVGMVKEVVRTDSLKGRRGRLPSKPKSPLQQEPSQPSPPSPPICMMNALVRALTDS-
NR4A1    KCLAVGMVKEVVRTDSLKGRRGRLPSKPKQ---------PPDASPANLLTSLVRAHLDSG
         ***:*********************. .           .* :.*  :::.:****  **

NR4A2    PAMTSLDYSRFQANPDYQMSGDDTQHIQQFYDLLTGSMEIIRGWAEKIPGFADLPKADQD
NR4A3    -TPRDLDYSRYCP-TDQAAAGTDAEHVQQFYNLLTASIDVSRSWAEKIPGFTDLPKEDQT
NR4A1    PSTAKLDYSKFQELVLPHFGKEDAGVQQFYDLLSGSLEVIRKWAEKIPGFAELSPADQD
          :  .****::        .  *: .:****:**:.*::: * *********:*. **

NR4A2    LLFESAFLELFVLRLAYRSNPVEGKLIFCNGVVLHRLQCVRGFGEWIDSIVEFSSNLQNM
NR4A3    LLIESAFLELFVLRLSIRSNTAEDKFVFCNGLVLHRLQCLRGFGEWLDSIKDFSLNLQSL
NR4A1    LLLESAFLELFILRLAYRSKPGEGKLIFCSGLVLHRLQCARGFGDWIDSILAFSRSLHSL
         **:********:***: **:.  *.*::**.*:******* ****:*:***   ** .*:.:

NR4A2    NIDISAFSCIAALAMVTERHGLKEPKRVEELQNKIVNCLKDHVTFNNGGLNRPNYLSKLL
NR4A3    NLDIQALACLSALSMITERHGLKEPKRVEELCNKITSSLKDHQSK---GQALEPTESKVL
NR4A1    LVDVPAFACLSALVLITDRHGLQEPRRVEELQNRIASCLKEHVAAVAGEPQPASCLSRLL
         :*: *::*:** ::**:*****:**:***** *::   ****   :            *::*

NR4A2    GKLPELRTLCTQGLQRIFYLKLEDLVPPPAIIDKLFLDTLPF
NR4A3    GALVELRKICTLGLQRIFYLKLEDLVSPPSIIDKLFLDTLPF
NR4A1    GKLPELRTLCTQGLQRIFYLKLEDLVPPPPIIDKIFMDTLPF
         * * ***.:** ***************.**.****:*:****
```

FIGURE 28

MEHQLLCCEVETIRRAYPDANLLNDRVLRAMLKAEETCAPSVSYFKCVQKEVLP
SMRKIVATWMLEVCEEQKCEEEVFPLAMNYLDRFLSLEPVKKSRLQLLGATCMF
VASKMKETIPLTAEKLCIYTDNSIRPEELLQMELLLVNKLKWNLAAMTPHDFIEH
FLSKMPEAEENKQIIRKHAQTFVALCATDVKFISNPPSMVAAGSVVAAVQGLNL
RSPNNFLSYYRLTRFLSRVIKCDPDCLRACQEQIEALLESSLRQAQQNMDPKAAE
EEEEEEEEVDLACTPTDVRDVDI

FIGURE 29

MELLCHEVDPVRRAVRDRNLLRDDRVLQNLLTIEERYLPQCSYFKCVQKDIQPY
MRRMVATWMLEVCEEQKCEEEVFPLAMNYLDRFLAGVPTPKSHLQLLGAVCM
FLASKLKETSPLTAEKLCIYTDNSIKPQELLEWELVVLGKLKWNLAAVTPHDFIE
HILRKLPQQREKLSLIRKHAQTFIALCATDFKFAMYPPSMIATGSVGAAICGLQQD
EEVSSLTCDALTELLAKITNTDVDCLKACQEQIEAVLLNSLQQYRQDQRDGSKSE
DELDQASTPTDVRDIDL

FIGURE 30

```
cyclinD1    MEHQLLCCEVETIRRAYPDANLLN-DRVLRAMLKAEETCAPSVSYFKCVQKEVLPSMRKI
cyclinD2    --MELLCHEVDPVRRAVRDRNLLRDDRVLQNLLTIEERYLPQCSYFKCVQKDIQPYMRRM
              :*** **:.:***   * ***. ****: :*. **    *. ********:: * **::

cyclinD1    VATWMLEVCEEQKCEEEVFPLAMNYLDRFLSLEPVKKSRLQLLGATCMFVASKMKETIPL
cyclinD2    VATWMLEVCEEQKCEEEVFPLAMNYLDRFLAGVPTPKSHLQLLGAVCMFLASKLKETSPL
            ******************************:  *. :** .*:*:* ** cyclinD1    TAEKLCIYTDNSIRPEELLQMELLLVNKLKWNLAAMTPHDFIEHFLSKMPEAEENKQIIR
cyclinD2    TAEKLCIYTDNSIKPQELLEWELVVLGKLKWNLAAVTPHDFIEHILRKLPQQREKLSLIR
            *************:*:***: **:::.********:********:* *:*: .*: ..:**

cyclinD1    KHAQTFVALCATDVKFISNPPSMVAAGSVVAAVQGLNLRSPNNFLSYYRLTRFLSRVIKC
cyclinD2    KHAQTFIALCATDFKFAMYPPSMIATGSVGAAICGLQQDEEVSSLTCDALTELLAKITNT
            ******:****** **    ****:*:*** **:: **:    .  . *:    **.:*::: :

cyclinD1    DPDCLRACQEQIEALLESSLRQAQQNMDPKAAEEEEEEEEEVDLACTPTDVRDVDI
cyclinD2    DVDCLKACQEQIEAVLLNSLQQYRQ-----DQRDGSKSEDELDQASTPTDVRDIDL
            * ***:*********:* .**:* :*        .: ..:.*:*:* *.*******:*:
```

FIGURE 31

MPLQGPQRRLLGSLNSTLPATPYLGLTTNQTEPPCLEVSIPDGLFLSLGLVSLVEN
VLVVTAIAKNRNLHSPMYYFICCLAVSDLLVSMSNVLEMAILLLLEAGVLATQA
SVLQQLDNIIDVLICGSMVSSLCFLGSIAVDRYISIFYALRYHSIMMLPRVWRAIV
AIWVVSVLSSTLFIAYYNHTAVLLCLVTFFVAMLVLMAVLYVHMLARACQHAR
GIARLHKRQHPIHQGFGLKGAATLTILLGVFFLCWGPFFLHLSLLILCPQHPTCGC
VFKNFKLFLTLILCSAIVDPLIYAFRSQELRKTLQEVLLCSW

FIGURE 32

TCTGGGCAGGTCCAGAGGAGGCCACACCTGGAGCAGAGGCCCAGCTGGGAG
TGCTGGTTGGCTGAGTACAGGGAGGCTGGGAGTGCAAAGGGGAGATGTCCTG
CTGTGTCTAGGAGTCTGGGGGCCCGGGGAGCCCAGACGGTCGTGGGTGCCAT
TTGCGCCACTTGGCGGCGGCGGCAGGAGGGTGTGTGGGCGCTCTGATGGTGC
CTTCCCGGGCACCCACCCATCATGTGACTGCCCTCAGGAGGAGGGGCTCCAT
GGAAGCCTTTAAAGATGCTGAGAAAGGCTCCATTCTTCCCAGTTTCCCCAACC
CACCCCTGCTCTGGGGAGGCAGGAGGCCTGGCAGGCCAGGAGGCAGCAAGA
GCTAGAGATGTGCGGACCTGAGCAACAGCACCTCCAGGGAGAGGCCGGGAG
GTGGGCTGAGAACCCAATGAGACTCCAGAGCCCAGAGGGTTGGTGCCACAG
AGCTTGGGTCTTGGCTGGGAAGTGACCAGACTCTGGTGGAGAGGCCAGGTTC
TCTGGCTGGGCCACGGTTGGGCCAACATTTTTCCAGCCAGGGAGAGCGTGAG
TGTGAGGGCAGCCCTGCGGGTGGCACCATGAGCTGAGTGGGACGCCTGGAGA
GTGAGGACCCCTTCCTGCTTCCTAGAGGGACT<u>ATG</u>CCTCTGCAGGGGCCCCA
GAGGAGGCTGCTGGGCTCCCTCAACTCCACCCTCCCAGCCACCCCCTACCTCG
GGCTGACCACCAACCAGACGGAGCCCCGTGCCTGGAAGTGTCCATTCCTGA
TGGGCTCTTCCTCAGCCTGGGGCTGGTGAGCCTAGTGGAAAATGTACTGGTG
GTGACTGCCATCGCCAAGAACCGCAACCTGCACTCACCCATGTACTACTTCAT
CTGCTGCCTGGCCGTGTCCGACCTGCTGGTGAGCATGAGCAACGTGCTGGAG
ATGGCAATCTTGCTGCTGCTGGAGGCCGGAGTCCTGGCCACCCAGGCCTCGG
TGTTGCAGCAGCTGGACAACATCATTGATGTGCTCATCTGCGGCTCCATGGTG
TCCAGCCTCTGCTTCCTGGGCAGCATTGCCGTAGACCGCTACATCTCCATCTT
CTATGCGCTGCGGTACCACAGCATCATGATGCTGCCCCGTGTGTGGCGTGCCA
TCGTGGCCATCTGGGTGGTTAGTGTCCTCTCTAGCACCCTCTTCATCGCTTACT
ACAACCACACGGCTGTCCTGCTCTGTCTCGTCACCTTCTTTGTGGCCATGCTG
GTGCTCATGGCAGTGCTGTACGTGCACATGCTCGCCAGGGCGTGCCAGCACG
CCCGGGGCATCGCCCGGCTCCACAAGAGGCAGCACCCCATCCACCAGGGCTT
TGGCCTCAAGGGTGCCGCCACCCTCACCATCCTGCTGGGCGTTTTCTTCCTCT
GCTGGGGCCCCTTTTTCCTGCACCTCTCACTCCTTATCCTCTGCCCTCAACACC
CCACCTGCGGCTGTGTCTTCAAGAACTTCAAGCTCTTCCTCACCCTCATCCTG
TGCAGCGCCATCGTCGACCCCCTCATCTATGCCTTCCGCAGCCAGGAACTTCG
AAAGACGCTCCAGGAGGTGCTGCTGTGCTCCTGG<u>TGA</u>GGGGAGGGGAGCCTG
CGGGCCAAGGCAGAGGGCTGTGCACAGGGAGGTGGTGACATCAGGGGCTC
GGTTCCTGTGTGACCGGGGCAGTCACTTGCCAAAGAGGGTGGCCTATA

ND MATERIALS RELATED TO

SEQUENCE LISTING

<160> NUMBER OF SEQ ID NOS: 145

<210> SEQ ID NO 1
<211> LENGTH: 12157
<212> TYPE: DNA
<213> ORGANISM: Equus caballus Grey allele

<400> SEQUENCE: 1

```
tgagtatata actgttttg gctcagagac gttagattaa taggataaga ggcttttata      60
aatcactagg cttttgatta ggattttaat agaagttaca atttgtaaga ctggtattga     120
accatggata gaagtctaac tgtcctcaaa ttccagatca attcaataaa catttattaa     180
gcacttgtta tataaaaggc actgtcttag gtgcttggca ttggggatct gacaaggttg     240
gataaagaaa gaaaggaagc atgctgtctg ccttcagggg tttacagtgg gtggagatat     300
gcttggaccc ccaaaactga aatttcaagt gtgattgtta aatgcaaaga caaggtatga     360
agagaagtat tatccgctcc aagggaagga ggcagggatt gtgaggtgga agcgtcaagg     420
gtagcttcac aagataggta gtatttgctt aagccttgaa aactgagtaa agtttccgca     480
ggtgggagag agggagtgca tttgaagaac gctgaacaaa gccttggagt agtgaagtgt     540
atggcctccc aggaatgaca agttctgcag tgtaaccaaa gcacaaggta ccatgggcaa     600
gcaaagcaga gtggctgagg gccaggttta gatggtactg aaggccatac caaagaattt     660
gcactttgta ggcattaagg agccaataca ggttttttgag caggttagag tgatgtgatc     720
ctgtccgtgt ttcaggaaga tcactgttag cggtatgagt aatggcctta agagaggagg     780
aggttatagg caggacagct agttaggagt cattgcaaga gttgcaccaa gagcaatggc     840
aatacaagtg tgaaggtaaa ggagagctga gaggcatttc tggggtgcac ttattaggaa     900
ttggaggaag atgaaagagt caaagataag aaacattaag gctttattcg gcataatcgg     960
gtagacagtg atactgttaa catagattag ggaacataaa gtagatttgg tgggaaagat    1020
agatttctg ttgttatttt tttaaattat tcttattttt ccttcccagg aattatggga    1080
aggttggata tgtggatgtg tgtgtatatg tatgtacata acaggctcga gcctgtttct    1140
gcttatgctt ctcttaggtt taattctttg ttcttgatca gactgtgatt tgagggttgc    1200
gcatctttga gttagggttt ccctgacatc tggctttaaa ttataagaag ttcccagatc    1260
acacaatctc agaattggaa tgaacttaa aaggacaact agtctaatcc ttctgctctt    1320
gcccaacttc tcaaatagat ggttttgcc tcttttgaa caattactgc aaggatgctt    1380
tctgcttcaa ccattccgtt tgaggctct aactccagaa gttattcctt gtacacagta    1440
agctctgccc tgtgataact tccctctggc actttggccc tctggagccg tatactgaac    1500
aaattttgtc ttttccat ataaatgtct ctactttttg agaccaacat tttcctcctt    1560
caccctaccc cacctcactg tattttcttc tcttaagaac ccttgactgt ctaatgtgtt    1620
ccttctagaa tgtgatttct agtctttta gtactggccc tttactctgc ttgttttcta    1680
gtttgtggat ttttcttgaa atgtaatgca aaaattgaa tgcagtaaat tgtttaaagc    1740
gttttctttt tttgatggct ttaagtcaga aaaagcaaaa tgtttgaagt ttatggagta    1800
gatatctgta caatatatta atatatttac gtataaaagg gaatgataca agaatcccaa    1860
actatttttg tttctagaat caagatttat tcaattattc taactcataa tctctgatct    1920
aatgtagttt ttaaaatctg taatgtatga ttacacaaat atatacattt gtcaaaagtc    1980
atcaatatgt acacattaca atgtgtgagt tacaatgtat gtgaattata cccaataaaa    2040
ttgatttaaa aaacaaacta aacatgtata aagttcttct cattcaagac aagtacgttt    2100
```

```
ccctcctagt gggatagaca catgaaagga aagttagggg tttgtggcca tgtaacagtt    2160
acatatccga ttaggttacg taagcagctc ctaaccccta atctaaggag gttcgtacag    2220
gaagactttg gccatagcca tagctctata caaatgtcct ttttataata atctgtaagg    2280
acatgagacg gaatgctatt aggcaaaagc tcaaggagaa acctctgatt actatcccca    2340
gggtgactga gttctcgtga ccacatggtc aaggattcac agaagctcca tttaggcacc    2400
aaatgacttg gaacataac cagagtgacc acacatcctc tcgttatcat cacatggtca    2460
tggtagtatc tgggccaatt aaccgtgtgt ttctggagca ctttctatgc gcatagtact    2520
gtgctaagct ccgtgaaaaa cagagaatcg tataaaaaga acctatagga tggtcgcggt    2580
agctgcacag catcgtggat gcgtttaatg tactgaactg tatatttaaa actgttaaaa    2640
gttcaagttt tatgttgtgc gtattttttac cacaatcaaa aagaaccttc aaggcccttg    2700
ggagatccag gtgtggtcca gtagatgtga ataaattcct atctactaag caccctgcat    2760
cgtctttcct ctgccattat tgctcaagtg ccctcttctc ttcctgtgac tgtgaagcca    2820
gccttatttc tagtcaaggg gatgtaaaga actgtgggcc agtcgcttaa tagcatggca    2880
cccttggtgc tggtccagtt ttgtctctcc ttttgcctta ttccttatgg cttttataat    2940 ctatttttact ctggatgcat aaaaactggg ttgtgatgga ttagatcaga ttcctccatt    3000
tattacctat gtgaccttcg gggtattgtg ttgacagcaa tgagctttgt aaaattaatc    3060
agaagactca atgagatagt gcctattact tcccaccccc ttctcttcta ctgaccccaa    3120
ctgcatttct gcttttgtcc ctctctcatt tgattccctc tgtggctcct tgcttagaat    3180
tctgcttttg ccaccatcat tatgtttaaa cattttagta cgtagttcct gactccctct    3240
tttattgctg gatctcttgc tgtcaacatt ttacttacct actctgttta ccgcctactc    3300
taggccaata taattcttac tgtgcctgta tgtcatagtg tttgtaagct tgtttctggg    3360
cttttctgtg tatataagtg catgtgatta aggagtatag attacttacc tttggagttc    3420
agaaccagga tagctcagtg ttatctggga tggtcaagct gtaagactag agctgctatt    3480
gaaagtagcc tggaagttag agagtcagaa ataaaggaaa ataccctagag ttctgatgtt    3540 agcttcttca aagaaacctg tagctttcca agcacattaa taaaactaca cagccactag    3600
caagactctc cgtgggagag catgtattat ggctccagaa ggatttgggg gtgggtttgt    3660
tgaatgcatt attgttgctt gatgcagaga atgctgggcc tacaagtgtc caccacaagc    3720
tttcaaggga aaaacttctt cattagtttt gacttcagat gcccaaactg cattataatt    3780
gaacaagtat taacttagta agtcaaattt tcttcaaaat cttaggtgct cctataactg    3840
ctcattaaga ttcacttatt tttttcacgc aggtaagggg acctaattca gtgtttctta    3900
aaatgaaatt catagacata ttcttagagt ctttgaaaat tcttttttctt taaaaaggaa    3960 agttttata gtactctagt ttgagaaaca ctacggtgtc cctcataaat ggtttagttc    4020
attgttaaag ggatgctgag aacatatatg aggtgccaaa gtataaaatg tcaggaaggg    4080
agtttgaagg ttgtcaaatg ttggaggccc agggaggtga aagcaaacat aagcacatcg    4140
gaagcaaaaa ggggaggttg gtggatagag gtgagaaggc tgctgagcca ccattgctgt    4200
cagcttggtt tcctatactg gggtaagttt gtgtatgtgt ggtttggccc agcataaaga    4260
gccaaagaca tagcggacaa gtggtgacca gattcagctc tgaatggatt ctagtttggc    4320
aatctctggg gagtgattaa caactttgac accagtttgc tgcctaacag taattgctgt    4380
gtcattgagt ccttcttact caagaagcag aatttgaaga tatgggcaaa gtttgggatt    4440
```

```
caaaccaagc aaaatagggga aggagcaggc agatctgtac aatgagggac gacttttgat    4500
cccagggtag aggctggtct tccctctgcc ttgtctccag gcccgtgttt aagcaagcgc    4560
cctgatgtca gtgaatgaat ccttacaggt gtgggctact ccccatggtg agacaggcct    4620
catcaggttc tgggattgcg gtgatgggga gcattgcagt tcaaataacc actgagctca    4680
ggcttcattt ggccctgtga tcctttctcc aattattcta aaggatcttt atgaaaaaat    4740
aataaagtaa aattttttaaa tttcacttaa aaaaactcat agagctgcaa tatgcaacct    4800
ttttaggaag gagcattaaa aaatatttcc ctgaggcctc gagattacac ttggggtaca    4860
gaaatggcaa taattatggc agattccacc atcttgacgg aacaattttg gggctgagag    4920
aaagacagtt ggctattttc cctctacgcc tcaacttgtc aagatacgga ggttgatgat    4980
cgagttttac atctgtgatt tatctggtag catagacttg atgcaagaac agaaagtgtt    5040
ggggatgtcc caaatagaaa caaggatagg gtatcagaaa tcctgacaag tggcacttat    5100
gcttctgtgg gttgggaaag gagagctaac attaaagaag ttttattgtc tgaggaaaat    5160
aaaaactgag tacatgaatg ctaggagaga tctaatgttt tagtgcccta gaattttcaa    5220
gcattatagg aaaaagttta atattttttt gatagcaaag aatgatgaga gttaagcttt    5280
ctttggaaga tcagcatgac ttttctatt tttcccctca tattctacag acactatctc    5340
attttatcct cacttcaact ctgtgaggta tgagtatcat tatcctcact tggcagacga    5400
gagtactgac atatagggag cttgagtagt ttatccaagg cacacagtg ctcgtgctgg    5460
gatctgaaca caggacatcc aaccaaaggt tgtgcccttta atcctatcat atatatatac    5520
ttgtggtttg tttttttctt tgcttaggaa gattcgccct gagctaactt ctgttgccaa    5580
ccttcctctt tttgcttgag gaagattcgc cctgagctaa catctgtgcc agtcttcctt    5640
tgttttgtat gtgggtcacc accacagtat ggctgccaaa gagtggtgta ggtctgcacc    5700
caggaaccaa accagggccg ccaaagcgga gcatgccgaa caaccatgag gccatgaggc    5760
tggccctgct agtggctttt aaagtttgag aatcatggac ttgtagtatc agcaccacct    5820
gggaactcat tagaaatgca aaatctcaga attggaattg aacttaaaag gacaactagt    5880
ctaatccttc tgctcttgcc caacttctca aatagatggt ttttgcctct ttttgaacaa    5940
ttactgcaag gatgctttct gcttcaacca ttccgttttg aggctctaac tccagaagtt    6000
attccttgta cacagtaagc tctgcccctgt gataacttcc ctctggcact ttggccctct    6060
ggagccgtat actgaacaaa ttttgtcttt ttcccatata aatgtctcta cttttttgaga    6120
ccaacatttt cctccttcac cctaccccac ctcactgtat tttcttctct taagaaccct    6180
tgactgtcta atgtgttcct tctagaatgt gatttctagt cttttttagta ctggcccttt    6240
actctgcttg ttttctagtt tgtggatttt tcttgaaatg taatgcaaaa aattgaatgc    6300
agtaaattgt ttaaagcgtt tttctttttt gatggcttta agtcagaaaa agcaaaatgt    6360
ttgaagttta tggagtagat atctgtacaa tatattaata tatttacgta taaaagggaa    6420
tgatacaaga atcccaaact attttttgttt ctagaatcaa gatttattca attattctaa    6480
ctcataatct ctgatctaat gtagttttta aaatctgtaa tgtatgatta cacaaatata    6540
tacatttgtc aaaagtcatc aatatgtaca cattacaatg tgtgagttac aatgtatgtg    6600
aattataccc aataaaattg atttaaaaaa caaactaaac atgtataaag ttcttctcat    6660
tcaagacaag tacgttttccc tcctagtggg atagacacat gaaaggaaag ttagggggttt    6720
gtggccatgt aacagttaca tatccgatta ggttacgtaa gcagctccta acccctaatc    6780
taaggaggtt cgtacaggaa gactttggcc atagccatag ctctatacaa atgtccttttt   6840
```

```
tataataatc tgtaaggaca tgagacggaa tgctattagg caaaagctca aaggagaacc      6900
tctgattact atccccaggg tgactgagtt ctcgtgacca catggtcaag gattcacaga      6960
agctccattt aggcaccaaa tgacttggga acataaccag agtgaccaca catcctctcg      7020
ttatcatcac atggtcatgg tagtatctgg gccaattaac cgtgtgtttc tggagcactt      7080
tctatgcgca tagtactgtg ctaagctccg tgaaaacag agaatcgtat aaaaagaacc       7140
tataggatgg tcgcggtagc tgcacagcat cgtggatgcg tttaatgtac tgaactgtat      7200
atttaaaact gttaaaagtt caagttttat gttgtgcgta tttttaccac aatcaaaaag      7260
aaccttcaag gcccttggga gatccaggtg tggtccagta gatgtgaata aattcctatc      7320
tactaagcac cctgcatcgt ctttcctctg ccattattgc tcaagtgccc tcttctcttc      7380
ctgtgactgt gaagccagcc ttatttctag tcaaggggat gtaaagaact gtgggccagt      7440
cgcttaatag catggcaccc ttggtgctgg tccagttttg tctctccttt tgccttattc      7500
cttatggctt ttataatcta ttttactctg gatgcataaa aactggggttg tgatggatta    7560
gatcagattc ctccatttat tacctatgtg accttcgggg tattgtgttg acagcaatga     7620
gctttgtaaa attaatcaga agactcaatg agatagtgcc tattacttcc cacccccttc     7680
tcttctactg accccaactg catttctgct tttgtccctc tctcatttga ttccctctgt     7740
ggctccttgc ttagaattct gcttttgcca ccatcattat gtttaaacat tttagtacgt    7800
agttcctgac tccctctttt attgctggat ctcttgctgt caacatttta cttacctact    7860
ctgtttaccg cctactctag gccaatataa ttcttactgt gcctgtatgt catagtgttt    7920
gtaagcttgt ttctgggctt ttctgtgtat ataagtgcat gtgattaagg agtatagatt    7980
acttacctttt ggagttcaga accaggatag ctcagtgtta tctgggatgg tcaagctgta   8040
agactagagc tgctattgaa agtagcctgg aagttagaga gtcagaaata aaggaaaata    8100
cctagagttc tgatgttagc ttcttcaaag aaacctgtag cttttccaagc acattaataa   8160
aactacacag ccactagcaa gactctccgt gggagagcat gtattatggc tccagaagga   8220
tttgggggtg ggtttgttga atgcattatt gttgcttgat gcagagaatg ctgggcctac   8280
aagtgtccac cacaagcttt caagggaaaa acttcttcat tagttttgac ttcagatgcc   8340
caaactgcat tataattgaa caagtattaa cttagtaagt caaattttct tcaaaatctt   8400
aggtgctcct ataactgctc attaagattc acttattttt ttcacgcagg taaggggacc   8460
taattcagtg tttcttaaaa tgaaattcat agacatattc ttagagtctt tgaaaattct   8520
ttttctttaa aaaggaaagt ttttatagta ctctagtttg agaaacacta cggtgtccct   8580
cataaatggt ttagttcatt gttaaaggga tgctgagaac atatatgagg tgccaaagta   8640
taaaatgtca ggaagggagt ttgaaggttg tcaaatgttg gaggcccagg gaggtgaaag   8700
caaacataag cacatcggaa gcaaaaaggg gaggttggtg gatagaggtg agaaggctgc   8760
tgagccacca ttgctgtcag cttggtttcc tatactgggg taagtttgtg tatgtgtggt   8820
ttggcccagc ataaagagcc aaagacatag cggacaagtg gtgaccagat tcagctctga   8880
atggattcta gtttggcaat ctctggggag tgattaacaa cttttgacacc agtttgctgc   8940
ctaacagtaa ttgctgtgtc attgagtcct tcttactcaa gaagcagaat ttgaagatat   9000
gggcaaagtt tgggattcaa accaagcaaa atagggaagg agcaggcaga tctgtacaat   9060
gagggacgac ttttgatccc agggtagagg ctggtcttcc ctctgccttg tctccaggcc   9120
cgtgtttaag caagcgccct gatgtcagtg aatgaatcct tacaggtgtg ggctactccc   9180
```

```
catggtgaga caggcctcat caggttctgg gattgcggtg atggggagca ttgcagttca    9240
aataaccact gagctcaggc ttcatttggc cctgtgatcc tttctccaat tattctaaag    9300
gatctttatg aaaaaataat aaagtaaaat ttttaaattt cacttaaaaa aactcataga    9360
gctgcaatat gcaaccttt  taggaaggag cattaaaaaa tatttccctg aggcctcgag    9420
attacacttg gggtacagaa atggcaataa ttatggcaga ttccaccatc ttgacggaac    9480
aattttgggg ctgagagaaa gacagttggc tattttccct ctacgcctca acttgtcaag    9540
atacggaggt tgatgatcga gttttacatc tgtgatttat ctggtagcat agacttgatg    9600
caagaacaga aagtgtttgg gatgtcccaa atagaaacaa ggatagggta tcagaaatcc    9660
tgacaagtgg cacttatgct tctgtgggtt gggaaaggag agctaacatt aaagaagttt    9720
tattgtctga ggaaaataaa aactgagtac atgaatgcta ggagagatct aatgttttag    9780
tgccctagaa ttttcaagca ttataggaaa aagtttaata tttttttgat agcaaagaat    9840
gatgagagtt aagctttctt tggaagatca gcatgacttt ttctattttt cccctcatat    9900
tctacagaca ctatctcatt ttatcctcac ttcaactctg tgaggtatga gtatcattat    9960
cctcacttgg cagacgagag tactgacata tagggagctt gagtagttta tccaagggca   10020
cacagtgctc gtgctgggat ctgaacacag gacatccaac caaaggttgt gcccttaatc   10080
ctatcatata tatatacttg tggtttgttt ttttctttgc ttaggaagat tcgccctgag   10140
ctaacttctg ttgccaacct tcctcttttt gcttgaggaa gattcgccct gagctaacat   10200
ctgtgccagt cttcctttgt tttgtatgtg ggtcaccacc acagtatggc tgccaaagag   10260
tggtgtaggt ctgcacccag gaaccaaacc agggccgcca agcggagca tgccgaacaa    10320 ccatgaggcc atgaggctgg ccctgctagt ggcttttaaa gtttgagaat catggacttg   10380
tagtatcagc accacctggg aactcattag aaatgcaaat tctcaggcct catcccaagc   10440
cccctgaatc agaaactctg gatgaagttc tccaggtgat tctggtgcac actccagtgt   10500
ggaaaccact gttgtattgg tctctgacga cgttagaaga agacttatag aggacttttt   10560
tagggattgt gttagagatg tcaagatggt ggagaatata gcaatgaagg gataccatga   10620
aaggtctaac ggtgaagagg tacatacctg gcgtctgaga agggaaggaa tgtcaataat   10680
gtgataggaa gcaactgtga ggaaacaatt agctgtgttg tttgggtgtc ctgttctcgg   10740
atgaaatgat gattggaatt agaagagtgt tggtcacata cgcttcacta taagtgacta   10800
ggtcagttat ataaggacaa tcaaatactt cagggttcaa attgaattat ttcacagtca   10860
tcgaagaagt tggcatttag ctaggatcaa agagggattc tcttcttttt ttctgtgaat   10920 taaaagact  agtctgtata ttgatgtgat ggtggttacg tgggtttatg catttatcag   10980
aaatcatcat actatacccct aaaatgggt  gcatattatt atatgtaaat tctgtctaaa   11040
taaagttgat ttaaaaatgg gaatgtgggg gctggccctg tgtgcccgag cggttaagtt   11100
cgcgccctcc gctgcaggcg gcccagtgtt tcgttggttc gaatcctggg cacggacatg   11160
acactgctca tcaaaccacg ctgaggcagc atcccacatg ccacaactag aaggacccac   11220
aacaaagaat atacaactat gtaccggggt gctttgggga gaaaaggaa aaaataaaat   11280 cttaaaaaaa aaaaaaaata gggtatagtg tactcgtggc cagttaatga gtttctgtca   11340
ctgaggtgtt tgagcagagg ttcagtaagc gcttgtcaga tatgtcgtag tggggcttcc   11400
cacatctgag ggagaaatcg cactcagcaa cctaaacatt ccttctaccc agaggttcca   11460
tgagtcacaa tttctgttgt gtcagccgca ggtgttgcca ttttgtgtag aatgcttggt   11520
taatatattt gatctgaaac attttaactt gtcatgattt taaaatgtat taaagtgtcc   11580
```

```
acgtgtgaaa cacaggacag tgaattcatt caccactccc tactgcatat cacaagtaga   11640
aagatttcat ggcagatcaa accatattgt attcttattc ctaaaacagt aatttgtatt   11700
tatcgtggca tcaagggtgt tttactccta aggcaaattt gcctgtttta aactgaatct   11760
tcaaagaaga taagttaggg aggattttttg ctttgatcct gttttttgttt ttttccatca   11820
```

```
acgtgtgaaa cacaggacag tgaattcatt caccactccc tactgcatat cacaagtaga   11640
aagatttcat ggcagatcaa accatattgt attcttattc ctaaaacagt aatttgtatt   11700
tatcgtggca tcaagggtgt tttactccta aggcaaattt gcctgtttta aactgaatct   11760
tcaaagaaga taagttaggg aggattttttg ctttgatcct gttttttgttt ttttccatca   11820
aacccaacat gacatgtaaa tacttatttg gactttttt ctttctcgaa agcagattta   11880
tttggagaac aatatgcttg tatgtttgaa tgaagtttag agtaagatgc ttttctctat   11940
aaaggtgcca ctctttttatt actgaataat taagtcacct tttttttatac aagtgaattt   12000
gtgctttcga cgtggtttgt cagatgctgt taaatgaact gctgttagac tccaaggctg   12060
cggcacacag gccctgatta caggagttaa aatagtgtgc attggctgac tgctgctccg   12120
cagcaggagc gctcactcat aattcctttg catctag                            12157

<210> SEQ ID NO 2
<211> LENGTH: 9154
<212> TYPE: DNA
<213> ORGANISM: Equus caballus

<400> SEQUENCE: 2
aatctcagaa ttggaattga acttaaaagg acaactagtc taatccttct gctcttgccc     60
aacttctcaa atagatggtt tttgccttctt tttgaacaat tactgcaagg atgctttctg   120
cttcaaccat tccgttttga ggctctaact ccagaagtta ttccttgtac acagtaagct   180
ctgcccgtgt ataacttccc tctggcactt tggccctctg gagccgtata ctgaacaaat   240
tttgtctttt tcccatataa atgtctctac ttttttgagac caacatttttc ctccttcacc   300
ctaccccacc tcactgtatt tcttctctct aagaaccctt gactgtctaa tgtgttcctt   360
ctagaatgtg atttctagtc ttttttagtac tggcccttta ctctgcttgt tttctagttt   420
gtggattttt cttgaaatgt aatgcaaaaa attgaatgca gtaaattgtt taaagcgttt   480
ttcttttttg atggctttaa gtcagaaaaa gcaaaatgtt tgaagtttat ggagtagata   540
tctgtacaat atattaatat atttacgtat aaaagggaat gatacaagaa tcccaaacta   600
tttttgtttc tagaatcaag attttattcaa ttattctaac tcataatctc tgatctaatg   660
tagttttttaa aatctgtaat gtatgattac acaaatatat acatttgtca aaagtcatca   720
atatgtacac attacaatgt gtgagttaca atgtatgtga attatacccca ataaaattga   780
tttaaaaaac aaactaaaca tgtataaagt tcttctcatt caagacaagt acgtttccct   840
cctagtggga tagacacatg aaaggaaagt taggggtttg tggccatgta acagttacat   900
atccgattag gttacgtaag cagctcctaa ccctaatct aaggaggttc gtacaggaag   960
actttggcca tagccatagc tctatacaaa tgtcctttttt ataataatct gtaaggacat  1020
gagacggaat gctattaggc aaaagctcaa aggagaacct ctgattacta tccccagggt  1080
gactgagttc tcgtgaccac atggtcaagg attcacagaa gctccattta ggcaccaaat  1140
gacttgggaa cataaccaga gtgaccacac atcctctcgt tatcatcaca tggtcatggt  1200
agtatctggg ccaattaacc gtgtgtttct ggagcacttt ctatgcgcat agtactgtgc  1260
taagctccgt gaaaaacaga gaatcgtata aaagaacct ataggatggt cgcggtagct  1320
gcacagcatc gtggatgcgt ttaatgtact gaactgtata tttaaaactg ttaaaagttc  1380
aagttttatg ttgtgcgtat ttttaccaca atcaaaaaga accttcaagg cccttgggag  1440
atccaggtgt ggtccagtag atgtgaataa attcctatct actaagcacc ctgcatcgtc  1500
```

```
tttcctctgc cattattgct caagtgccct cttctcttcc tgtgactgtg aagccagcct   1560
tatttctagt caaggggatg taaagaactg tgggccagtc gcttaatagc atggcaccct   1620
tggtgctggt ccagttttgt ctctcctttt gccttattcc ttatggcttt tataatctat   1680
tttactctgg atgcataaaa actgggttgt gatggattag atcagattcc tccatttatt   1740
acctatgtga ccttcggggt attgtgttga cagcaatgag ctttgtaaaa ttaatcagaa   1800
gactcaatga gatagtgcct attacttccc acccccttct cttctactga ccccaactgc   1860
atttctgctt ttgtccctct ctcatttgat tccctctgtg gctccttgct tagaattctg   1920
cttttgccac catcattatg tttaaacatt ttagtacgta gttcctgact ccctctttta   1980
ttgctggatc tcttgctgtc aacattttac ttacctactc tgtttaccgc ctactctagg   2040
ccaatataat tcttactgtg cctgtatgtc atagtgtttg taagcttgtt tctgggcttt   2100
tctgtgtata taagtgcatg tgattaagga gtatagatta cttacctttg gagttcagaa   2160
ccaggatagc tcagtgttat ctgggatggt caagctgtaa gactagagct gctattgaaa   2220
gtagcctgga agttagagag tcagaaataa aggaaaatac ctagagttct gatgttagct   2280
tcttcaaaga aacctgtagc tttccaagca cattaataaa actacacagc cactagcaag   2340
actctccgtg ggagagcatg tattatggct ccagaaggat ttgggggtgg gtttgttgaa   2400
tgcattattg ttgcttgatg cagagaatgc tgggcctaca agtgtccacc acaagctttc   2460
aagggaaaaa cttcttcatt agttttgact tcagatgccc aaactgcatt ataattgaac   2520
aagtattaac ttagtaagtc aaattttctt caaaatctta ggtgctccta taactgctca   2580
ttaagattca cttattttt tcacgcaggt aaggggacct aattcagtgt tcttaaaat    2640 gaaattcata gacatattct tagagtcttt gaaaattctt tttcttaaa aaggaaagtt   2700 tttatagtac tctagtttga gaaacactac ggtgtccctc ataaatggtt tagttcattg   2760
ttaaagggat gctgagaaca tatatgaggt gccaaagtat aaaatgtcag gaagggagtt   2820
tgaaggttgt caaatgttgg aggcccaggg aggtgaaagc aaacataagc acatcggaag   2880
caaaaagggg aggttggtgg atagaggtga gaaggctgct gagccaccat tgctgtcagc   2940
ttggtttcct atactggggt aagtttgtgt atgtgtggtt tggcccagca taaagagcca   3000
aagacatagc ggacaagtgg tgaccagatt cagctctgaa tggattctag tttggcaatc   3060
tctggggagt gattaacaac tttgacacca gtttgctgcc taacagtaat tgctgtgtca   3120
ttgagtcctt cttactcaag aagcagaatt tgaagatatg ggcaaagttt gggattcaaa   3180
ccaagcaaaa tagggaagga gcaggcagat ctgtacaatg agggacgact tttgatccca   3240
gggtagaggc tggtcttccc tctgccttgt ctccaggccc gtgtttaagc aagcgccctg   3300
atgtcagtga atgaatcctt acaggtgtgg gctactcccc atggtgagac aggcctcatc   3360
aggttctggg attgcggtga tggggagcat tgcagttcaa ataaccactg agctcaggct   3420
tcatttggcc ctgtgatcct ttctccaatt attctaaagg atctttatga aaaaataata   3480
aagtaaaatt tttaaatttc acttaaaaaa actcatagag ctgcaatatg caacctttt    3540 aggaaggagc attaaaaaat atttccctga ggcctcgaga ttacacttgg ggtacagaaa   3600
tggcaataat tatggcagat tccaccatct tgacggaaca attttggggc tgagagaaag   3660
acagttggct attttccctc tacgcctcaa cttgtcaaga tacggaggtt gatgatcgag   3720
ttttacatct gtgatttatc tggtagcata gacttgatgc aagaacagaa agtgttgggg   3780
atgtcccaaa tagaaacaag gatagggtat cagaaatcct gacaagtggc acttatgctt   3840
ctgtgggttg ggaaaggaga gctaacatta agaagttttt attgtctgag gaaaataaaa   3900
```

```
actgagtaca tgaatgctag gagagatcta atgttttagt gccctagaat tttcaagcat   3960
tataggaaaa agtttaatat tttttgata gcaaagaatg atgagagtta agctttcttt   4020
ggaagatcag catgactttt tctattttc ccctcatatt ctacagacac tatctcattt   4080
tatcctcact tcaactctgt gaggtatgag tatcattatc ctcacttggc agacgagagt   4140
actgacatat agggagcttg agtagtttat ccaagggcac acagtgctcg tgctgggatc   4200
tgaacacagg acatccaacc aaaggttgtg cccttaatcc tatcatatat atatacttgt   4260
ggtttgtttt tttctttgct taggaagatt cgccctgagc taacttctgt tgccaacctt   4320
cctcttttg cttgaggaag attcgccctg agctaacatc tgtgccagtc ttcctttgtt   4380
ttgtatgtgg gtcaccacca cagtatggct gccaaagagt ggtgtaggtc tgcacccagg   4440
aaccaaacca gggccgccaa agcggagcat gccgaacaac catgaggcca tgaggctggc   4500
cctgctagtg gcttttaaag tttgagaatc atggacttgt agtatcagca ccacctggga   4560
actcattaga aatgcaaaat ctcagaattg gaattgaact taaaaggaca actagtctaa   4620
tccttctgct cttgcccaac ttctcaaata gatggttttt gcctcttttt gaacaattac   4680
tgcaaggatg ctttctgctt caaccattcc gttttgaggc tctaactcca gaagttattc   4740
cttgtacaca gtaagctctg ccctgtgata acttccctct ggcactttgg ccctctggag   4800
ccgtatactg aacaaatttt gtcttttcc catataaatg tctctacttt ttgagaccaa   4860
cattttcctc cttcacccta ccccacctca ctgtatttc ttctcttaag aacccttgac   4920
tgtctaatgt gttccttcta gaatgtgatt tctagtcttt ttagtactgg ccctttactc   4980
tgcttgtttt ctagtttgtg gatttttctt gaaatgtaat gcaaaaatt gaatgcagta   5040
aattgtttaa agcgttttc tttttgatg gctttaagtc agaaaagca aatgtttga   5100
agtttatgga gtagatatct gtacaatata ttaatatatt tacgtataaa agggaatgat   5160
acaagaatcc caaactattt ttgtttctag aatcaagatt tattcaatta ttctaactca   5220
taatctctga tctaatgtag ttttaaaat ctgtaatgta tgattacaca aatatataca   5280
tttgtcaaaa gtcatcaata tgtacacatt acaatgtgtg agttacaatg tatgtgaatt   5340
atacccaata aaattgattt aaaaaacaaa ctaaacatgt ataaagttct tctcattcaa   5400
gacaagtacg tttccctcct agtgggatag acacatgaaa ggaaagttag gggtttgtgg   5460
ccatgtaaca gttacatatc cgattaggtt acgtaagcag ctcctaaccc ctaatctaag   5520
gaggttcgta caggaagact ttggccatag ccatagctct atacaaatgt cctttttata   5580
ataatctgta aggacatgag acggaatgct attaggcaaa agctcaaagg agaacctctg   5640
attactatcc ccagggtgac tgagttctcg tgaccacatg gtcaaggatt cacagaagct   5700
ccatttaggc accaaatgac ttgggaacat aaccagagtg accacacatc ctctcgttat   5760
catcacatgg tcatggtagt atctgggcca attaaccgtg tgtttctgga gcactttcta   5820
tgcgcatagt actgtgctaa gctccgtgaa aaacagagaa tcgtataaaa agaacctata   5880
ggatggtcgc ggtagctgca cagcatcgtg gatgcgttta atgtactgaa ctgtatattt   5940
aaaactgtta aaagttcaag ttttatgttg tgcgtatttt taccacaatc aaaaagaacc   6000
ttcaaggccc ttgggagatc caggtgtggt ccagtagatg tgaataaatt cctatctact   6060
aagcaccctg catcgtcttt cctctgccat tattgctcaa gtgccctctt ctcttcctgt   6120
gactgtgaag ccagccttat ttctagtcaa ggggatgtaa agaactgtgg gccagtcgct   6180
taatagcatg gcaccctggg tgctggtcca gttttgtctc tccttttgcc ttattcctta   6240
```

-continued

```
tggctttat  aatctattt   actctggatg  cataaaaact  gggttgtgat  ggattagatc  6300
agattcctcc  attattacc   tatgtgacct  tcggggtatt  tgtgttgacag  caatgagctt  6360
tgtaaaatta  atcagaagac  tcaatgagat  agtgcctatt  acttcccacc  cccttctctt  6420
ctactgaccc  caactgcatt  tctgcttttg  tccctctctc  atttgattcc  ctctgtggct  6480
ccttgcttag  aattctgctt  ttgccaccat  cattatgttt  aaacatttta  gtacgtagtt  6540
cctgactccc  tcttttattg  ctggatctct  tgctgtcaac  attttactta  cctactctgt  6600
ttaccgccta  ctctaggcca  atataattct  tactgtgcct  gtatgtcata  gtgtttgtaa  6660
gcttgtttct  gggcttttct  gtgtatataa  gtgcatgtga  ttaaggagta  tagattactt  6720
acctttggag  ttcagaacca  ggatagctca  gtgttatctg  ggatggtcaa  gctgtaagac  6780
tagagctgct  attgaaagta  gcctggaagt  tagagagtca  gaaataaagg  aaaatacca  6840
gagttctgat  gttagcttct  tcaaagaaac  ctgtagcttt  ccaagcacat  taataaaact  6900
acacagccac  tagcaagact  ctccgtggga  gagcatgtat  tatggctcca  gaaggatttg  6960
ggggtgggtt  tgttgaatgc  attattgttg  cttgatgcag  agaatgctgg  gcctacaagt  7020
gtccaccaca  agctttcaag  ggaaaaactt  cttcattagt  tttgacttca  gatgcccaaa  7080
ctgcattata  attgaacaag  tattaactta  gtaagtcaaa  ttttcttcaa  aatcttaggt  7140
gctcctataa  ctgctcatta  agattcactt  attttttca   cgcaggtaag  gggacctaat  7200
tcagtgttc   ttaaaatgaa  attcatagac  atattcttag  agtctttgaa  aattcttttt  7260
cttaaaaag   gaaagttttt  atagtactct  agtttgagaa  acactacggt  gtccctcata  7320
aatggtttag  ttcattgtta  aagggatgct  gagaacatat  atgaggtgcc  aaagtataaa  7380
atgtcaggaa  gggagtttga  aggttgtcaa  atgttggagg  cccagggagg  tgaaagcaaa  7440
cataagcaca  tcggaagcaa  aaaggggagg  ttggtggata  gaggtgagaa  ggctgctgag  7500
ccaccattgc  tgtcagcttg  gtttcctata  ctggggtaag  tttgtgtatg  tgtggtttgg  7560
cccagcataa  agagccaaag  acatagcgga  caagtggtga  ccagattcag  ctctgaatgg  7620
attctagttt  ggcaatctct  ggggagtgat  taacaacttt  gacaccagtt  tgctgcctaa  7680
cagtaattgc  tgtgtcattg  agtccttctt  actcaagaag  cagaatttga  agatatgggc  7740
aaagtttggg  attcaaacca  agcaaaatag  ggaaggagca  ggcagatctg  tacaatgagg  7800
gacgactttt  gatcccaggg  tagaggctgg  tcttccctct  gccttgtctc  caggcccgtg  7860
tttaagcaag  cgccctgatg  tcagtgaatg  aatccttaca  ggtgtgggct  actccccatg  7920
gtgagacagg  cctcatcagg  ttctgggatt  gcggtgatgg  ggagcattgc  agttcaaata  7980
accactgagc  tcaggcttca  tttggccctg  tgatcctttc  tccaattatt  ctaaaggatc  8040
tttatgaaaa  aataataaag  taaaatttt   aaatttcact  taaaaaaact  catagagctg  8100
caatatgcaa  ccttttagg   aaggagcatt  aaaaaatatt  tccctgaggc  ctcgagatta  8160
cacttggggt  acagaaatgg  caataattat  ggcagattcc  accatcttga  cggaacaatt  8220
ttggggctga  gagaaagaca  gttggctatt  ttccctctac  gcctcaactt  gtcaagatac  8280
ggaggttgat  gatcgagttt  tacatctgtg  atttatctgg  tagcatagac  ttgatgcaag  8340
aacagaaagt  gttggggatg  tcccaaatag  aaacaaggat  agggtatcag  aaatcctgac  8400
aagtggcact  tatgcttctg  tgggttggga  aggagagct   aacattaaag  aagttttatt  8460
gtctgaggaa  aataaaaact  gagtacatga  atgctaggag  agatctaatg  ttttagtgcc  8520
ctagaatttt  caagcattat  aggaaaaagt  ttaaatttt   tttgatagca  aagaatgatg  8580
agagttaagc  tttctttgga  agatcagcat  gacttttct   atttttcccc  tcatattcta  8640
```

| | |
|---|---:|
| cagacactat ctcattttat cctcacttca actctgtgag gtatgagtat cattatcctc | 8700 |
| acttggcaga cgagagtact gacatatagg gagcttgagt agtttatcca agggcacaca | 8760 |
| gtgctcgtgc tgggatctga acacaggaca tccaaccaaa ggttgtgccc ttaatcctat | 8820 |
| catatatata tacttgtggt ttgttttttt ctttgcttag gaagattcgc cctgagctaa | 8880 |
| cttctgttgc caaccttcct cttttttgctt gaggaagatt cgccctgagc taacatctgt | 8940 |
| gccagtcttc ctttgttttg tatgtgggtc accaccacag tatggctgcc aaagagtggg | 9000 |
| gtaggtctgc acccaggaac caaaccaggg ccgccaaagc ggagcatgcc gaacaaccat | 9060 |
| gaggccatga ggctggccct gctagtggct tttaaagttt gagaatcatg gacttgtagt | 9120 |
| atcagcacca cctgggaact cattagaaat gcaa | 9154 |

<210> SEQ ID NO 3
<211> LENGTH: 7582
<212> TYPE: DNA
<213> ORGANISM: Equus caballus

<400> SEQUENCE: 3

| | |
|---|---:|
| tgagtatata actgttttg gctcagagay gttagattaa taggataaga ggcttttata | 60 |
| aatcactagg cttttgatta ggattttaat agaagttaca atttgtaaga ctggtattga | 120 |
| accatggata gaagtctaac tgtcctcaaa ttccagatca attcaataaa catttattaa | 180 |
| gcacttgtta tataaaaggc actgtcttag gtgcttggca ttggggatct gacaaggttg | 240 |
| gataaagaaa gaaggaagc atgctgtctg ccttcagggg tttacagtgg gtggagatat | 300 |
| gcttggaccc ccaaaactga aatttcaagt gtgattgtta aatgcaaaga caaggtatga | 360 |
| agagaagtat tatccgctcc aagggaagga ggcagggatt gtgaggtgga agcgtyaagg | 420 |
| gyagcttcac aasataggta gtatttgctt aagccttgaa aaytgagtaa agtktccgca | 480 |
| ggtgggagag agggagtgca tttgaagaac gctgaacaaa gccttggagt agtgaagtgt | 540 |
| atggcctccc aggaatgaca agttctgcag tgtaaccaaa gcacaaggta ccayggggcaa | 600 |
| gcaaagcaga gyggctgagg gccaggttta gatggtactg aaggccatac caaagaattt | 660 |
| gcactttgta ggcattaagg agccaataca ggttttttgag caggttagag tgatgtgatc | 720 |
| ctgtccgtgt ttcaggaaga tcactgttag cggtrtgrrt aatggcctta agagaggagg | 780 |
| aggttatagg caggacagct agttaggagt cattgcaaga gttgcaccaa gagcaatggc | 840 |
| aatacaagtg tgaaggtaaa ggagagctga gaggcatttc tggggtgcac ttattaggaa | 900 |
| ttggaggaag atgaaagagt caaagataag aaacattaag gctttattcg gcataatcgg | 960 |
| gtagacagtg atactgttaa catagattag ggaacataaa gtagatttgg tgggaaagat | 1020 |
| agattttctg ttgttatttt tttaaattat tcttattttt ccttcccagg aattatggga | 1080 |
| aggttggata tgtggatgtg tgtgtatatg tatgtacata acaggctcga gcctgtttct | 1140 |
| gcttatgctt ctcttaggtt taattctttg ttccttgatca gactgtgatt tgagggttgc | 1200 |
| gcatctttga gttagggttt ccctgacatc tggctttaaa ttataagaag ttcccagatc | 1260 |
| acacaatctc agaattggaa ttgaacttaa aaggacaact agtctaatcc ttctgctctt | 1320 |
| gcccaacttc tcaaatagat ggttttttgcc tctttttgaa caattactgc aaggatgctt | 1380 |
| tctgcttcaa ccattccgtt ttgaggctct aactccagaa gttattcctt gtacacagta | 1440 |
| agctctgccc tgtgataact tccctctggc actttggccc tctggagccg tatactgaac | 1500 |
| aaattttgtc ttttttcccat ataaatgtct ctacttttttg agaccaacat tttcctcctt | 1560 |

```
caccctaccc cacctcactg tattttcttc tcttaagaac ccttgactgt ctaatgtgtt    1620
ccttctagaa tgtgatttct agtctttta gtactggccc tttactctgc ttgttttcta    1680
gtttgtggat ttttcttgaa atgtaatgca aaaaattgaa tgcagtaaat tgtttaaagc    1740 gttttttcttt tttgatggct ttaagtcaga aaaagcaaaa tgtttgaagt ttatggagta    1800
gatatcygta caatatatta atatatttac gtataaaagg gaatgataca agaatcccaa    1860 actattttttg tttctagrat caagatttat tcaattattc taactcataa tctctgatct    1920
aatgtagttt ttaaaatctg taatgtatga ttacacaaat atatacattt gtcaaaagtc    1980
atcaatatgt acacattaca atgtgtgagt tacaatgtat gtgaattata cccaataaaa    2040
ttgatttaaa aaacaaacta acatgtata aagttcttct cattcaagac aagtacgttt    2100
ccctcctagt gggatagaca catgaaagga aagttagggg tttgtggcca tgtaacagtt    2160
acatatccga ttaggttacg taagcagctc ctaaccccta atctaaggag gttcgtacag    2220
gaagactttg gccatagcca tagctctata caaatgtcct ttttataata atctgtaagg    2280
acatgagacg gaatgctatt aggcaaaagc tcaaggaga acctctgatt actatcccca    2340
gggtgactga gttctcgtga ccacatggtc aaggattcac agaagctcca tttaggcacc    2400
aaatgacttg gaacataac cagagtgacc acacatcctc tcgttatcat cacatggtca    2460
tggtagtatc tgggccaatt aaccgtgtgt ttctggagca ctttctatgc gcatagtact    2520
gtgctaagct ccgtgaaraa cagagaatcr tataaaaaga acctatagga tggtcgcggt    2580
agctgcacag catcgtggat gcgtttaatg tactgaactg tatatttaaa actgttaaaa    2640
gttcaagttt tatgttgtgc gtattttttac cacaatcaaa aagaaccttc aaggcccttg    2700
ggagatccag gtgtggtcca gtagatgtga ataaattcct atctactaag caccctgcrt    2760
cgtctttcct ctgccrttat tgctcaagtg ccctcttctc ttcctgtgac tgtgaagcca    2820
gccttatttc tagtcaaggg gatgtaaaga actgtgggcc agtcgcttaa tagcatggca    2880
cccttggtgc tggtccagtt ttgtctctcc ttttgcctta ttccytatgg cttttataat    2940
ctattttact ctggatgcat aaaaactggg ttgtgatgga ttagatcaga ttcctccatt    3000
tattacctat gtgaccttcg gggtattgtg ttgacagcaa tgagcttttgt aaaattaatc    3060 agaagactca atgagatagt gyctattact tcccaccccc ttctcttcta ctgaccccaa    3120
ctgcatttct gcttttgtcc ctcyctcatt tgattccctc tgtggctcct tgcttagaat    3180
tctgcttttg ccaccatcat tatgtttaaa catttagta cgtagttcct gactccctct    3240
tttattgctg gatctcttgc tgtcaacatt ttacttacct actctgttta ccgcctactc    3300
taggccaata taatycttac tgtgcctgta tgtcatagtg tttgtaagct tgtttctggg    3360
cttttctgtg tatataagtg catgtgatta aggagtatrg attacttacc tttggagttc    3420
agaaccagga tagctcagtg ttatctggga tggtcaagct gtaagactag agctgctatt    3480
gaaagtagcc tggaagttag agagtcagaa ataaggaaa ataccagag ttctgatgtt    3540 agcttcttca aagaaacctg tagctttcca agcacattaa taaaactaca cagccactag    3600
caagactctc cgtgggagag catgtattat ggctccagaa ggatttgggg gtgggtttgt    3660
tgaatgcatt attgttgctt gatgcagaga atgctgggcc tacaagtgtc caccacaagc    3720
tttcaaggga aaaacttctt cattagtttt gacttcagat gcccaaactg cattataatt    3780
gaacaagtat taacttagta agtcaaattt tcttcaaaat cttaggtgct cctataactg    3840
ctcattaaga ttcacttatt tttttcacgc aggtaagggg acctaattca gtgtttctta    3900
aaatgaaatt catagacata ttcttagagt ctttgaaaat tcttttttctt taaaaaggaa    3960
```

```
agtttttata gtactctagt ttgagaaaca ctacggtgtc cctcataaat ggtttagytc    4020
attgttaaag ggatgctgag aacatatatg aggtgccaaa gtataaaatg tcaggaaggg    4080
agtttgaagg ttgtcaaatg ttggaggccc agggaggtga aagcaaacat aagcacatcg    4140
gaagcaaaaa ggggaggttg gtggatagag gtgagaaggc tgctgagcca ccattgctgt    4200
cagcttggtt tcctatactg gggtaagttt gtgtatgtgt ggtttggccc agcataaaga    4260
gccaaagaca tagcggacaa gtggtgacca gattcagctc tgaatggatt ctagtttggc    4320
aatctctggg gagtgattaa caactttgac accagtttgc tgcctaacag taattgctgt    4380
gtcattgagt ccttcttact caagaagcag aatttgaaga tatgggcaaa gtttgggatt    4440
caaaccaagc aaaataggga aggagcaggc agatctgtac aatgagggac gacttttgat    4500
cckagggtag aggctggtct tccctctgcc ttgtctccag gcccgtgttt aagcaagcgc    4560
cctgatgtca gtgaatgaat ccttacaggt gtgggctact ccccatggtg agacaggcct    4620
catcaggttc tgggattgcg gtgatgggga gcattgcagt tcaaataacc actgagctca    4680
ggcttcattt ggccctgtga tcctttctcc aattattcta aaggatcttt atgaaaaaat    4740
aataaagtaa aattttttaaa tttcactkaa aaaaactcat agagctgcaa tatgcaacct    4800
ttttaggaag gagcattaaa aaatatttcc ctgaggcctc gagattacac ttggggtaca    4860
gaaatggcaa taattatggc agattccacc atcttgacgg aacaattttg gggctgagag    4920
aaagacagtt ggctatttc cctctacgcc tsaactygtc aagatacgga ggttgatgat    4980
cgagttttac atctgtgatt tatctggtag catagacttg atgcaagaac rgaaagtgtt    5040
ggggatgtcc caaatagaaa caaggatagg gtatcagaaa tcctgacaag tggcacttat    5100
gcttctgtgg gttgggaaag gagagctaac attaaagaak ttttattgtc tgaggaaaat    5160
aaaaactgag trcatgaatg ctaggagaga tctaatgttt tagtgcccta gaattttcaa    5220
gcwmttatag gaaaaagttt aatatttttt tgatagcaaa gaatgatgag agttaagctt    5280
tctttggaag atcagcmtga cttttttctat ttttccccctc atattctaca gacactatct    5340
cattttatcc tcacttcaac tctgtgaggt atgagtatca ttatcctcac ttggcagacg    5400
agagtactga catatagrga gcttgagtag tttatccaag ggcacacagt gctcgtgctg    5460
ggatctgaac acaggacatc caaccaaagg ttgtgccctt aatcctatca tatatatata    5520
ctygtggttt gttttttct ttgcttagga agattcrccc tgagctaact tctgttgcca    5580
accttcctct ttttgcttga ggaagattcg ccctgagcta acatctgtgc cagtcttcct    5640
ytgttttgta tgtgggtcac caccacagta tggctgccaa agagtggygt aggtctgcac    5700
ccaggaacca aaccagggcc gccaaagcrg agcatgccga acaaccatga aggccatgag    5760
gctggccctg ctagtggctt ttaaagtktg agaatcatgg acttgtagta tcagcaccac    5820
ctgggaactc attagaaatg caaattctca ggcctcaycc caagcccct gaatcagaaa    5880 ctctggatga agttctccag gtgattctgg tgcacactcc agtgtggaaa ccactgttgt    5940
attggtctct gacgacgtta aagaagact tatagaggac ttttttaggg attgtgttag    6000
agatgtcaag atggtggaga atatagcaat gaagggatac catgaaaggt ctaacggtga    6060
agaggtacat acctggcgtc tgagaaggga aggaatgtca ataatgtgat aggaagcaac    6120
tgtgaggaaa caattagctg tgttgtttgg gtgtcctgtt ctcggatgaa atgatgattg    6180
gaattagaag agtgttggtc acatacgctt cactataagt gactaggtca gttatataag    6240
gacaatcaaa tacttcaggg ttcaaattga attatttcac agtcatcgaa gaagttggca    6300
```

```
tttagctagg atcaaagagg gattctcttc ttttttttctg tgaattaaaa agactagtct    6360
gtatattgat gtgatggtgg ttacgtgggt ttatgcattt atcagaaatc atcatactat    6420
acccttaaaa tgggtgcata ttattatatg taaattctgt ctaaataaag ttgatttaaa    6480
aatgggaatg tgggggctgg cccygtgtgc ccgagcggtt aagttcgcgc sctccgctgc    6540
aggcggccca gtgtttcgtt ggttcraatc ctgggcacgg acatgacact gctcatcaaa    6600
ccacgctgag gcagcatccc acatgccaca actagaagga cccacaacaa agaatatacm    6660
actatgtacc ggggtgcttt ggggagaaaa aggaaaaaat aaaatcttaa aaaaaaaaaa    6720
aaataggta tagtgtactc gtggccagtt aatgagtttc tgtcactgag gtgtttgagc    6780
agaggttcag taagcgcttg tcagatatgt cgtagtgggg cttcccacat ctgagggaga    6840
aatcgcactc agcaacctaa acattccttc tacccagagg ttccatgagt cacaatttct    6900
gttgtgtcag ccgcaggtgt tgccattttg tgtagaatgc ttggttaata tatttgatct    6960
gaaacatttt aacttgtcat gatttttaaaa tgtattaaag tgtccacgtg tgaaacacag    7020
gacagygaat tcattcaccr ctccctactg catatcacaa gtagaaagat ttcatggcag    7080
atcaaaccat attgtattct tattcctaaa acagtaattt gtatttatcg tggcatcaag    7140
ggtgttttac tcctaaggca aatttgcctg ttttaaactg aatcttcaaa gaagataagt    7200
tagggaggat ttttgctttg atcctgtttt tgtttttttc catcaaaccc aacatgacat    7260
gtaaatactt atttggactt ttttttcttc tcgaaagcag atttatttgg agaacaatat    7320
gcttgtatgt ttgaatgaag tttagagtaa gatgcttttt cctataaagg tgccactctt    7380
ttattactga ataattaagt caccttttt tatacaagtg aatttgtgct ttcgacgtgg    7440
tttgtcagat gctgttaaat gaactgctgt tagactccaa ggctgcggca cacaggccct    7500
gattrcagga gttaaaatag tgtgcattgg ctgactgctg ctccgcagca ggagcgctca    7560
ctcataattc ctttgcatct ag                                            7582
```

```
<210> SEQ ID NO 4
<211> LENGTH: 4578
<212> TYPE: DNA
<213> ORGANISM: Equus caballus

<400> SEQUENCE: 4
```

```
aatctcagaa ttggaattga acttaaaagg acaactagtc taatccttct gctcttgccc      60
aacttctcaa atagatggtt tttgcctctt tttgaacaat tactgcaagg atgctttctg     120
cttcaaccat tccgttttga ggctctaact ccagaagtta ttccttgtac acagtaagct     180
ctgccctgtg ataacttccc tctggcactt tggccctctg gagccgtata ctgaacaaat     240
tttgtctttt tccatataaa atgtctctac tttttgagac caacattttc ctccttcacc     300
ctaccccacc tcactgtatt tcttctctt aagaacccctt gactgtctaa tgtgttcctt     360
ctagaatgtg atttctagtc ttttagtac tggcccttta ctctgcttgt tttcagtttt     420
gtggattttt cttgaaatgt aatgcaaaaa attgaatgca gtaaattgtt taagcgtttt     480
ttcttttttg atggctttaa gtcagaaaaa gcaaatgtt tgaagtttat ggagtagata     540
tcygtacaat atattaatat atttacgtat aaaagggaat gatacaagaa tcccaaacta     600
tttttgtttc tagratcaag atttattcaa ttattctaac tcataatctc tgatctaatg     660
tagttttta aatctgtaat gtatgattac acaatatat acatttgtca aaagtcatca     720
atatgtacac attacaatgt gtgagttaca atgtatgtga attataccca ataaaattga     780
tttaaaaaac aaactaaaca tgtataaagt tcttctcatt caagacaagt acgtttccct     840
```

```
cctagtggga tagacacatg aaaggaaagt taggggtttg tggccatgta acagttacat    900
atccgattag gttacgtaag cagctcctaa cccctaatct aaggaggttc gtacaggaag    960
actttggcca tagccatagc tctatacaaa tgtcctttt ataataatct gtaaggacat    1020
gagacggaat gctattaggc aaaagctcaa aggagaacct ctgattacta tccccagggt    1080
gactgagttc tcgtgaccac atggtcaagg attcacagaa gctccattta ggcaccaaat    1140
gacttgggaa cataaccaga gtgaccacac atcctctcgt tatcatcaca tggtcatggt    1200
agtatctggg ccaattaacc gtgtgtttct ggagcacttt ctatgcgcat agtactgtgc    1260
taagctccgt gaaraacaga aatcrtata aaaagaacct ataggatggt cgcggtagct    1320
gcacagcatc gtggatgcgt ttaatgtact gaactgtata tttaaaactg ttaaaagttc    1380
aagttttatt ttgtgcgtat ttttaccaca atcaaaaaga accttcaagg cccttgggag    1440
atccaggtgt ggtccagtag atgtgaataa attcctatct actaagcacc ctgcrtcgtc    1500
tttcctctgc crttattgct caagtgcccc cttctcttcc tgtgactgtg aagccagcct    1560
tatttctagt caaggggatg taaagaactg tgggccagtc gcttaatagc atggcaccct    1620
tggtgctggt ccagttttgt ctctcctttt gccttattcc ytatggcttt tataatctat    1680
tttactctgg atgcataaaa actgggttgt gatggattag atcagattcc tccatttatt    1740
acctatgtga ccttcggggt attgtgttga cagcaatgag ctttgtaaaa ttaatcagaa    1800
gactcaatga gatagtgyct attacttccc acccccttct cttctactga ccccaactgc    1860
atttctgctt ttgtccctcy ctcatttgat tccctctgtg gctccttgct tagaattctg    1920
cttttgccac catcattatg tttaaacatt ttagtacgta gttcctgact ccctctttta    1980
ttgctggatc tcttgctgtc aacattttac ttacctactc tgtttaccgc ctactctagg    2040
ccaatataat ycttactgtg cctgtatgtc atagtgtttg taagcttgtt tctgggcttt    2100
tctgtgtata taagtgcatg tgattaagga gtatrgatta cttacctttg gagttcagaa    2160
ccaggatagc tcagtgttat ctgggatggt caagctgtaa gactagagct gctattgaaa    2220
gtagcctgga agttagagag tcagaaataa aggaaaatac ctagagttct gatgttagct    2280
tcttcaaaga aacctgtagc tttccaagca cattaataaa actacacagc cactagcaag    2340
actctccgtg ggagagcatg tattatggct ccagaaggat ttgggggtgg gtttgttgaa    2400
tgcattattg ttgcttgatg cagagaatgc tgggcctaca agtgtccacc acaagctttc    2460
aagggaaaaa cttcttcatt agtttttgact tcagatgccc aaactgcatt ataattgaac    2520
aagtattaac ttagtaagtc aaattttctt caaaatctta ggtgctccta taactgctca    2580
ttaagattca cttattttt tcacgcaggt aaggggacct aattcagtgt ttcttaaaat    2640
gaaattcata gacatattct tagagtcttt gaaaattctt tttctttaaa aaggaaagtt    2700
tttatagtac tctagtttga gaaacactac ggtgtccctc ataaatggtt tagytcattg    2760
ttaaagggat gctgagaaca tatgaggt gccaaagtat aaaatgtcag gaagggagtt    2820
tgaaggttgt caaatgttgg aggcccaggg aggtgaaagc aaacataagc acatcggaag    2880
caaaaagggg aggttggtgg atagaggtga gaaggctgct gagccaccat tgctgtcagc    2940
ttggtttcct atactggggt aagtttgtgt atgtgtggtt tggcccagca taaagagcca    3000
aagacatagc ggacaagtgg tgaccagatt cagctctgaa tggattctag tttggcaatc    3060
tctggggagt gattaacaac tttgacacca gtttgctgcc taacagtaat tgctgtgtca    3120
ttgagtcctt cttactcaag aagcagaatt tgaagatatg ggcaaagttt gggattcaaa    3180
```

```
ccaagcaaaa tagggaagga gcaggcagat ctgtacaatg agggacgact tttgatccka    3240
gggtagaggc tggtcttccc tctgccttgt ctccaggccc gtgtttaagc aagcgccctg    3300
atgtcagtga atgaatcctt acaggtgtgg gctactcccc atggtgagac aggcctcatc    3360
aggttctggg attgcggtga tggggagcat tgcagttcaa ataaccactg agctcaggct    3420
tcatttggcc ctgtgatcct ttctccaatt attctaaagg atctttatga aaaataata     3480
aagtaaaatt tttaaatttc actkaaaaaa actcatagag ctgcaatatg caaccttttt    3540
aggaaggagc attaaaaaat atttccctga ggcctcgaga ttacacttgg ggtacagaaa    3600
tggcaataat tatggcagat tccaccatct tgacggaaca attttggggc tgagagaaag    3660
acagttggct atttttccctc tacgcctsaa ctygtcaaga tacggaggtt gatgatcgag    3720
ttttacatct gtgatttatc tggtagcata gacttgatgc aagaacrgaa agtgttgggg    3780
atgtcccaaa tagaaacaag gatagggtat cagaaatcct gacaagtggc acttatgctt    3840
ctgtggttg ggaaggaga gctaacatta aagaaktttt attgtctgag gaaaataaaa      3900
actgagtrca tgaatgctag gagagatcta atgttttagt gccctagaat tttcaagcwm    3960
ttataggaaa aagtttaata ttttttttgat agcaaagaat gatgagagtt aagctttctt   4020
tggaagatca gcmtgacttt ttctatttt cccctcatat tctacagaca ctatctcatt    4080
ttatcctcac ttcaactctg tgaggtatga gtatcattat cctcacttgg cagacgagag   4140
tactgacata tagrgagctt gagtagttta tccaagggca cacagtgctc gtgctgggat   4200
ctgaacacag gacatccaac caaaggttgt gcccttaatc ctatcatata tatatactyg   4260
tggtttgttt ttttctttgc ttaggaagat tcrccctgag ctaacttctg ttgccaacct   4320
tcctcttttt gcttgaggaa gattcgccct gagctaacat ctgtgccagt cttcctytgt   4380
tttgtatgtg ggtcaccacc acagtatggc tgccaaagag tggygtaggt ctgcacccag   4440
gaaccaaacc agggccgcca agcrgagca tgccgaacaa ccatgaaggc catgaggctg     4500
gccctgctag tggcttttaa agtktgagaa tcatggactt gtagtatcag caccacctgg   4560
gaactcatta gaaatgca                                                  4578

<210> SEQ ID NO 5
<211> LENGTH: 1957
<212> TYPE: DNA
<213> ORGANISM: Equus caballus

<400> SEQUENCE: 5
gaaatcaccg aaaccggcct ccagcgcccc ggccggaggt ttttctgtat gagtggagaa      60
gacagttgtt acaagtagaa gtgacacaac attttttag gatgtctgaa gatgaagaaa     120
aagtgaaatt acgccgtctt gagccagcta tccagaaatt cattaagata gtaatcccaa    180
cagacctgga gaggttaaga aagcaccaga taaatattga gaagtatcaa aggtgcagaa    240
tctgggataa gttacatgaa gaacatatca atgcaggacg tacagttcag caactccgct    300
ccaatattcg agaaatggag aaactttgtt tgaaagtccg aaaggatgat gtaggacttc    360
taaagagaat gatagatcct gttaaagaag aagcatcagt agcaacagca gaatttctcc    420
agctccatct ggaatctgta gaagaactta agaaacagtt taatgatgaa gaaactttgt    480
tacagccttc tctgaccaga tccatgactg ttggtggagc ttttcacact gctgaagctg    540
aaaccgatcc tcagagtgtg actcagatat acgcattgcc tgaaatccct cgagatcaaa    600
atgctgccga atcctgggaa accttagaag cggacttaat cgaacttagc caactggtca    660
ctgatttctc tctcctagta aattcccagc aggagaagat tgacagcatt gaagaccatg    720
```

```
tcaacactgc tgctgtgaat gttgaagtgg gaaccaaaaa cttggggaag gctgcaaaat      780
acaagctggc agctctgcct gtggcaggtg cactcatcgg aggagcggta gggggtccga      840
ttggcctcct tgcaggcttc aaagtggcag gaattgcagc tgcacttggt ggtgggtgt       900 tgggcttcac aggtggaaaa ttgatacaaa gaaaaaaaca gaaaatgatg gagaagctcg      960
cttccagctg tccagatctt cccagccaaa gtgacaaaaa atgcagttaa aaaccaaact     1020
ttagtattat tggtgccaac atgtctatcc taatgaggac ctttctgct gttgacact       1080 cagtcagctt ttgaacatg attatatcaa atagtggct gtagatgctc cagtgggact      1140
gaactgtgat gagcgggtat atttcgttgt ttactgggtt tttaatggag atgttagaga    1200
tcaaggagcc tgggctgagg gtgtataatg gttgtcaggt aaagtttaaa gagtgccagg    1260
gagcagattt tctacctgga aatatgaaaa ctgaacccat aactttgata aggtcttgag    1320
atgtgtggac atgttgggtt acagaagaat agtttcttcc ataaccttga cttggaaacc    1380
ctagggctaa gcatattgca aatatgctta tttgtctcct aaatatggga gattatttag    1440
gcctgttagc aaggaaagaa tgggagttca ggagcctatc ttgtcaaata gggagatcag    1500
gatccagcga gatcctggtg agctacataa cacagtccat ttggtgaacc ctattacagt    1560
ttggtccaac tgtacttctg gtgaaggaaa ctaataatgt aagaaatgg aaagagaggc     1620 ccagcttctc tttcagatat cttaatttgt gatactggct tcttctctga actcttcctt    1680
ctgcctctct ttaaataaag aacactgaat ctcaaatggt aggagactta ttagcccagt    1740
cactaagctt gctctgtcag cctgtatctt aagacctcaa agatccagtg ccctgtgtct    1800 ttcctcccttt gtaattttga aaaggtctta gacttgtagg gtgaattta cccatgtgta    1860 atgaggactt ttctcataat ctcctttttt gtactgtctc ccatctctgt tcacccttc     1920 ctgtagcccc taggtggaaa aaaaaaaaaa aaaaaaa                             1957
```

<210> SEQ ID NO 6
<211> LENGTH: 2271
<212> TYPE: DNA
<213> ORGANISM: Equus caballus
<220> FEATURE:
<221> NAME/KEY: misc_feature
<222> LOCATION: 920
<223> OTHER INFORMATION: n = A,T,C or G

<400> SEQUENCE: 6

```
catgacactg ctcatcaaac cacgctgagg cagcatccca catgccacaa ctagaaggac       60
ccacaacaaa gaatatacaa ctatgtaccg gggtgctttg gggagaaaaa ggaaaaaata      120
aaatcttaaa aaaaaaaaaa aatagggtat agtgtacctg tggccagtaa tgagtttctg      180
tcactgaggt gtttgagcag aggttcagta agcgcttgtc agaatgtcgt agtgggcttt      240
cccacatctg agggagaaat cgcactcagc aacctaaaca ttccttctac ccagaggttc      300
catgagtcac aatttctgtt gtgtcagccg caggtgttgc catttgtgt agaatgcttg       360 gttaatatat ttgatctgaa acattttaac ttgtcatgat tttaaaatgt ataaagtgtc      420
cacgtgtgaa acacaggaca gtgaattcat tcaccactcc ctactgcata tcacaagtag     480
aaagatttca tggcagatca aaccatattg tattcttatt cctaaaacag taatttgtat     540
ttatcgtggc atcaagggtg ttttactcct aaggcaaatt tgcctgtttt aaactgaatc    600
ttcaaagaag ataagttagg gaggattttt gctttgatcc tgttttgtt ttttccatc      660 aaacccaaca tgacatgtaa atacttattt ggactttttt tctttctcga aagcagattt   720
```

-continued

| | |
|---|---|
| atttggagaa caatatgctt gtatgtttga atgaagttta gagtaagatg cttttttccta | 780 |
| taaaggtgcc actcttttat tactgaataa ttaagtcacc ttttttttata caagtgaatt | 840 |
| tgtgctttcg acgtggtttg tcagatgctg ttaatgaact gctgttagac tccaaggctg | 900 |
| cggcacacag gccctgattn caggagttaa aatagtgtgc attggctgac tgctgctccg | 960 |
| cagcaggagc gctcactcat aattcctttg catctagtcc cagcaggaga agattgacag | 1020 |
| cattgaagac catgtcaaca ctgctgctgt gaatgttgaa gtgggaacca aaaacttggg | 1080 |
| gaaggctgca aaatacaagc tggcagctct gcctgtggca ggtgcactca tcggaggagc | 1140 |
| ggtagggggt ccgattggcc tccttgcagg cttcaaagtg gcaggaattg cagctgcact | 1200 |
| tggtggtggg gtgttgggct tcacaggtgg aaaattgata caaagaaaaa aacagaaaat | 1260 |
| gatggagaag ctcgcttcca gctgtccaga tcttcccagc caaagtgaca aaaaatgcag | 1320 |
| ttaaaaacca aactttagta ttattggtgc caacatgtct atcctaatga ggaccttttc | 1380 |
| tgctgttgga cactcagtca gcttttggaa catgattata tcaaaatagt ggctgtagat | 1440 |
| gctccagtgg gactgaactg tgatgagcgg gtatatttcg ttgtttactg ggttttttaat | 1500 |
| ggagatgtta gagatcaagg agcctgggct gagggtgtat aatggttgtc aggtaaagtt | 1560 |
| taaagagtgc cagggagcag attttctacc tggaaatatg aaaactgaac ccataacttt | 1620 |
| gataaggtct tgagatgtgt ggacatgttg ggttacagaa gaatagtttc ttccataacc | 1680 |
| ttgacttgga aaccctaggg ctaagcatat tgcaaatatg cttatttgtc tcctaaatat | 1740 |
| gggagattat ttaggcctgt tagcaaggaa agaatgggag ttcaggagcc tatcttgtca | 1800 |
| aatagggaga tcaggatcca gcgagatcct ggtgagctac ataacacagt ccatttggtg | 1860 |
| aaccctatta cagtttggtc caactgtact tctggtgaag gaaactaata atgtaagaaa | 1920 |
| atggaaagag aggcccagct tctctttcag atatcttaat ttgtgatact ggcttcttct | 1980 |
| ctgaactctt ccttctgcct ctctttaaat aaagaacact gaatctcaaa tggtaggaga | 2040 |
| cttattagcc cagtcactaa gcttgctctg tcagcctgta tcttaagacc tcaaagatcc | 2100 |
| agtgccctgt gtctttcctc ccttgtaatt ttgaaaaggt cttagacttg tagggtgaat | 2160 |
| tttacccatg tgtaatgagg acttttctca taatctcctt ttttgtactg tctcccatct | 2220 |
| ctgttcaccc tttcctgtag cccctaggtg gaaaaaaaaa aaaaaaaaa a | 2271 |

<210> SEQ ID NO 7
<211> LENGTH: 302
<212> TYPE: PRT
<213> ORGANISM: Equus caballus

<400> SEQUENCE: 7

Met Ser Glu Asp Glu Glu Lys Val Lys Leu Arg Arg Leu Glu Pro Ala
1               5                   10                  15

Ile Gln Lys Phe Ile Lys Ile Val Ile Pro Thr Asp Leu Glu Arg Leu
            20                  25                  30

Arg Lys His Gln Ile Asn Ile Glu Lys Tyr Gln Arg Cys Arg Ile Trp
        35                  40                  45

Asp Lys Leu His Glu His Ile Asn Ala Gly Arg Thr Val Gln Gln
    50                  55                  60

Leu Arg Ser Asn Ile Arg Glu Met Glu Lys Leu Cys Leu Lys Val Arg
65                  70                  75                  80

Lys Asp Asp Val Gly Leu Leu Lys Arg Met Ile Asp Pro Val Lys Glu
                85                  90                  95

Glu Ala Ser Val Ala Thr Ala Glu Phe Leu Gln Leu His Leu Glu Ser

|     |     |     |     | 100 |     |     |     |     | 105 |     |     |     |     | 110 |
| --- | --- | --- | --- | --- | --- | --- | --- | --- | --- | --- | --- | --- | --- | --- |

Val Glu Glu Leu Lys Lys Gln Phe Asn Asp Glu Glu Thr Leu Leu Gln
            115                      120                      125

Pro Ser Leu Thr Arg Ser Met Thr Val Gly Gly Ala Phe His Thr Ala
130                      135                      140

Glu Ala Glu Thr Asp Pro Gln Ser Val Thr Gln Ile Tyr Ala Leu Pro
145                      150                      155                      160

Glu Ile Pro Arg Asp Gln Asn Ala Ala Glu Ser Trp Glu Thr Leu Glu
                  165                      170                      175

Ala Asp Leu Ile Glu Leu Ser Gln Leu Val Thr Asp Phe Ser Leu Leu
                  180                      185                      190

Val Asn Ser Gln Gln Glu Lys Ile Asp Ser Ile Glu Asp His Val Asn
                  195                      200                      205

Thr Ala Ala Val Asn Val Glu Val Gly Thr Lys Asn Leu Gly Lys Ala
210                      215                      220

Ala Lys Tyr Lys Leu Ala Ala Leu Pro Val Ala Gly Ala Leu Ile Gly
225                      230                      235                      240

Gly Ala Val Gly Gly Pro Ile Gly Leu Leu Ala Gly Phe Lys Val Ala
                  245                      250                      255

Gly Ile Ala Ala Ala Leu Gly Gly Gly Val Leu Gly Phe Thr Gly Gly
                  260                      265                      270

Lys Leu Ile Gln Arg Lys Lys Gln Lys Met Met Glu Lys Leu Ala Ser
                  275                      280                      285

Ser Cys Pro Asp Leu Pro Ser Gln Ser Asp Lys Lys Cys Ser
290                      295                      300

<210> SEQ ID NO 8
<211> LENGTH: 2207
<212> TYPE: DNA
<213> ORGANISM: Equus caballus

<400> SEQUENCE: 8

```
atatgccctg cgtgcaagcc cagtatagcc cttcgcctcc aggttccagt tatgcagcgc      60
agacctacgg ctcagcggaa tacaccaccg agatcatgaa ccccgactac accaagctga     120
ccatggacct cggcagcacc gagatcacgg ccacggccac acgtccctg cccagcttca     180
gtaccttcat ggagggctac tcgagcaact acgaactcaa gccctcctgc ctgtaccaaa     240
tgccgccatc ggggccgcgg cccttgatca agatggagga gggccgcgcg cacggctacc     300
accatcacca ccatcaccac caccaccacc accatcacca gcagcagcag cagcagccat     360
ccattccgcc ccctccggc ccggaggacg aggtgctgcc cagcacctcc atgtacttca     420
agcagtcccc gccgtccacc ccgaccacgc cgggcttccc ccgcaggcg ggggcgctgt     480
gggacgacgc gctgccctcc gcgcagggct gcctcgcgcc cggcccgctg ctcgacccgc     540
cgatgaaggc ggtgcccacg gtggccggcg cgcgcttccc gctcttccac ttcaagacct     600
cgccgccgca cccgcctgcg cccagcccgg ccggcggcca ccacctggcc tacgacccga     660
cggccgccgc cgcgctcagc ctgccgcttg agccgccgc cgccgcgggc agccaggccg     720
ccgcgctcga gggccactcg tacgggctgc cgctgcccaa gagggcggcc gcgctggcct     780
tctcgccgct cggcctcacc gcctccccca ccgcgtccag cctgctggcc gagagcccca     840
gcctgccgtc gccgcccaac aggagtttgt cgtcgggcga gggaacgtgc gccgtgtgcg     900
gggacaacgc cgcctgccag cactacgcgc tgcgaacctg cgagggctgc aagggctttt     960
tcaagagaac ggtgcagaaa aatgcaaaat atgtttgcct ggcaaataaa aactgccctg    1020
```

```
tagacaagag acgtcgaaac cgatgtcagt actgtcgatt cagaagtgt  ctcagtgtcg    1080 gaatggttaa agaagttgtc cgtacagata gtctgaaagg gaggagaggt cggctgcctt    1140
ccaaaccaaa gagcccgtta cagcaggaac cttctcagcc ctctccaccg tctcctccga    1200
tctgcatgat gaatgccctt gtccgagctt aacagactc  aacgcccaga gatctcgatt    1260
attccagata ctgccccact gaccaggccg ctgccggcac agatgctgag catgtgcaac    1320
agttctacaa ccttctgaca gcctccattg atgtatccag aagctgggca gaaaagattc    1380
ccggatttac tgatctcccc aagaagatc  agacattact tatagaatca gccttttttgg   1440 agctgtttgt tctcagactt tccatcaggt cgaacactgc tgaagataag tttgtgttct    1500
gcaatggact tgtcctgcat cgacttcagt gccttcgtgg atttggggag tggctcgact    1560
ccattaaaga cttttcctta agtttgcaga gcctgaacct ggatatccaa gccttagcat    1620
gcctgtcagc actgagcatg atcacagaac gacatgggtt aaaagaacca agagagtgg    1680 aggagctatg caacaagatc acaagcagct taaaagacca ccagagcaag ggcaggctt    1740 tggagcccac ggagcccaag gtcctgcgcg ccctggtaga actgcggaag atatgcaccc    1800
tgggcctcca gcgcatcttc tacctgaagc tggaagactt ggtgtctcca ccttccatca    1860
tcgacaagct cttcctggac accctgcctt tctgagcagg agcagcctca tctgctagca    1920
cctgcttgct aagcagcaga gggatgggtc tggacaccta ccattttctg tccttcctta    1980
agagaaaaag cagctcctgt agaaaagaaa gactttttt  tttttctgg cacttttcct     2040 tacaagctaa agccagaaaa cttgcagagt attgtgttgg ggttgtgttt tatatttagg    2100
ctttggggtt ggggtgggag gtgggtatag ttcatgaggg ttttctaaga aattgctaac    2160
agagcacttt tggacgatgc tatcccagca ggaaaaaaaa aaaaaaa                  2207
```

<210> SEQ ID NO 9
<211> LENGTH: 630
<212> TYPE: PRT
<213> ORGANISM: Equus caballus

<400> SEQUENCE: 9

```
Met Pro Cys Val Gln Ala Gln Tyr Ser Pro Ser Pro Gly Ser Ser
  1               5                  10                  15

Tyr Ala Ala Gln Thr Tyr Gly Ser Ala Glu Tyr Thr Thr Glu Ile Met
             20                  25                  30

Asn Pro Asp Tyr Thr Lys Leu Thr Met Asp Leu Gly Ser Thr Glu Ile
             35                  40                  45

Thr Ala Thr Ala Thr Thr Ser Leu Pro Ser Phe Ser Thr Phe Met Glu
     50                  55                  60

Gly Tyr Ser Ser Asn Tyr Glu Leu Lys Pro Ser Cys Leu Tyr Gln Met
 65                  70                  75                  80

Pro Pro Ser Gly Pro Arg Pro Leu Ile Lys Met Glu Glu Gly Arg Ala
                 85                  90                  95

His Gly Tyr His His His His His His His His His His His His His
                100                 105                 110

Gln Gln Gln Gln Gln Gln Pro Ser Ile Pro Pro Ser Gly Pro Glu
            115                 120                 125

Asp Glu Val Leu Pro Ser Thr Ser Met Tyr Phe Lys Gln Ser Pro Pro
        130                 135                 140

Ser Thr Pro Thr Thr Pro Gly Phe Pro Pro Gln Ala Gly Ala Leu Trp
145                 150                 155                 160
```

```
Asp Asp Ala Leu Pro Ser Ala Gln Gly Cys Leu Ala Pro Gly Pro Leu
            165                 170                 175

Leu Asp Pro Pro Met Lys Ala Val Pro Thr Val Ala Gly Ala Arg Phe
        180                 185                 190

Pro Leu Phe His Phe Lys Thr Ser Pro Pro His Pro Pro Ala Pro Ser
            195                 200                 205

Pro Ala Gly Gly His His Leu Ala Tyr Asp Pro Thr Ala Ala Ala Ala
    210                 215                 220

Leu Ser Leu Pro Leu Gly Ala Ala Ala Ala Gly Ser Gln Ala Ala
225                 230                 235                 240

Ala Leu Glu Gly His Ser Tyr Gly Leu Pro Leu Pro Lys Arg Ala Ala
                245                 250                 255

Ala Leu Ala Phe Ser Pro Leu Gly Leu Thr Ala Ser Pro Thr Ala Ser
            260                 265                 270

Ser Leu Leu Ala Glu Ser Pro Ser Leu Pro Ser Pro Asn Arg Ser
        275                 280                 285

Leu Ser Ser Gly Glu Gly Thr Cys Ala Val Cys Gly Asp Asn Ala Ala
    290                 295                 300

Cys Gln His Tyr Gly Val Arg Thr Cys Glu Gly Cys Lys Gly Phe Phe
305                 310                 315                 320

Lys Arg Thr Val Gln Lys Asn Ala Lys Tyr Val Cys Leu Ala Asn Lys
                325                 330                 335

Asn Cys Pro Val Asp Lys Arg Arg Arg Asn Arg Cys Gln Tyr Cys Arg
            340                 345                 350

Phe Gln Lys Cys Leu Ser Val Gly Met Val Lys Glu Val Val Arg Thr
        355                 360                 365

Asp Ser Leu Lys Gly Arg Arg Gly Arg Leu Pro Ser Lys Pro Lys Ser
    370                 375                 380

Pro Leu Gln Gln Glu Pro Ser Gln Pro Ser Pro Pro Ser Pro Pro Ile
385                 390                 395                 400

Cys Met Met Asn Ala Leu Val Arg Ala Leu Thr Asp Ser Thr Pro Arg
                405                 410                 415

Asp Leu Asp Tyr Ser Arg Tyr Cys Pro Thr Asp Gln Ala Ala Ala Gly
            420                 425                 430

Thr Asp Ala Glu His Val Gln Gln Phe Tyr Asn Leu Leu Thr Ala Ser
        435                 440                 445

Ile Asp Val Ser Arg Ser Trp Ala Glu Lys Ile Pro Gly Phe Thr Asp
    450                 455                 460

Leu Pro Lys Glu Asp Gln Thr Leu Leu Ile Glu Ser Ala Phe Leu Glu
465                 470                 475                 480

Leu Phe Val Leu Arg Leu Ser Ile Arg Ser Asn Thr Ala Glu Asp Lys
                485                 490                 495

Phe Val Phe Cys Asn Gly Leu Val Leu His Arg Leu Gln Cys Leu Arg
            500                 505                 510

Gly Phe Gly Glu Trp Leu Asp Ser Ile Lys Asp Phe Ser Leu Ser Leu
        515                 520                 525

Gln Ser Leu Asn Leu Asp Ile Gln Ala Leu Ala Cys Leu Ser Ala Leu
    530                 535                 540

Ser Met Ile Thr Glu Arg His Gly Leu Lys Glu Pro Lys Arg Val Glu
545                 550                 555                 560

Glu Leu Cys Asn Lys Ile Thr Ser Ser Leu Lys Asp His Gln Ser Lys
                565                 570                 575

Gly Gln Ala Leu Glu Pro Thr Glu Pro Lys Val Leu Arg Ala Leu Val
```

```
                580             585             590
        Glu Leu Arg Lys Ile Cys Thr Leu Gly Leu Gln Arg Ile Phe Tyr Leu
                    595             600             605

Lys Leu Glu Asp Leu Val Ser Pro Pro Ser Ile Ile Asp Lys Leu Phe
                610             615             620

Leu Asp Thr Leu Pro Phe
        625             630

<210> SEQ ID NO 10
<211> LENGTH: 2678
<212> TYPE: DNA
<213> ORGANISM: Homo Sapiens

<400> SEQUENCE: 10
```

| | | | | | |
|---|---|---|---|---|---|
| ggcctcgagc | gccccggcgg | gaggttttc | tatatgagtg | gagaagacag | ctgttaccag | 60 |
| ggaggtcata | caacattttt | ttaggatgtc | tgaagatgaa | gaaaaagtga | aattacgccg | 120 |
| tcttgaacca | gctatccaga | aattcattaa | gatagtaatc | ccaacaaacc | tggaaaggtt | 180 |
| aagaaagcac | cagataaata | ttgagaagta | tcaaaggtgc | agaatctggg | acaagttgca | 240 |
| tgaagagcat | atcaatgcag | gacgtacagt | tcagcaactc | cgatccaata | tccgagaaat | 300 |
| tgagaaactt | tgtttgaaag | tccgaaagga | tgacctagta | cttctgaaga | gaatgataga | 360 |
| tcctgttaaa | gaagaagcat | cagcagcaac | agcagaattt | ctccaactcc | atttggaatc | 420 |
| tgtagaagaa | cttaagaagc | aatttaatga | tgaagaaact | ttgctacagc | ctcctttgac | 480 |
| cagatccatg | actgttggtg | gagcatttca | tactactgaa | gctgaagcta | gttctcagag | 540 |
| tttgactcag | atatatgcct | tacctgaaat | tcctcaagat | caaaatgctg | cagaatcgcg | 600 |
| ggaaacctta | gaagcggact | taattgaact | tagccaactg | gtcactgact | tctctctcct | 660 |
| agtgaactct | cagcaggaga | agattgacag | cattgcagac | catgtcaaca | gtgctgctgt | 720 |
| gaatgttgaa | gagggaacca | aaaacttagg | gaaggctgca | aaatacaagc | tggcagctct | 780 |
| gcctgtggca | ggtgcactca | tcgggggaat | ggtaggggt | cctattggcc | tccttgcatg | 840 |
| cttcaaagtg | gcaggaattg | cagctgcact | tggtggtggg | gtgttgggct | tcacaggtgg | 900 |
| aaaaattgata | caaagaaaga | aacagaaaat | gatggagaag | ctcacttcca | gctgtccaga | 960 |
| tcttcccagc | caaactgaca | agaaatgcag | ttaaaaacca | aatttcagta | ttattggtgc | 1020 |
| caacatgtct | atcctgagga | cctttgctgc | tgttggacac | tccgtcacct | tttgaacac | 1080 |
| aagtatatca | agatagtggc | tactgatgtt | caagtgggat | tgaagtgtga | taaatggata | 1140 |
| tatttgttg | tttgctgggg | tgttcatgga | gatgttaaga | gattgaggcc | ctgggctgag | 1200 |
| ggtatataat | gtatgtcagg | taaagtttga | agactgccaa | ggagcagatt | ttctcccgg | 1260 |
| aaatgtgaaa | actgaaccta | taactctgat | aaggacttga | gatgtgtaga | aacgttgggt | 1320 |
| tatggaagac | tagtttcttc | cataaccctg | aattggagac | cttaatgcta | agtgtagatt | 1380 |
| attgaggttt | gttagtgagg | aaaagaataa | gagttcagaa | gcctttgtta | tcagatagcg | 1440 |
| aaatcagggc | ctagtgagga | gcacaggtcg | actacataat | ggagtccatt | ggcgaaccct | 1500 |
| attgcaattt | ggtccaacta | tatcttctgg | tgaaggaaat | taatgatgta | agaaaatgca | 1560 |
| agaggctcaa | cttctcttcc | aaaaatcttc | tggcttctga | actcttcctc | tgcctctctt | 1620 |
| taaataaata | acacagaatt | tcaagtggta | ggagacttat | taagccagtc | accaagcttg | 1680 |
| gtctgtcagc | ctgtcttcta | acacctcaaa | gatcttgtgc | cctgtgctgt | ccctcccttg | 1740 |
| taattatgaa | aagttctttg | gtttctgggg | tgaactctac | ccatgtataa | tgaggaattc | 1800 |

```
tctcataacc ttttttgtct tgtctgtcat ctctgttcat cccctcctat aacctctagg    1860
taaaaagaaa agaaaaaaag aaatttcgag atattttcaa cattgttaga gtttgggcta    1920
aaatgagcaa ggagaaaaaa accaccaaga acatttcctg gggcatgttc cagttttgag    1980
gggtgatata tctgccagat agggggtatc tgacccagtc ttcttttcag ctggtctctg    2040
gggggagctg agaactcgct tgctacctca catccttttc cccagacttt ttatctccta    2100
tgcatccctt tgcttctat agctggtgtt cttccccaa aatggcgttc ccatgcttac    2160
ctttctcaca ttctagacaa tgatggacaa agacgcatgc aagactcaga cccggggaat    2220
ggtgtggtgc taatctcaac acctgacatt cacagcaagc atgcccagc ccaaccgcat    2280 gtctatctca aaccgcagaa aggctttaat actggaaaaa aagaattcaa gactacaggc    2340
agctcccctc tgtaccccaa ctcatttaaa ataggaggaa tcacttttg ccttacttaa    2400 cgctttttc tgagcacagg gatgggcacc tgcacccag aaggtgtgag ctgtctctct    2460
gccaggagct aaggttcatt aggggattgg atggtttatc acttcttct ttctgagttt    2520 acttttagta acttttattg atggctacct ttcatgtccc tgtctaaaga acttctctct    2580
ttcatacgtc ttaaatctca tcaatgaaat ccagtgaaac agcaccattt cttagtatca    2640
ttaaataact agaaagtatc aaaaaaaaaa aaaaaaa                             2678

<210> SEQ ID NO 11
<211> LENGTH: 2940
<212> TYPE: DNA
<213> ORGANISM: Homo sapiens

<400> SEQUENCE: 11
tcatactata ccattaaaag cagtacttgt tatatgtaaa ttctatctaa ataaagttga      60
attaaaaatg ggaatgtgtt cctacagcaa gtaatgagtt cgtgtcactg gaggtatctg    120
agcagaggtt cagtaaccac ttgtcaggaa tgttacagta gggcttcgca catcagagag    180
gagattgacc tgatgacctc aacattcctt ctacccagag attccatgag tcacagttgc    240
tgttgtgcca gcacaggtgt tgccatttta tgtagaatgc tttattaata tatttgatct    300
gaaacatttt aaactgtcat gattttaaaa tgtattaaga tacacaggtg taaagcacag    360
aacagtgatt tcattcactg ttccctactg catattacaa atggaaagat ctcataatag    420
atcaaaccgt attgtagtct tgttcctgaa acataacaat ttgtatttat tggaccaagg    480
gcattttact cctaaggtaa atgtgcctga tttaaactga atcctcaaag aaggtaagtt    540
agggaggtat tttgggggttt gattttgttg ggttttttt ttccatcaaa cccaacatga    600
catgtaaatg cttatttgga ttttttttt ctggaaagta gattcatttg gagaataata    660
tgtttgtatg tttgagtgaa ttttagcgtg agatgctttt tgctgtaaag ttgccaccct    720
tttattacct aataattaag acccccccct ttttttatg aaagttaatt tgtcctttcg    780
acatggctta tcagatgcta ttaatgaacc actattaaga tggcaaggct gcagtaccca    840
gggccctgat tacaggaatt aaaatagtgt gtgttggctc cctgctgctc cccagcagga    900
ccgctcactc ataattcctt tgcatctagt ctcagcagga aagattgac agcattgcag    960 accatgtcaa cagtgctgct gtgaatgttg aagaggaac caaaaactta gggaaggctg   1020
caaaatacaa gctggcagct ctgcctgtgg caggtgcact catcggggga atggtagggg   1080
gtcctattgg cctccttgca ggcttcaaag tggcaggaat tgcagctgca cttggtggtg   1140
gggtgttggg cttcacaggt ggaaaattga tacaaagaaa gaaacagaaa atgatggaga   1200
agctcacttc cagctgtcca gatcttccca gccaaactga caagaaatgc agttaaaaac   1260
```

-continued

```
caaatttcag tattattggt gccaacatgt ctatcctgag gacctttgct gctgttggac   1320
actccgtcac cttttggaac acaagtatat caagatagtg gctactgatg ttcaagtggg   1380
attgaagtgt gataaatgga tatattttgt tgtttgctgg ggtgttcatg agatgttaa    1440
gagattgagg ccctgggctg agggtatata atgtatgtca ggtaaagttt gaagactgcc   1500
aaggagcaga ttttctccct ggaaatgtga aaactgaacc tataactctg ataaggactt   1560
gagatgtgta gaaacgttgg gttatggaag actagtttct tccataaccc tgaattggag   1620
accttaatgc taagtgtaga ttattgaggt ttgttagtga ggaaaagaat aagagttcag   1680
aagcctttgt tatcagatag cgaaatcagg gcctagtgag gagcacaggt cgactacata   1740
atggagtcca ttggcgaacc ctattgcaat ttggtccaac tatatcttct ggtgaaggaa   1800
attaatgatg taagaaaatg caagaggctc aacttctctt ccaaaaatct tctggcttct   1860
gaactcttcc tctgcctctc tttaaataaa taacacagaa tttcaagtgg taggagactt   1920
attaagccag tcaccaagct tggtctgtca gcctgtcttc taacacctca agatcttgt    1980
gccctgtgct gtccctccct tgtaattatg aaaagttctt tggtttctgg ggtgaactct   2040
acccatgtat aatgaggaat tctctcataa cctttttgt cttgtctgtc atctctgttc    2100
atcccctcct ataacctcta ggtaaaaaga aagaaaaaa agaaatttcg agatattttc    2160
aacattgtta gagtttgggc taaaatgagc aaggagaaaa aaaccaccaa gaacatttcc   2220
tggggcatgt tccagttttg aggggtgata tatctgccag atagggggta tctgacccag   2280
tcttcttttc agctggtctc tgggggagc tgagaactcg cttgctacct cacatccttt    2340
tccccagact ttttatctcc tatgcatccc tttgctttct atagctggtg tttcttcccc   2400
aaaatggcgt tccatgctt acctttctca cattctagac aatgatggac aaagacgcat    2460
gcaagactca gacccgggga atggtgtggt gctaatctca acacctgaca ttcacagcaa   2520
gcatggccca gcccaaccgc atgtctatct caaaccgcag aaaggcttta atactggaaa   2580
aaaagaattc aagactacag gcagctcccc tctgtacccc aactcattta aaataggagg   2640
aatcactttt tgccttactt aacgcttttt tctgagcaca gggatgggca cctgcacccc   2700
agaaggtgtg agctgtctct ctgccaggag ctaaggttca ttaggggatt ggatggttta   2760
tcacttcttt ctttctgagt ttactttag taacttttat tgatggctac ctttcatgtc    2820
cctgtctaaa gagactttct ctttcatacg tcttaaatct catcaatgaa atccagtgaa   2880
acagcaccat ttcttagtat cattaaataa ctagaaagta tcaaaaaaaa aaaaaaaaa    2940
```

<210> SEQ ID NO 12
<211> LENGTH: 302
<212> TYPE: PRT
<213> ORGANISM: Homo sapiens

<400> SEQUENCE: 12

```
Met Ser Glu Asp Glu Glu Lys Val Lys Leu Arg Arg Leu Glu Pro Ala
  1               5                  10                  15

Ile Gln Lys Phe Ile Lys Ile Val Ile Pro Thr Asn Leu Glu Arg Leu
             20                  25                  30

Arg Lys His Gln Ile Asn Ile Glu Lys Tyr Gln Arg Cys Arg Ile Trp
         35                  40                  45

Asp Lys Leu His Glu Glu His Ile Asn Ala Gly Arg Thr Val Gln Gln
     50                  55                  60

Leu Arg Ser Asn Ile Arg Glu Ile Glu Lys Leu Cys Leu Lys Val Arg
 65                  70                  75                  80
```

```
Lys Asp Asp Leu Val Leu Leu Lys Arg Met Ile Asp Pro Val Lys Glu
                 85                  90                  95
Glu Ala Ser Ala Ala Thr Ala Glu Phe Leu Gln Leu His Leu Glu Ser
            100                 105                 110
Val Glu Glu Leu Lys Lys Gln Phe Asn Asp Glu Thr Leu Leu Gln
        115                 120                 125
Pro Pro Leu Thr Arg Ser Met Thr Val Gly Gly Ala Phe His Thr Thr
130                 135                 140
Glu Ala Glu Ala Ser Ser Gln Ser Leu Thr Gln Ile Tyr Ala Leu Pro
145                 150                 155                 160
Glu Ile Pro Gln Asp Gln Asn Ala Ala Glu Ser Arg Glu Thr Leu Glu
                165                 170                 175
Ala Asp Leu Ile Glu Leu Ser Gln Leu Val Thr Asp Phe Ser Leu Leu
            180                 185                 190
Val Asn Ser Gln Gln Glu Lys Ile Asp Ser Ile Ala Asp His Val Asn
        195                 200                 205
Ser Ala Ala Val Asn Val Glu Glu Gly Thr Lys Asn Leu Gly Lys Ala
210                 215                 220
Ala Lys Tyr Lys Leu Ala Ala Leu Pro Val Ala Gly Ala Leu Ile Gly
225                 230                 235                 240
Gly Met Val Gly Gly Pro Ile Gly Leu Leu Ala Cys Phe Lys Val Ala
                245                 250                 255
Gly Ile Ala Ala Ala Leu Gly Gly Gly Val Leu Gly Phe Thr Gly Gly
            260                 265                 270
Lys Leu Ile Gln Arg Lys Lys Gln Lys Met Met Glu Lys Leu Thr Ser
        275                 280                 285
Ser Cys Pro Asp Leu Pro Ser Gln Thr Asp Lys Lys Cys Ser
290                 295                 300

<210> SEQ ID NO 13
<211> LENGTH: 6382
<212> TYPE: DNA
<213> ORGANISM: Homo sapiens

<400> SEQUENCE: 13
ataaatgacg tgccgagaga gcgagcgaac gcgcagccgg gagagcggag tctcctgcct      60
cccgccccc accctccag ctcctgctcc tcctccgctc cccatacaca gacgcgctca      120
cacccgctcc ctcactcgca cacagaca caagcgcgca cacaggctcc gcacacacac      180
ttcgctctcc cgcgcgctca caccctctt gccctgagcc cttgccggtg cagcgcggcg      240
ccgcagctgg acgcccctcc cgggctcact ttgcaacgct gacggtgccg gcagtggccg      300
tggaggtggg aacagcggcg gcatcctccc ccctggtcac agcccaagcc aggacgcccg      360
cggaacctct cggctgtgct ctcccatgag tcggatcgc agcatccccc accagccgct      420
caccgcctcc gggagccgct gggcttgtac accgcagccc ttccgggaca gcagctgtga      480
ctcccccca gtgcagattt cgggacagct ctctagaaac tcgctctaaa gacggaaccg      540
ccacagcact caaagcccac tgcggaagag ggcagcccgg caagcccggg ccctgagcct      600
ggaccccttag cggtgccggg cagcactgcc ggcgcttcgc ctcgccggac gtccgctcct      660
cctacactct cagcctccgc tggagagacc cccagcccca ccattcagcg cgcaagatag      720
tgtgtatata tatatatatg ggtgggtgtt ttgttgcagc tgctgatctt tttctttgca      780
gatggtacaa actctcccga gtcaatttcc tgggcctatg tccccaccta gctgactgaa      840
```

```
gttatcaaca ggggtccagt tgtgcaggc tgctagccct attggaagag tggggatgag      900
gtgggagaaa gcaaccacaa cgtgtgtggg caacctcaat tggcactcat aaaatgttag      960
aatgtcaact ctctcccttg gccactaaat ctctcacagg gtagtttttc ttgcctaact     1020
caggtttaca aatcaatgtg tatgccttgg gggaccaatg gcctctttcc tcccaaataa     1080
accactggct ttctctttgt cccccctaggt tatagctgag gagcccactc caattagttt     1140
ataggattca aagcctcttt ttaaaaacat ctctgagctt atgaggaaag acttcaagtt     1200
tcccaaatct agtggaggac agggcaaggg aggaaagata ggtacaggag tccacaggag     1260
gccaggtttt ggcaccccctt tgtcaggaat tcagcttcct tactagggat gaagaaaata     1320
agtgtggggc tttgtgtcta tgctaccaga aggaggagag gatgacactt cctctctgtt     1380
tcccagatta gagaacagtg aacccaatgc tgcctgttgg ctagaaaaca agtgttaact     1440
tgcttctgag agacccttttt ctctgtccct gcagatatgc cctgcgtcca agcccaatat     1500
agcccttccc ctccaggttc cagttatgcg gcgcagacat acagtctgga atacaccacg     1560
gagatcatga acccccgacta caccaagctg accatggacc ttggcagcac tgagatcacg     1620
gctacagcca ccacgtccct gcccagcatc agtaccttcg tggagggcta ctcgagcaac     1680
tacgaactca agccttcctg cgtgtaccaa atgcagcggc ccttgatcaa agtggaggag     1740
gggcgggcgc ccagctacca tcaccatcac caccaccacc accaccacca ccaccatcac     1800
cagcagcagc atcagcagcc atccattcct ccagcctcca gcccgaggga cgaggtgctg     1860
cccagcacct ccatgtactt caagcagtcc ccaccgtcca cccccaccac gccggccttc     1920
cccccgcagg cggggggcgtt atgggacgag gcactgccct cggcgccccgg ctgcatcgca     1980
cccggcccgc tgctggaccc gccgatgaag gcggtcccca cggtggccgg cgcgcgcttc     2040
ccgctcttcc acttcaagcc ctcgccgccg catcccccccg cgcccagccc ggccggcggc     2100
caccacctcg gctacgaccc gacggccgct gccgcgctca gcctgccgct gggagccgca     2160
gccgccgcgg gcagccaggc cgccgcgctt gagagccacc cgtacgggct gccgctggcc     2220
aagagggcgg ccccgctggc cttcccgcct ctcggcctca cgccctcccc taccgcgtcc     2280
agcctgctgg gcgagagtcc cagcctgccg tcgccgccca gcaggagctc gtcgtctggc     2340
gagggcacgt gtgccgtgtg cgggggacaac gccgcctgcc agcactacgg cgtgcgaacc     2400
tgcgagggct gcaagggctt tttcaagaga acagtgcaga aaaatgcaaa atatgtttgc     2460
ctggcaaata aaaactgccc agtagacaag agacgtcgaa accgatgtca gtactgtcga     2520
tttcagaagt gtctcagtgt tggaatggta aaagaagttg tccgtacaga tagtctgaaa     2580
gggaggagag gtcgtctgcc ttccaaacca aagagcccat tacaacagga accttctcag     2640
ccctctccac cttctcctcc aatctgcatg atgaatgccc ttgtccgagc tttaacagac     2700
tcaacacccca gagatcttga ttattccaga tactgtccca ctgaccaggc tgctgcaggc     2760
acagatgctg agcatgtgca acaattctac aacctcctga cagcctccat tgatgtatcc     2820
agaagctggg cagaaaagat tccgggattt actgatctcc ccaaagaaga tcagacatta     2880
cttattgaat cagcctttttt ggagctgttt gtcctcagac tttccatcag gtcaaacact     2940
gctgaagata agtttgtgtt ctgcaatgga cttgtcctgc atcgacttca gtgccttcgt     3000
ggatttgggg agtggctcga ctctattaaa gacttttcct taaatttgca gagcctgaac     3060
cttgatatcc aagccttagc ctgcctgtca gcactgagca tgatcacaga aagacatggg     3120
ttaaaagaac caaagagagt cgaagagcta tgcaacaaga tcacaagcag tttaaaagac     3180
caccagagta agggacaggc tctggagccc accgagtcca aggtcctggg tgccctggta     3240
```

```
gaactgagga agatctgcac cctgggcctc cagcgcatct tctacctgaa gctggaagac    3300
ttggtgtctc caccttccat cattgacaag ctcttcctgg acaccctacc tttctaatca    3360
ggagcagtgg agcagtgagc tgcctcctct cctagcacct gcttgctacg cagcaaaggg    3420
ataggtttgg aaacctatca tttcctgtcc ttccttaaga ggaaaagcag ctcctgtaga    3480
aagcaaagac tttctttttt ttctggctct tttccttaca acctaaagcc agaaaacttg    3540
cagagtattg tgttggggtt gtgttttata tttaggcatt gggggatggg gtgggagggg    3600
gttatagttc atgagggttt tctaagaaat tgctaacaaa gcacttttgg acaatgctat    3660
cccagcagga aaaaaagga taatataact gttttaaaac tctttctggg gaatccaatt    3720
atagttgctt tgtatttaaa acaagaaca gccaagggtt gttcgccagg gtaggatgtg    3780
tcttaaagat tggtcccttg aaaatatgct tcctgtatca aggtacgta tgtggtgcaa    3840 acaaggcaga aacttccttt taatttcctt cttcctttat tttaacaaat ggtgaaagat    3900
ggaggattac ctacaaatca gacatggcaa acaataatg gctgtttgct tccataaaca    3960
agtgcaattt tttaaagtgc tgtcttacta agtcttgttt attaactctc ctttattcta    4020
tatgaaaata aaaaggaggc agtcatgtta gcaaatgaca cgttaatatc cctagcagag    4080
gctgtgttca ccttccctgt cgatcccttc tgaggtatgg cccatccaag acttttaggc    4140
cattcttgat ggaaccagat ccctgccctg actgtccagc tatcctgaaa gtggatcaga    4200
ttataaactg gattacatgt aactgttttg gttgtgttct atcaacccca ccagagttcc    4260
ctaaacttgc ttcagttata gtaactgact ggtatattca ttcagaagcg ccataagtca    4320
gttgagtatt tgatccctag ataagaacat gcaaatcagc aggaactggt catacagggt    4380
aagcaccagg gacaataagg attttttatag atataattta attttgtta ttggttaagg    4440 agacaatttt ggagagcaag caaatctttt taaaaaatag tatgaatgtg aatactagaa    4500
aagatttaaa aaatagtatg agtgtgagta ctaggaagga ttagtgggct gcgtttcaac    4560
attccgtgtt cgtactccct tttgtatgtt tctactgtta atgccatatt actatgagat    4620
aatttgttgc atagtgtcct tatttgtata acatttgta tgcacgttat attgtaatag    4680 cttttgcctgt atttattgca agaccaccag ctcctggaag ctgagttaca gagtaattaa    4740
atggggtgtt cacagtgact tggatacacc aattagaaat taaataagca aatatatata    4800
tatatataaa tatagcaggt tacatatata tatttataat gtgtcttttt attaaccatt    4860
tgtacaataa atgtcacttc ccatgccgtt attttatggt tcatttgcag tgacttttaa    4920
ggcagtactg tttagcactt tgatattaaa attttgctta tgttttgcta aattcgaata    4980
atgtttgaag atttttaggt ctaaaagtct ttatattata tactctgtat caagtcaaaa    5040
tatctttggc cattttgcta agaaacaaac tttgaatgtc aaactgatgt cacagtagtt    5100
tttgttagct ttaaatcatt tttgctttag tcttttaaa ggaaaataac aaaactatgc    5160
tgtttatatt gtcattaaat tatacaatca aacaatgcc aaatgaattg cctaattgct    5220
gcaaagtata acccagatag gaaatcatat gttttttcc aagagtcatt ctaatatttg    5280
attatgttat gtgtgctttt atgaaagatt gttatttta tatatcaaga tgatagaacc    5340
tggaatgtta ggattttgaa atgttagact tggaaggggc ctggtctgtc aactagtcca    5400
accccttaaa attcatagag gagcaaactg gggcccattg aagggtgaag agttactcaa    5460
ggtcaaacag ctggtaacag aatcaagact aagacctaat ttacctttcc atactctttt    5520
tttttctcaa cttcatctat ataaaatcag gcttttaaac ataaccacta atatttacct    5580
```

-continued

```
gaagataacc atgagtaaag tatacttttg cattaatttt ttgagcttat atgcaaacat    5640
aataaatatt attaaatatc aggaaagcta acatttcata caagatagct tcagaccaaa    5700
ttcaaattga atttgaataa attagaaata ctgtgcatac ataaccttct tgtgcaccat    5760
gagtatttgg aaagttaatc cttgtttttg tcgtgtctat aaaggaagaa caaaacaaaa    5820
taaaaacaga gccctagaga atgctgtta cttttatttt ttacacccat cagatttaag     5880
gaaaagactt tttagccatt ataatctagt ggttggaagg aatgaagaag ctttttagt     5940 aataggtcca gatatgagtg ctaaaaataa agatgatagc atgttcttct gtcttccata    6000
gttattacaa ctatgagagc ctcccaagtc atcttatcaa ctcaactccc ttttttttgt    6060
cttaatgttg cacataagtt tatacagagt ggatgaccac actagcacag aagagaacaa    6120
catgtattaa agcaggtgat tcctcccctt ggcgggagag ctctctcagt gtgaacatgc    6180
cttctgtggg cggaaatcag gaagccacca gctgttaatg gagagtgcct tgcttttatt    6240
tcagacagca gagttttcca aagtttctct gctcctctaa cagcattgct ctttagtgtg    6300
tgttaacctg tggtttgaaa gaaatgctct tgtacattaa caatgtaaat ttaaatgatt    6360
aaattacatt ttatcaatgg ca                                              6382
```

<210> SEQ ID NO 14
<211> LENGTH: 626
<212> TYPE: PRT
<213> ORGANISM: Homo sapiens

<400> SEQUENCE: 14

```
Met Pro Cys Val Gln Ala Gln Tyr Ser Pro Ser Pro Pro Gly Ser Ser
 1               5                  10                  15

Tyr Ala Ala Gln Thr Tyr Ser Ser Glu Tyr Thr Thr Glu Ile Met Asn
             20                  25                  30

Pro Asp Tyr Thr Lys Leu Thr Met Asp Leu Gly Ser Thr Glu Ile Thr
         35                  40                  45

Ala Thr Ala Thr Thr Ser Leu Pro Ser Ile Ser Thr Phe Val Glu Gly
     50                  55                  60

Tyr Ser Ser Asn Tyr Glu Leu Lys Pro Ser Cys Val Tyr Gln Met Gln
 65                  70                  75                  80

Arg Pro Leu Ile Lys Val Glu Glu Gly Arg Ala Pro Ser Tyr His His
                 85                  90                  95

His His His His His His His His His His Gln Gln Gln His
            100                 105                 110

Gln Gln Pro Ser Ile Pro Pro Ala Ser Ser Pro Glu Asp Glu Val Leu
        115                 120                 125

Pro Ser Thr Ser Met Tyr Phe Lys Gln Ser Pro Ser Thr Pro Thr
    130                 135                 140

Thr Pro Ala Phe Pro Pro Gln Ala Gly Ala Leu Trp Asp Glu Ala Leu
145                 150                 155                 160

Pro Ser Ala Pro Gly Cys Ile Ala Pro Gly Pro Leu Leu Asp Pro Pro
                165                 170                 175

Met Lys Ala Val Pro Thr Val Ala Gly Ala Arg Phe Pro Leu Phe His
            180                 185                 190

Phe Lys Pro Ser Pro His Pro Ala Pro Ser Pro Ala Gly Gly
        195                 200                 205

His His Leu Gly Tyr Asp Pro Thr Ala Ala Ala Leu Ser Leu Pro
    210                 215                 220

Leu Gly Ala Ala Ala Ala Ala Gly Ser Gln Ala Ala Ala Leu Glu Ser
```

```
            225                 230                 235                 240
        His Pro Tyr Gly Leu Pro Leu Ala Lys Arg Ala Ala Pro Leu Ala Phe
                        245                 250                 255
        Pro Pro Leu Gly Leu Thr Pro Ser Pro Thr Ala Ser Ser Leu Leu Gly
                        260                 265                 270
        Glu Ser Pro Ser Leu Pro Ser Pro Pro Ser Arg Ser Ser Ser Ser Gly
                        275                 280                 285
        Glu Gly Thr Cys Ala Val Cys Gly Asp Asn Ala Ala Cys Gln His Tyr
                        290                 295                 300
        Gly Val Arg Thr Cys Glu Gly Cys Lys Gly Phe Phe Lys Arg Thr Val
        305                 310                 315                 320
        Gln Lys Asn Ala Lys Tyr Val Cys Leu Ala Asn Lys Asn Cys Pro Val
                        325                 330                 335
        Asp Lys Arg Arg Arg Asn Arg Cys Gln Tyr Cys Arg Phe Gln Lys Cys
                        340                 345                 350
        Leu Ser Val Gly Met Val Lys Glu Val Val Arg Thr Asp Ser Leu Lys
                        355                 360                 365
        Gly Arg Arg Gly Arg Leu Pro Ser Lys Pro Lys Ser Pro Leu Gln Gln
                        370                 375                 380
        Glu Pro Ser Gln Pro Ser Pro Pro Ser Pro Pro Ile Cys Met Met Asn
        385                 390                 395                 400
        Ala Leu Val Arg Ala Leu Thr Asp Ser Thr Pro Arg Asp Leu Asp Tyr
                        405                 410                 415
        Ser Arg Tyr Cys Pro Thr Asp Gln Ala Ala Ala Gly Thr Asp Ala Glu
                        420                 425                 430
        His Val Gln Gln Phe Tyr Asn Leu Leu Thr Ala Ser Ile Asp Val Ser
                        435                 440                 445
        Arg Ser Trp Ala Glu Lys Ile Pro Gly Phe Thr Asp Leu Pro Lys Glu
                        450                 455                 460
        Asp Gln Thr Leu Leu Ile Glu Ser Ala Phe Leu Glu Leu Phe Val Leu
        465                 470                 475                 480
        Arg Leu Ser Ile Arg Ser Asn Thr Ala Glu Asp Lys Phe Val Phe Cys
                        485                 490                 495
        Asn Gly Leu Val Leu His Arg Leu Gln Cys Leu Arg Gly Phe Gly Glu
                        500                 505                 510
        Trp Leu Asp Ser Ile Lys Asp Phe Ser Leu Asn Leu Gln Ser Leu Asn
                        515                 520                 525
        Leu Asp Ile Gln Ala Leu Ala Cys Leu Ser Ala Leu Ser Met Ile Thr
                        530                 535                 540
        Glu Arg His Gly Leu Lys Glu Pro Lys Arg Val Glu Glu Leu Cys Asn
        545                 550                 555                 560
        Lys Ile Thr Ser Ser Leu Lys Asp His Gln Ser Lys Gly Gln Ala Leu
                        565                 570                 575
        Glu Pro Thr Glu Ser Lys Val Leu Gly Ala Leu Val Glu Leu Arg Lys
                        580                 585                 590
        Ile Cys Thr Leu Gly Leu Gln Arg Ile Phe Tyr Leu Lys Leu Glu Asp
                        595                 600                 605
        Leu Val Ser Pro Pro Ser Ile Ile Asp Lys Leu Phe Leu Asp Thr Leu
                        610                 615                 620
        Pro Phe
        625

<210> SEQ ID NO 15
```

<211> LENGTH: 598
<212> TYPE: PRT
<213> ORGANISM: Homo sapiens

<400> SEQUENCE: 15

Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
            20                  25                  30

Pro Thr Met Asp Leu Ala Ser Pro Glu Ala Ala Pro Ala Ala Pro Thr
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
            100                 105                 110

Pro Gly Pro Leu Ser Gly Pro Val Asp Glu Ala Leu Ser Ser Ser Gly
        115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270

Asn Ala Ser Cys Gln His Tyr Gly Val Arg Thr Cys Glu Gly Cys Lys
        275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala

```
385                 390                 395                 400
Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Ala Asp Gln Asp Leu Leu Leu Glu Ser Ala Phe Leu Glu Leu Phe Ile
        435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
        515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
        595
```

<210> SEQ ID NO 16
<211> LENGTH: 598
<212> TYPE: PRT
<213> ORGANISM: Homo sapiens

<400> SEQUENCE: 16

```
Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160
```

His Met Ile Glu Gln Arg Lys Thr Pro Val Ser Arg Leu Ser Leu Phe
            165                 170                 175

Ser Phe Lys Gln Ser Pro Pro Gly Thr Pro Val Ser Ser Cys Gln Met
        180                 185                 190

Arg Phe Asp Gly Pro Leu His Val Pro Met Asn Pro Glu Pro Ala Gly
    195                 200                 205

Ser His His Val Val Asp Gly Gln Thr Phe Ala Val Pro Asn Pro Ile
210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
            245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
            325                 330                 335

Ser Leu Lys Gly Arg Arg Gly Arg Leu Pro Ser Lys Pro Lys Ser Pro
            340                 345                 350

Gln Glu Pro Ser Pro Pro Ser Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
            405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
            485                 490                 495

Asn Ile Asp Ile Ser Ala Phe Ser Cys Ile Ala Ala Leu Ala Met Val
        500                 505                 510

Thr Glu Arg His Gly Leu Lys Gly Pro Lys Arg Val Glu Glu Leu Gln
    515                 520                 525

Asn Lys Ile Val Asn Cys Leu Lys Asp His Val Thr Phe Asn Asn Gly
530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
            565                 570                 575

Lys Leu Glu Asp Leu Val Pro Pro Pro Ala Ile Ile Asp Lys Leu Phe

Leu Asp Thr Leu Pro Phe
        595

<210> SEQ ID NO 17
<211> LENGTH: 295
<212> TYPE: PRT
<213> ORGANISM: Homo sapiens

<400> SEQUENCE: 17

Met Glu His Gln Leu Leu Cys Cys Glu Val Glu Thr Ile Arg Arg Ala
 1               5                  10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
        275                 280                 285

Asp Val Arg Asp Val Asp Ile
    290                 295

<210> SEQ ID NO 18
<211> LENGTH: 289
<212> TYPE: PRT
<213> ORGANISM: Homo sapiens

<400> SEQUENCE: 18

Met Glu Leu Leu Cys His Glu Val Asp Pro Val Arg Arg Ala Val Arg

```
            1               5              10              15

Asp Arg Asn Leu Leu Arg Asp Asp Arg Val Leu Gln Asn Leu Leu Thr
                        20                  25                  30

Ile Glu Glu Arg Tyr Leu Pro Gln Cys Ser Tyr Phe Lys Cys Val Gln
                        35                  40                  45

Lys Asp Ile Gln Pro Tyr Met Arg Arg Met Val Ala Thr Trp Met Leu
         50                      55                  60

Glu Val Cys Glu Gln Lys Cys Glu Glu Val Phe Pro Leu Ala
         65                      70                  75                  80

Met Asn Tyr Leu Asp Arg Phe Leu Ala Gly Val Pro Thr Pro Lys Ser
                        85                  90                  95

His Leu Gln Leu Leu Gly Ala Val Cys Met Phe Leu Ala Ser Lys Leu
                        100                 105                 110

Lys Glu Thr Ser Pro Leu Thr Ala Glu Lys Leu Cys Ile Tyr Thr Asp
                        115                 120                 125

Asn Ser Ile Lys Pro Gln Glu Leu Leu Glu Trp Glu Leu Val Val Leu
                        130                 135                 140

Gly Lys Leu Lys Trp Asn Leu Ala Ala Val Thr Pro His Asp Phe Ile
        145                     150                 155                 160

Glu His Ile Leu Arg Lys Leu Pro Gln Gln Arg Glu Lys Leu Ser Leu
                        165                 170                 175

Ile Arg Lys His Ala Gln Thr Phe Ile Ala Leu Cys Ala Thr Asp Phe
                        180                 185                 190

Lys Phe Ala Met Tyr Pro Pro Ser Met Ile Ala Thr Gly Ser Val Gly
                        195                 200                 205

Ala Ala Ile Cys Gly Leu Gln Gln Asp Glu Val Ser Ser Leu Thr
        210                     215                 220

Cys Asp Ala Leu Thr Glu Leu Leu Ala Lys Ile Thr Asn Thr Asp Val
        225                     230                 235                 240

Asp Cys Leu Lys Ala Cys Gln Glu Gln Ile Glu Ala Val Leu Leu Asn
                        245                 250                 255

Ser Leu Gln Gln Tyr Arg Gln Asp Gln Arg Asp Gly Ser Lys Ser Glu
                        260                 265                 270

Asp Glu Leu Asp Gln Ala Ser Thr Pro Thr Asp Val Arg Asp Ile Asp
                        275                 280                 285

Leu

<210> SEQ ID NO 19
<211> LENGTH: 317
<212> TYPE: PRT
<213> ORGANISM: Equus caballus

<400> SEQUENCE: 19

Met Pro Leu Gln Gly Pro Gln Arg Arg Leu Leu Gly Ser Leu Asn Ser
         1               5                  10                  15

Thr Leu Pro Ala Thr Pro Tyr Leu Gly Leu Thr Thr Asn Gln Thr Glu
                        20                  25                  30

Pro Pro Cys Leu Glu Val Ser Ile Pro Asp Gly Leu Phe Leu Ser Leu
                        35                  40                  45

Gly Leu Val Ser Leu Val Glu Asn Val Leu Val Thr Ala Ile Ala
         50                      55                  60

Lys Asn Arg Asn Leu His Ser Pro Met Tyr Tyr Phe Ile Cys Cys Leu
         65                      70                  75                  80

Ala Val Ser Asp Leu Leu Val Ser Met Ser Asn Val Leu Glu Met Ala
```

```
                        85                  90                  95
Ile Leu Leu Leu Leu Glu Ala Gly Val Leu Ala Thr Gln Ala Ser Val
                100                 105                 110

Leu Gln Gln Leu Asp Asn Ile Ile Asp Val Leu Ile Cys Gly Ser Met
            115                 120                 125

Val Ser Ser Leu Cys Phe Leu Gly Ser Ile Ala Val Asp Arg Tyr Ile
130                 135                 140

Ser Ile Phe Tyr Ala Leu Arg Tyr His Ser Ile Met Met Leu Pro Arg
145                 150                 155                 160

Val Trp Arg Ala Ile Ala Ile Trp Val Val Ser Val Leu Ser Ser
                165                 170                 175

Thr Leu Phe Ile Ala Tyr Tyr Asn His Thr Ala Val Leu Leu Cys Leu
            180                 185                 190

Val Thr Phe Phe Val Ala Met Leu Val Leu Met Ala Val Leu Tyr Val
        195                 200                 205

His Met Leu Ala Arg Ala Cys Gln His Ala Arg Gly Ile Ala Arg Leu
    210                 215                 220

His Lys Arg Gln His Pro Ile His Gln Gly Phe Gly Leu Lys Gly Ala
225                 230                 235                 240

Ala Thr Leu Thr Ile Leu Leu Gly Val Phe Phe Leu Cys Trp Gly Pro
                245                 250                 255

Phe Phe Leu His Leu Ser Leu Leu Ile Leu Cys Pro Gln His Pro Thr
            260                 265                 270

Cys Gly Cys Val Phe Lys Asn Phe Lys Leu Phe Leu Thr Leu Ile Leu
        275                 280                 285

Cys Ser Ala Ile Val Asp Pro Leu Ile Tyr Ala Phe Arg Ser Gln Glu
    290                 295                 300

Leu Arg Lys Thr Leu Gln Glu Val Leu Leu Cys Ser Trp
305                 310                 315

<210> SEQ ID NO 20
<211> LENGTH: 1721
<212> TYPE: DNA
<213> ORGANISM: Equus caballus

<400> SEQUENCE: 20
tctgggcagg tccagaggag gccacacctg gagcagaggc ccagctggga gtgctggttg     60
gctgagtaca gggaggctgg gagtgcaaag gggagatgtc ctgctgtgtc taggagtctg    120
ggggcccggg gagcccagac ggtcgtgggt gccatttgcg ccacttggcg gcggcggcag    180
gagggtgtgt gggcgctctg atggtgcctt cccgggcacc cacccatcat gtgactgccc    240
tcaggaggag gggctccatg gaagccttta aagatgctga aaaggctcc attcttccca     300 gtttccccaa cccacccctg ctctggggag gcaggaggcc tggcaggcca ggaggcagca    360
agagctagag atgtgcggac ctgagcaaca gcacctccag ggagaggccg ggaggtgggc    420
tgagaaccca atgagactcc agagcccaga gggttggtgc cacagagctt gggtcttggc    480
tgggaagtga ccagactctg gtggagaggc caggttctct ggctgggcca cggttgggcc    540
aacatttttc cagccaggga gagcgtgagt gtgaggcag ccctgcgggt ggcaccatga     600
gctgagtggg acgcctggag agtgaggacc ccttcctgct tcctagaggg actatgcctc    660
tgcaggggcc ccagaggagg ctgctgggct ccctcaactc caccctccca gccacccct    720 acctcgggct gaccaccaac cagacggagc ccccgtgcct ggaagtgtcc attcctgatg    780
ggctcttcct cagcctgggg ctggtgagcc tagtggaaaa tgtactggtg gtgactgcca    840
```

```
tcgccaagaa ccgcaacctg cactcaccca tgtactactt catctgctgc ctggccgtgt    900
ccgacctgct ggtgagcatg agcaacgtgc tggagatggc aatcttgctg ctgctggagg    960
ccggagtcct ggccacccag gcctcggtgt tgcagcagct ggacaacatc attgatgtgc    1020
tcatctgcgg ctccatggtg tccagcctct gcttcctggg cagcattgcc gtagaccgct    1080
acatctccat cttctatgcg ctgcggtacc acagcatcat gatgctgccc cgtgtgtggc    1140
gtgccatcgt ggccatctgg gtggttagtg tcctctctag caccctcttc atcgcttact    1200
acaaccacac ggctgtcctg ctctgtctcg tcaccttctt tgtggccatg ctggtgctca    1260
tggcagtgct gtacgtgcac atgctcgcca gggcgtgcca gcacgcccgg ggcatcgccc    1320
ggctccacaa gaggcagcac cccatccacc agggctttgg cctcaagggt gccgccaccc    1380
tcaccatcct gctgggcgtt ttcttcctct gctggggccc ctttttcctg cacctctcac    1440
tccttatcct ctgccctcaa caccccacct gcggctgtgt cttcaagaac ttcaagctct    1500
tcctcaccct catcctgtgc agcgccatcg tcgaccccct catctatgcc ttccgcagcc    1560
aggaacttcg aaagacgctc caggaggtgc tgctgtgctc ctggtgaggg gaggggagcc    1620
tgcgggccaa ggcagagggc tgtgcacagg gaggtggtga catcagggg ctcggttcct    1680 gtgtgaccgg ggcagtcact tgccaaagag ggtggcctat a                        1721

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
ttgtagtatc agcaccacct gggaactc                                         28

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
tcatgtgtct atcccactag gaggga                                           26

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
gtaggtctgc acccaggaac                                                  20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agaagttggg caagagcaga                                                  20
```

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cacagtatgg ctgccaaaga                                                  20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
caaagtgcca gagggaagtt                                                  20

<210> SEQ ID NO 27
<211> LENGTH: 50
<212> TYPE: DNA
<213> ORGANISM: Artificial Sequence
<220> FEATURE:
<223> OTHER INFORMATION: Probe sequence

<400> SEQUENCE: 27
acctgggaac tcattagaaa tgcaaaatct cagaattgga attgaactta                 50

<210> SEQ ID NO 28
<211> LENGTH: 40
<212> TYPE: DNA
<213> ORGANISM: Artificial Sequence
<220> FEATURE:
<223> OTHER INFORMATION: Probe sequence

<400> SEQUENCE: 28
ggaactcatt agaaatgcaa aatctcagaa ttggaattga                            40

<210> SEQ ID NO 29
<211> LENGTH: 36
<212> TYPE: DNA
<213> ORGANISM: Artificial Sequence
<220> FEATURE:
<223> OTHER INFORMATION: Probe sequence

<400> SEQUENCE: 29
aactcattag aaatgcaaaa tctcagaatt ggaatt                                36

<210> SEQ ID NO 30
<211> LENGTH: 30
<212> TYPE: DNA
<213> ORGANISM: Artificial Sequence
<220> FEATURE:
<223> OTHER INFORMATION: Probe sequence

<400> SEQUENCE: 30
tcattagaaa tgcaaaatct cagaattgga                                       30

<210> SEQ ID NO 31
<211> LENGTH: 28
<212> TYPE: DNA
<213> ORGANISM: Artificial Sequence
<220> FEATURE:
<223> OTHER INFORMATION: Probe sequence

```
<400> SEQUENCE: 31
cattagaaat gcaaaatctc agaattgg                                          28

<210> SEQ ID NO 32
<211> LENGTH: 20
<212> TYPE: DNA
<213> ORGANISM: Artificial Sequence
<220> FEATURE:
<223> OTHER INFORMATION: Probe sequence

<400> SEQUENCE: 32
agaaatgcaa aatctcagaa                                                   20

<210> SEQ ID NO 33
<211> LENGTH: 16
<212> TYPE: DNA
<213> ORGANISM: Artificial Sequence
<220> FEATURE:
<223> OTHER INFORMATION: Probe sequence

<400> SEQUENCE: 33
aaatgcaaaa tctcag                                                       16

<210> SEQ ID NO 34
<211> LENGTH: 10
<212> TYPE: DNA
<213> ORGANISM: Artificial Sequence
<220> FEATURE:
<223> OTHER INFORMATION: Probe sequence

<400> SEQUENCE: 34
tgcaaaatct                                                              10

<210> SEQ ID NO 35
<211> LENGTH: 17
<212> TYPE: DNA
<213> ORGANISM: Artificial Sequence
<220> FEATURE:
<223> OTHER INFORMATION: Probe sequence

<400> SEQUENCE: 35
gaaatgcaaa atctcag                                                      17

<210> SEQ ID NO 36
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 36

Ser Pro Arg Arg Ser Glu Arg Leu Gly Trp
1               5                   10

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ggaacataaa gtagatttgg tgggaaag                                          28
```

```
<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
ttctgataaa tgcataaacc cacgtaac                                      28

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
ttccaattct gagattttgc atttctaa                                      28

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
cctgccacag gcagagct                                                 18

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
tggtcactga tttctctctc ctagtaaa                                      28

<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
gctcactcat aattcctttg catct                                         25

<210> SEQ ID NO 43
<211> LENGTH: 30
<212> TYPE: DNA
<213> ORGANISM: Artificial Sequence
<220> FEATURE:
<223> OTHER INFORMATION: Probe sequence

<400> SEQUENCE: 43
cttgtatttt gcagccttcc ccaagttttt                                    30

<210> SEQ ID NO 44
<211> LENGTH: 22
<212> TYPE: DNA
<213> ORGANISM: Artificial Sequence
<220> FEATURE:
<223> OTHER INFORMATION: Primer
```

```
<400> SEQUENCE: 44
gaatcagcct ttttggagct gt                                              22

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
cattgcagaa cacaaactta tcttc                                           25

<210> SEQ ID NO 46
<211> LENGTH: 31
<212> TYPE: DNA
<213> ORGANISM: Artificial Sequence
<220> FEATURE:
<223> OTHER INFORMATION: Probe Sequence

<400> SEQUENCE: 46
tgttctcaga ctttccatca ggtcgaacac t                                    31

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
agtccctgcc ctttgtacac a                                               21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
gatccgaggg cctcactaaa c                                               21

<210> SEQ ID NO 49
<211> LENGTH: 23
<212> TYPE: DNA
<213> ORGANISM: Artificial Sequence
<220> FEATURE:
<223> OTHER INFORMATION: Probe Sequence

<400> SEQUENCE: 49
cgcccgtcgc tactaccgat tgg                                             23

<210> SEQ ID NO 50
<211> LENGTH: 1669
<212> TYPE: DNA
<213> ORGANISM: Equus caballus

<400> SEQUENCE: 50
gagacttcag tcagatgacc atgcttagga aatatcctta tcccttcctc atatgaatgt     60
gcagtctaaa cttttccgtc tgaacatgtt taaagtgtat atatgtataa gttttataca    120
tctttatggt tttcttcttt cagcgacctt tttcaataaa ttggtcaacc taacacgyta    180
taaaagaggg ctcctgctgt atttaaaaac acagatagtg cattccagat aggggygagt    240
```

| | | | |
|---|---|---|---|
| ggaagggaa | tacaccatgg | atataggtca | agttgacgtg gagaaggacc tccaatgtca | 300 |
| cagtgaggaa | tttggacatt | gcaataagca | ataagggaac agtaagaggt tgtcgttttg | 360 |
| tcatttgata | gtacagattt | ttgagcatat | caaaggacat gcccttatg aaattagttt | 420 |
| ggcagctagt | aggcttgctg | ctccggtccc | cgtagtccac gtcattcctc ccatagcaa | 480 |
| aggctgctgg | agtcttgctc | cttaggctcc | agacctgcgc tgtccaatag gtagcggtag | 540 |
| ccacatgtgg | ctattgagca | cttaaacgtg | gctagccgga actgagatgt gctgtaagtg | 600 |
| taaaataaac | ccagatttca | gagacttagt | atgagaaaag gaatgtaaaa tatcttatta | 660 |
| acgatgtttt | attgcttaca | tgttgaaacg | atgatagcat atactgggtt aaataaaata | 720 |
| tactattaaa | attcattttcc | acttatttct | ttttactttt ttaaaatgtg actacttgaa | 780 |
| aatttagaac | tttaacatgt | agctcggcat | ctggaggctc acattatatt tatctttctg | 840 |
| gacagaaatg | gctctagttc | tagatcaatc | ctgacacgag ataggagagt tgagccatcc | 900 |
| tgcccctag | cccaatgctt | tgggactcat | ttctcctact gggtgtctga tttcaaataa | 960 |
| agaatctttg | tcacactcct | ctttctccac | tttgggatgt ggtctggttt ccttgatttc | 1020 |
| tgctttgtaa | tgtttaaggc | tcaggttgct | ggctccttag agatttgtct tctctctcat | 1080 |
| tttccgtcat | gcacaaatcc | atgtttcctc | cttatgatga ctccttcctc tggagaagca | 1140 |
| gacacttcca | gaaagatgga | gatcaacaat | agggcattgg atttggtgat cagggaatca | 1200 |
| ctacctttaa | gagaacgacc | atatcaacta | tttgagcgga cggctgagca gttgtcagga | 1260 |
| ttgccacacc | aacgatctca | taggcttaaa | gaccagaaga aaaaccaaat cacacccttag | 1320 |
| ccaatggtag | aacaatgaca | agcacactgg | cacatccctc acccagtctt tgtctaccgg | 1380 |
| tggaactgag | acttccagaa | tgaagggcct | cctccctgtc atttattatt ttgaagtagt | 1440 |
| gttaccaagt | gctcactttg | aagaagcatt | cagctagaca gttagggatc acaatcaagt | 1500 |
| taaaagaaa | aggaaataag | tttgcagcac | tggggctgca ttcagaaatg ggagagacat | 1560 |
| ccccacaagt | cacgtcaccc | tcatgcaagc | aaagctgaat acacctgatt tatttgccta | 1620 |
| tccagggacc | tggccagatt | ttttctaaac | tctggaggca gtcttggtt | 1669 |

<210> SEQ ID NO 51
<211> LENGTH: 1429
<212> TYPE: DNA
<213> ORGANISM: Equus caballus

<400> SEQUENCE: 51

| | | | |
|---|---|---|---|
| tgacttgtta | gaggcggttc | taattctctt | gggctgctgg ggaatctcaa cagaaaatgg | 60 |
| tttagtacgt | atgagcacgt | gcatatctga | gtgtacgtac atatgcctcc atcttatgtg | 120 |
| tgtacgtgtg | tttatgcatc | agggcacagt | agctgataca atgcaataga tacctaaaaa | 180 |
| cacggcacca | acaaaatcaa | aatggactat | tcactagaaa ataacaccaa cgaggttggc | 240 |
| taggtatatg | tgttttattt | tgtcttcatt | tttttaagtc cccacattga actgcataac | 300 |
| ctcttacatt | tcatcttaaa | gaatttcata | acatcttgta aaaagctrct tccttctgtt | 360 |
| cttcagtctt | gcaaagtgct | cactgacgtt | gctgttgcag tctggaagaa ttgaaagctt | 420 |
| tagcattcgg | ttctcaagga | gctctcccctc | ctgaccacat tgaaggcagc atggcgtggt | 480 |
| acaaagggtc | ctaaacagtg | agccacagga | catgggttta agccagaatc ctacccattg | 540 |
| tgaagttagg | ctagaccctc | acagccctga | gtctatttcc tcatttgtaa aaagggcta | 600 |
| ataaccttg | acctgtcctt | aaaaagagtc | tctgggaatg ggcttcgtaa actctgcagc | 660 |

```
actgaggcaa gccatggaaa gggattagta ccgccacaat tgtggaagta agtctcacgc     720
ctaagaagca gtcccagcga ggaggttttc ggtacaggga gacaggaagg aaagcrcagg     780
attccaacac acacctgtga cttcattcat gaaattcagg ggagaaattt aaaatatttc     840
cctagacttc cctcagaact acattggctt caaaggaggc aaaagtcaag atgtaacagg     900 aattttttatt ctgatttgtt ctgaaatatg ggttttcaat catcatgatt ccttaaatta    960
gaatggatct gcaaaaatag atacatgcaa acattttttc ctaaattttt ttcatgtaag    1020
agtatgcagc ctgctgtgta atgtcacaca ctaaaataac attggcatag aatgggagta    1080
aaatcctttc tctggaaata agcatatgtt attaaaatta tatatcattt gtakccaact    1140
actagaaaag aatccacact gcagtgttta agtttaggat tgacttggcg tactgtgaca    1200
ttgtgcaatc aaggatagga ccaggaggca agggcttgag ttctacttcc agctattccg    1260
ctaaytaacc tggtgacttg aataaagcat tggcctccat gagctttatt tcttccatgg    1320
ggaaaatgaa ttaccacatg tgcctactca cctgcttcat agggttctta tggggatcaa    1380
atgaaagtgt ctatgaaaat ggctctctat aactatgaaa tggttgggt                1429

<210> SEQ ID NO 52
<211> LENGTH: 1048
<212> TYPE: DNA
<213> ORGANISM: Equus caballus
<220> FEATURE:
<223> OTHER INFORMATION: Synthetically generated oligonucleotide

<400> SEQUENCE: 52
agaagttgtg ggagctctaa tgtggcagtg gaggtgaagg tggggcccac ttgctacgaa      60
cagtctgctc tcacaaaaaa tttaaagcaa ggcaatattt ttgcacactt ttctgtaatt     120
gaatatcatt aaggtactaa atagataatg ccccttgcct ttctttttt tcaaaaacta     180 tttattgaat gcctactata taccaggmat tgtgcaagag ataaagggat aaaatggtga     240
tcaaagaaaa agagcaaaga aagctaaaag acagtcgagt ggaaagagta ggaatggaaa     300
agaaaaagcg gattgctggt gggctccttt attgccaaag tctttgtatg ttttggggtc     360
cttgagtcag gaaaaaagt agttatgctg gatccctctg acaygtatgg caaggagtgt      420
gtgtgtgtgt gcatgcatgc acgtgtgtgt ggtgtgtttt ggagaagatg agagagcata     480
aggagaatac ctcaatttct gyccaataga agtgggagga tggaatcact gatgttccag     540
aagctaagaa aggaaaaatg taaattattt tctttacgca tgtggtttgc acaacatcct     600
ccaacataag actcccactt gggtcctaaa gttggaaaaa tctagggagt acggagaaag     660
agaacagagc aacaagacga cacagtatac caggtgtcag cgctagcaca tcaactccga     720
aagggagacc tttgcaagac attctccagg ttcactagcc atgtgcatta cgaatctgga     780
attaatgcta tttacctaaa ttataaagac gtatttctca cataagtccc ttatgtgcaa     840
gcagggtagc aaaggaagag ttcttatatt gggggtaact tgaagagccc taagaatttt    900
cctaccccaa atagttcact gaaattcttc attttgtttc gctctttgga acctgtcttt     960
aattatctcc ctatgaccac agaagcagtt ataacacagt acagtaatta aagattctga    1020
aatcagattg cttttgttcac cctgggct                                      1048

<210> SEQ ID NO 53
<211> LENGTH: 862
<212> TYPE: DNA
<213> ORGANISM: Equus caballus

<400> SEQUENCE: 53
```

```
gaatcatcgc actgtggtgg attcatgttc cagaagctaa gaaggaaaaa tgtaaattat      60
tttctttacg catgtggttt gcacaacatc ctccaacata agactcccac ttgggtccta     120
aagttggaaa atctagggta gtacggagaa agagaacaga gcaacaagac gacacagtat     180
accaggtgtc agcgctagca catcaactcc gaaagggaga cctttgcaag acattctcca     240
ggttcactag ccatgtgcat tacgaatctg gaattaatgc tatttaccta aattataaag     300
acgtatttct cacataagtc cctaatgtgc aagcagggta gcaaggaag agttctttat      360 atggggtaa cttgaagagc ccctaagaat ttcctacccc aaatagttca ctgaaattct      420
tcattttgtt tcgctctttg gaacctgtct ttaattatct ccctatgacc acagaagcag     480
ttataacaca gtacagtaat taaagattct gaaatcagat tgctttgttc accctgggct     540
tcaccactag tcactcctgt gattattggg tatgcttctt actaacagct aagaattaca     600
tttattgagc atgtaatcac ttagcaacta taggcacaag cattttacat gtattggcag     660
gtatcattaa tcctcacaat accccatga ggtatgacgt aggtrtcatg atcatgatgt      720
catcttacgg atgaggaaac tgaggcacat atggaacttt caggtccaaa agtaataaga     780
gtgagctgaa attcaaacct aaacagactt aactatatac tacaggcccc tcacttaaac     840
gctctaagcc accataccta ct                                               862

<210> SEQ ID NO 54
<211> LENGTH: 793
<212> TYPE: DNA
<213> ORGANISM: Equus caballus

<400> SEQUENCE: 54 cgcgttttttt agcctcgatt cgggtgccac aaaacggcgg tgaacgcact gggtgctggg     60
caacccatac tcggctcccc caaggcggtg taatgcttct tgcccaggga ctccgttcac    120
cttaagcact gctttcttac ccttataatt ctttgtaatt aacgtagcat tcctcgaggc    180
ccccaccaac accccaacgc gcccggccca ggccgcggtg accccgcctg gtcccgctgt    240
gacctctgtc ctctctcccg gtgcccgcag agcccactgc ggaagagcgc agccggcaa     300 gccccaggcc tgagactgga ccctcggcag agccgggcag caccgcagcc gcttcgcctc    360
gccrgacgtc ccccgcttct acactctcag cctccgctgg agagaccccc agccccacca    420
ttcagcgcgc aagatatcct ccaggtaggt ctgaaggcac gaccccttat tcctcgcagg    480
ctggaagaag tgggggaggg gatgggccct gggtccctgg caggggcggg ctggtcgact    540
tgcctagcgc caggacagtg actgctggcc gagcatttca cagcacaggt ggcttctttg    600
cacgaagctc ctctggatac cacaccctgt tgctaccgag tggaggagcc agattaaatt    660
aagcgttgca tttttcaaaa atattttttcc taagaaaaat gcaaatacac cgatagatta    720
ggatctttta atacactgta atgtcatgtt tgctgtcctt ttatatccgg tttacgcatt     780
taagagtatt ggg                                                       793

<210> SEQ ID NO 55
<211> LENGTH: 1231
<212> TYPE: DNA
<213> ORGANISM: Equus caballus

<400> SEQUENCE: 55
ttaaaataca ggaaaggcaa agttaaggta tggaccacat agagttcaga ttagtcacgc      60
ctgatactca tcaagctcct cttgtgtacc aggcactggg crtgggctttt caaatctttt   120
```

```
astttacagt catgcatcac ttaacaacag aggtatgctc tgagaaacgc atcattaggt    180
gattttatca ttatgcgaac atcgtagagt ggactaacac aaatctggac ggcatagcct    240
rctacacacc taggctctrt ggtactaatc ttatgggagc acggtcgcat atgtggtccg    300
tcgttgactg aatgttgtta tgcagcacat gactctattt aattcccaca acgatcgtag    360
gaggtagcaa ttagaagtcc tgttttatac ataaggaaaa ggaagcccag agagattaga    420
agtgcccagg gcccctagc taggtggtga tgtttcacca gaagtttcag ggtgtctttc    480
atgagagaga gaagagtggg atgattatgg acataatata aactatcacg gcagatttag    540
aaacagccct ccgcagcccc cctgttaaaa gcagagaggg taatacaaaa taagctctct    600 tttcactta aggcgcttgt cagtttctga ttgacttctg gcggtcgcag tgactcggtg    660
gttttagagt ctgcacaatg gaattgtagt gtctagcgtc aggccttatc agtttctgac    720
attcaaggaa atgaggggga agtcctggtg agggagcgct aaagagaaca gtctcaggtt    780
catggcagag gccacgcact gggcttcact tccacagtct gtgagcgcct gctcctctgt    840
gtcccgtccc aggggggagcc agtaattgac tctagtaata agaaatcagg tgccccaccg    900
ccagcttccc cggggggctga tgctcagcaa gaaagttagc acagacgcct ggtggtggct    960
gtgcatccct ggagtaccct cttcttcctc gagggcaccc gggcagattt cacaacacca   1020
cactacttct gaacgctgcc ccatggctgt gcgggtatct ctgtggtgtg atggtgtcct   1080
gtccgacaga ccgaacagac ctgtctaacg tatctccatc ctccgccccc cacgactttg   1140
tcttgtaggt cgaacactgc tgaagataag tttgtgttct gcaatggact tgtcctgcat   1200
cgacttcagt gccttcgtgg atttggggag t                                  1231

<210> SEQ ID NO 56
<211> LENGTH: 722
<212> TYPE: DNA
<213> ORGANISM: Equus caballus

<400> SEQUENCE: 56
tatagtttta accgtaattt gaatacacgt ctagtataat ctatagtttt atacatgtta     60
gtgttcacag tcatagaatt ttagtatcga agggaacctc aaagcatcat cttgtgctaa    120
tgcaaacctt tcaaagtaac gatggggact yagaggcctg aaggcgcaga ggcgtttagt    180
gacagagctg ggactagaga gccctggtcc ccgggcctta tcggcctgtt ttgtgttcag    240
cctgggaccc aaattcaaaa aactgctccc atgatctgtg atcataactc atacctgaat    300
cagaatagcc atctcccagg ccttctgggg tataaattaa cctgctactt gccagataat    360
aaggagtgct agggtttttt tttgcttta ggaagattag ccctgagcta actgctgcca    420
gtcctctttt tgctggggaa gactggcagt gagctaacat ccatgcccat cctcctctac    480
tttatatgtg ggacgcctac cacagcatgg cttgccaagc ggtgccatgt ccacacccgg    540
gatctgaact ggcgaaccct gggccgccaa gaagcggacc gagcgaactt aactgctgca    600
ccactgggcc ggcctctggg agtgctaggt ttttaaccct tagctgagaa gttaagtatg    660
tctgaaccta gaaggagctc cttaggccca agacaatggt ggccacaact aagaggcaaa    720
aa                                                                  722

<210> SEQ ID NO 57
<211> LENGTH: 154
<212> TYPE: DNA
<213> ORGANISM: Equus caballus

<400> SEQUENCE: 57
```

```
ttactgaact ggcaagacta cgagggacga acacctcttc attttgcagt cgccgatggg    60
aatgtgacgg tggttgatgt cttgacctcg tacgagagct gcaacataac rtcttatgat   120
aacttatttc gaaccccact tcactgggca gctc                               154
```

<210> SEQ ID NO 58
<211> LENGTH: 1460
<212> TYPE: DNA
<213> ORGANISM: Equus caballus

<400> SEQUENCE: 58

```
cggagatatg gacagatgga accaagagtg catggtattg ctcctccagg tctggaggaa    60
ggaactgcaa gtaaaacccc caaagattat cccagtaagc aggaccacca agagtccatc   120
caagggcatc tcgggcacaa agtccaccag gcactcagtg ctcaagcaaa tctatggtaa   180
ctatccttct gggcactttg tagtttacar ttagcacccc cagagagtgt cacgtcataa   240
tctggaatgg gatttaatta cattgggcaa acatccattc aggtaggaac tttattatac   300
ctccaggcac caagagaatc ctcagcacca catttagtgc ctccctccca gccattctgg   360
gtcagaattg gtttcataag acattctggc atcacaacaa agagcttctc tgctgggctc   420
catgactgaa agcctcaccr tctctccagg ccattgcttg ggtcttcccc ttacattgtc   480
ctcttggagg aacccaggca cagaccaacc ttgcctgcct cacttggacs tttcctatgc   540
tacgayagtg cagggttgtc catctgtggg actgccccag accgagcacc gcagtaaaca   600
cgcgtttagc agatgaactg ctccacctct ggaagagccc acccagagaa aggcagcagg   660
caacaagtct ggctggctcc crrcagaaga aagttgagct gaggcaccgt tagaaacaat   720
ctgtgaacag gcaggaaact ctcaggagtt gacctgggtc tacatggtat ttccatacca   780
tgcctaattt atcttggcag acacctgaag cctcaagcct tcacctcaac aaagaattca   840
gaacctggtc aggccacagc tctcakggtc agagatacat gattattgtt ggttgattgc   900
aggttgttct caagaaggga agtacatca tcccacaaga tcttcaaaag ctcattctgt   960
gctgcgtctc aactcaggta aggcaaacca ctgcactggc aaaaaaaacg ttagaacaga  1020
gatggccagg ggttcccaaa ggtcattttg atttccacta ggcatgggtt tcatcccgt   1080 ttcatggagt tgttactgca gtcaacatct gtctctataa ggggcaagtt attttccaaa  1140
taaaagctaa cattacctcc agtagaaact tgttcacata aaggaagggg gaaatgaaaa  1200
tgctatcgtt cttcaaagta ataccttggg aattcttgtt tcattttggt ttcacattag  1260
katcctccag ttccttccca aagatgacaa aaagtccttt accacaaatt ctggcttttg  1320 cctttttagga cctactccat aaagatgtgt aatatttaat agcatgttca gctcaggctc  1380
agctgtgcac attttcactc atccaagagc agctcaggga actttctttt cagccacaag  1440
acaggagtgy ttactcagag                                             1460
```

<210> SEQ ID NO 59
<211> LENGTH: 809
<212> TYPE: DNA
<213> ORGANISM: Equus caballus

<400> SEQUENCE: 59

```
cttacaacct gcaatcagct attcaatcaa aaaacaaaac aaaagcttcg accgcctgyg    60
gaggaagact gtgtccaggg gcgctggaat agctagtgca gagtgctaat tctccgctca   120
ttatctccga catcttggga aaacgttaat acccatgcct gcagccttac tggcctgaaa   180
```

| | |
|---|---|
| acgtgttaac aactgaaaga gaatgtcaga atrtttcctt tctgctctca cacagcactg | 240 |
| ttttgtaaat tctcttagcc tgagctcaag gaccaggga aactatgcct gtgcaaaact | 300 |
| gcccagctgt ctgccttcac ctcagtcacg acggctggaa agaagaattt ataattaacg | 360 |
| gtaaagtcta agtaacacta agaacatagg tgctaaagag gctgctgggt tgggatttcg | 420 |
| gccagccagc tgctgctggc ctggtgtttt ggttccagtg aagaactgga atcagatgag | 480 |
| gaggagcctg tcctacagta gctgccttgt ttcactactt ttctggaatc taatgcaaca | 540 |
| aacttcctta gagataccgc atcctgttat tccaacatta ttagttttaa attttagacc | 600 |
| agaatcataa tccagccttt gcttttagaa actgcaagac cataagaggt atactgttga | 660 |
| ttccttacat ttacagttcc catgttggcc tctgaaggcc acaggttgct gcctcgtcct | 720 |
| ctcagaatgg tgttctcgtc gctgagcacc agcagcagta ttgggcacta aggaatcagt | 780 |
| cgggcaggtt tacagaccag accattcat | 809 |

<210> SEQ ID NO 60
<211> LENGTH: 781
<212> TYPE: DNA
<213> ORGANISM: Equus caballus

<400> SEQUENCE: 60

| | |
|---|---|
| cgtctgcaga gaaaacaaca gcaatgtgac actgcacccg aacygctgtc tcctcaccgt | 60 |
| attcttcaca cccaaacgaa cagtatcctc atctgtaagt caccacagga aatcttactg | 120 |
| gaaaagggga cctattaact gggcattacc acaggcagcg aaaattccta gttacgacct | 180 |
| caagtacaag tactacyggt ttctcgtttg gtctgtgccc tcccatacat gctagagact | 240 |
| aatgaaattt caccatcaac aatcctacac tccagactcc cccmccttg gcattctagt | 300 |
| ctctcgctct ctgcactcaa atcaactgag aacacttcca cagagccgcc tgccaagtcc | 360 |
| tgtcattctc ttccttatgg aggtgagctg attctctaac ctcagaataa tccaaattct | 420 |
| tgactttct tcccttctac tatttctgaa ttattattat atataccaat taataaaccc | 480 |
| ccccaatcma ataccctatac aaaaaaccct ctaactctcc caaaccaaaa acaccaaaag | 540 |
| gaatcctaga ttacagagct gcctccacaa cacagagaac caagctccag acaaagctga | 600 |
| agctgtgact tccttcttcc aacttcttct tactctccgg tgaactaagt gactagagat | 660 |
| tggcctaaaa tttattactg ccaaataatt tccctaatga cagctagcat ttggtgagca | 720 |
| cttaataaat gttagctata ctaaaaacat tatttggatt atctcattta acggtcacca | 780 |
| a | 781 |

<210> SEQ ID NO 61
<211> LENGTH: 768
<212> TYPE: DNA
<213> ORGANISM: Equus caballus

<400> SEQUENCE: 61

| | |
|---|---|
| ttttctgtta cacaaaaaaa gagattcatt ggtaaagatt gggtttgcca tagccaggag | 60 |
| tgagtgagtc tycagaagtc taagcttaat acattccatg gcctttcaca gcatgatgct | 120 |
| gtggcaagaa ctgagaaatc ttggtgtttt cctggctgc taactaatta attctgtgcc | 180 |
| cttgggaaaa tctcttttcc caggacctta ctttctacat ctgtgcaatg aaggaccttg | 240 |
| aaattctacc tcagatcctt ctgtcttgta atgctttaat taacatgtgt ctggtgtcag | 300 |
| tgtattgtga atccagcatc cagactgggg tctaattttc acctagagct ttggggtcta | 360 |
| aagctgggat gtcacctggc aggctcaagg cctartcact ggaagcaggg agctcagcca | 420 |

```
tgagcctgac ttgtcttctg gccagtctct tgttccctcg gtattaaatt cacactaggt    480
atgcctgggt ttttgctttt aacttcttcc agtgtttcca ctttgacctc tggctttat     540 tataataatt tattaagtgc aaggaaggga tcacaaactt tatcttccag aggactttca    600
cctgtttgga tattttcag gcgtatctat tccctctttt ctttaaatat tattttcctt    660
aagttggaag agtactgctt tgaattcccc gtgctctttt ctccctgctc tcaaacttcc    720
aatccttagc ccgtgtgtct ccaaagatcc ccacttttt ttaacctg                  768
```

<210> SEQ ID NO 62
<211> LENGTH: 564
<212> TYPE: DNA
<213> ORGANISM: Equus caballus

<400> SEQUENCE: 62

```
gagcaactta agaagatgg gacacttcca acaaacaata gaaagcttaa cataaaggta     60
agtcwtaagt gttgttttga taaaataaga ttttctttca aatcatctrg aatgttgtgt   120
ttttgtgaaa agttgtttta actcttaggg tttattaatg gctgaagttt ggagttcatc   180
tgttattcat atgtgatgtt gccatggcag ctttcccacc tcgtccagaa agacttgctc   240
agctaaaccc acagtggttt ctccctgtct acttatttga tgatttaata tatcatctca   300
aagkarttct tgtgtttaac tttttgatgt gtcaaggtgt ttttttttgtt tgtttgtttt   360 ggtgaggaag attggcccta cactaacatc tgttgccagt cctcctcttt ttagttgaag   420
aagattgtta ctgagctaat actgtgctag tcttcctcta ttttgtgtgt gccacacact   480
gccacastgt ggcttaacga gtggtgctag gtctgcgcca tggatccgaa cctgcaaacc   540
tygggctccc aaagcagagg acat                                          564
```

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63

```
agcatggttt agctgttttt taaa                                           24
```

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64

```
ctgtgtggta gtaatggaat g                                              21
```

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65

```
cccaaaggac ataaaggaca                                                20
```

<210> SEQ ID NO 66

```
<211> LENGTH: 17
<212> TYPE: DNA
<213> ORGANISM: Artificial Sequence
<220> FEATURE:
<223> OTHER INFORMATION: Primer

<400> SEQUENCE: 66
aagwgaaaca tcattcc                                                    17

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
caataaattg gtcaacctaa cacg                                            24

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
catggtgtat tccccttcca                                                 20

<210> SEQ ID NO 69
<211> LENGTH: 16
<212> TYPE: DNA
<213> ORGANISM: Artificial Sequence
<220> FEATURE:
<223> OTHER INFORMATION: Primer

<400> SEQUENCE: 69
ytataaaaag agggct                                                     16

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
caataaattg gtcaacctaa cacg                                            24

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
catggtgtat tccccttcca                                                 20

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
```

-continued

| | |
|---|---|
| cacagatagt gcattccaga tagg | 24 |

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73

| | |
|---|---|
| ggtcgagatg gagggggaata | 20 |

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74

| | |
|---|---|
| ctgcagtgtt taagtttagg attga | 25 |

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75

| | |
|---|---|
| taaagctcat ggaggccaat | 20 |

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76

| | |
|---|---|
| ttctacttcc agctattccg ct | 22 |

<210> SEQ ID NO 77
<211> LENGTH: 15
<212> TYPE: DNA
<213> ORGANISM: Artificial Sequence
<220> FEATURE:
<223> OTHER INFORMATION: Primer

<400> SEQUENCE: 77

| | |
|---|---|
| aaytaacctg gtgac | 15 |

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78

| | |
|---|---|
| tgcaccttgc ctttctttt | 20 |

<210> SEQ ID NO 79
<211> LENGTH: 20
<212> TYPE: DNA

```
<213> ORGANISM: Artificial Sequence
<220> FEATURE:
<223> OTHER INFORMATION: Primer

<400> SEQUENCE: 79
cagcaatccg ctttttcttt                                                     20

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
tccctttatc tcttgcacaa t                                                   21

<210> SEQ ID NO 81
<211> LENGTH: 14
<212> TYPE: DNA
<213> ORGANISM: Artificial Sequence
<220> FEATURE:
<223> OTHER INFORMATION: Primer

<400> SEQUENCE: 81
kcctggtata tagt                                                           14

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
gcattttaca tgtattggca ggt                                                 23

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
cctcagtttc ctcatccgta a                                                   21

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
cccatgaggt atgacgtagg                                                     20

<210> SEQ ID NO 85
<211> LENGTH: 18
<212> TYPE: DNA
<213> ORGANISM: Artificial Sequence
<220> FEATURE:
<223> OTHER INFORMATION: Primer

<400> SEQUENCE: 85
trtcatgatc atgatgtc                                                       18
```

```
<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
tgtgacctct gtcctctctc c                                              21

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
atatcttgcg cgctgaatg                                                 19

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
gtgtagaagc ggggacgtc                                                 20

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
yggcgaggcg aagcggctg                                                 19

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
catgcatcac ttaacaacag agg                                            23

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
gtcaacgacg gaccacata                                                 19

<210> SEQ ID NO 92
<211> LENGTH: 17
<212> TYPE: DNA
<213> ORGANISM: Artificial Sequence
<220> FEATURE:
```

```
<223> OTHER INFORMATION: Primer

<400> SEQUENCE: 92
ctacacacct aggctct                                                    17

<210> SEQ ID NO 93
<211> LENGTH: 14
<212> TYPE: DNA
<213> ORGANISM: Artificial Sequence
<220> FEATURE:
<223> OTHER INFORMATION: Primer

<400> SEQUENCE: 93
rtggtactaa tctt                                                       14

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
aacctcaaag catcatcttg tg                                              22

<210> SEQ ID NO 95
<211> LENGTH: 18
<212> TYPE: DNA
<213> ORGANISM: Artificial Sequence
<220> FEATURE:
<223> OTHER INFORMATION: Primer

<400> SEQUENCE: 95
tctctagtcc cagctctg                                                   18

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
tcaaagtaac gatggggact                                                 20

<210> SEQ ID NO 97
<211> LENGTH: 17
<212> TYPE: DNA
<213> ORGANISM: Artificial Sequence
<220> FEATURE:
<223> OTHER INFORMATION: Primer

<400> SEQUENCE: 97
yagaggcctg aaggcgc                                                    17

<210> SEQ ID NO 98
<211> LENGTH: 21
<212> TYPE: DNA
<213> ORGANISM: Artificial Sequence
<220> FEATURE:
<223> OTHER INFORMATION: Primer

<400> SEQUENCE: 98
gtacgagagc tgcaacataa c                                               21
```

```
<210> SEQ ID NO 99
<211> LENGTH: 18
<212> TYPE: DNA
<213> ORGANISM: Artificial Sequence
<220> FEATURE:
<223> OTHER INFORMATION: Primer

<400> SEQUENCE: 99
gagctgccca gtgaagtg                                                        18

<210> SEQ ID NO 100
<211> LENGTH: 24
<212> TYPE: DNA
<213> ORGANISM: Artificial Sequence
<220> FEATURE:
<223> OTHER INFORMATION: Primer

<400> SEQUENCE: 100
ggttcgaaat aagttatcat aaga                                                 24

<210> SEQ ID NO 101
<211> LENGTH: 12
<212> TYPE: DNA
<213> ORGANISM: Artificial Sequence
<220> FEATURE:
<223> OTHER INFORMATION: Primer

<400> SEQUENCE: 101
ygttatgttg ca                                                              12

<210> SEQ ID NO 102
<211> LENGTH: 22
<212> TYPE: DNA
<213> ORGANISM: Artificial Sequence
<220> FEATURE:
<223> OTHER INFORMATION: Primer

<400> SEQUENCE: 102
tcagtgctca agcaaatcta tg                                                   22

<210> SEQ ID NO 103
<211> LENGTH: 22
<212> TYPE: DNA
<213> ORGANISM: Artificial Sequence
<220> FEATURE:
<223> OTHER INFORMATION: Primer

<400> SEQUENCE: 103
aatcccattc cagattatga cg                                                   22

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
ctgggcactt tgtagtttac a                                                    21

<210> SEQ ID NO 105
<211> LENGTH: 15
<212> TYPE: DNA
<213> ORGANISM: Artificial Sequence
<220> FEATURE:
<223> OTHER INFORMATION: Primer
```

```
<400> SEQUENCE: 105
rttagcaccc ccaga                                                   15

<210> SEQ ID NO 106
<211> LENGTH: 19
<212> TYPE: DNA
<213> ORGANISM: Artificial Sequence
<220> FEATURE:
<223> OTHER INFORMATION: Primer

<400> SEQUENCE: 106
agaacctggt caggccaca                                               19

<210> SEQ ID NO 107
<211> LENGTH: 23
<212> TYPE: DNA
<213> ORGANISM: Artificial Sequence
<220> FEATURE:
<223> OTHER INFORMATION: Primer

<400> SEQUENCE: 107
tcttgtggga tgatgtactt tcc                                          23

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
ataatcatgt atctctgacc                                              20

<210> SEQ ID NO 109
<211> LENGTH: 11
<212> TYPE: DNA
<213> ORGANISM: Artificial Sequence
<220> FEATURE:
<223> OTHER INFORMATION: Primer

<400> SEQUENCE: 109
mtgagagctg t                                                       11

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
caagagcagc tcagggaact                                              20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
ctggcattag ctgctgacag                                              20

<210> SEQ ID NO 112
<211> LENGTH: 20
```

```
<212> TYPE: DNA
<213> ORGANISM: Artificial Sequence
<220> FEATURE:
<223> OTHER INFORMATION: Primer

<400> SEQUENCE: 112
tcagccacaa gacaggagtg                                               20

<210> SEQ ID NO 113
<211> LENGTH: 11
<212> TYPE: DNA
<213> ORGANISM: Artificial Sequence
<220> FEATURE:
<223> OTHER INFORMATION: Primer

<400> SEQUENCE: 113
yttactcaga g                                                        11

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
catgcctgca gccttactg                                                19

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
ggtccttgag ctcaggctaa                                               20

<210> SEQ ID NO 116
<211> LENGTH: 22
<212> TYPE: DNA
<213> ORGANISM: Artificial Sequence
<220> FEATURE:
<223> OTHER INFORMATION: Primer

<400> SEQUENCE: 116
ctgtgtgaga gcagaaagaa aa                                            22

<210> SEQ ID NO 117
<211> LENGTH: 15
<212> TYPE: DNA
<213> ORGANISM: Artificial Sequence
<220> FEATURE:
<223> OTHER INFORMATION: Primer

<400> SEQUENCE: 117
yattctgaca ttcac                                                    15

<210> SEQ ID NO 118
<211> LENGTH: 18
<212> TYPE: DNA
<213> ORGANISM: Artificial Sequence
<220> FEATURE:
<223> OTHER INFORMATION: Primer

<400> SEQUENCE: 118
```

```
cgtctgcaga gaaaacaa                                                    18

<210> SEQ ID NO 119
<211> LENGTH: 18
<212> TYPE: DNA
<213> ORGANISM: Artificial Sequence
<220> FEATURE:
<223> OTHER INFORMATION: Primer

<400> SEQUENCE: 119
gaggatactg ttcgtttg                                                    18

<210> SEQ ID NO 120
<211> LENGTH: 19
<212> TYPE: DNA
<213> ORGANISM: Artificial Sequence
<220> FEATURE:
<223> OTHER INFORMATION: Primer

<400> SEQUENCE: 120
tgtgacactg cacccgaac                                                   19

<210> SEQ ID NO 121
<211> LENGTH: 15
<212> TYPE: DNA
<213> ORGANISM: Artificial Sequence
<220> FEATURE:
<223> OTHER INFORMATION: Primer

<400> SEQUENCE: 121
ygctgtctcc tcacc                                                       15

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ggggtctaaa gctgggatgt                                                  20

<210> SEQ ID NO 123
<211> LENGTH: 19
<212> TYPE: DNA
<213> ORGANISM: Artificial Sequence
<220> FEATURE:
<223> OTHER INFORMATION: Primer

<400> SEQUENCE: 123
cagtctcttg ttccctcgg                                                   19

<210> SEQ ID NO 124
<211> LENGTH: 18
<212> TYPE: DNA
<213> ORGANISM: Artificial Sequence
<220> FEATURE:
<223> OTHER INFORMATION: Primer

<400> SEQUENCE: 124
tggcaggctc aaggccta                                                    18

<210> SEQ ID NO 125
<211> LENGTH: 16
<212> TYPE: DNA
<213> ORGANISM: Artificial Sequence
```

```
<220> FEATURE:
<223> OTHER INFORMATION: Primer

<400> SEQUENCE: 125
rtcactggaa gcaggg                                                        16

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
tgggacactt ccaacaaaca                                                    20

<210> SEQ ID NO 127
<211> LENGTH: 24
<212> TYPE: DNA
<213> ORGANISM: Artificial Sequence
<220> FEATURE:
<223> OTHER INFORMATION: Primer

<400> SEQUENCE: 127
ccaaacttca gccattaata aacc                                               24

<210> SEQ ID NO 128
<211> LENGTH: 18
<212> TYPE: DNA
<213> ORGANISM: Artificial Sequence
<220> FEATURE:
<223> OTHER INFORMATION: Primer

<400> SEQUENCE: 128
ttatcaaaac aacactta                                                      18

<210> SEQ ID NO 129
<211> LENGTH: 19
<212> TYPE: DNA
<213> ORGANISM: Artificial Sequence
<220> FEATURE:
<223> OTHER INFORMATION: Primer

<400> SEQUENCE: 129
wgacttacct ttatgttaa                                                     19

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130
cctatgtcga caatctttgt ac                                                 22

<210> SEQ ID NO 131
<211> LENGTH: 24
<212> TYPE: DNA
<213> ORGANISM: Artificial Sequence
<220> FEATURE:
<223> OTHER INFORMATION: Primer

<400> SEQUENCE: 131
attagtagca gaacgaagaa attc                                               24
```

```
<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
tgagaaatat ttgatgcttt                                                20

<210> SEQ ID NO 133
<211> LENGTH: 13
<212> TYPE: DNA
<213> ORGANISM: Artificial Sequence
<220> FEATURE:
<223> OTHER INFORMATION: Primer

<400> SEQUENCE: 133
rttggctttt tta                                                       13

<210> SEQ ID NO 134
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 134
cugcugcugu gaauguugat t                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 135
ucaacauuca cagcagcagt g                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 136
guuuuaaacu gaaucuucat t                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 137
ugaagauuca guuuaaaaca g                                              21

<210> SEQ ID NO 138
<211> LENGTH: 21
<212> TYPE: DNA
<213> ORGANISM: Artificial Sequence
<220> FEATURE:
<223> OTHER INFORMATION: Synthetically generated oligonucleotide
```

```
<400> SEQUENCE: 138
gaucaaacca uauuguauut t                                              21

<210> SEQ ID NO 139
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 139
aauacaauau gguuugauct g                                              21

<210> SEQ ID NO 140
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 140
cacugagcau gaucacagat t                                              21

<210> SEQ ID NO 141
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 141
ucugugauca ugcucagugc t                                              21

<210> SEQ ID NO 142
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 142
cauuaaagac uuuuccuuat t                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 143
uaaggaaaag ucuuuaaugg a                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 144
ccacgagaaa uaugacaaut t                                              21
```

-continued

```
<210> SEQ ID NO 145
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 145
auugucauau uucucguggt t                                          21
```

METHODS AND MATERIALS RELATED TO HAIR PIGMENTATION AND CANCER

CROSS-REFERENCE TO RELATED APPLICATIONS

This application is a continuation of U.S. application Ser. No. 12/663,138, filed Jun. 24, 2010, which is a National Stage application under 35 U.S.C. §371 of International Application No. PCT/EP2008/057034, having an International Filing Date of Jun. 5, 2008, which claims the benefit of U.S. Provisional Application Ser. No. 60/942,080, filed Jun. 5, 2007. The disclosures of the prior applications are considered part of (and are incorporated by reference in) the disclosure of this application.

BACKGROUND

1. Technical Field

This document relates to methods and materials involved in detecting genetic mutations involved in loss of hair pigmentation and increased cancer susceptibility (e.g., increase susceptibility to form melanomas). This document also relates to methods and materials involved in treating cancer (e.g., melanoma).

2. Background Information

Grey horses are born colored but gradually loose hair pigmentation and eventually, by the age of 6-8 years, become shining white. The dominant Grey allele, manifested as a splendid white horse, has had a high impact on human culture and has left numerous marks in art and literature (e.g., Pegasus and the Unicorn) from Asia and Europe. It has most certainly been selected by humans due to the prestige of riding a white horse with its mystic charisma. Numerous kings, emperors, and other prominent people have been portrayed on a white horse. The mutation appears to have arisen more than 2,000 years ago since white horses are mentioned in ancient Greek literature as well as in the Bible; the Grey locus is by far the most common cause of white coat color in horses (Sponenberg, "Equine Coat Color Genetics," (Blackwell, Ames, Iowa, 2003)).

Grey causes a gradual loss of hair pigmentation whereas dark skin pigmentation is maintained. Furthermore, Grey horses can exhibit vitiligo and a very high incidence of dermal melanomas. It has been estimated that 70-80% of Grey horses older than 15 years of age possess melanomas (Sutton and Coleman, 1-34, R1RDC, Barton, Australia (1997) and Fleury et al., *Pigment Cell Res.*, 13:47-51 (2000)) and that the Grey mutation reduces longevity (Comfort, *Nature*, 182:1531-1532 (1958)).

The melanomas occur primarily as jet black firm nodules in the dermis of glabrous skin (e.g., under the tail root, in the anal, perianal, and genital regions, perineum, lips, and eyelids; Seltenhammer et al., *Pigment Cell Res.*, 17:674-681 (2004)). Initially, these primary multiple melanomas are benign but some develop metastases in several internal organs.

SUMMARY

This document relates to methods and materials for determining whether or not a horse contains a Grey allele. For example, this 5 document provides diagnostic methods such as nucleic acid-based detection methods and materials such as nucleic acid probes and primer pairs that can be used to determine whether or not a horse contains a duplication in intron 6 of STX17 nucleic acid. The presence of a duplication in intron 6 of STX17 nucleic acid can indicate that the horse contains a Grey allele and can gradually loose hair pigmentation and eventually, by the age of 6-8 years, become shining white. The presence of a duplication in intron 6 of STX17 nucleic acid also can indicate that the horse is susceptible to developing cancer (e.g., melanoma). Identifying horses that are heterozygous or homozygous for a Grey allele can provide horse breeders and horse owners important information about individual horses and their offspring. For example, a newborn horse that is born pigmented can be assessed as described herein to determine whether or not that horse will loose its pigment and become a shining white horse.

This document also relates to methods and materials for treating a mammal having or being likely to develop cancer (e.g., benign, malignant, or metastatic cancer). For example, this document provides methods and materials for treating cancer in a mammal by administering an agent having the ability to reduce expression of an STX17 polypeptide and/or an NR4A polypeptide (e.g., an NR4A3 polypeptide) in the mammal. Having the ability to treat cancer can help clinicians reduce the considerable morbidity and mortality associated with cancer.

The methods and materials provided herein are based, in part, on the discovery that a duplication in intron 6 of STX17 nucleic acid is responsible for the phenotype observed in horses that are homozygous or heterozygous for a Grey allele. The horse STX17 gene is located at chromosome 25 between positions 28,971,292 and 29,022,566 bp on the horse genome assembly as presented on the UCSC server at "genome.ucsc.edu" (Build January 2007 (equCab1) assembly), and nucleic acid sequences for an intron 6 of an STX17 nucleic acid from a Grey allele and a non-Grey allele are provided in FIGS. 11 and 12, respectively. The methods and materials provided herein also are based, in part, on the discovery that a duplication in intron 6 of STX17 nucleic acid can be a cis-acting mutation that allows for over-expression of both STX17 nucleic acid and neighboring NR4A3 nucleic acid in melanomas from Grey horses. NR4A3 polypeptides are members of the NR4A orphan nuclear receptor family. Over-expression of an STX17 nucleic acid (e.g., over-expression of an STX17 polypeptide or STX17 RNA sequence) or an NR4A3 nucleic acid (e.g., over-expression of an NR4A3 polypeptide or NR4A3 RNA sequence) can be a cause for the Grey phenotypes. Without being limited to any particular mechanism of action, the Grey allele can cause premature hair graying, due to a hyperproliferation of melanocytes in hair follicles depleting the pool of melanocyte stem cells, and melanomas, due to the proliferation of certain dermal melanocytes present in glabrous skin.

In general, one aspect of this document features a method for identifying a horse having a Grey allele. The method comprises, or consists essentially of; obtaining sequence information from the region of nucleic acid located between single nucleotide polymorphisms NR4A3.2 and INVS.3 (see, e.g., Table 4) to determine whether or not the horse comprises a duplication in intron 6 of STX17 nucleic acid, wherein the presence of the duplication indicates that the horse contains the Grey allele. The horse can be a foal. The horse can comprise black, brown, or chestnut hair. The obtaining sequence information step can comprise sequencing a portion of the intron 6 to determine whether or not the horse comprises the duplication. The obtaining sequence information step can comprise determining whether or not the horse comprises a polymorphism linked to the duplication. The obtaining sequence information step can comprise using a nucleic acid probe capable of detecting a breakpoint of the duplication to determine whether or not the horse comprises the duplication.

The nucleic acid probe can comprise the nucleic acid sequence set forth in SEQ ID NO:32. The obtaining sequence information step can comprise using a nucleic acid primer pair capable of amplifying nucleic acid comprising a breakpoint of the duplication to determine whether or not the horse comprises the duplication. The method can comprise determining whether or not the horse is homozygous for the duplication. The method can comprise determining whether or not the horse is heterozygous for the duplication.

In another aspect, this document features a method for genotyping a horse. The method comprises, or consists essentially of, (a) determining whether or not the horse comprises a duplication in intron 6 of STX17 nucleic acid, and (b) classifying the horse as containing a Grey allele if the horse comprises the duplication, and classifying the horse as lacking a Grey allele if the horse does not comprise the duplication. The horse can be a foal. The horse can comprise black, brown, or chestnut hair. The determining step can comprise sequencing a portion of the intron 6. The determining step can comprise determining whether or not the horse comprises a polymorphism linked to the duplication. The determining step can comprise using a nucleic acid probe capable of detecting a breakpoint of the duplication. The nucleic acid probe can comprise the nucleic acid sequence set forth in SEQ ID NO:32. The determining step can comprise using a nucleic acid primer pair capable of amplifying nucleic acid comprising a breakpoint of the duplication. The method can comprise determining whether or not the horse is homozygous for the duplication. The method can comprise classifying the horse as being homozygous for the Grey allele if the horse is homozygous for the duplication. The method can comprise determining whether or not the horse is heterozygous for the duplication. The method can comprise classifying the horse as being heterozygous for the Grey allele if the horse is heterozygous for the duplication.

In another aspect, this document features an isolated nucleic acid molecule comprising, or consisting essentially of, a nucleic acid sequence, wherein the nucleic acid sequence comprises a sequence present in a duplication of intron 6 of STX17 nucleic acid of a Grey allele from a horse, and wherein the nucleic acid molecule is capable of detecting a breakpoint of the duplication. The isolated nucleic acid molecule can comprise a label. The isolated nucleic acid molecule can be between 15 and 100 nucleotides in length.

In another aspect, this document features an isolated nucleic acid primer pair comprising a first primer and a second primer, wherein each of the first and second primers comprises a sequence present in a duplication of intron 6 of STX17 nucleic acid of a Grey allele from a horse, and wherein the primer pair is capable of amplifying nucleic acid containing a breakpoint of the duplication.

In another aspect, this document features a method for treating a mammal having cancer. The method comprises, or consists essentially of, administering, to the mammal, a composition comprising an agent having the ability to reduce an NR4A3 polypeptide activity or an STX17 polypeptide activity in the mammal. The mammal can be a horse or a human. The cancer can be melanoma. The agent can comprise a nucleic acid molecule capable of inducing RNA interference against expression of a NR4A3 polypeptide. The agent can comprise a nucleic acid molecule capable of inducing RNA interference against expression of a STX17 polypeptide. The composition can comprise a nucleic acid molecule capable of inducing RNA interference against expression of a NR4A3 polypeptide and a nucleic acid molecule capable of inducing RNA interference against expression of a STX17 polypeptide. The composition can comprise a nucleic acid molecule having a nucleic acid sequence capable of inducing RNA interference against expression of a NR4A3 polypeptide and a nucleic acid sequence capable of inducing RNA interference against expression of a STX17 polypeptide. The agent can comprise an anti-NR4A3 antibody. The agent can comprise an anti-STX17 antibody. The composition can comprise an anti-NR4A3 antibody and an anti-STX17 antibody. The composition can comprise a cyclin D2 inhibitor. The cyclin D2 inhibitor can be selected from the group consisting of flavopiridols, nucleic acid molecules capable of inducing RNA interference against expression of a cyclin D2 polypeptide, anti-cyclin D2 antibodies, suberoylanilide hydroxamic acid, rapamycin, Rugosin E, and THRX-165724. The composition can comprise a MC1R inhibitor. The MC inhibitor can be selected from the group consisting of nucleic acid molecules capable of inducing RNA interference against expression of a MC1R polypeptide, anti-MC1R antibodies, and polypeptide antagonists of MC1R polypeptide activity.

In another aspect, this document features a method for treating a horse suspected to develop a melanoma. The method comprises, or consists essentially of, administering, to the horse, a composition comprising an agent having the ability to reduce an NR4A3 polypeptide activity or an STX17 polypeptide activity in the horse. The horse can comprise a homozygous Grey allele genotype. The horse can comprise a heterozygous Grey allele genotype. The agent can comprise a nucleic acid molecule capable of inducing RNA interference against expression of a NR4A3 polypeptide. The agent can comprise a nucleic acid molecule capable of inducing RNA interference against expression of a STX17 polypeptide. The composition can comprise a nucleic acid molecule capable of inducing RNA interference against expression of a NR4A3 polypeptide and a nucleic acid molecule capable of inducing RNA interference against expression of a STX17 polypeptide. The composition can comprise a nucleic acid molecule having a nucleic acid sequence capable of inducing RNA interference against expression of a NR4A3 polypeptide and a nucleic acid sequence capable of inducing RNA interference against expression of a STX17 polypeptide. The agent can comprise an anti-NR4A3 antibody. The agent can comprise an anti-STX17 antibody. The composition can comprise an anti-NR4A3 antibody and an anti-STX17 antibody. The composition can comprise a cyclin D2 inhibitor. The cyclin D2 inhibitor can be selected from the group consisting of flavopiridols, nucleic acid molecules capable of inducing RNA interference against expression of a cyclin D2 polypeptide, anti-cyclin D2 antibodies, suberoylanilide hydroxamic acid, rapamycin, Rugosin E, and THRX-165724. The composition can comprise a MC1R inhibitor. The MC inhibitor can be selected from the group consisting of nucleic acid molecules capable of inducing RNA interference against expression of a MC1R polypeptide, anti-MC1R antibodies, and polypeptide antagonists of MC1R polypeptide activity.

In another aspect, this document features a method for identifying an agent for treating cancer. The method comprises, or consists essentially of, (a) identifying a test agent as having the ability to reduce an NR4A3 polypeptide activity or an STX17 polypeptide activity in a mammal, (b) administering the test agent to a horse comprising a Grey allele and a melanoma, and (c) determining whether or not the melanoma is reduced in the horse, wherein a reduction in the melanoma indicates that the test agent is the agent for treating cancer.

In another aspect, this document features a method for identifying an agent for reducing the probability of developing cancer. The method comprises, or consists essentially of, (a) administering a test agent to a population of horses having a heterozygous or homozygous Grey allele genotype, wherein the population of horses comprises horses without observable melanomas, and (b) determining whether or not the population of horses develops melanomas at a lower degree of incidence than a control population of horses not administered the test agent, wherein a presence of the lower degree of incidence indicates that the test agent is the agent for reducing the probability of developing cancer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 11 is a sequence listing of a nucleotide sequence for an intron 6 of an STX17 nucleic acid from a Grey allele (SEQ ID NO:1). Polymorphic positions that are different for Grey alleles plus ancestral, non-grey alleles versus non-ancestral, non-Grey alleles are shaded. The first copy of the duplication is singly underlined (SEQ ID NO:2), and the second copy of the duplication is doubly underlined (SEQ ID NO:2). The breakpoint between the two copies is indicated by an arrow.

FIG. 12 is a sequence listing of a nucleotide sequence for an intron 6 of an STX17 nucleic acid from a non-Grey allele (SEQ ID NO:3). Polymorphic positions that are different for Grey alleles plus ancestral non-Grey alleles versus non-ancestral, non-Grey alleles are shaded. The sequence duplicated in the nucleic acid sequence of a Grey allele is underlined (SEQ ID NO:4).

FIG. 13 is a sequence listing of a nucleotide sequence of a cDNA of a horse 5 STX17 nucleic acid (SEQ ID NO:5). The start and stop codons are underlined.

FIG. 14 is a sequence listing of a nucleotide sequence of a cDNA of a horse short STXI7 nucleic acid (SEQ ID NO:6). The start and stop codons are underlined.

FIG. 15 is a sequence listing of an amino acid sequence of a horse STXI7 polypeptide (SEQ ID NO:7).

FIG. 16 is a sequence listing of a nucleotide sequence of a cDNA of a horse NR4A3 nucleic acid (SEQ ID NO:8). The start and stop codons are underlined.

FIG. 17 is a sequence listing of an amino acid sequence of a horse NR4A3 polypeptide (SEQ ID NO:9).

FIG. 18 is a sequence listing of a nucleotide sequence of a cDNA of a human STX17 nucleic acid (SEQ ID NO:10). The start and stop codons are underlined.

FIG. 19 is a sequence listing of a nucleotide sequence of a cDNA of a human short STXI7 nucleic acid (SEQ ID NO:11). The start and stop codons are underlined.

FIG. 20 is a sequence listing of an amino acid sequence of a human STX17 polypeptide (SEQ ID NO:12).

FIG. 21 is a sequence listing of a nucleotide sequence of a cDNA of a human NR4A3 nucleic acid (SEQ ID NO:13). The start and stop codons are underlined.

FIG. 22 is a sequence listing of an amino acid sequence of a human NR4A3 polypeptide (SEQ ID NO:14).

FIG. 23 is a sequence alignment of amino acid sequences of a human STX17 polypeptide (SEQ ID NO:12) and a horse STX17 polypeptide (SEQ ID NO:7). The "*" indicates positions that have a single, fully conserved residue. The ":" indicates that the amino acid difference between the horse and human sequences is a highly conservative difference within one of the following groups of amino acid residues: STA; NEQK; NHQK; NDEQ; QHRK; MILV; MILF; HY; and FYW. The "." indicates that the amino acid difference between the horse and human sequences is a moderately conservative difference within one of the following groups of amino acid residues: CSA; ATV; SAG; STNK; STPA; SGND; SNDEQK; NDEQHK; NEQHRK; FVLIM; and HFY.

FIG. 24 is a sequence alignment of amino acid sequences of a human NR4A3 polypeptide (SEQ ID NO:14) and a horse NR4A3 polypeptide (SEQ ID NO:9). The "*" indicates positions that have a single, fully conserved residue. The ":" indicates that the amino acid difference between the horse and human sequences is a highly conservative difference within one of the following groups of amino acid residues: STA; NEQK; NHQK; NDEQ; QHRK; MILV; MILF; HY; and FYW. The "." indicates that the amino acid difference between the horse and human sequences is a moderately conservative difference within one of the following groups of amino acid residues: CSA; ATV; SAG; STNK; STPA; SGND; SNDEQK; NDEQHK; NEQHRK; FVLIM; and HFY.

FIG. 25 is a sequence listing of an amino acid sequence of a human NR4A1 polypeptide (SEQ ID NO:15).

FIG. 26 is a sequence listing of an amino acid sequence of a human NR4A2 polypeptide (SEQ ID NO:16).

FIG. 27 is a sequence alignment of amino acid sequences of a human NR4A1 polypeptide (SEQ ID NO:15), a human NR4A2 polypeptide (SEQ ID NO:16), and a human NR4A3 polypeptide (SEQ ID NO:14). The "*" indicates positions that have a single, fully conserved residue. The ":" indicates that the amino acid difference is a highly conservative difference within one of the following groups of amino acid residues: STA; NEQK; NHQK; NDEQ; QHRK; MILV; MILF; HY; and FYW. The "." indicates that the amino acid difference is a moderately conservative difference within one of the following groups of amino acid residues: CSA; ATV; SAG; STNK; STPA; SGND; SNDEQK; NDEQHK; NEQHRK; FVLIM; and HFY.

FIG. 28 is a sequence listing of an amino acid sequence of a human cyclin D1 polypeptide (SEQ ID NO:17).

FIG. 29 is a sequence listing of an amino acid sequence of a human cyclin D2 polypeptide (SEQ ID NO:18).

FIG. 30 is a sequence alignment of amino acid sequences of a human cyclin D1 polypeptide (SEQ ID NO:17) and a human cyclin D2 polypeptide (SEQ ID NO:18). The "*" indicates positions that have a single, fully conserved residue. The ":" indicates that the amino acid difference is a highly conservative difference within one of the following groups of amino acid residues: STA; NEQK; NHQK; NDEQ; QHRK; MILV; MILF; HY; and FYW. The "." indicates that the amino acid difference is a moderately conservative difference within one of the following groups of amino acid residues: CSA; ATV; SAG; STNK; STPA; SGND; SNDEQK; NDEQHK; NEQHRK; FVLIM; and HFY.

FIG. 31 is a sequence listing of an amino acid sequence of a horse MC1R polypeptide (SEQ ID NO:19).

FIG. 32 is a sequence listing of a nucleotide sequence of a cDNA of a horse MC1R nucleic acid (SEQ ID NO:20). The start and stop codons are underlined.

DETAILED DESCRIPTION

Figure 1:
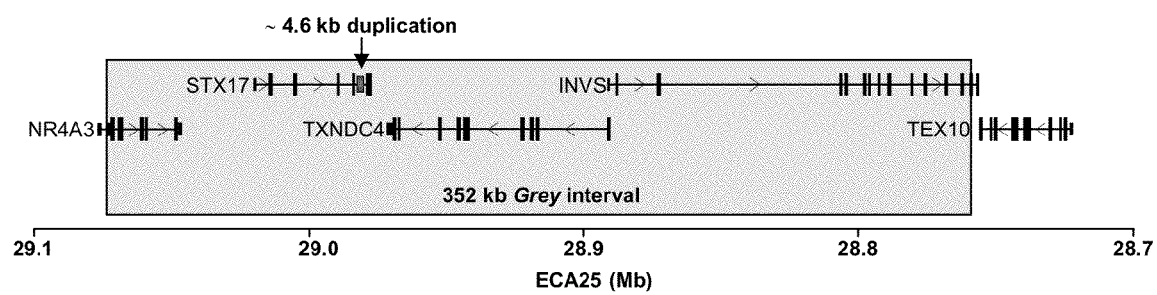
FIG. 1 is a schematic diagram of the gene content of the Grey interval based on the human genome assembly as presented on the UCSC server at "genome.ucsc.edu"; Build March 2006 (hg 18) assembly/NCBI Build 36.1; Karolchik et al., *Nucl. Acids Res.*, 31(1):51-54 (2003)). The 472 kb region exhibiting complete association with Grey is indicated by a box, and the location of the 4.6 kb duplication in STX17 intron 6 is marked with an arrow.

This document relates to methods and materials for determining whether or not a horse contains a Grey allele (e.g., contains a heterozygous Grey allele genotype or a homozygous Grey allele genotype). For example, this document provides diagnostic methods and materials such as nucleic acid probes and primer pairs that can be used to determine whether or not a horse contains a duplication in intron 6 of STX17 nucleic acid. The presence of a duplication in intron 6 of STX17 nucleic acid can indicate that the horse contains a Grey allele and can gradually loose hair pigmentation and eventually, by the age of 6-8 years, become shining white.

The methods and materials provided herein can be used to determine whether or not any type of horse contains a Grey allele. For example, the horse can be an American quarter horse, an American standard bred horse, an Arabian horse, an Hanoverian horse, a Morgan horse, a Palomino horse, a Thoroughbred horse, a Miniature horse, a Mustang horse, a Lippizaner horse, a Connemara horse, or an Icelandic horse. In some cases, the horse can be a horse fetus, a newborn horse, a foal, a colt, a filly, a stallion, a mare, or an adult horse. The horse can be any color including, without limitation, white, grey, black, brown, or chestnut. In some cases, a newborn horse that is black, brown, or chestnut can be assessed using the methods and materials provided herein to determine whether or not it has a heterozygous or homozygous Grey allele genotype. In some cases, an adult horse that gradually changed from a dark colored horse (e.g., brown colored horse) to a light colored horse (e.g., a white colored horse) can be assessed using the methods and materials provided herein to confirm the presence of a Grey allele or to distinguish between a heterozygous Grey allele genotype and a homozygous Grey allele genotype.

The term "intron 6 of STX17 nucleic acid" as used herein refers to a non-STX17 polypeptide-encoding nucleic acid sequence located between exons 6 and 7 of STX17 polypeptide-encoding nucleic acid. Examples of horse nucleic acid sequences for an intron 6 of an STX17 nucleic acid from a Grey allele and a non-Grey allele are provided in FIGS. 11 and 12, respectively. The nucleic acid sequence set forth in FIG. 11 contains a 4,577 nucleotide duplication. As described herein, a duplication present in intron 6 of STX17 nucleic acid such as the 4,577 nucleotide duplication set forth in FIG. 11 can be the genetic mutation responsible for the Grey allele in horses and the phenotypic characteristics associated with the Grey allele.

Any appropriate method can be used to detect a duplication in intron 6 of STXI7 nucleic acid and the presence of a Grey allele. For example, a duplication can be detected by nucleic acid sequencing, denaturing high performance liquid chromatography (DHPLC; Underhill et al., *Genome Res.*, 7:996-1005 (1997)), allele-specific hybridization (Stoneking et al., *Am. J. Hum. Genet.*, 48:370-382 (1991); and Prince et al., *Genome Res.*, 11(1): 152-162 (2001)), allele-specific restriction digests, polymorphism specific polymerase chain reactions, single-stranded conformational polymorphism detection (Schafer et al., *Nat. Biotechnol.*, 15:33-39 (1998)), infrared matrix-assisted laser desorption/ionization mass spectrometry (WO 99/57318), and combinations of such methods.

Genomic DNA can be used to detect a duplication in intron 6 of STXI7 nucleic acid. Genomic DNA can be extracted from a biological sample such as peripheral blood samples, hair roots, or tissues (e.g., mucosal scrapings of the lining of the mouth or from renal or hepatic tissue). Any appropriate method can be used to extract genomic DNA from a blood or tissue sample, including, for example, phenol extraction. In some cases, genomic DNA can be extracted with kits such as the QIAamp® Tissue Kit (Qiagen, Chatsworth, Calif.), the Wizard® Genomic DNA purification kit (Promega, Madison, Wis.), the Puregene DNA Isolation System (Gentra Systems, Minneapolis, Minn.), or the A.S.A.P.3 Genomic DNA isolation kit (Boehringer Mannheim, Indianapolis, Ind.).

Amplification methods such as PCR techniques can be used to determine whether or not a horse contains a duplication in intron 6 of STXl7 nucleic acid. For example, a primer pair designed to amplify PCR products containing a duplication breakpoint can be used to detect the presence of a duplication in intron 6 of STXl7 nucleic acid. Such a primer pair can contain a first primer that anneals upstream of the duplication breakpoint such that extension from that primer proceeds toward the duplication breakpoint and a second primer that anneals downstream of the duplication breakpoint such that extension from that primer also proceeds toward the duplication breakpoint. When a sample contains nucleic acid with the duplication, an appropriately sized PCR product containing the duplication breakpoint can be generated and detected, thereby identifying the sample as containing a duplication in intron 6 of STX17 nucleic acid. When a sample contains nucleic acid lacking the duplication, an appropriately sized PCR product containing the duplication breakpoint will not be generated and detected, thereby the sample can be identified as lacking a duplication in intron 6 of STX17 nucleic acid.

Examples of primer pairs that can be used to detect the presence of a duplication in intron 6 of STXl7 nucleic acid can include, without limitation, those set forth in Table 1.

TABLE 1

Primer pairs

| Primer pair | Sequence | | SEQ ID NO: | Tm | Product size (bp) |
|---|---|---|---|---|---|
| #1 | Forward | 5'-TTGTAGTATCAGCACCACCTGGGAACTC-3' | 21 | 68 | 902 |
|    | Reverse | 5'-TCATGTGTCTATCCCACTAGGAGGGA-3' | 22 | | |
| #2 | Forward | 5'-GTAGGTCTGCACCCAGGAAC-3' | 23 | 60 | 221 |
|    | Reverse | 5'-AGAAGTTGGGCAAGAGCAGA-3' | 24 | | |
| #3 | Forward | 5'-CACAGTATGGCTGCCAAAGA-3' | 25 | 59 | 391 |
|    | Reverse | 5'-CAAAGTGCCAGAGGGAAGTT-3' | 26 | | |

The nucleic acid sequences set forth in FIGS. 11 and 12 can be used to confirm that a particular primer pair can produce amplification product that can be used to distinguish between nucleic acid of a Grey allele and nucleic acid of a non-Grey allele.

Any appropriate method can be used to detect the presence or absence of amplification products. For example, a gel electrophoresis or real-time PCR techniques that include the use of dyes such as Sybergreen can be used.

The term "duplication breakpoint" as used herein refers to a nucleotide junction site of duplicated nucleic acid that is (1) present in the nucleic acid containing the duplication and (2) is not present in nucleic acid lacking the duplication. The duplication breakpoint for the nucleic acid set forth in FIG. 11 is the labeled CAA↓AAT duplication breakpoint. The arrow represents the junction between the two copies of the duplicated nucleic acid.

In some cases, a nucleic acid probe having the ability to hybridize to nucleic acid containing a duplication in intron 6 of STXl7 nucleic acid can be used to detect the presence of a duplication in intron 6 of STX17 nucleic acid. For example, a nucleic acid probe having the ability to hybridize to the duplication breakpoint of a Grey allele and not to nucleic acid from a non-Grey allele can be used to detect the presence of a duplication in intron 6 of STX17 nucleic acid. Such a nucleic acid probe can contain the 5'-CAA↓AAT-3' duplication breakpoint set forth in FIG. 11 or its complement. Examples of nucleic acid probes that can be used to detect the presence of a duplication in intron 6 of STX17 nucleic acid can include, without limitation, 5'-ACCTGGGAACTCATTAGAAATG-CAA↓AATCTCAGAATTGGAATTGAACTTA-3' (SEQ ID NO:27); 5'-GGAACTCATTAGAAATGCAA↓AATCTCA-GAATTGGAATTGA-3' (SEQ ID NO:28); 5'-AACTCATT-AGAAATGCAA↓AATCTCAGAATTG GAATT-3' (SEQ ID NO:29); 5'-TCATTAGAAATGCAA↓AATCTCAGAATTG-GA-3' (SEQ ID NO:30); 5'-CATTAGAAATGCAA↓AATC-TCAGAATTGG-3' (SEQ ID NO:31); 5'-AGAAATGCAA↓AATCTCAGAA-3' (SEQ ID NO:32); 5'-AAATGCAA↓AA-TCTCAG-3' (SEQ ID NO:33); 5'-TGCAA↓AATCT-3' (SEQ ID NO:34); 5'-GAAATGCAA↓AATCTCAG-3' (SEQ ID NO:35), and complements thereof. The nucleic acid sequences set forth in FIGS. 11 and 12 can be used to confirm that a particular nucleic acid probe can distinguish between nucleic acid of a Grey allele and nucleic acid of a non-Grey allele.

An amplification process can be performed before proceeding with a detection method. For example, nucleic acid such as nucleic acid from intron 6 of STX17 nucleic acid can be amplified and then directly sequenced. Dye primer sequencing can be used to increase the accuracy of detecting heterozygous samples. In some cases, an amplification process can be performed to amplify a duplication breakpoint, if present, and a nucleic acid probe having the ability to hybridize to the duplication breakpoint of a Grey allele and not to nucleic acid from a non-Grey allele can be used to detect the presence or absence of a duplication in intron 6 of STX17 nucleic acid.

In some cases, a polymorphism that co-segregates with a duplication in intron 6 of STX17 nucleic acid can be used as a marker to detect the presence or absence of the duplication in intron 6 of STX17 nucleic acid. Such a polymorphism can be present in the region of nucleic acid located between NR4A3.2 and INVS.3. Any appropriate method can be used to identify nucleic acid containing a polymorphism versus nucleic acid not containing the polymorphism. For example, a polymorphism in the region of nucleic acid located between NR4A3.2 and INVS.3 can be detected by, for example, DHPLC analysis. Genomic DNA can be isolated from a horse and sequences from a region of nucleic acid located between NR4A3.2 and INVS.3 can be amplified (e.g., by PCR) using primer pairs. After amplification, PCR products can be denatured and reannealed, such that an allele containing a polymorphism can reanneal with a wild-type allele to form a heteroduplex (i.e., a double-stranded nucleic acid with a mismatch at one or more positions). The reannealed products then can be subjected to DHPLC, which detects heteroduplexes based on their altered melting temperatures, as compared to homoduplexes that do not contain mismatches. Samples containing heteroduplexes can be sequenced by standard methods to identify mutant nucleotides.

Allele specific hybridization also can be used to detect a polymorphism in the region of nucleic acid located between NR4A3.2 and INVS.3. For example, samples of DNA or RNA from a horse can be amplified using a primer pair, and the resulting amplification products can be immobilized on a substrate (e.g., in discrete regions). Hybridization conditions can be selected such that a nucleic acid probe specifically binds to the sequence of interest, e.g., a region of nucleic acid located between NR4A3.2 and INVS.3 containing a particular polymorphism. Such hybridizations typically are performed under high stringency, as nucleotide polymorphisms can include only a single nucleotide difference versus a wild-type sequence. High stringency conditions can include the use of low ionic strength solutions and high temperatures for washing. For example, nucleic acid molecules can be hybridized at 42° C. in 2×SSC (0.3 M NaCl/0.03 M sodium citrate/ 0.1% sodium dodecyl sulfate (SDS)) and washed in 0.1×SSC (0.015 M NaCl/0.0015 M sodium citrate) with 0.1% SDS at 65° C. Hybridization conditions can be adjusted to account for unique features of the nucleic acid molecule, including length and sequence composition. Probes can be labeled (e.g., fluorescently) to facilitate detection. In some cases, one of the primers used in the amplification reaction can be biotinylated (e.g., 5' end of reverse primer), and the resulting biotinylated amplification product can be immobilized on an avidin or streptavidin coated substrate.

Allele-specific restriction digests can be performed in the following manner. For polymorphisms that introduce a restriction site into nucleic acid, a restriction digest with the particular restriction enzyme can differentiate alleles.

Other methods also can be used to detect a polymorphism in the region of nucleic acid located between NR4A3.2 and INVS.3. For example, conventional and field-inversion electrophoresis can be used to visualize base pair changes. In some cases, quantitative PCR analysis of the genomic copy number for the 4,577 nucleotide duplication set forth in FIG. 11 can be used to detect the presence or absence of a duplication in intron 6 of STX17 nucleic acid.

In some cases, polypeptide or mRNA levels can be determined to detect the presence or absence of a duplication in intron 6 of STX17 nucleic acid and the presence or absence of a Grey allele. For example, STX17 polypeptide levels, STX17 mRNA levels, NR4A3 polypeptide levels, NR4A3 mRNA levels, or a combination thereof can be used to detect the presence or absence of a duplication in intron 6 of STX17 nucleic acid. In such cases, an elevated level of STX17 or NR4A3 expression in a horse can indicate that that horse contains a duplication in intron 6 of STX17 nucleic acid.

The term "elevated level" as used herein with respect to a level of STX17 or NR4A3 expression is any level of STX17 or NR4A3 expression that is greater than a median level of STX17 or NR4A3 polypeptide or STX17 or NR4A3 RNA expression in a random population of horses (e.g., a random population of 5, 10, 20, 30, 40, 50, 100, or more horses) that lack Grey alleles (e.g., horses homozygous for non-Grey alleles). In some cases, an elevated level of STX17 or NR4A3 expression can be a level of STX17 or NR4A3 expression that is at least one (e.g., at least 1.0, 1.2, 1.4, 1.6, 1.8, 2.0, or 2.2) standard deviation greater than a mean level of STX17 or NR4A3 expression in a random population of horses that do not contain a Grey allele. It will be appreciated that STX17 or NR4A3 expression levels from comparable samples (e.g., blood samples) are used when determining whether or not a particular STX17 or NR4A3 expression level is an elevated level. For example, an mRNA level of STX17 expression in a skin biopsy from a horse is compared to the median mRNA level of STX17 expression in skin biopsies from a random population of horses that do not contain a Grey allele. STX17 or NR4A3 expression levels can be compared to a median STX17 or NR4A3 expression level measured using the same or a comparable method. Any appropriate method can be used to assess STX17 or NR4A3 mRNA levels including, without limitation, PCR-based methods (e.g., RT-PCR and quantitative PCR), Northern blotting, and in-situ hybridization techniques. The level of STX17 or NR4A3 mRNA expression in a sample (e.g., blood sample, plasma sample, or tissue biopsy sample such as a skin biopsy) from a horse can be determined by measuring the level of an STX17 or NR4A3 mRNA, or any fragment of an STX17 or NR4A3 mRNA. A horse STX17 mRNA can have an RNA sequence corresponding to the nucleic acid sequence set forth in FIG. 13 or 14. A horse NR4A3 mRNA can have an RNA sequence corresponding to the nucleic acid sequence set forth in FIG. 16. Any appropriate method can be used to assess STX17 or NR4A3 polypeptide levels including, without limitation, immunological methods, chromatographic methods, and spectroscopic methods. The level of STX17 or NR4A3 polypeptide expression in a sample (e.g., blood sample, plasma sample, or tissue biopsy sample such as a skin biopsy) from a horse can be determined by measuring the level of an STX17 or NR4A3 polypeptide, or any fragment of an STX17 or NR4A3 polypeptide. A horse STX17 polypeptide can have the amino acid sequence set forth in FIG. 15. A horse NR4A3 polypeptide can have the amino acid sequence set forth in FIG. 17.

In some cases, mass spectrometry can be used to determine a level of an STX17 or NR4A3 polypeptide. In some cases, a level of an STX17 or NR4A3 polypeptide can be detected using a method that relies on an anti-STX17 polypeptide antibody or an anti-NR4A3 polypeptide antibody. Such methods include, without limitation, FACS, Western blotting, ELISA, immunohistochemistry, and immunoprecipitation. Antibody based assays (e.g., sandwich enzyme-linked immunosorbent assays) can include using combinations of antibodies that bind to one or more sites of the amino-terminal, central, and carboxy-terminal portions of a STX17 or NR4A3 polypeptide or a fragment thereof. An anti-STX17 polypeptide antibody or an anti-NR4A3 polypeptide antibody can be labeled for detection. For example, an anti-STX17 polypeptide antibody can be labeled with a radioactive molecule, a fluorescent molecule, or a bioluminescent molecule. STX17 or NR4A3 polypeptides can also be detected indirectly using a labeled antibody that binds to an anti-STX17 polypeptide antibody or an anti-NR4A3 polypeptide antibody that binds to a STX17 or NR4A3 polypeptide, respectively.

An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. An antibody can be naturally occurring, recombinant, or synthetic. Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. An anti-STX17 polypeptide antibody can bind to a STX17 polypeptide at an affinity of at least $10^4$ mol$^{-1}$ (e.g., at least $10^5$, $10^6$, $10^7$, $10^8$, $10^9$, $10^{10}$, $10^{11}$ or $10^{12}$ mol$^{-1}$). An anti-NR4A3 polypeptide antibody can bind to a NR4A3 polypeptide at an affinity of at least $10^4$ mol$^{-1}$ (e.g., at least $10^5$, $10^6$, $10^7$, $10^8$, $10^9$, $10^{10}$, $10^{11}$ or $10^{12}$ mol$^{-1}$).

An anti-STX17 polypeptide antibody or an anti-NR4A3 polypeptide antibody provided herein can be prepared using any appropriate method. For example, any substantially pure STX17 or NR4A3 polypeptide (e.g., horse STX17 or NR4A3 polypeptide), or fragment thereof (e.g., a truncated STXI7 or NR4A3 polypeptide), can be used as an immunogen to elicit an immune response in an animal such that specific antibodies are produced. Thus, a horse STX17 or NR4A3 polypeptide or a fragment thereof can be used as an immunizing antigen. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1-5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, CURRENT PROTOCOLS IN IMMUNOLOGY, Wiley Interscience, 1994).

The preparation of monoclonal antibodies also is well-known to those skilled in the art. See, e.g., Kohler & Milstein, Nature 256:495 (1975); Coligan et al., sections 2.5.12.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, Vol. 10, pages 79-104 (Humana Press 1992).

Once hybridoma clones that produce antibodies to an antigen of interest (e.g., a horse STX17 or NR4A3 polypeptide) have been selected, further selection can be performed for clones that produce antibodies having a particular specificity. For example, clones can be selected that produce antibodies that bind to a horse STX17 or NR4A3 polypeptide and lack detectable binding to a human STX17 or NR4A3 polypeptide.

The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

Once a horse is determined to contain a duplication in intron 6 of STX17 nucleic acid, the horse can be classified as having an elevated risk of developing cancer (e.g., melanomas). Horses classified as having an elevated risk of developing cancer can be inspected frequently (e.g., daily, weekly, or monthly) for signs of cancer. For example, a horse determined to contain a duplication in intron 6 of STX17 nucleic acid can be inspected by a veterinarian for signs of melanomas every other month. In some cases, a horse determined to contain a duplication in intron 6 of STX17 nucleic acid can be treated using the methods and materials provided herein to reduce the chance of developing cancer, to reduce the progression of cancer, or to reduce the severity of cancer.

This document also provides isolated nucleic acids having a nucleotide sequence of at least about contiguous 20 nucleotides (e.g., at least about 20, 25, 30, 40, 50, 75, 100, 150, 300, 500, or more nucleotides) from an intron 6 of an STX17 nucleic acid (e.g., an intron 6 of an STX17 nucleic acid having the nucleic acid sequence set forth in FIG. 11). In some cases, an isolated nucleic acid can contain the CAA↓AAT duplication breakpoint for the nucleic acid set forth in FIG. 11. For example, an isolated nucleic acid provided herein can contain the following sequence: 5'-AGAAATGCAA↓AAT CTCA-GAA-3' (SEQ ID NO:32). Such a nucleic acid can be between 10 and 500 nucleotides in length (e.g., between 15 and 500 nucleotides in length, between 20 and 500 nucleotides in length, between 25 and 500 nucleotides in length, between 50 and 500 nucleotides in length, between 25 and 450 nucleotides in length, between 25 and 400 nucleotides in length, or between 25 and 300 nucleotides in length).

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

Isolated nucleic acids can be produced by standard techniques, including, without limitation, common molecular cloning and chemical nucleic acid synthesis techniques. For example, polymerase chain reaction techniques can be used to obtain an isolated nucleic acid containing the CAA↓AAT duplication breakpoint for the nucleic acid set forth in FIG. 11.

Isolated nucleic acids provided herein can be used for diagnostic purposes. For example, an isolated nucleic acid comprising a portion of a intron 6 of STX17 nucleic acid (e.g., a PCR amplicon) can be used in DHPLC or allele specific hybridization analyses. In some cases, an isolated nucleic acid containing a portion of a intron 6 of STX17 nucleic acid containing a duplication breakpoint can be labeled (e.g., with a fluorescent label) and used to determine whether or not a horse contain the duplication.

This document also provides kits that can be used to determine whether or not a horse contains a duplication in intron 6 of STX17 nucleic acid. Such kits can include nucleic acid molecules (e.g., primer pairs or probes), antibodies (e.g., anti-STX17 polypeptide antibodies or anti-NR4A3 polypeptide antibodies), secondary antibodies, control nucleic acid molecules (e.g., nucleic acid representing a Grey homozygote, nucleic acid representing a Grey heterozygote, or nucleic acid representing a non-Grey homozygote), control polypeptides (e.g., horse STXI7 or NR4A3 polypeptides), DNA aptamers, microarrays, ELISA plates, or data analysis software optionally together with any other appropriate reagents, tools, or instructions for performing the methods described herein. Appropriate informational material can be descriptive, instructional, marketing, or other materials that relate to the methods described herein or the use of the reagents for the methods described herein. For example, the informational material can relate to performing a genetic analysis on a horse and subsequently classifying the horse as being at risk (or not) for developing melanomas. In addition, or in an alternative, the informational material of a kit can be contact information, for example, a physical address, email address, website, or telephone number, where a user of the kit can obtain substantive information about performing a genetic analysis and interpreting the results.

The informational material of the kits can be in any form. In some cases, the informational material, for example, instructions, can be provided in printed matter (e.g., a printed text, drawing, photograph, or label). Informational material can be provided in other formats, such as Braille, computer readable materials, video recordings, or audio recordings. Informational material also can be provided in any combination of formats.

The kit can include one or more containers for the reagents for performing a genetic analysis, such as reagents for performing PCR, FISH, CGH, or any appropriate method described herein. The kit can contain separate containers, dividers, or compartments for the reagents and informational material. A container can be labeled for use for the genotyping of horses.

This document also provides methods and materials to assist horse owners or horse breeders in determining whether or not breed two particular horses. A horse owner or horse breeder can be assisted by (1) determining each horse's genotype (e.g., determining whether or not each horse to be mated contains a duplication in intron 6 of STX17 nucleic acid, is homozygous for a duplication in intron 6 of STX17 nucleic acid, or is heterozygous for a duplication in intron 6 of STX17 nucleic acid), and (2) communicating information about each horse's genotype to that professional.

Any appropriate method can be used to communicate information to another person (e.g., a horse owner or horse breeder). For example, information can be given directly or indirectly to a horse owner or horse breeder. In addition, any type of communication can be used to communicate the information. For example, mail, e-mail, telephone, and face-to-face interactions can be used. The information also can be communicated to a horse owner or horse breeder by making that information electronically available to the horse owner or horse breeder. For example, the information can be communicated to a horse owner or horse breeder by placing the information on a computer database such that the horse owner or horse breeder can access the information. In addition, the information can be communicated to a clinic or research facility serving as an agent for a horse owner or horse breeder.

This document provides methods and materials for treating cancer in mammals and for reducing the likelihood that a mammal will develop cancer. For example, this document provides methods and materials related to the use of agents that reduce STX17 polypeptide activity, STX17 polypeptide expression, STX17 RNA expression, NR4A polypeptide activity (e.g., NR4AI, NR4A2, or NR4A3 polypeptide activity), NR4A polypeptide expression (e.g., NR4AI, NR4A2, or NR4A3 polypeptide expression), NR4A RNA expression (e.g., NR4AI, NR4A2, or NR4A3 RNA expression), or combinations thereof to treat cancer in a mammal. In some cases, a human having melanoma can be treated by administering an agent that reduces human STXI7 polypeptide activity, human STXI7 polypeptide expression, human STXI7 RNA expression, human NR4A polypeptide activity (e.g., a human NR4AI, NR4A2, or NR4A3 polypeptide activity), human NR4A polypeptide expression (e.g., a human NR4AI, NR4A2, or NR4A3 polypeptide expression), human NR4A RNA expression (e.g., a human NR4A1, NR4A2, or NR4A3 RNA expression), or a combination thereof.

A human STX17 mRNA can have an RNA sequence corresponding to the nucleic acid sequence set forth in FIG. 18 or 19. A human STX17 polypeptide can have the amino acid sequence set forth in FIG. 20. A human NR4A3 mRNA can have an RNA sequence corresponding to the nucleic acid sequence set forth in FIG. 21. A human NR4A3 polypeptide can have the amino acid sequence set forth in FIG. 22. A human NR4AI polypeptide and a human NR4A2 polypeptide can have the amino acid sequence set forth in FIG. 25 and FIG. 26, respectively. An alignment of amino acid sequences of a human STXI7 polypeptide and a horse STXI7 polypeptide is provided (FIG. 23). An alignment of amino acid sequences of a human NR4A3 polypeptide and a horse NR4A3 polypeptide is provided (FIG. 24). An alignment of amino acid sequences of a human NR4AI polypeptide, a human NR4A2 polypeptide, and a human NR4A3 polypeptide is provided (FIG. 27).

The methods and materials provided herein can be used to treat cancer (e.g., skin cancer) in any type of mammal including, without limitation, dogs, cats, horses, cows, pigs, monkeys, and humans. Any type of cancer, such as melanoma, brain tumors, colon cancer, and leukemia, can be treated. For example, stage I, stage II, stage III, or stage IV melanoma can be treated. In some cases, a lymph node positive, a lymph node negative, or a metastatic melanoma can be treated.

In general, cancer (e.g., melanoma) can be treated by administering an agent that reduces the activity or expression of an STX17 polypeptide or RNA or an NR4A polypeptide or RNA. Such agents can include, without limitation, antibodies (e.g., anti-STX17 polypeptide antibodies or anti-NR4A3 polypeptide antibodies), antisense oligonucleotides (e.g., antisense oligonucleotides targeting STX17 or NR4A expression), siRNA molecules (siRNA molecules targeted against STX17 or NR4A expression), or nucleic acid constructs having the ability to induce RNA interference against STX17 or NR4A expression.

In some cases, cancer (e.g., melanoma) can be treated by administering a cyclin inhibitor (e.g., a cyclin D1 inhibitor or a cyclin D2 inhibitor) to a mammal having cancer. A human cyclin D1 polypeptide and a human cyclin D2 polypeptide can have the amino acid sequence set forth in FIG. 28 and FIG. 29, respectively. An alignment of amino acid sequences of a human cyclin D1 polypeptide and a human cyclin D2 polypeptide is provided (FIG. 30). Examples of cyclin D1 inhibitors includes, without limitation, nucleic acid molecules capable of inducing RNA interference against expression of a cyclin D1 polypeptide, anti-cyclin D1 antibodies, all-trans-retinoic acid, dihydro-β-carboline, and Leptomycin B. Examples of cyclin D2 inhibitors includes, without limitation, flavopiridols, nucleic acid molecules capable of inducing RNA interference against expression of a cyclin D2 polypeptide, anti-cyclin D2 antibodies, suberoylanilide hydroxamic acid, rapamycin, Rugosin E, and THRX-165724 (Theravance, Inc., CA).

In some cases, cancer (e.g., melanoma) can be treated by administering a MC1R inhibitor to a mammal having cancer. A horse MC polypeptide can have the amino acid sequence set forth in FIG. 31. A human MC1R mRNA can have an RNA sequence corresponding to the nucleic acid sequence set forth in FIG. 32. Examples of MC1R inhibitors includes, without limitation, nucleic acid molecules capable of inducing RNA interference against expression of a MC polypeptide, anti-MC1R antibodies, and polypeptide antagonists of MC1R polypeptide activity. A polypeptide antagonist of MC polypeptide activity can contain the following amino acid sequence: SPRRSERLGW (SEQ ID NO:36; Bonetto et al., *Peptides*, 26:2302-2313 (2005)). Additional examples of a polypeptide antagonist of MC1R polypeptide activity can be designed and obtained as described elsewhere (e.g., Mayorov et al., *Chem. Bio!. Drug Des.*, 67(5):329-35 (2006) and Thirumoorthy et al., *J. Med. Chem.*, 44(24):4114-24 (2001)).

An agent having the ability to reduce the activity or expression of an STX17 polypeptide or RNA or an NR4A polypeptide or RNA can be administered individually or in combination with one or more other agents having the ability to reduce the activity or expression of an STX17 polypeptide or RNA or an NR4A polypeptide or RNA. For example, an anti-STX17 polypeptide antibody can be administered together with an anti-NR4A3 polypeptide antibody. In some cases, an agent having the ability to reduce the activity or expression of an STX17 polypeptide or RNA or an NR4A polypeptide or RNA can be administered together with a cyclin inhibitor (e.g., a cyclin D2 inhibitor) and/or a MC inhibitor.

Any appropriate method can be used to administer an agent having the ability to reduce the activity or expression of an STX17 polypeptide or RNA or an NR4A polypeptide or RNA, a cyclin inhibitor (e.g., a cyclin D2 inhibitor), or a MC1R inhibitor. For example, an NR4A3 siRNA molecule and a cyclin D2 inhibitor can be administered orally or via injection (e.g., subcutaneous injection, intramuscular injection, intravenous injection, or intrathecal injection). In some cases, an agent having the ability to reduce the activity or expression of an STX17 polypeptide or RNA or an NR4A polypeptide or RNA, a cyclin inhibitor (e.g., a cyclin D2 inhibitor), and a MC1R inhibitor can be administered by different routes. For example, a cyclin D2 inhibitor can be administered orally, and an anti-NR4A3 polypeptide antibody can be administered via injection.

Before administering an agent or inhibitor described herein to a mammal, the mammal can be assessed to determine whether or not the mammal has cancer or is likely to develop cancer. Any appropriate method can be used to determine whether or not a mammal has cancer (e.g., skin cancer such as melanoma). For example, a mammal (e.g., human) can be identified as having cancer using standard diagnostic techniques. In some cases, a tissue biopsy can be collected and analyzed to determine whether or not a mammal has skin cancer such as melanoma.

After identifying a mammal as having cancer, the mammal can be administered an agent or inhibitor described herein orally combination thereof. For example, agents having the ability to reduce STX17 and NR4A3 polypeptide expression can be administered prior to or in lieu of surgical resection of a tumor. In some cases, agents having the ability to reduce STX17 and NR4A3 polypeptide expression can be administered following resection of a tumor. An agent or inhibitor described herein can be administered to a mammal in any amount, at any frequency, and for any duration effective to achieve a desired outcome (e.g., to increase progression-free survival or to increase the time to progression). In some cases, an agent or inhibitor described herein can be administered to a mammal having cancer to reduce the progression rate of melanoma by 5, 10, 25, 50, 75, 100, or more percent. For example, the progression rate can be reduced such that no additional cancer progression is detected. Any method can be used to determine whether or not the progression rate of cancer is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of skin cancer after treatment can be determined and compared to the stage before treatment to determine whether or not the progression rate was reduced.

In some cases, an agent or inhibitor described herein can be administered to a mammal having cancer (e.g., skin cancer) under conditions where progression-free survival or time to progression is increased (e.g., by 5, 10, 25, 50, 75, 100, or more percent) as compared to the median progression-free survival or time to progression, respectively, of corresponding mammals having untreated cancer (e.g., skin cancer). Progression-free survival and time to progression can be increased by any amount (e.g., 5%, 7.5%, 10%, 25%, 50%, 75%, 100%, or more). Progression-free survival can be measured over any length of time (e.g., one month, two months, three months, four months, five months, six months or longer).

An effective amount of an agent or inhibitor described herein can be any amount that treats cancer (e.g., reduces the progression rate of cancer, increases the progression-free survival rate, or increases the median time to progression) without producing significant toxicity to the mammal. Typically, an effective amount of an agent or inhibitor described herein can be from about 1 ng/kg to about 500 mg/kg (e.g., between about 10 ng/kg and 500 mg/kg, between about 100 ng/kg and 500 mg/kg, between about 1 µg/kg and 500 mg/kg, between about 10 µg/kg and 500 mg/kg, between about 100 µg/kg and 500 mg/kg, between about 1 ng/kg and 250 µg/kg, between about 1 ng/kg and 10 mg/kg, between about 1 ng/kg and 1 mg/kg, between about 1 ng/kg and 100 µg/kg, between about 10 ng/kg and 100 µg/kg, between about 100 ng/kg and 100 µg/kg, or between about 1 µg/kg and 100 µg/kg). If a particular mammal fails to respond to a particular amount, then the amount can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that treats cancer without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. In some case, multiple agents and/or inhibitors can be administered with the frequency of administration of each being the same or different. For example, a cyclin D2 inhibitor can be administered daily, while an anti-NR4A3 polypeptide antibody can be administered two times a week. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering an agent or inhibitor described herein can be any duration that treats cancer without producing significant toxicity to the mammal. Thus, the effective duration can vary from several days to several weeks, months, or years. In general, the effective duration for the treatment of cancer (e.g., skin cancer) can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

A composition containing au agent or inhibitor described herein can be in any appropriate form. For example, a composition containing au agent or inhibitor described herein can be in the form of a solution or powder with or without a diluent to make an injectable suspension. A composition containing an agent or inhibitor described herein also can contain additional ingredients including, without limitation, pharmaceutically acceptable vehicles. A pharmaceutically acceptable vehicle can be, for example, saline, water, lactic acid, and mannitol.

After administering a composition containing an agent or inhibitor described herein provided herein to a mammal, the mammal can be monitored to determine whether or not the cancer was treated. For example, a mammal can be assessed after treatment to determine whether or not the progression rate of cancer (e.g., melanoma) was reduced (e.g., stopped). As described herein, any method can be used to assess progression and survival rates.

In some cases, the treatment methods and materials provided herein can be used to reduce a mammal's risk of developing cancer. For example, a combination of agents and inhibitors described herein can be administered to a mammal at risk for cancer under conditions that reduce that mammal's risk for developing cancer.

The invention will be further described in the following examples, which do not limit the scope of the invention described in the claims.

EXAMPLES

Example 1

Cis-Acting Regulatory Mutation Causes Premature Hair Greying and Susceptibility to Melanoma in the Horse Genotyping Long range PCR using Expand Long Template PCR system Mix 1 (Roche Diagnostics GmbH, Mannheim, Germany) was performed to genotype the 4.6 kb duplication. One forward primer (Fwd 5'-GGAACATAAAGTAGATTTGG TGGGAAAG-3'; SEQ ID NO:37) and two different reverse primers (N-Rev: 5'-TTCTGATAAATGCATAAACCCACG-TAAC-3 (SEQ ID NO:38) for the normal copy and D-Rev: 5'-TTCCAATTCTGAGATTTTGCATTTCTAA-3', (SEQ ID NO:39) for the duplicated copy) were used in the same reaction. The PCR was performed using 125 ng of genomic DNA and the primer content was 3.75 pmoles of Fwd primer, 2.5 pmoles of N-Rev primer, and 5 pmoles of D-Rev primer.

Western Blotting

Rabbit polyclonal antibodies against amino acids 1-229 of horse STXI7 were generated by immunization (AgriSera, Sweden) with purified soluble bacterially expressed amino-terminal cytoplasmic domain of horse STXI7 (amino acids 1-229) produced as a GST-STX17 fusion polypeptide. For affinity purification, the antiserum was incubated with the 6×His-tagged amino-terminal portion of horse STXI7 (amino acids 1-229) coupled to CNBr-activated Sepharose beads (Amersham, Sweden; 2 mg protein/mL beads). The beads were then washed extensively, and bound antibodies were eluted in 0.1 M glycine pH 2.7 and quickly neutralized.

The following primary antibodies were used for Western blot analysis: murine monoclonal ANTI-FLAG (M2; Sigma, Saint Louis, Mo.); rabbit polyclonal anti-phospho-p44/42 Map Kinases (Thr202/Tyr204; Cell Signalling Technology, Inc.), and rabbit anti-ERK2 (EET) (Leevers and Marshall, *EMBO J.*, 11:569-574 (1992).

Equal amounts of lysates were boiled with SDS sample buffer containing dithiothreitol and separated by SDS-PAGE. Samples were electro-transferred to Immobilon-P membranes (Millipore) and blocked in 5% bovine serum albumin in tris-buffered saline solution containing 0.1% Tween 20. Primary antibodies were used at concentrations and buffers recommended by the suppliers and incubated overnight at 4° C. After washing, the membranes were incubated with horseradish peroxidase-conjugated anti-mouse or anti-rabbit IgG antibodies (both from Amersham Biosciences), and polypeptides were visualized using ECL Western blotting detection system from Roche Applied Science on a cooled charge-coupled device (CCD) camera (Fuji). For detection of total amount of polypeptides after analysis of phosphorylation status, membranes were stripped with 0.4 M NaOH for 10 minutes at room temperature, blocked, and incubated with the corresponding antibody.

Northern Blot Hybridizations

Total RNA from horse tissues was extracted according to the TRIzol® (Life Technologies, Inc.) protocol. mRNA was prepared using Oligotex® mRNA kit (QIAGEN GmbH, Germany) following the manufacturer's protocol. Poly A+ RNA was electrophoretically separated on a denaturing formaldehyde agarose gel, transferred to a nylon membrane (Nybond N+; Amersham Biosciences, Inc.), and immobilized by UV irradiation. A random-primed 32p probe was generated using full-length coding region for each of NR4A3, STX17, TXNDC4, INVS, CCND1, CCND2, and β-actin. Hybridizations and washings were performed using ExpressHyb™ (CLONTECH Laboratories, Inc.).

Real-Time PCR

Relative expression of STX17, NR4A3, and 18S-RNA were analyzed by comparative $C_T$ method using the primers and probes given in Table 2. The PCR was performed in 25 µL reaction volumes using the TaqMan Buffer A (Applied Biosystems), 0.7 µL of both forward and reverse primer, 0.25 µL of TaqMan probe, 3.5 mM $MgCl_2$, 0.2 mM dNTPs, and 0.625 units of AmpliTaq Gold DNA polymerase (Applied Biosystems). The PCR reactions were performed using the ABI7700 instrument (Applied Biosystems), and cycling conditions were 50° hold for 5 seconds and 95° hold for 10 minutes, followed by 40 cycles of 95° for 15 seconds and 60° for 1 minute. All samples were analyzed in triplicates.

Primers and Template Sequences

Primers were designed and used for pyrosequencing (Table 3). Template sequences for the pyrosequencing are as follows with polymorphisms identified:

SNP.1&2:

(SEQ ID NO: 50)
GAGACTTCAGTCAGATGACCATGCTTAGGAAATATCCTTATCCCTTCCTC

ATATGAATGTGCAGTCTAAACTTTTCCGTCTGAACATGTTTAAAGTGTAT

ATATGTATAAGTTTTATACATCTTTATGGTTTTCTTCTTTCAGCGACCTT

TTTCAATAAATTGGTCAACCTAACACGT/CTATAAAAGAGGGCTCCTGCT

GTATTTAAAAACACAGATAGTGCATTCCAGATAGGGGT/CGAGTGGAAGG

GGAATACACCATGGATATAGGTCAAGTTGACGTGGAGAAGGACCTCCAAT

GTCACAGTGAGGAATTTGGACATTGCAATAAGCAATAAGGGAACAGTAAG

AGGTTGTCGTTTTGTCATTTGATAGTACAGATTTTTGAGCATATCAAAGG

ACATGCCCTTTATGAAATTAGTTTGGCAGCTAGTAGGCTTGCTGCTCCGG

TCCCCGTAGTCCACGTCATTCCTCCCCATAGCAAAGGCTGCTGGAGTCTT

GCTCCTTAGGCTCCAGACCTGCGCTGTCCAATAGGTAGCGGTAGCCACAT

GTGGCTATTGAGCACTTAAACGTGGCTAGCCGGAACTGAGATGTGCTGTA

AGTGTAAAATAAACCCAGATTTCAGAGACTTAGTATGAGAAAAGGAATGT

AAAATATCTTATTAACGATGTTTTATTGCTTACATGTTGAAACGATGATA

GCATATACTGGGTTAAATAAAATATACTATTAAAATTCATTTCCACTTAT

TTCTTTTTACTTTTTTAAAATGTGACTACTTGAAAATTTAGAACTTTAAC

ATGTAGCTCGGCATCTGGAGGCTCACATTATATTTATCTTTCTGGACAGA

AATGGCTCTAGTTCTAGATCAATCCTGACACGAGATAGGAGAGTTGAGCC

TABLE 2

Primers and probes for real-time PCR analysis of NR4A3 and STX17 in Grey and non-grey horses

| Primer/Probe | Sequence |
| --- | --- |
| STXForward | 5'-CCTGCCACAGGCAGAGCT-3' (SEQ ID NO: 40) |
| STXLongReverse | 5'-TGGTCACTGATTTCTCTCTCCTAGTAAA-3' (SEQ ID NO: 41) |
| STXShortReverse | 5'-GCTCACTCATAATTCCTTTGCATCT-3' (SEQ ID NO: 42) |
| STSTaqMan probe | 5'-FAM-CTTGTATTTTGCAGCCTTCCCCAAGTTTT TTAMRA-3' (SEQ ID NO: 43) |
| NR4Forward | 5'-GAATCAGCCTTTTTGGAGCTGT-3' (SEQ ID NO: 44) |
| NR4Reverse | 5'-CATTGCAGAACACAAACTTATCTTCA-3' (SEQ ID NO: 45) |
| NR4TaqMan probe | 5'-FAM-TGTTCTCAGACTTTCCATCAGGTCGAAC ACTTAMRA-3' (SEQ ID NO: 46) |
| 18SForward | 5'-AGTCCCTGCCCTTTGTACACA-3' (SEQ ID NO: 47) |
| 18SReverse | 5'-GATCCGAGGGCCTCACTAAAC-3' (SEQ ID NO: 48) |
| 18STaqMan probe | 5'-FAM-CGCCCGTCGCTACTACCGATTGG-TAMRA-3' (SEQ ID NO: 49) |

ATCCTGCCCCCTAGCCCAATGCTTTGGGACTCATTTCTCCTACTGGGTGT
CTGATTTCAAATAAAGAATCTTTGTCACACTCCTCTTTCTCCACTTTGGG
ATGTGGTCTGGTTTCCTTGATTTCTGCTTTGTAATGTTTAAGGCTCAGGT
TGCTGGCTCCTTAGAGATTTGTCTTCTCTCATTTTCCGTCATGCACAA
ATCCATGTTTCCTCCTTATGATGACTCCTTCCTCTGGAGAAGCAGACACT
TCCAGAAAGATGGAGATCAACAATAGGGCATTGGATTTGGTGATCAGGGA
ATCACTACCTTTAAGAGAACGACCATATCAACTATTTGAGCGGACGGCTG
AGCAGTTGTCAGGATTGCCACACCAACGATCTCATAGGCTTAAAGACCAG
AAGAAAAACCAAATCACACCTTAGCCAATGGTAGAACAATGACAAGCACA
CTGGCACATCCCTCACCCAGTCTTTGTCTACCGGTGGAACTGAGACTTCC
AGAATGAAGGGCCTCCTCCCTGTCATTTATTATTTTGAAGTAGTGTTACC
AAGTGCTCACTTTGAAGAAGCATTCAGCTAGACAGTTAGGGATCACAATC
AAGTTAAAAAGAAAAGGAAATAAGTTTGCAGCACTGGGGCTGCATTCAGA
AATGGGAGAGACATCCCCACAAGTCACGTCACCCTCATGCAAGCAAAGCT
GAATACACCTGATTTATTTGCCTATCCAGGGACCTGGCCAGATTTTTTCT
AAACTCTGGAGGCAGTCTTGGTT

SNP.3:

(SEQ ID NO: 51)
TGACTTGTTAGAGGCGGTTCTAATTCTCTTGGGCTGCTGGGGAATCTCAA
CAGAAAATGGTTTAGTACGTATGAGCACGTGCATATCTGAGTGTACGTAC
ATATGCCTCCATCTTATGTGTGTACGTGTGTTTATGCATCAGGGCACAGT
AGCTGATACAATGCAATAGATACCTAAAAACACGGCACCAACAAAATCAA
AATGGACTATTCACTAGAAAATAACACCAACGAGGTTGGCTAGGTATATG
TGTTTTATTTTGTCTTCATTTTTTTAAGTCCCCACATTGAACTGCATAAC
CTCTTACATTTCATCTTAAAGAATTTCATAACATCTTGTAAAAAGCTA/G
CTTCCTTCTGTTCTTCAGTCTTGCAAAGTGCTCACTGACGTTGCTGTTGC
AGTCTGGAAGAATTGAAAGCTTTAGCATTCGGTTCTCAAGGAGCTCTCCC
TCCTGACCACATTGAAGGCAGCATGGCGTGGTACAAAGGGTCCTAAACAG
TGAGCCACAGGACATGGGTTTAAGCCAGAATCCTACCCATTGTGAAGTTA
GGCTAGACCCTCACAGCCCTGAGTCTATTTCCTCATTTGTAAAAAAGGGC
TAATAACCCTTGACCTGTCCTTAAAAAGAGTCTCTGGGAATGGGCTTCGT
AAACTCTGCAGCACTGAGGCAAGCCATGGAAAGGGATTAGTACCGCCACA
ATTGTGGAAGTAAGTCTCACGCCTAAGAAGCAGTCCCAGCGAGGAGGTTT
TCGGTACAGGGAGACAGGAAGGAAAGCA/GCAGGATTCCAACACACACCT
GTGACTTCATTCATGAAATTCAGGGGAGAAATTTAAAATATTTCCCTAGA
CTTCCCTCAGAACTACATTGGCTTCAAAGGAGGCAAAAGTCAAGATGTAA
CAGGAATTTTTATTCTGATTTGTTCTGAAATATGGGTTTTCAATCATCAT
GATTCCTTAAATTAGAATGGATCTGCAAAAATAGATACATGCAAACATTT
TTTCCTAAATTTTTTTCATGTAAGAGTATGCAGCCTGCTGTGTAATGTCA
CACACTAAAATAACATTGGCATAGAATGGGAGTAAAATCCTTTCTCTGGA
AATAAGCATATGTTATTAAAATTATATATCATTTGTAT/GCCAACTACTA
GAAAAGAATCCACACTGCAGTGTTTAAGTTTAGGATTGACTTGGCGTACT
GTGACATTGTGCAATCAAGGATAGGACCAGGAGGCAAGGGCTTGAGTTCT
ACTTCCAGCTATTCCGCTAAC/TTAACCTGGTGACTTGAATAAAGCATTG
GCCTCCATGAGCTTTATTTCTTCCATGGGAAAATGAATTACCACATGTG
CCTACTCACCTGCTTCATAGGGTTCTTATGGGGATCAAATGAAAGTGTCT
ATGAAAATGGCTCTCTATAACTATGAAATGGTTGGGT

SNP.4:

(SEQ ID NO: 52)
AGAAGTTGTGGGAGCTCTAATGTGGCAGTGGAGGTGAAGGTGGGGCCCAC
TTGCTACGAACAGTCTGCTCTCACAAAAAATTTAAAGCAAGGCAATATTT
TTGCACACTTTTCTGTAATTGAATATCATTAAGGTACTAAATAGATAATG
CACCTTGCCTTTCTTTTTTTTCAAAAACTATTTATTGAATGCCTACTATA
TACCAGGC/AATTGTGCAAGAGATAAAGGGATAAAATGGTGATCAAAGAA
AAAGAGCAAAGAAAGCTAAAAGACAGTCGAGTGGAAAGAGTAGGAATGGA
AAAGAAAAAGCGGATTGCTGGTGGGCTCCTTTATTGCCAAAGTCTTTGTA
TGTTTTGGGGTCCTTGAGTCAGGAAAAAAAGTAGTTATGCTGGATCCCTC
TGACAT/CGTATGGCAAGGAGTGTGTGTGTGTGCATGCATGCACGTGT
GTGTGGTGTGTTTTGGAGAAGATGAGAGAGCATAAGGAGAATACCTCAAT
TTCTGC/TCCAATAGAAGTGGGAGGATGGAATCACTGATGTTCCAGAAGC
TAAGAAAGGAAAAATGTAAATTATTTTCTTTACGCATGTGGTTTGCACAA
CATCCTCCAACATAAGACTCCCACTTGGGTCCTAAAGTTGGAAAAATCTA
GGGAGTACGGAGAAAGAGAACAGAGCAACAAGACGACACAGTATACCAGG
TGTCAGCGCTAGCACATCAACTCCGAAAGGGAGACCTTTGCAAGACATTC
TCCAGGTTCACTAGCCATGTGCATTACGAATCTGGAATTAATGCTATTTA
CCTAAATTATAAAGACGTATTTCTCACATAAGTCCCTTATGTGCAAGCAG
GGTAGCAAAGGAAGAGTTCTTTATATGGGGGTAACTTGAAGAGCCCCTAA
GAATTTCCTACCCCAAATAGTTCACTGAAATTCTTCATTTTGTTTCGCTC
TTTGGAACCTGTCTTTAATTATCTCCCTATGACCACAGAAGCAGTTATAA
CACAGTACAGTAATTAAAGATTCTGAAATCAGATTGCTTTGTTCACCCTG
GGCT

SNP.5:

(SEQ ID NO: 53)
GAATCATCGCACTGTGGTGGATTCATGTTCCAGAAGCTAAGAAGGAAAAA
TGTAAATTATTTTCTTTACGCATGTGGTTTGCACAACATCCTCCAACATA
AGACTCCCACTTGGGTCCTAAAGTTGGAAAAATCTAGGGAGTACGGAGAA
AGAGAACAGAGCAACAAGACGACACAGTATACCAGGTGTCAGCGCTAGCA
CATCAACTCCGAAAGGGAGACCTTTGCAAGACATTCTCCAGGTTCACTAG
CCATGTGCATTACGAATCTGGAATTAATGCTATTTACCTAAATTATAAAG
ACGTATTTCTCACATAAGTCCCTAATGTGCAAGCAGGGTAGCAAAGGAAG

AGTTCTTTATATGGGGGTAACTTGAAGAGCCCCTAAGAATTTCCTACCCC
AAATAGTTCACTGAAATTCTTCATTTTGTTTCGCTCTTTGGAACCTGTCT
TTAATTATCTCCCTATGACCACAGAAGCAGTTATAACACAGTACAGTAAT
TAAAGATTCTGAAATCAGATTGCTTTGTTCACCCTGGGCTTCACCACTAG
TCACTCCTGTGATTATTGGGTATGCTTCTTACTAACAGCTAAGAATTACA
TTTATTGAGCATGTAATCACTTAGCAACTATAGGCACAAGCATTTTACAT
GTATTGGCAGGTATCATTAATCCTCACAATACCCCCATGAGGTATGACGT
AGGTA/GTCATGATCATGATGTCATCTTACGGATGAGGAAACTGAGGCAC
ATATGGAACTTTCAGGTCCAAAAGTAATAAGAGTGAGCTGAAATTCAAAC
CTAAACAGACTTAACTATATACTACAGGCCCCTCACTTAAACGCTCTAAG
CCACCATACCTACT

NR4A3.2

(SEQ ID NO: 54)
CGCGTTTTTTAGCCTCGATTCGGGTGCCACAAAACGGCGGTGAACGCACT
GGGTGCTGGGCAACCCATACTCGGCTCCCCCAAGGCGGTGTAATGCTTCT
TGCCCAGGGACTCCGTTCACCTTAAGCACTGCTTTCTTACCCTTATAATT
CTTTGTAATTAACGTAGCATTCCTCGAGGCCCCCACCAACACCCCAACGC
GCCCGGCCCAGGCCGCGGTGACCCCGCCTGGTCCCGCTGTGACCTCTGTC
CTCTCTCCCGGTGCCCGCAGAGCCCACTGCGGAAGAGCGCAGCCCGGCAA
GCCCCAGGCCTGAGACTGGACCCTCGGCAGAGCCGGGCAGCACCGCAGCC
GCTTCGCCTCGCCA/GGACGTCCCCCGCTTCTACACTCTCAGCCTCCGCT
GGAGAGACCCCCAGCCCCACCATTCAGCGCGCAAGATATCCTCCAGGTAG
GTCTGAAGGCACGACCCCTTATTCCTCGCAGGCTGGAAGAAGTGGGGGAG
GGGATGGGCCCTGGGTCCCTGGCAGGGGCGGGCTGGTCGACTTGCCTAGC
GCCAGGACAGTGACTGCTGGCCGAGCATTTCACAGCACAGGTGGCTTCTT
TGCACGAAGCTCCTCTGGATACCACACCCTGTTGCTACCGAGTGGAGGAG
CCAGATTAAATTAAGCGTTGCATTTTTCAAAAATATTTTTCCTAAGAAAA
ATGCAAATACACCGATAGATTAGGATCTTTTAATACACTGTAATGTCATG
TTTGCTGTCCTTTTATATCCGGTTTACGCATTTAAGAGTATTGGG

NR43.1:

(SEQ ID NO: 55)
TTAAAATACAGGAAAGGCAAAGTTAAGGTATGGACCACATAGAGTTCAGA
TTAGTCACGCCTGATACTCATCAAGCTCCTCTTGTGTACCAGGCACTGGG
CA/GTGGGCTTTCAAATCTTTTAC/GTTACAGTCATGCATCACTTAACA
ACAGAGGTATGCTCTGAGAAACGCATCATTAGGTGATTTTATCATTATGC
GAACATCGTAGAGTGGACTAACACAAATCTGGACGGCATAGCCTG/ACTA
CACACCTAGGCTCTG/ATGGTACTAATCTTATGGGAGCACGGTCGCATAT
GTGGTCCGTCGTTGACTGAATGTTGTTATGCAGCACATGACTCTATTTAA
TTCCCACAACGATCGTAGGAGGTAGCAATTAGAAGTCCTGTTTTATACAT
AAGGAAAAGGAAGCCCAGAGAGATTAGAAGTGCCCAGGGCCCCTTAGCTA

GGTGGTGATGTTTCACCAGAAGTTTCAGGGTGTCTTTCATGAGAGAGAGA
AGAGTGGGATGATTATGGACATAATATAAACTATCACGGCAGATTTAGAA
ACAGCCCTCCGCAGCCCCCCTGTTAAAAGCAGAGAGGGTAATACAAAATA
AGCTCTCTTTTCACTTTAAGGCGCTTGTCAGTTTCTGATTGACTTCTGGC
GGTCGCAGTGACTCGGTGGTTTTAGAGTCTGCACAATGGAATTGTAGTGT
CTAGCGTCAGGCCTTATCAGTTTCTGACATTCAAGGAAATGAGGGGGAAG
TCCTGGTGAGGGAGCGCTAAAGAGAACAGTCTCAGGTTCATGGCAGAGGC
CACGCACTGGGCTTCACTTCCACAGTCTGTGAGCGCCTGCTCCTCTGTGT
CCCGTCCCAGGGGGAGCCAGTAATTGACTCTAGTAATAAGAAATCAGGTG
CCCCACCGCCAGCTTCCCCGGGGGCTGATGCTCAGCAAGAAAGTTAGCAC
AGACGCCTGGTGGTGGCTGTGCATCCCTGGAGTACCCTCTTCTTCCTCGA
GGGCACCCGGGCAGATTTCACAACACCACACTACTTCTGAACGCTGCCCC
ATGGCTGTGCGGGTATCTCTGTGGTGTGATGGTGTCCTGTCCGACAGACC
GAACAGACCTGTCTAACGTATCTCCATCCTCCGCCCCCCACGACTTTGTC
TTGTAGGTCGAACACTGCTGAAGATAAGTTTGTGTTCTGCAATGGACTTG
TCCTGCATCGACTTCAGTGCCTTCGTGGATTTGGGGAGT

TXNDC4.

(SEQ ID NO: 56)
TATAGTTTTAACCGTAATTTGAATACACGTCTAGTATAATCTATAGTTTT
ATACATGTTAGTGTTCACAGTCATAGAATTTTAGTATCGAAGGGAACCTC
AAAGCATCATCTTGTGCTAATGCAAACCTTTCAAAGTAACGATGGGGACT
T/CAGAGGCCTGAAGGCGCAGAGGCGTTTAGTGACAGAGCTGGGACTAGA
GAGCCCTGGTCCCCGGGCCTTATCGGCCTGTTTTGTGTTCAGCCTGGGAC
CCAAATTCAAAAAACTGCTCCCATGATCTGTGATCATAACTCATACCTGA
ATCAGAATAGCCATCTCCCAGGCCTTCTGGGGTATAAATTAACCTGCTAC
TTGCCAGATAATAAGGAGTGCTAGGGTTTTTTTTGCTTTTAGGAAGATT
AGCCCTGAGCTAACTGCTGCCAGTCCTCTTTTTGCTGGGGAAGACTGGCA
GTGAGCTAACATCCATGCCCATCCTCCTCTACTTTATATGTGGGACGCCT
ACCACAGCATGGCTTGCCAAGCGGTGCCATGTCCACACCCGGGATCTGAA
CTGGCGAACCCTGGGCCGCCAAGAAGCGGACCGAGCGAACTTAACTGCTG
CACCACTGGGCCGGCCTCTGGGAGTGCTAGGTTTTTAACCCTTAGCTGAG
AAGTTAAGTATGTCTGAACCTAGAAGGAGCTCCTTAGGCCCAAGACAATG
GTGGCCACAACTAAGAGGCAAAAA

INVS.1:

(SEQ ID NO: 57)
TTACTGAACTGGCAAGACTACGAGGGACGAACACCTCTTCATTTTGCAGT
CGCCGATGGGAATGTGACGGTGGTTGATGTCTTGACCTCGTACGAGAGCT
GCAACATAACA/GTCTTATGATAACTTATTTCGAACCCCACTTCACTGGG
CAGCTC

INVS.2&3&4:

(SEQ ID NO: 58)
CGGAGATATGGACAGATGGAACCAAGAGTGCATGGTATTGCTCCTCAGG
TCTGGAGGAAGGAACTGCAAGTAAAACCCCCAAAGATTATCCCAGTAAGC
AGGACCACCAAGAGTCCATCCAAGGGCATCTCGGGCACAAAGTCCACCAG
GCACTCAGTGCTCAAGCAAATCTATGGTAACTATCCTTCTGGGCACTTTG
TAGTTTACAA/GTTAGCACCCCAGAGAGTGTCACGTCATAATCTGGAAT
GGGATTTAATTACATTGGGCAAACATCCATTCAGGTAGGAACTTTATTAT
ACCTCCAGGCACCAAGAGAATCCTCAGCACCACATTTAGTGCCTCCCTCC
CAGCCATTCTGGGTCAGAATTGGTTTCATAAGACATTCTGGCATCACAAC
AAAGAGCTTCTCTGCTGGGCTCCATGACTGAAAGCCTCACCG/ATCTCTC
CAGGCCATTGCTTGGGTCTTCCCCTTACATTGTCCTCTTGGAGGAACCCA
GGCACAGACCAACCTTGCCTGCCTCACTTGGACC/GTTTCCTATGCTACG
AT/CAGTGCAGGGTTGTCCATCTGTGGGACTGCCCCAGACCGAGCACCGC
AGTAAACACGCGTTTAGCAGATGAACTGCTCCACCTCTGGAAGAGCCCAC
CCAGAGAAAGGCAGCAGGCAACAAGTCTGGCTGGCTCCCG/AAGCAGAA
GAAAGTTGAGCTGAGGCACCGTTAGAAACAATCTGTGAACAGGCAGGAAA
CTCTCAGGAGTTGACCTGGGTCTACATGGTATTTCCATACCATGCCTAAT
TTATCTTGGCAGACACCTGAAGCCTCAAGCCTTCACCTCAACAAAGAATT
CAGAACCTGGTCAGGCCACAGCTCTCAG/TGGTCAGAGATACATGATTAT
TGTTGGTTGATTGCAGGTTGTTCTCAAGAAGGGAAAGTACATCATCCCAC
AAGATCTTCAAAAGCTCATTCTGTGCTGCGTCTCAACTCAGGTAAGGCAA
ACCACTGCACTGGCAAAAAAAACGTTAGAACAGAGATGGCCAGGGGTTCC
CAAAGGTCATTTTGATTTCCACTAGGCATGGGTTTCATCCCCGTTTCATG
GAGTTGTTACTGCAGTCAACATCTGTCTCTATAAGGGGCAAGTTATTTTC
CAAATAAAAGCTAACATTACCTCCAGTAGAAACTTGTTCACATAAAGGAA
GGGGGAAATGAAAATGCTATCGTTCTTCAAAGTAATACCTTGGGAATTCT
TGTTTCATTTTGGTTTCACATTAGG/TATCCTCCAGTTCCTTCCCAAAGA
TGACAAAAGTCCTTTACCACAAATTCTGGCTTTTGCCTTTTAGGACCTA
CTCCATAAAGATGTGTAATATTTAATAGCATGTTCAGCTCAGGCTCAGCT
GTGCACATTTTCACTCATCCAAGAGCAGCTCAGGGAACTTTCTTTTCAGC
CACAAGACAGGAGTGC/TTACTCAGAG

INVS.UTR:

(SEQ ID NO: 59)
CTTACAACCTGCAATCAGCTATTCAATCAAAAACAAAACAAAAGCTTCG
ACCGCCTGC/TGGAGGAAGACTGTGTCCAGGGGCGCTGGAATAGCTAGTG
CAGAGTGCTAATTCTCCGCTCATTATCTCCGACATCTTGGGAAAACGTTA
ATACCCATGCCTGCAGCCTTACTGGCCTGAAAACGTGTTAACAACTGAAA
GAGAATGTCAGAATG/ATTTTCTTTCTGCTCTCACACAGCACTGTTTTGT
AAATTCTCTTAGCCTGAGCTCAAGGACCAGGGGAAACTATGCCTGTGCAA
AACTGCCCAGCTGTCTGCCTTCACCTCAGTCACGACGGCTGGAAAGAAGA
ATTTATAATTAACGGTAAAGTCTAAGTAACACTAAGAACATAGGTGCTAA
AGAGGCTGCTGGGTTGGGATTTCGGCCAGCCAGCTGCTGCTGGCCTGGTG
TTTTGGTTCCAGTGAAGAACTGGAATCAGATGAGGAGGAGCCTGTCCTAC
AGTAGCTGCCTTGTTTCACTACTTTTCTGGAATCTAATGCAACAAACTTC
CTTAGAGATACCGCATCCTGTTATTCCAACATTATTAGTTTTAAATTTTA
GACCAGAATCATAATCCAGCCTTTGCTTTTAGAAACTGCAAGACCATAAG
AGGTATACTGTTGATTCCTTACATTTACAGTTCCCATGTTGGCCTCTGAA
GGCCACAGGTTGCTGCCTCGTCCTCTCAGAATGGTGTTCTCGTCGCTGAG
CACCAGCAGCAGTATTGGGCACTAAGGAATCAGTCGGGCAGGTTTACAGA
CCAGACCATTCAT

TEX10.3:

(SEQ ID NO: 60)
CGTCTGCAGAGAAAACAACAGCAATGTGACACTGCACCCGAACC/TGCTG
TCTCCTCACCGTATTCTTCACACCCAAACGAACAGTATCCTCATCTGTAA
GTCACCACAGGAAATCTTACTGGAAAAGGGGACCTATTAACTGGGCATTA
CCACAGGCAGCGAAAATTCCTAGTTACGACCTCAAGTACAAGTACTAC
C/TGGTTTCTCGTTTGGTCTGTGCCCTCCCATACATGCTAGAGACTAATG
AAATTTCACCATCAACAATCCTACACTCCAGACTCCCCCCA/CCCTTGGC
ATTCTAGTCTCTCGCTCTCTGCACTCAAATCAACTGAGAACACTTCCACA
GAGCCGCCTGCCAAGTCCTGTCATTCTCTTCCTTATGGAGGTGAGCTGAT
TCTCTAACCTCAGAATAATCCAAATTCTTGACTTTTCTTCCCTTCTACTA
TTTCTGAATTATTATTATATATACCAATTAATAAACCCCCCCAATCC/AA
ATACCTATACAAAAAACCCTCTAACTCTCCCAAACCAAAAACACCAAAAG
GAATCCTAGATTACAGAGCTGCCTCCACAACACAGAGAACCAAGCTCCAG
ACAAAGCTGAAGCTGTGACTTCCTTCTTCCAACTTCTTCTTACTCTCCGG
TGAACTAAGTGACTAGAGATTGGCCTAAAATTTATTACTGCCAAATAATT
TCCCTAATGACAGCTAGCATTTGGTGAGCACTTAATAAATGTTAGCTATA
CTAAAAACATTATTTGGATTATCTCATTTAACGGTCACCAA

TEX10.1:

(SEQ ID NO: 61)
TTTTCTGTTACACAAAAAAGAGATTCATTGGTAAAGATTGGGTTTGCCA
TAGCCAGGAGTGAGTGAGTCTT/CCAGAAGTCTAAGCTTAATACATTCCA
TGGCCTTTCACAGCATGATGCTGTGGCAAGAACTGAGAAATCTTGGTGTT
TTTCCTGGCTGCTAACTAATTAATTCTGTGCCCTTGGGAAAATCTCTTTT
CCCAGGACCTTACTTTCTACATCTGTGCAATGAAGGACCTTGAAATTCTA
CCTCAGATCCTTCTGTCTTGTAATGCTTTAATTAACATGTGTCTGGTGTC
AGTGTATTGTGAATCCAGCATCCAGACTGGGGTCTAATTTTCACCTAGAG
CTTTGGGGTCTAAAGCTGGGATGTCACCTGGCAGGCTCAAGGCCTAG/AT
CACTGGAAGCAGGGAGCTCAGCCATGAGCCTGACTTGTCTTCTGGCCAGT
CTCTTGTTCCCTCGGTATTAAATTCACACTAGGTATGCCTGGGTTTTTGC

-continued

TTTTAACTTCTTCCAGTGTTTCCACTTTGACCTCTGGCTTTTATTATAAT

AATTTATTAAGTGCAAGGAAGGGATCACAAACTTTATCTTCCAGAGGACT

TTCACCTGTTTGGATATTTTTCAGGCGTATCTATTCCCTCTTTTCTTTAA

ATATTATTTTCCTTAAGTTGGAAGAGTACTGCTTTGAATTCCCCGTGCTC

TTTTCTCCCTGCTCTCAAACTTCCAATCCTTAGCCCGTGTGTCTCCAAAG

ATCCCCACTTTTTTTTAACCTG

TEX10.2:

(SEQ ID NO: 62)
GAGCAACTTAAAGAAGATGGGACACTTCCAACAAACAATAGAAAGCTTAA

CATAAAGGTAAGTCA/TTAAGTGTTGTTTTGATAAAATAAGATTTTCTTT

CAAATCATCTA/GGAATGTTGTGTTTTTGTGAAAAGTTGTTTTAACTCTT

AGGGTTTATTAATGGCTGAAGTTTGGAGTTCATCTGTTATTCATATGTGA

TGTTGCCATGGCAGCTTTCCCACCTCGTCCAGAAAGACTTGCTCAGCTAA

ACCCACAGTGGTTTCTCCCTGTCTACTTATTTGATGATTTAATATATCAT

CTCAAAGT/GAA/GTTCTTGTGTTTAACTTTTTGATGTGTCAAGGTGTTT

TTTTGTTTGTTTGTTTGGTGAGGAAGATTGGCCCTACACTAACATCTG

TTGCCAGTCCTCCTCTTTTTAGTTGAAGAAGATTGTTACTGAGCTAATAC

TGTGCTAGTCTTCCTCTATTTTGTGTGTGCCACACACTGCCACAC/GTGT

GGCTTAACGAGTGGTGCTAGGTCTGCGCCATGGATCCGAACCTGCAAACC

TT/CGGGCTCCCAAAGCAGAGGACAT

TABLE 3

Primers for pyrosequencing

| Gene | Primers | Tm | SEQ ID NO: |
|---|---|---|---|
| TGFBR1 | F: AGCATGGTTTAGCTGTTTTTTAAA | | 63 |
| | Rbio: CTGTGTGGTAGTAATGGAATG | | 64 |
| | Seq: CCCAAAGGACATAAAGGACA | | 65 |
| | T: AAG/TGAAACATCATTCC | 56/54 | 66 |
| SNP.1 | F: CAATAAATTGGTCAACCTAACACG | | 67 |
| | Rbio: CATGGTGTATTCCCCTTCCA | | 68 |
| | Seq: CAATAAATTGGTCAACCTAACACG | | 67 |
| | T: T/CTATAAAAGAGGGCT | 58/55 | 69 |
| SNP.2 | F: CAATAAATTGGTCAACCTAACACG | | 70 |
| | Rbio: CATGGTGTATTCCCCTTCCA | | 71 |
| | Seq: CACAGATAGTGCATTCCAGATAGG | | 72 |
| | T: GGT/CGAGATGGAGGGGAATA | 58/55 | 73 |
| SNP.3 | F: CTGCAGTGTTTAAGTTTAGGATTGA | | 74 |
| | Rbio: TAAAGCTCATGGAGGCCAAT | | 75 |
| | Seq: TTCTACTTCCAGCTATTCCGCT | | 76 |
| | T: AAC/TTAACCTGGTGAC | 58/55 | 77 |
| SNP.4 | Fbio: TGCACCTTGCCTTTCTTTTT | | 78 |
| | R: CAGCAATCCGCTTTTTCTTT | | 79 |
| | Seq: TCCCTTTATCTCTTGCACAAT | | 80 |
| | T: T/GCCTGGTATATAGT | 60/58 | 81 |

TABLE 3-continued

Primers for pyrosequencing

| Gene | Primers | Tm | SEQ ID NO: |
|---|---|---|---|
| SNP.5 | F: GCATTTTACATGTATTGGCAGGT | | 82 |
| | Rbio: CCTCAGTTTCCTCATCCGTAA | | 83 |
| | Seq: CCCATGAGGTATGACGTAGG | | 84 |
| | T: TA/GTCATGATCATGATGTC | 60/58 | 85 |
| NR4A3.2 | Fbio: TGTGACCTCTGTCCTCTCTCC | | 86 |
| | R: ATATCTTGCGCGCTGAATG | | 87 |
| | Seq: GTGTAGAAGCGGGGGACGTC | | 88 |
| | T: T/CGGCGAGGCGAAGCGGCTG | 60/58 | 89 |
| NR4A3.1 | F: CATGCATCACTTAACAACAGAGG | | 90 |
| | Rbio: GTCAACGACGGACCACATA | | 91 |
| | Seq: CTACACACCTAGGCTCT | | 92 |
| | T: A/GTGGTACTAATCTT | 58/56 | 93 |
| TXNDC4 | F: AACCTCAAAGCATCATCTTGTG | | 94 |
| | Rbio: TCTCTAGTCCCAGCTCTG | | 95 |
| | Seq: TCAAAGTAACGATGGGGACT | | 96 |
| | T: C/TAGAGGCCTGAAGGCGC | 57/55 | 97 |
| INVS.1 | Fbio: GTACGAGAGCTGCAACATAAC | | 98 |
| | R: GAGCTGCCCAGTGAAGTG | | 99 |
| | Seq: GGTTCGAAATAAGTTATCATAAGA | | 100 |
| | T: T/CGTTATGTTGCA | 59/58 | 101 |
| INVS.2 | F: TCAGTGCTCAAGCAAATCTATG | | 102 |
| | Rbio: AATCCCATTCCAGATTATGACG | | 103 |
| | Seq: CTGGGCACTTTGTAGTTTACA | | 104 |
| | T: A/GTTAGCACCCCCAGA | 57/55 | 105 |
| INVS.3 | Fbio: AGAACCTGGTCAGGCCACA | | 106 |
| | R: TCTTGTGGGATGATGTACTTTCC | | 107 |
| | Seq: ATAATCATGTATCTCTGACC | | 108 |
| | T: C/ATGAGAGCTGT | 59/57 | 109 |
| INVS.4 | F: CAAGAGCAGCTCAGGGAACT | | 110 |
| | Rbio: CTGGCATTAGCTGCTGACAG | | 111 |
| | Seq: TCAGCCACAAGACAGGAGTG | | 112 |
| | T: C/TTTACTCAGAG | 60/58 | 113 |
| INVS.UTR | Fbio: CATGCCTGCAGCCTTACTG | | 114 |
| | R: GGTCCTTGAGCTCAGGCTAA | | 115 |
| | Seq: CTGTGTGAGAGCAGAAAGAAAA | | 116 |
| | T: T/CATTCTGACATTCAC | 59/57 | 117 |
| TEX10.3 | F: CGTCTGCAGAGAAAACAA | | 118 |
| | Rbio: GAGGATACTGTTCGTTTG | | 119 |
| | Seq: TGTGACACTGCACCCGAAC | | 120 |
| | T: C/TGCTGTCTCCTCACC | 52/50 | 121 |
| TEX10.1 | F: GGGGTCTAAAGCTGGGATGT | | 122 |
| | Rbio: CAGTCTCTTGTTCCCTCGG | | 123 |
| | Seq: TGGCAGGCTCAAGGCCTA | | 124 |
| | T: G/ATCACTGGAAGCAGGG | 59/58 | 125 |
| TEX10.2 | Fbio: TGGGACACTTCCAACAAACA | | 126 |
| | R: CCAAACTTCAGCCATTAATAAACC | | 127 |
| | Seq: TTATCAAAACAACACTTA | | 128 |
| | T: T/AGACTTACCTTTATGTTAA | 60/58 | 129 |

TABLE 3-continued

Primers for pyrosequencing

| Gene | Primers | Tm | SEQ ID NO: |
|---|---|---|---|
| TMEFF1 | F: CCTATGTCGACAATCTTTGTAC | | 130 |
| | Rbio: ATTAGTAGCAGAACGAAGAAATTC | | 131 |
| | Seq: TGAGAAATATTTGATGCTTT | | 132 |
| | T: A/GTTGGCTTTTTA | 58/57 | 133 |

F refers to forward primer; Fbio refers to biotinylated forward primer; R refers to reverse primer; Rbio refers to biotinylated reverse primer; Seq refers to sequencing primer; and T refers to target sequence to be analyzed.

Identical-by-Descent (IBD) Mapping Assigns Grey to a ~350 kb Region

Grey was first assigned to horse chromosome 25 (Swinburne et al., *Animal Genetics*, 33:338-342 (2002); Henner et al., *Mamm. Genome*, 13:535-537 (2002); and Locke et al., *Anim. Genet.*, 33:329-337 (2002)) and subsequently fine-mapped to a region corresponding to 6.9 Mbp on human chromosome 9q (Pielberg et al., *Anim. Genet.*, 36:390-395 (2005)). The region did not harbour any identifiable candidate genes for a pigmentation phenotype. It was hypothesized that Grey represents a single mutation event, because of its unique phenotypic characteristics and the presumed strong selection, and consequently that all Grey horses have inherited the mutation from a common ancestor.

Coding sequences from the 6.9 Mbp region in human were aligned with homologous sequences in other mammals and PCR primers were designed for sequencing and detection of Single Nucleotide Polymorphisms (SNPs). SNPs were screened on a panel of Grey (G/G or G/g) and non-grey (g/g) horses. SNPs in the interval from position 29,095,813 to 28,743,518 on horse chromosome 25 and approximately corresponding to position 101.6 to 102.1 Mbp (~470 kb) on human chromosome 9q31 defined the Grey critical interval since markers within this interval exhibited complete linkage disequilibrium (LD) with Grey (Table 4). The Grey interval is surprisingly large given the fact that the material includes as divergent populations as Icelandic and Arabian horses that have been separated for at least 1,000 years. The results implicate a very low rate of recombination in the region as also indicated in a linkage study (Pielberg et al., *Anim. Genet.*, 36:390-395 (2005)). Based on these results, it was concluded that the causative mutation is located in this ~350 kb interval and that all Grey horses tested (>700 from eight breeds) have inherited Grey from a common ancestor. Interestingly, one non-grey haplotype was identical to the Grey haplotype for all tested SNPs, suggesting that it may represent the ancestral haplotype for Grey.

TABLE 4

Single Nucleotide Polymorphisms tested for association with the Grey allele on horse chromosome 25. NR4A3.2 and INVS.3 (in bold italics) represent the flanking markers for the Grey interval.

| | | Allele[b] | | Grey horses | | | Non-grey horses | | |
|---|---|---|---|---|---|---|---|---|---|
| Marker | Position* | A | B | AA | AB | BB | AA | AB | BB |
| TGRBR1 | 29,687,971 | A | T | 9 | 18 | 11 | 4 | 8 | 20 |
| SNPgrey1 | 29,243,371 | T | C | 32 | 6 | 0 | 27 | 4 | 1 |
| SNPgrey2 | 29,243,313 | T | C | 7 | 24 | 7 | 2 | 8 | 22 |
| SNPgrey3 | 29,240,577 | C | T | 12 | 20 | 6 | 6 | 9 | 17 |
| SNPgrey4 | 29,121,942 | T | G | 28 | 12 | 0 | 14 | 12 | 5 |
| SNPgrey5 | 29,120,937 | A | G | 33 | 7 | 0 | 13 | 16 | 4 |
| *NR4A3.2* | *29,095,813* | *C* | *T* | *26* | *6* | *2* | *26* | *3* | *1* |
| NR4A3.1 | 29,076,114 | G | A | 33 | 8 | 0 | 15 | 17 | 6 |
| TXNDC4 | 28,940,160 | T | C | 30 | 13 | 0 | 12 | 18 | 8 |
| INVS.1 | 28,800,463 | T | C | 29 | 13 | 0 | 7 | 16 | 9 |
| INVS.2 | 28,744,174 | A | G | 33 | 11 | 0 | 15 | 17 | 6 |
| *INVS.3* | *28,743,518* | *C* | *A* | *24* | *17* | *2* | *17* | *14* | *7* |
| INVS.4 | 28,742,934 | T | C | 6 | 33 | 4 | 0 | 4 | 34 |
| INVS.UTR | 28,740,562 | C | T | 10 | 30 | 4 | 1 | 10 | 27 |
| TEX10.3 | 28,738,799 | T | C | 13 | 25 | 1 | 2 | 17 | 13 |
| TEX10.1 | 28,730,901 | A | G | 27 | 14 | 0 | 9 | 16 | 6 |
| TEX10.2 | 28,686,743 | T | A | 6 | 29 | 15 | 2 | 8 | 20 |
| TMEFF1 | 28,524,848 | A | G | 3 | 19 | 15 | 2 | 8 | 20 |

[a]Position in the horse genome (see internet site: "genome.ucsc.edu"; Build January 2007 (equCab1) assembly).
[b]Definition of the SNP alleles for each marker.

The Grey Critical Region Contains Four Genes

Figure 2:
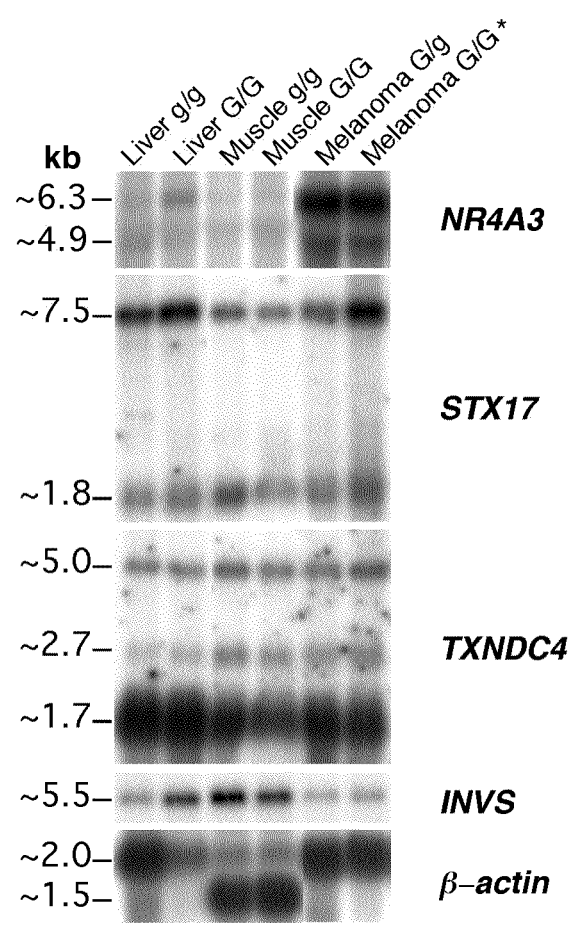
FIG. 2 is a photograph of a multiple-tissue Northern blot analysis of the genes in the Grey critical region and from horses of the indicated genotype. β-actin was used as internal control. The estimated transcript sizes are indicated.
Figure 3:
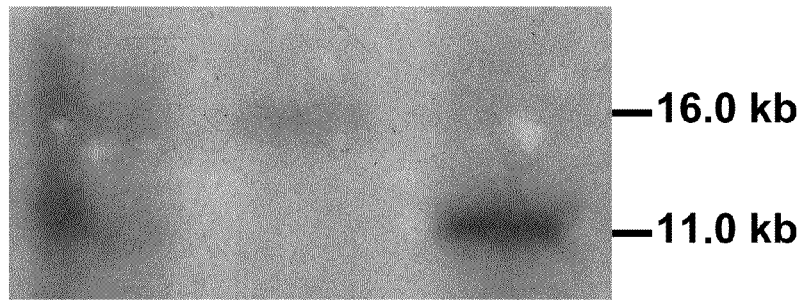
FIG. 3 is a photograph of a Southern blot analysis of genomic DNA restricted with BamHI and probed with a horse STX17 cDNA fragment (exon 2-8). Three horses representing the three different genotypes at the Grey locus are shown. The fragment sizes of the two fragments in kilobases are indicated.

The corresponding region in humans, mice, and dogs contains four known genes: NR4A3 (nuclear receptor subfamily 4, group A, member 3), STX17 (syntaxin 17), TXNDC4 (thioredoxin domain containing 4), and INKS (inversin) (FIG. 1). SNPs were developed for these genes and genetic analysis confirmed that they are all located in the Grey critical interval (Table 4). None of the genes has previously been associated with pigmentation defects or development of melanoma. Northern blot and reverse transcriptase (RT)-PCR analysis revealed that all four genes are expressed in Grey melanoma tissue and no variant transcript was detected in Grey horses (FIG. 2). However, the high expression of NR4A3 in melanomas from Grey horses was striking A 4.6 kb Duplication in STX17 Intron 6 Exhibits a Complete Association with Grey Sequence analysis of all exons from the four genes (as defined in the human assembly) revealed no unique sequence polymorphism associated with Grey. Southern blot analysis of genomic DNA revealed no polymorphism for NR4A3, TXNDC4, or INV but a ~4.6 kb duplication was present within STX17 (FIG. 3). Fine mapping of the duplication revealed that it is located in intron 6. The entire intron was sequenced from several horses to determine the exact position of the duplication. The sequenced Grey alleles exhibited 39 SNPs in comparison with non-grey haplotypes. The "ancestral" non-grey haplotype exhibited an identical sequence as Grey but did not include the duplication. A diagnostic PCR-based test for the STX17 duplication was used to screen more than 43 Grey horses and more than 100 non-grey horses representing eight breeds. The duplication was detected in the homozygous or heterozygous condition in all Grey horses but in none of the non-grey horses (Table 5) and thus qualifies as a candidate causal mutation.

TABLE 5

Complete association between the 436 kb duplication in intron 6 of STX17 and the Grey allele across breeds.

| Breed | n | Genotype | | |
|---|---|---|---|---|
| | | D/D | D/— | —/— |
| Grey horses | | | | |
| Arabian | 22 | 4 | 18 | 0 |
| Connemara | 3 | 0 | 3 | 0 |
| Icelandic | 1 | 0 | 1 | 0 |
| Lipizzaner | 10 | 5 | 5 | 0 |
| New forest pony | 1 | 0 | 1 | 0 |
| Shetland pony | 1 | 0 | 1 | 0 |
| Thoroughbred | 3 | 0 | 3 | 0 |
| Welsh | 2 | 1 | 1 | 0 |
| Total: | 43 | 10 | 33 | 0 |
| Non-grey horses | | | | |
| Arabian | 18 | 0 | 0 | 18 |
| Connemaa | 4 | 0 | 0 | 4 |
| Fjord horse | 10 | 0 | 0 | 10 |
| Friesian | 5 | 0 | 0 | 5 |
| Haflinlger | 10 | 0 | 0 | 10 |
| Icelandic | 11 | 0 | 0 | 11 |
| Morgan horse | 10 | 0 | 0 | 10 |
| New forest pony | 10 | 0 | 0 | 10 |
| North Swedish Horse | 10 | 0 | 0 | 10 |
| Shetland pony | 10 | 0 | 0 | 10 |
| Swedish warmblood | 4 | 0 | 0 | 4 |
| Thoroughbred | 7 | 0 | 0 | 7 |
| Welsh | 4 | 0 | 0 | 4 |
| Total: | 113 | 0 | 0 | 113 |

D = presence of STX17 duplication

Characterization of STX17

Figure 4:
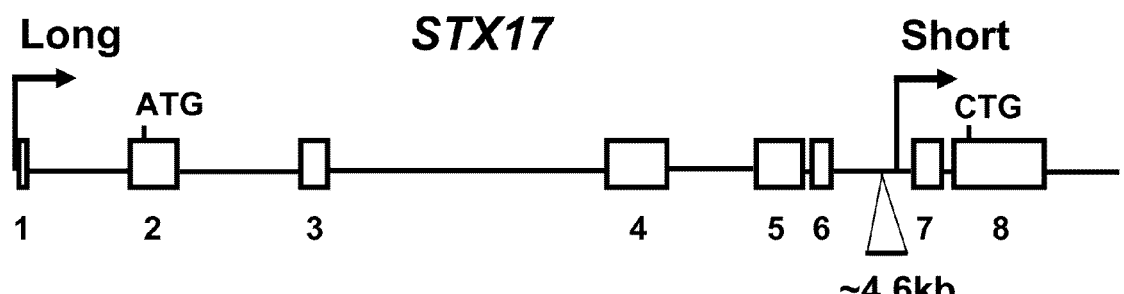
FIG. 4 is a schematic diagram of an STX17 exon/intron organization including the start of transcription for long and short isoforms. The location of the 4.6 kb duplication in intron 6 associated with Grey is indicated.

ESTs from several mammals, including humans, revealed that an alternative STX17 transcript can be initiated just downstream of the Grey duplication breakpoint (FIG. 4). The expression of this transcript was continued both in normal tissues from all horses and in melanoma tissue from Grey horses. This truncated transcript was spliced exactly as the long transcript and includes a part of intron 6 and exons 7 and 8. The only ATG codons in frame with the coding sequence could only generate short polypeptides (20 or 21 residues). There was a putative alternative CTG start codon in exon 8 that may generate a polypeptide with 74 residues. This CTG was confirmed to be used as a start codon by transfection experiments using two different vectors in which FLAG was fused to the N-terminal end directly followed by the CTG codon in frame, or by keeping the entire 5'UTR from the alternative transcript and fusing FLAG in frame at the 3' end. These two constructs generated recombinant polypeptides of identical molecular weights as determined by Western blot analysis. These results indicate that the alternative transcript is translated into a short polypeptide of 74 amino acids. Interestingly, the part of the 5'UTR of the short transcript encoded by intron 6 is evolutionary well conserved down to fishes. The EvoFold program (Pedersen et al., PLoS Computat. Biol., 2:e33 (2006)) predicted an evolutionary conserved RNA structure for this 5'UTR sequence.

Figure 5:
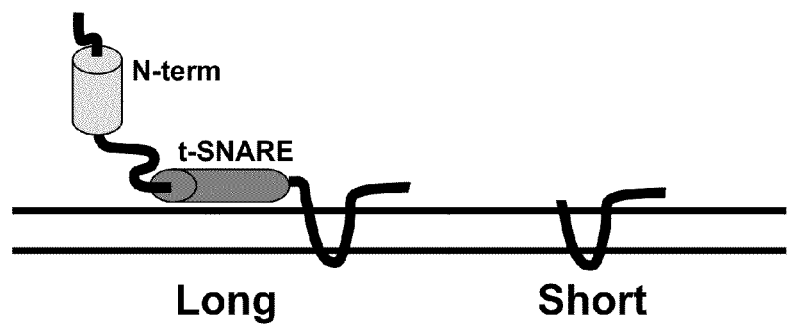
FIG. 5 is a schematic diagram of the predicted polypeptide corresponding to the two different STX17 transcripts.

The full-length transcript encodes a polypeptide of 302 amino acids with an N-terminal region of unknown function, a well conserved syntaxin domain followed by two transmembrane regions and a carboxyterminal tail (FIG. 5). The short transcript only includes the transmembrane regions and the carboxyterminal tail. The presence of two transmembrane regions implies that the N-terminal domains and the carboxy-terminal tails are located on the same side of the membrane (FIG. 5). STX17 is the only syntaxin with such a carboxyterminal tail (Steegmaier et al., J. Biol. Chem., 273:34171-34179 (1998)), suggesting that it has a distinct function.

Expression of Both STX17 and NR4A3 from Grey Chromosomes are Upregulated in Melanomas.

STX17 and NR4A3 were further investigated for their involvement in the Grey phenotype due to the presence of a duplication in the former (FIG. 3) and the high expression in Grey melanoma of the latter (FIG. 2). Syntaxins contain SNARE domains and are involved in intracellular membrane trafficking (Bonifacino and Glick, Cell, 116:153-166 (2004)). Syntaxin 17 was first isolated in a two-hybrid screen using STX3 as bait (Steegmaier et al., J. Biol. Chem., 273:34171-34179 (1998)). It is a divergent member of the syntaxin family with a broad tissue distribution. STX17 was reported to be partially associated with the endoplasmic reticulum and exhibited a nuclear localization in some malignant cells (Zhang et al., J. Histochem. Cytochem., 53:1371-1382 (2005)). NR4A3, also denoted NOR-1, belongs to the NR4A subgroup of the nuclear hormone receptor superfamily (Maxwell and Muscat, Nucl. Recept. Signal., 4:e002 (2006)).

Figure 6:
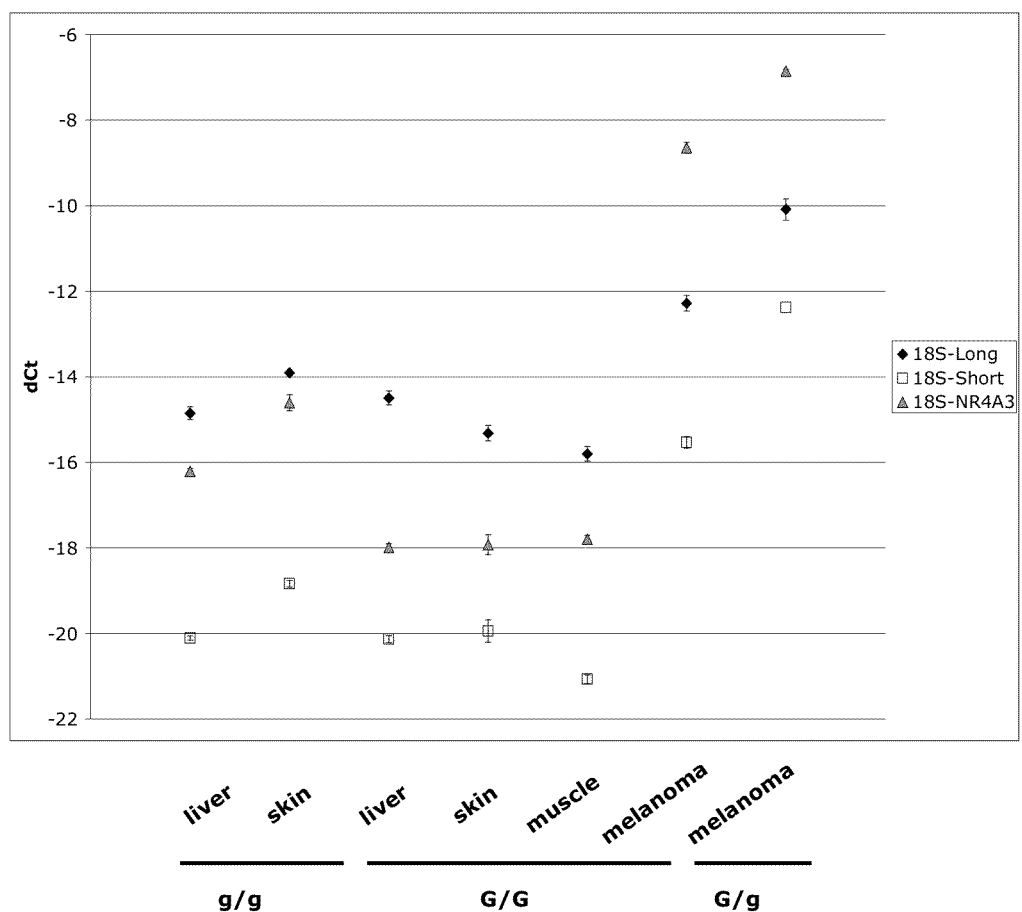
FIG. 6 is a graph plotting real-time PCR analysis of STX17 (short and long 5 transcripts) and NR4A3 expression in relation to the expression of 18S-rRNA in different tissues from Grey and non-grey horses.
Figure 7:
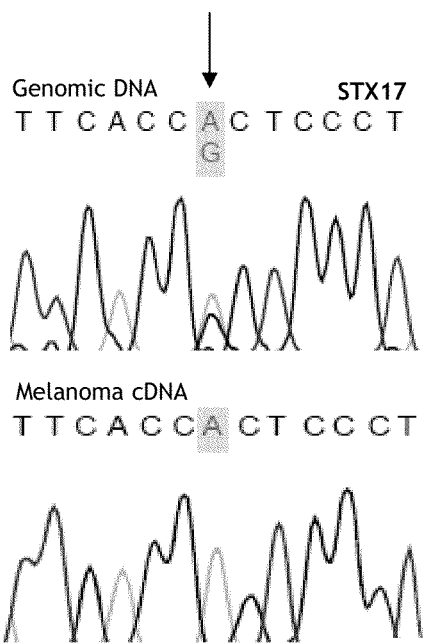
FIG. 7 contains results from a differential expression analysis for STX17 using melanoma tissue from a G/g heterozygous horse. The upper case letter "G" is an abbreviation for the dominant allele causing Grey coat color. The lower case letter "g" is an abbreviation for the recessive wild-type allele at this locus. Genomic DNA was used as reference.

The STX17 duplication in Grey horses is located in intron 6 just upstream of the initiation of a short alternative transcript. A bioinformatic analysis of the duplicated region did not reveal any obvious protein- or microRNA-coding sequences. However, the region contains several elements that are well conserved among mammals indicating that the duplication may include regulatory elements. The relative expression of the long and short isoform of STX17 in different tissues from Grey and non-grey horses was assessed by real-time PCR analysis using 18S as an internal control (FIG. 6). The long isoform was clearly the predominant form in all tissues tested, and there was a strong correlation between the expressions levels of the two forms. Both the long and short isoforms of STX17 were markedly upregulated in melanoma tissue from Grey horses compared with skin, liver, and muscle from both Grey and non-grey horses (FIG. 6). In order to more directly study differential expression between alleles, the relative expression of alleles in Grey heterozygotes was quantified using SNPs located in the part of intron 6 encoding the 5'UTR of the short transcript. This analysis was not possible for the long form due to the lack of suitable polymorphisms. Sequence analysis of genomic DNA from three Gig heterozygotes confirmed that they were heterozygous for two SNPs in this region. However, sequence analysis of cDNA from melanoma tissue revealed only expression of one allele, demonstrating differential expression of the short isoform in these three Grey heterozygotes (FIG. 7). The strong correlation between the two isoforms (FIG. 7) implies that this differential expression can occur for the long form as well.

Figure 8:
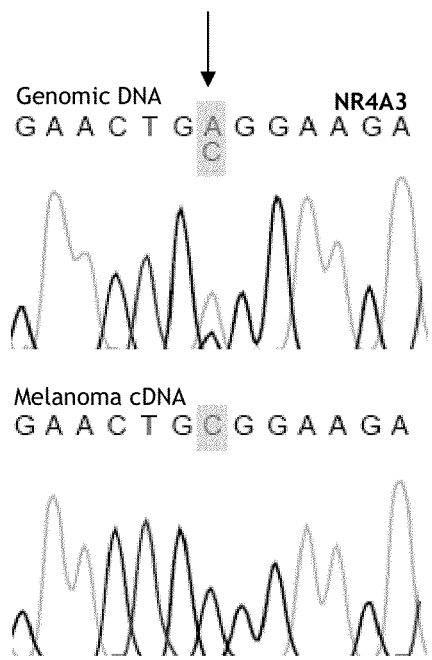
FIG. 8 contains results from a differential expression analysis for NR4A3 using melanoma tissue from a G/g heterozygous horse. Genomic DNA was used as reference.
Figure 9:
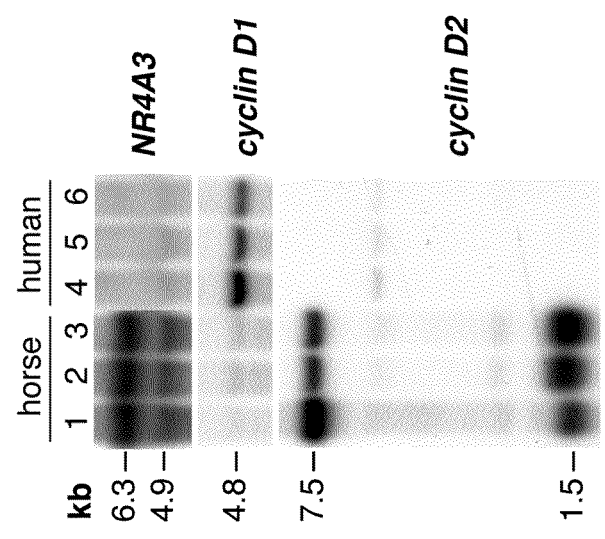
FIG. 9 contains photographs of a Northern blot analysis demonstrating that enhanced expression of NR4A3 nucleic acid is associated with high expression of a cyclin D2 transcript but not a cyclin D 1 transcript in Grey horse melanoma. Lanes 1, 2, and 3: horse melanoma; Lanes 4, 5, and 6: human melanoma.
Figure 10:
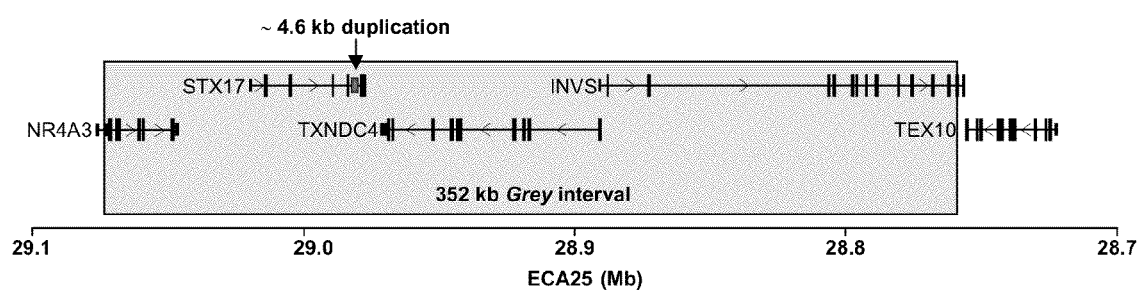
FIG. 10 is a schematic diagram of the gene content of the Grey interval based on the horse genome assembly as presented on the UCSC server at "genome.ucsc.edu"; Build January 2007 (equCab1) assembly); Karolchik et al., Nucl. Acids Res., 31(1):51-54 (2003)). The 352 kb region exhibiting complete association with Grey is indicated by a box, and the location of the 4.6 kb duplication in STX17 intron 6 is marked with an arrow.

Northern blot analysis revealed a high expression of NR4A3 in horse melanomas (FIG. 2) whereas no expression of another NR4A member (NR4A1) was detected. This result was confirmed by real-time PCR analysis (FIG. 6). Sequence analysis of cDNA from Grey heterozygotes revealed only NR4A3 expression from the Grey allele demonstrating that a cis-acting regulatory mutation is underlying the upregulation of expression (FIG. 8). The expression levels of cyclin D1 and D2 in Grey melanoma cells were investigated, and both Northern blot analysis revealed high expression of cyclin D2 but not D1 (FIG. 9).

The results provided herein demonstrate that Greying with age in horses is caused by a cis-acting regulatory mutation since the two neighbouring genes STX17 and NR4A3 both exhibit differential expression in horse melanomas. The 4.6 kb duplication in intron 6 of STX17 constitutes this regulatory mutation because (i) a complete association to Grey was found for >100 horses, (ii) the duplication is the only observed difference between the Grey and non-grey "ancestral" haplotypes, and (iii) tandem duplications are notoriously unstable (Bailey et al., *Science,* 297:1003-1007 (2002)); it appears extremely unlikely that such a complete association between the duplication and the phenotype could have been maintained over thousands of years unless it is the causative mutation. In fact, the observed "ancestral" haplotype may not be an ancestral haplotype but a Grey haplotype that has lost the duplication and thereby the association with the Grey phenotype. There appears to be no documented cases of revertants (e.g., a homozygous Grey stallion that produces a non-grey progeny) although such events are difficult to verify in an outbred species like the horse. However, somatic revertants are expected to cause pigmented spots and, interestingly, speckling is a characteristic feature of the Grey phenotype.

The results provided herein also demonstrate that overexpression of STX17 or NR4A3 can be a cause for the phenotypes associated with greying with age. The results that cyclin D2, which has been shown to be a target gene for NR4A3 (Nomiyama et al., *J. Biol. Chem.,* 281:33467-33476 (2006)), is upregulated in melanomas from Grey horses suggests a plausible mechanism for how the Grey mutation predisposes horses to the development of melanoma. For example, the overexpression of NR4A3 can result in over expression of cyclin D2, which can to promote cell proliferation and thereby lead to melanoma development.

Example 2

Silencing of STX17 and NR4A3 in a Grey Melanoma Cell Line Inhibits Proliferation siRNA Treatment Synthetic double-stranded small interfering RNAs (Ambion Silencer® Select Pre-designed siRNA, cat. 4392420) were designed to silence the expression of NR4A3 (siNR4A3__1 aud__2) and the short form of STX17 (siSTX-short 1, 2, 3). Scrambled siRNA (Ambion Silencer® Select Negative Control siRNA, cat. 4390843) and siRNA for GAPDH (Ambion Silencer® Select Pre-designed siRNA, cat. 4392420) were used as negative controls.

Melanoma cells from a Grey horse (provided by Monika H. Seltenhammer, University of Veterinary Medicine, Vienna, Austria) were split to 75-cm2 tissue culture plates (NUNC) three days before transfection. Cell suspension (5×10s cells per 1 mL growth medium without antibiotics) was harvested by trypsinizing with 0.05% Trypsin-EDTA solution (Invitrogen), suspended, centrifuged at 1500 rpm for 5 minutes, and re-suspended in growth medium. The cell suspension was added to an equal volume of the transfection solution that consisted of 5-20 pmol siRNA and 5 µL lipofectamine-2000 CD (Invitrogen) per 0.5 mL OptiMEM (Invitrogen) in 12-well plates. After 24 hours, the solution was replaced with fresh growth medium, and the transfected cells were incubated for an additional 2-3 days. PBS was used to wash and collect cells for silencing validation by qPCR and Western blotting. For each treatment with every single siRNA oligonucleotides, biological triplicates were prepared for statistical analysis.

Proliferation Assay

Every 24 hours after transfection, growth medium with 10% AlamarBlue (Invitrogen) was added 4 hours before absorbance reading at wavelengths 570 and 600 nm using Sunrise microplate reader (Tecan). Proliferation curves after silencing were generated according to the manufacturer's protocol.

Results

Figure 33:
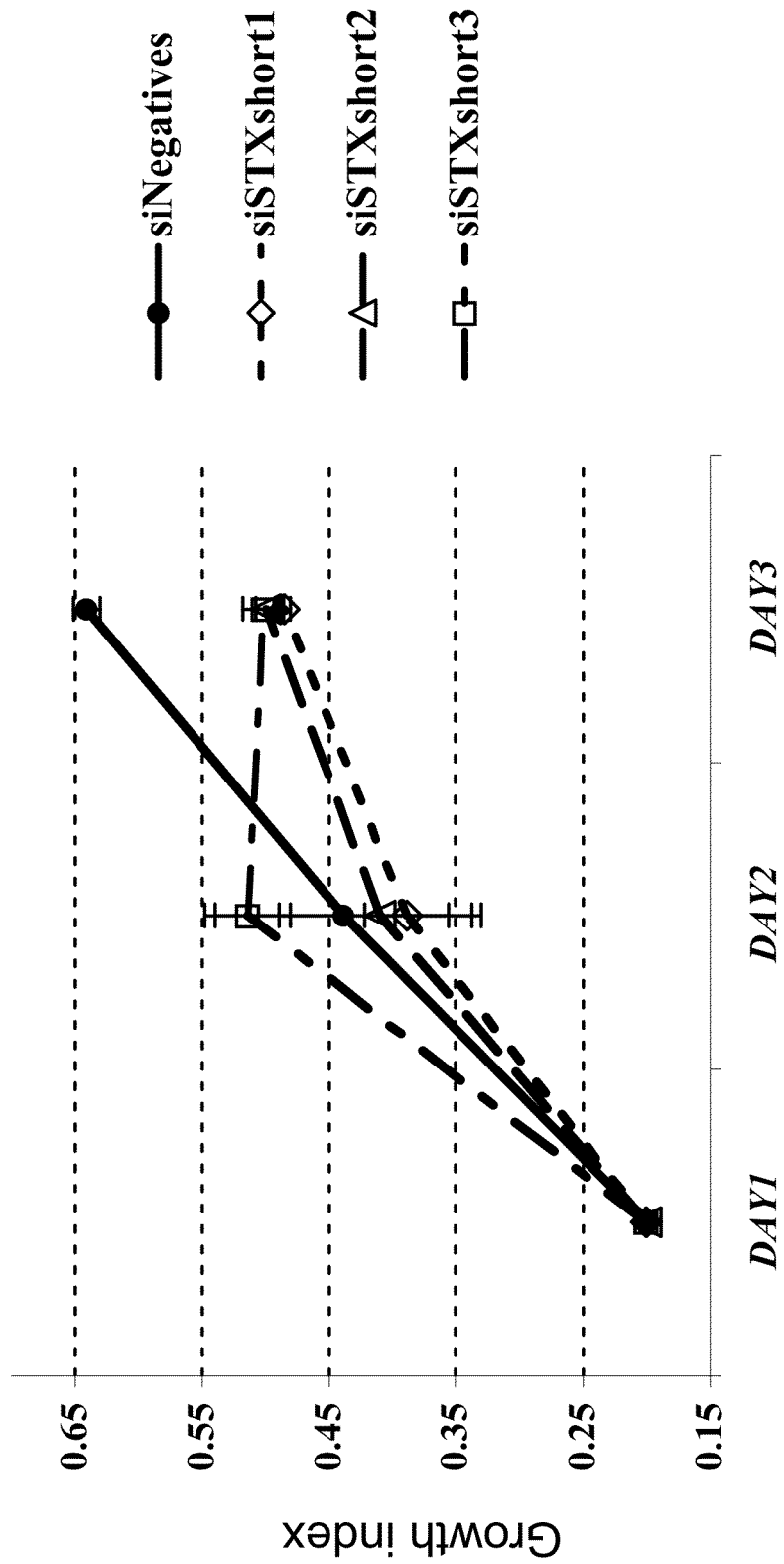
FIG. 33 is a graph showing the results of silencing the STX17 short transcript. The solid line represents the negative control, and the broken lines represent the results obtained using three different siRNA oligonucleotides. The differences at day 3 are statistically significant (P<0.05).
Figure 34:
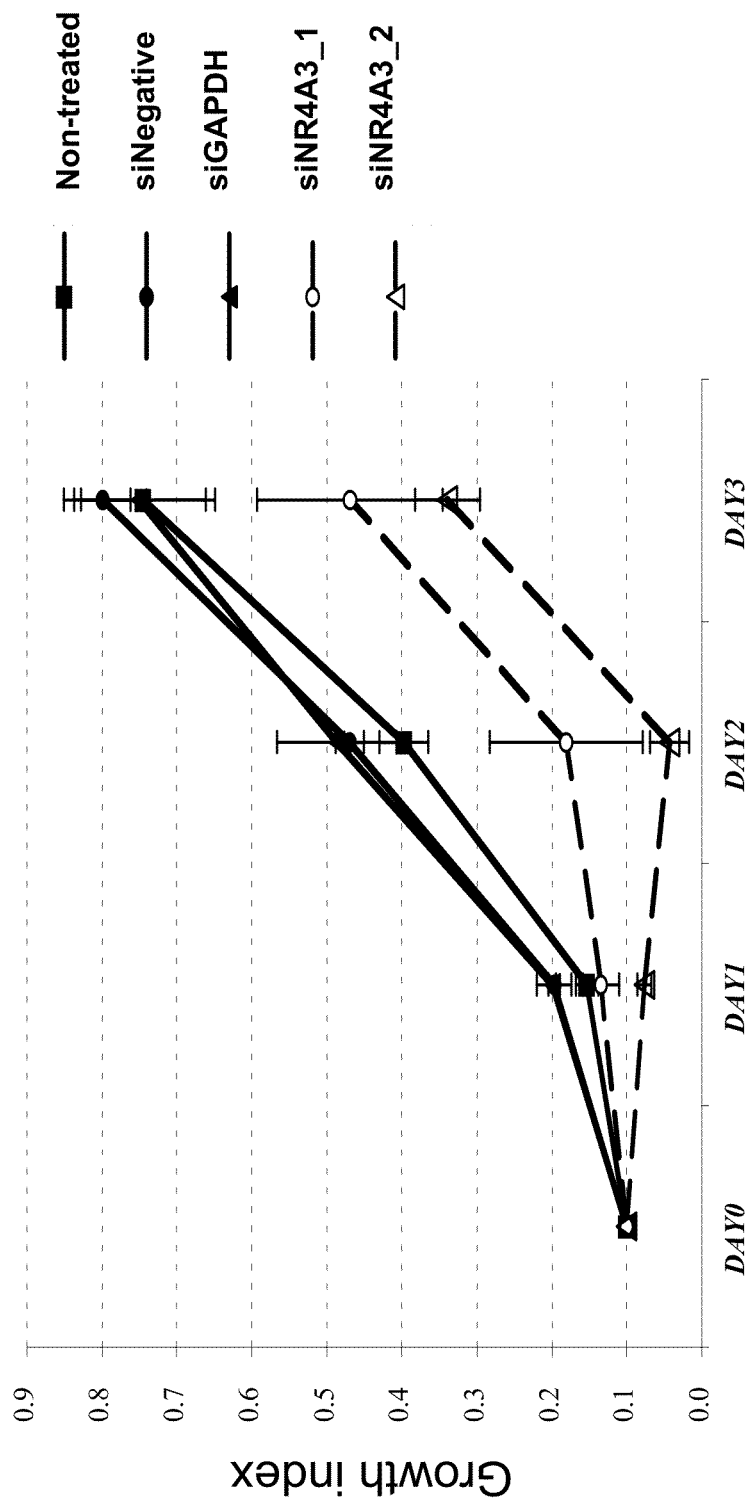
FIG. 34 is a graph showing the results of silencing the NR4A3 transcript using two different siRNA oligonucleotides. The solid lines represent negative controls, and the broken lines represent the results obtained using two different siRNA oligonucleotides. The differences at day 3 are statistically significant (P<0.05).

Silencing of the short form of STX17 using three different oligonucleotides led in all cases to significant inhibition of proliferation of the grey melanoma cell line (FIG. 33). Similarly, silencing of NR4A3 also inhibited the proliferation of the Grey melanoma cell line significantly (FIG. 34). These results indicate that RNA interference against STX17 and/or NR4A3 can be used to treat Grey melanomas.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 6

List of siRNA oligonucleotides used for silencing STX17 and NR4A3

| siRNAs ID | Target | senseSeq | antisenseSeq |
|---|---|---|---|
| s219844 | STXshort3 | CUGCUGCUGUGAAUGUUGAtt (SEQ ID NO: 134) | UCAACAUUCACAGCAGCAGtg (SEQ ID NO: 135) |
| s219846 | STXshort1 | GUUUUAAACUGAAUCUUCAtt (SEQ ID NO: 136) | UGAAGAUUCAGUUUAAAACag (SEQ ID NO: 137) |
| s219848 | STXshort2 | GAUCAAACCAUAUUGUAUUtt (SEQ ID NO: 138) | AAUACAAUAUGGUUUGAUCtg (SEQ ID NO: 139) |
| s219856 | NR4A3_1 | CACUGAGCAUGAUCACAGAtt (SEQ ID NO: 140) | UCUGUGAUCAUGCUCAGUGct (SEQ ID NO: 141) |
| s219857 | NR4A3_2 | CAUUAAAGACUUUUCCUUAtt (SEQ ID NO: 142) | UAAGGAAAAGUCUUUAAUGga (SEQ ID NO: 143) |
| s219852 | GAPDH | CCACGAGAAAUAUGACAAUtt (SEQ ID NO: 144) | AUUGUCAUAUUUCUCGUGGtt (SEQ ID NO: 145) |

What is claimed is:

1. A method for treating a mammal having cancer, wherein said method comprises administering, to said mammal, a composition comprising an agent having the ability to reduce an STX17 polypeptide activity in said mammal.

2. The method of claim 1, wherein said mammal is a horse.

3. The method of claim 1, wherein said mammal is a human.

4. The method of claim 1, wherein said cancer is a melanoma.

5. The method of claim 1, wherein said agent comprises a nucleic acid molecule capable of inducing RNA interference against expression of a STX17 polypeptide.

6. The method of claim 1, wherein said agent comprises an anti-STX17 antibody.

* * * * *